United States Patent
Di Lucrezia et al.

(10) Patent No.: US 11,111,238 B2
(45) Date of Patent: *Sep. 7, 2021

(54) COUMARIN DERIVATIVES, PROCESSES FOR THEIR PREPARATION AND USES THEREOF FOR THE TREATMENT OF CANCER

(71) Applicants: Lead Discovery Center GmbH, Dortmund (DE); Max Planck Gesellschaft zur Förderung der Wissenschaften e. V., Munich (DE); SOTIO a.s., Prague (CZ)

(72) Inventors: Raffaella Di Lucrezia, Wuppertal (DE); Tim Bergbrede, Dortmund (DE); Peter Nussbaumer, Dortmund (DE); Uwe Koch, Dortmund (DE); Bert Klebl, Dortmund (DE); Axel Choidas, Herdecke (DE); Anke Unger, Dortmund (DE); Nils-Göran Larsson, Sollentuna (SE); Maria Falkenberg-Gustafsson, Mölndal (SE); Claes M. Gustafsson, Mölndal (SE)

(73) Assignees: Lead Discovery Center GmbH, Dortmund (DE); Max Planck Gesellschaft zur Förderung der Wissenschften e.V., Munich (DE); SOTIO a.s., Prague (CZ)

( * ) Notice: Subject to any disclaimer, the term of this patent is extended or adjusted under 35 U.S.C. 154(b) by 0 days.

This patent is subject to a terminal disclaimer.

(21) Appl. No.: 16/648,348

(22) PCT Filed: Sep. 20, 2018

(86) PCT No.: PCT/EP2018/075473
§ 371 (c)(1),
(2) Date: Mar. 18, 2020

(87) PCT Pub. No.: WO2019/057821
PCT Pub. Date: Mar. 28, 2019

(65) Prior Publication Data
US 2020/0291011 A1   Sep. 17, 2020

(30) Foreign Application Priority Data

Sep. 20, 2017 (EP) .................................. 17001565

(51) Int. Cl.
| | |
|---|---|
| A61K 45/06 | (2006.01) |
| C07D 413/14 | (2006.01) |
| C07D 311/18 | (2006.01) |
| C07D 405/12 | (2006.01) |
| C07D 409/04 | (2006.01) |
| C07D 409/14 | (2006.01) |
| C07D 491/052 | (2006.01) |

(52) U.S. Cl.
CPC .......... *C07D 413/14* (2013.01); *C07D 311/18* (2013.01); *C07D 405/12* (2013.01); *C07D 409/04* (2013.01); *C07D 409/14* (2013.01); *C07D 491/052* (2013.01); *A61K 45/06* (2013.01)

(58) Field of Classification Search
None
See application file for complete search history.

(56) References Cited

FOREIGN PATENT DOCUMENTS

CN   106674176 A   5/2017

OTHER PUBLICATIONS

International Search Report and Written Opinion for International Application No. PCT/EP2018/075473, dated Dec. 19, 2018 (12 pages).
Ismail et al., "Synthesis and docking studies of novel benzopyran-2-ones with anticancer activity", European Journal of Medicinal Chemistry, vol. 45, pp. 3950-3959, (11 pages).
Leonetti et al., "Design, Synthesis, and 3D QSAR of Novel Potent and Selective Aromatase Inhibitors", Journal of Medicinal Chemistry, vol. 47, No. 27, pp. 6792-6803, Jul. 12, 2004, (12 pages).
E-Space English Language Abstract for CN 106674176.

*Primary Examiner* — Samantha L Shterengarts
(74) *Attorney, Agent, or Firm* — Kagan Binder, PLLC

(57) ABSTRACT

The invention provides novel coumarin derivatives as specific mitochondrial RNA polymerase inhibitors for the treatment of cancer.

20 Claims, 2 Drawing Sheets

Figure 1:
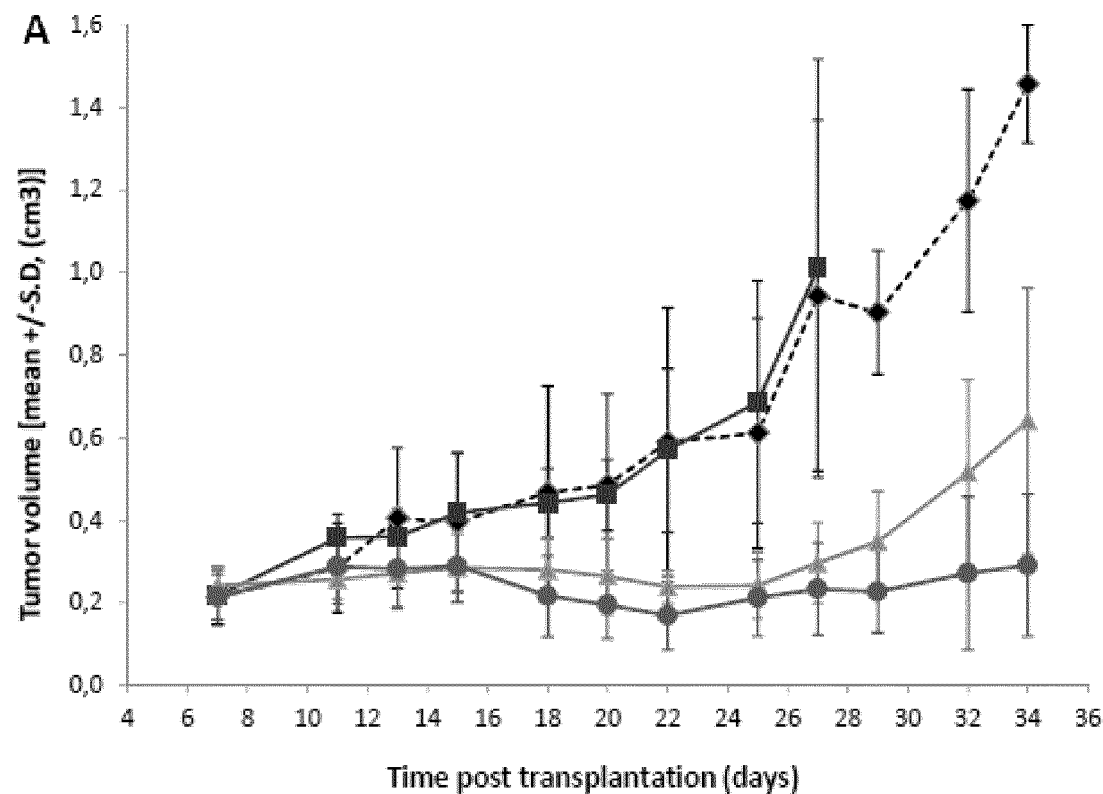
Figure 1:
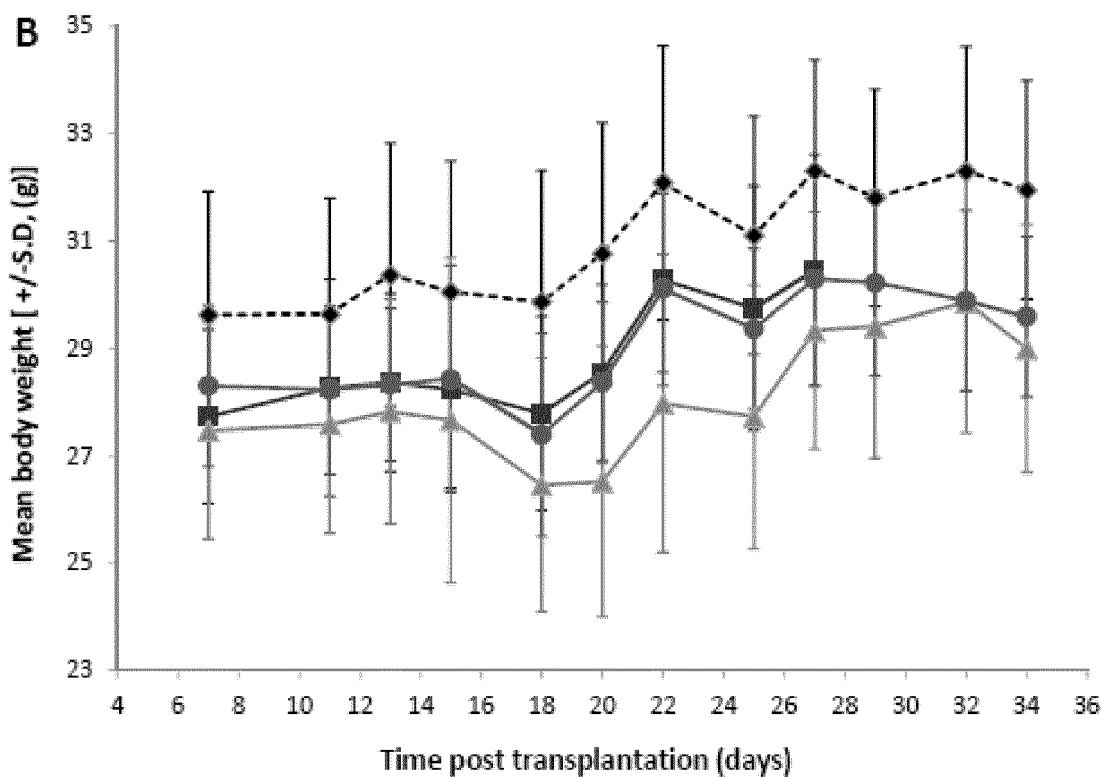

Specification includes a Sequence Listing.

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Fluorescent-donor probe biotinylated

<400> SEQUENCE: 1
aacacatctc tgccaaaccc ca                                              22

<210> SEQ ID NO 2
<211> LENGTH: 20
<212> TYPE: DNA
<213> ORGANISM: Artificial Sequence
<220> FEATURE:
<223> OTHER INFORMATION: Fluorescent-acceptor probe conjugated to
      ATTO647N
```

```
<400> SEQUENCE: 2
acaaagaacc ctaacaccag                                             20
```

COUMARIN DERIVATIVES, PROCESSES FOR THEIR PREPARATION AND USES THEREOF FOR THE TREATMENT OF CANCER

CROSS-REFERENCE TO RELATED APPLICATIONS

This application claims priority to International Application No. PCT/EP2018/075473, filed Sep. 20, 2018 and titled "COUMARIN DERIVATIVES, PROCESSES FOR THEIR PREPARATION AND USES THEREOF FOR THE TREATMENT OF CANCER," which in turn claims priority from a European Patent Application having Ser. No. 17/001,565.5, filed Sep. 20, 2017, titled "COUMARIN DERIVATIVES, PROCESSES FOR THEIR PREPARATION AND USES THEREOF FOR THE TREATMENT OF CANCER," both of which are incorporated herein by reference in their entireties.

REFERENCE TO SEQUENCE LISTING

This application contains a Sequence Listing submitted via EFS-Web. The entire contents of the sequence listing in ASCII text file is entitled "IBH0003US Sequence Listing.txt," created on Mar. 9, 2020 and is 1 kilobyte in size and is incorporated herein by reference in its entirety.

FIELD OF THE INVENTION

The present invention relates to compounds of the general formula (I)

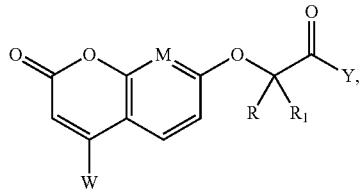

wherein W, M, R, $R_1$ and Y have the designations cited below, or a pharmaceutically or veterinary acceptable salt, hydrate or solvate thereof, and to processes for the preparation of compounds of the general formula (I) or a pharmaceutically or veterinary acceptable salt, hydrate or solvate thereof. The invention also relates to compounds of the general formula (I) or a pharmaceutically or veterinary acceptable salt, hydrate or solvate thereof for use as a medicament. Further, the invention relates to compounds of the general formula (I) or a pharmaceutically or veterinary acceptable salt, hydrate or solvate thereof for use in the treatment of cancer. Moreover, the invention relates to compounds of the general formula (I) or a pharmaceutically or veterinary acceptable salt, hydrate or solvate thereof for treating cancer in simultaneous, alternating or subsequent combination with another cancer therapy.

BACKGROUND OF THE INVENTION

Despite enormous research efforts during the last decades and advanced cancer treatments, cancer remains a major public health problem worldwide and is the second leading cause of death in the United States. In the US population, incidence and death rates are even increasing for several cancer types, including liver and pancreas—two of the most fatal cancers (Siegel et al., 2016). Thus, there is still an urgent need to obtain additional and improved treatment options for fighting cancer besides the established chemotherapies, radiation and upcoming immunotherapies.

Interfering with the cancer metabolism is another principle to tackle tumor growth. In contrast to normal differentiated cells, which rely primarily on mitochondrial oxidative phosphorylation to generate energy, most cancer cells instead rely on aerobic glycolysis, a phenomenon termed "the Warburg effect" (Vander Heiden et al., 2009). Aerobic glycolysis in the cytoplasm leads to pyruvate generated from glucose, which is not transported into mitochondria for total oxidation for yielding more energy but is converted to lactate, originally described by Warburg (Hsu and Sabatini, 2008). Lactate is transferred to the liver, where the carbon skeleton is used to synthesize glucose known as the "neoplastic or pathological Cori cycle" contributing to the clinical metabolic state of Cachexia, a condition existing in neoplastic patients who suffer massive loss of normal body mass as the neoplasm continues its growth (Tisdale, 2002). Consequently, inhibiting aerobic glycolysis (Warburg effect) and/or neoplastic anabolism (pathological Cori cycle) may be another effective way to interfere with cancer metabolism and effectively treat cancer patients. The inhibition of glycolysis in connection with the Warburg effect for cancer treatment has been described by Pelicano, H. et al. (2006) and Scatena et al. (2008).

However, the relevance of mitochondrial respiration in tumors is varied depending on tumor type. An oxidative class of tumors and tumors with dual capacity for glycolytic and oxidative metabolism is evident and the importance of mitochondria in tumor cell survival and proliferation, including utilization of alternative oxidizable substrates such as glutamine and fatty acids, has been increasingly appreciated. The diversity of carbon substrate utilization pathways in tumors is indicative of metabolic heterogeneity that may not only be relevant across different types of cancer but also manifest within a group of tumors that otherwise share a common diagnosis (Caro et al., 2012). Accordingly, tumors show heterogeneity in fuel utilization even within the same disease entity with some having a significant mitochondrial component, marked by elevated oxidative phosphorylation (OXPHOS), increased contribution of mitochondria to total cellular energy budget, greater incorporation of fatty acid- and glucose-derived carbons into the TCA cycle, and increased lipogenesis from these carbon substrates (Caro et al., 2012).

Indeed, recent evidence supports the hypothesis that acquired resistance to therapy is accompanied by a metabolic shift from aerobic glycolysis toward respiratory metabolism, suggesting that metabolic plasticity can have a role in survival of cells responsible for tumor relapse, suggesting that metabolic plasticity can have a role in survival of cells responsible for tumor relapse. For example, it has been observed that several drug-resistant tumor cells show a higher respiratory activity than parental cells. The metabolic adaptation allows OXPHOS-addicted cancer cells to easily survive drug treatments, but leaves cells susceptible to inhibitors of OXPHOS (Denise et al., 2015).

Cancer cell mitochondria are structurally and functionally different from their normal counterparts. Moreover, tumor cells exhibit an extensive metabolic reprogramming that renders them more susceptible to mitochondrial perturbations than non-immortalized cells. Based on these premises, mitochondrially-targeted agents emerge as a means to selectively target tumors. The correction of cancer-associated mitochondrial dysfunctions and the (re)activation of cell death programs by pharmacological agents that induce or facilitate mitochondrial membrane permeabilization represent attractive strategies for cancer therapy. Further, autophagy in the tumor stroma and oxidative mitochondrial metabolism (OXPHOS) in cancer cells can both dramatically promote tumor growth, independently of tumor angiogenesis (Salem et al., 2012) and that cancer-associated fibroblasts undergo aerobic glycolysis, thereby producing lactate, which is utilized as a metabolic substrate by adjacent cancer cells. In this model, "energy transfer" or "metabolic-coupling" between the tumor stroma and epithelial cancer cells "fuels" tumor growth and metastasis, via oxidative mitochondrial metabolism in anabolic cancer cells, the "reverse Warburg effect" (Whitaker-Menezes et al., 2011).

Accordingly, these findings provide a rationale and for novel strategies for anti-cancer therapies by employing inhibitors of OXPHOS and mitochondrial functions. Mitochondrial targeted anti-cancer drugs are reviewed by Fulda et al. (2010) and Weinberg and Chandel (2015) including inhibitors of mitochondrial complex 1, inhibitors of the electron transfer chain (ETC) complex, inhibitors of mitochondrial ribosomal machinery, inhibitors of the translation of ETC subunits, inhibitors of mitochondrial chaperone proteins, inhibitors of glutaminases, aminotransferases or glutamate dehydrogenases, short term inhibition of autophagy, mitochondrial-targeted antioxidants.

Recently, mitochondrial RNA polymerase (POLRMT, also known as h-mtRNAP) has been proposed as a new target in acute myeloid leukemia (Bralha et al., 2015). POLRMT is responsible for the transcription of the 13 subunits of the OXPHOS complexes, two rRNAs and 22 tRNAs required for mitochondrial translation and acts as the RNA primase for mitochondrial DNA replication (Wanrooij and Falkenberg, 2010, Scarpulla, 2008). Therefore, this enzyme is of fundamental importance for both expression and replication of the human mitochondrial genome (Arnold et al., 2012).

A number of nucleoside analogues used as antiviral agents to target viral RNA polymerases demonstrate off-target inhibition of POLRMT (Arnold et al., 2012); POLRMT is distantly related to bacteriophage T7 class of single-subunit RNAPs. The finding that treatment with 2-C-methyladenosine, identified as an inhibitor of the RNA-dependent RNA polymerase of hepatitis C virus (Carroll et al., 2003), triggers the death of AML cells allegedly through rather unspecific inhibition of mitochondrial transcription confirms this rational (Bralha et al., 2015).

Thus, there is a need for alternative novel compounds, which specifically inhibit POLRMT and are suitable for use as a medicament. In particular, a need exists for novel compounds that can be used in the treatment of cancer, preferably melanoma, metastatic melanoma, pancreatic cancer, hepatocellular carcinoma, lymphoma, acute myeloid leukemia, breast cancer, glioblastoma, cervical cancer, renal cancer, colorectal cancer or ovarian cancer. Furthermore, POLRMT inhibitors are of interest, which can be used in a method for treating cancer in simultaneous, alternating or subsequent combination with another cancer therapy.

Accordingly, the present invention provides specific POLRMT inhibitors for the treatment of cancer.

SUMMARY OF THE INVENTION

The present invention, in one aspect, relates to a compound of the general formula (I)

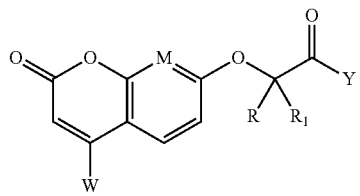

wherein
R is —$C_1$-$C_4$-alkyl, preferably -methyl or -ethyl, in particular -methyl;
$R_1$ is —H, or -methyl, preferably —H;
M is CH or N;
W is

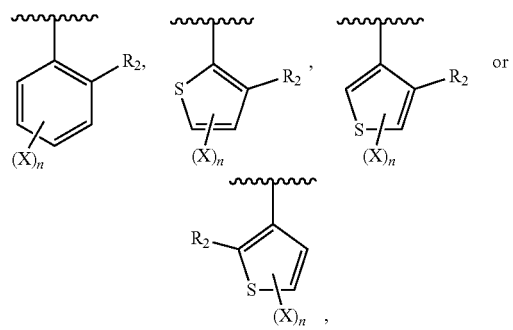

with
$R_2$ is $C_1$-$C_4$-alkyl, -halogen, —CN, preferably -methyl, -ethyl, —Cl, or —Br;
X is -halogen, or —CN, preferably —Cl, —Br, or —F, in particular —F, with n=1 or 2;
n=0, 1, or 2, preferably 0 or 1;
Y is —$NR_3R_4$ with
$R_3$ is —H, or —$C_1$-$C_4$-alkyl, preferably —H or -methyl, and
$R_4$ is —$C_1$-$C_4$-alkyl or —$C_3$-$C_6$-cycloalkyl, preferably -methyl, -ethyl, -isopropyl, or -cyclopropyl; or
an unsubstituted or substituted pyridine residue; or
an unsubstituted or substituted phenyl residue, preferably substituted at the para position;
Y is —$NR_3R_4$ with N, $R_3$ and $R_4$ forming an unsubstituted or substituted 5- or 6-membered saturated heterocycle; or
Y is —$OR_{11}$, with $R_{11}$ is —H or —$C_1$-$C_4$-alkyl, preferably —H, -methyl, -ethyl, or -isopropyl, or a pharmaceutically or veterinary acceptable salt, hydrate or solvate thereof.

In one embodiment, the invention relates to a compound of the general formula (I) as defined above, wherein
R is —$C_1$-$C_4$-alkyl, preferably -methyl or -ethyl, in particular -methyl;
$R_1$ is —H, or -methyl, preferably —H;
M is —CH;
W is

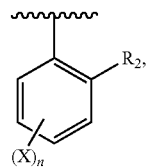

with
R$_2$ is methyl, -halogen, —CN, preferably -methyl, —Cl, or —Br;
X is -halogen, or —CN, preferably —Cl, —Br, or —F, in particular —F, with n=1 or 2;
n=0, 1, or 2, preferably 0 or 1;
Y is —NR$_3$R$_4$ with
R$_3$ is —H, or —C$_1$-C$_4$-alkyl, preferably —H or -methyl, and
R$_4$ is —C$_1$-C$_4$-alkyl or —C$_3$-C$_6$-cycloalkyl, preferably -methyl, -ethyl, -isopropyl, or -cyclopropyl; or
an unsubstituted or substituted pyridine residue; or
an unsubstituted or substituted phenyl residue, preferably substituted at the para position;
Y is —NR$_3$R$_4$ with N, R$_3$ and R$_4$ forming an unsubstituted or substituted 5- or 6-membered saturated heterocycle; or
Y is —OR$_{11}$, with R$_{11}$ is —H or —C$_1$-C$_4$-alkyl, preferably —H, -methyl, -ethyl, or -isopropyl, or a pharmaceutically or veterinary acceptable salt, hydrate or solvate thereof.

In another embodiment, the invention relates to a compound of the general formula (I) as defined above, wherein Y is —NR$_3$R$_4$, with
R$_3$ is —H, or —C$_1$-C$_4$-alkyl, preferably —H or -methyl, and
R$_4$ is a pyridine residue; or a phenyl residue each optionally and independently substituted with —COOH; —COO—C$_1$-C$_4$-alkyl;
—(CH$_2$)$_p$OH with p=1 or 2; or
—C$_1$-C$_4$-alkyl or —C$_3$-C$_6$-cycloalkyl, preferably -methyl, -ethyl, -isopropyl or -cyclopropyl.

In another embodiment, the invention relates to a compound of the general formula (I) as defined above, wherein Y is —NR$_3$R$_4$, with
R$_3$ is —H, or —C$_1$-C$_4$-alkyl, preferably —H or -methyl, and
R$_4$ is a pyridine residue; or a phenyl residue substituted with —(CH$_2$)$_p$OH with p=1 or 2;
or
—C$_1$-C$_4$-alkyl or —C$_3$-C$_6$-cycloalkyl, preferably -methyl, -ethyl, -isopropyl or -cyclopropyl.

In another embodiment, the invention relates to a compound of the general formula (I) as defined above, wherein N, R$_3$ and R$_4$ together form an unsubstituted or substituted piperidine, piperazine or pyrrolidine residue, each optionally and independently substituted with one or more, preferably with one of the following residues:
—C$_1$-C$_4$-alkyl;
—(CH$_2$)$_m$—COOR$_5$ with R$_5$ is —H, —C$_2$-C$_4$-alkyl-N-morpholine or the group

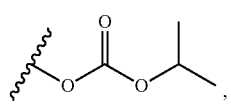 [SMILES: *OC(=O)OC(C)C]

preferably —H, -methyl, -ethyl, -isopropyl, -tert-butyl, -n-heptyl, 2-morpholinoethyl or -isopropoxycarbonyloxymethyl;
—(CH$_2$)$_m$CONR$_6$R$_7$ with R$_6$ and R$_7$ is independently —H, or —C$_1$-C$_4$-alkyl, preferably —H or -methyl;
—CO—(C$_2$-C$_4$-alkenyl); —CO—CH$_2$—Cl; —CO—CH$_2$—CH$_3$,
—NH—CO—(C$_2$-C$_4$-alkenyl); —NH—CO—CH$_2$—Cl; —NH—CO—CH$_2$—CH$_3$;
—F;
—CN;
—SO$_3$H;
—SO$_2$NR$_8$R$_9$ with R$_8$ and R$_9$ independently are —H, or —C$_1$-C$_4$-alkyl, preferably —H or -methyl;
—SONHR$_{10}$ with R$_{10}$ is —C$_1$-C$_4$-alkyl, preferably -methyl; or

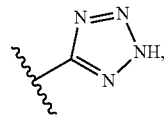 [SMILES: *c1nn[nH]n1]

and
m=0, 1, or 2, preferably 0 or 1.

In another embodiment, the invention relates to a compound of the general formula (I) as defined above, wherein N, R$_3$ and R$_4$ together form an unsubstituted or substituted piperidine or pyrrolidine residue, each optionally and independently substituted with one or more, preferably with one of the following residues:
—C$_1$-C$_4$-alkyl;
—(CH$_2$)$_m$—COOR$_5$ with R$_5$ is —H, —C$_2$-C$_4$-alkyl-N-morpholine or the group

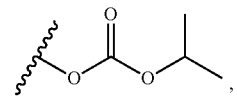 [SMILES: *OC(=O)OC(C)C]

preferably —H, -methyl, -ethyl, -isopropyl, -tert-butyl, -n-heptyl, 2-morpholinoethyl or -isopropoxycarbonyloxymethyl;
—(CH$_2$)$_m$CONR$_6$R$_7$ with R$_6$ and R$_7$ is independently —H, or —C$_1$-C$_4$-alkyl, preferably —H or -methyl;
—F;
—CN;
—SO$_3$H;
—SO$_2$NR$_8$R$_9$ with R$_8$ and R$_9$ independently are —H, or —C$_1$-C$_4$-alkyl, preferably —H or -methyl;
—SONHR$_{10}$ with R$_{10}$ is —C$_1$-C$_4$-alkyl, preferably -methyl; or

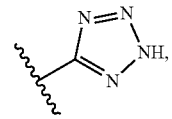

and
m=0, 1, or 2, preferably 0 or 1.

In another embodiment, the invention relates to a compound of the general formula (I) as defined above, wherein R is -methyl, preferably (R)-methyl;
R$_1$ is —H;
m=0, or 1;
W is

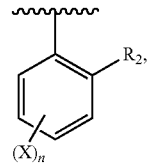

with
R$_2$ is methyl, or —Cl;
X is —F with n=1;
Y is —NR$_3$R$_4$
with
R$_3$ is —H, and
R$_4$ is a pyridine residue,
a phenyl residue substituted at the para position, preferably substituted with —(CH$_2$)$_2$OH, or
a cyclopropyl or isopropyl residue;
or with
N, R$_3$ and R$_4$ forming together a piperidine residue, or a pyrrolidine residue, each optionally and independently substituted with one of the following residues: —COOH, —COOCH$_3$, —COOC$_2$H$_5$, —CH$_2$COOH, —CH$_2$COOCH$_3$, —CH$_2$COOCH$_2$CH$_3$, —CONH$_2$, —CONHCH$_3$, —CON(CH$_3$)$_2$, —CH$_2$CONHCH$_3$, —SO$_2$NH$_2$, —SO$_2$NHCH$_3$, or —CN.

In another embodiment, the invention relates to a compound of the general formula (I) as defined above, wherein
R is (R)-methyl;
R$_1$ is —H;
W is

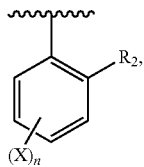

with
R$_2$ is methyl, or —Cl, preferably —Cl;
X is —F with n=1;
Y is —NR$_3$R$_4$
with
N, R$_3$ and R$_4$ forming a piperidine residue, or a pyrrolidine residue, each optionally and independently substituted with one of the following residues: —COOH, —CH$_2$COOH, —CONHCH$_3$, —CH$_2$CONHCH$_3$, —SO$_2$NH$_2$, —SO$_2$NHCH$_3$, or —CN, preferably —COOH, —CH$_2$COOH, —CONHCH$_3$ or —CH$_2$CONHCH$_3$, more preferably (S)—COOH, (R)—COOH, (S)—CH$_2$COOH or (R)—CH$_2$COOH, especially a piperidine residue substituted with (S)—COOH, (R)—COOH, (S)—CH$_2$COOH or (R)—CH$_2$COOH.

In another embodiment, the invention relates to a compound of the general formula (I) as defined above, wherein the piperidine residue or the pyrrolidine residue is substituted at the 3-position.

In another embodiment, the invention relates to a compound of the general formula (I) as defined above, wherein X is at the para-position of the phenyl ring.

In another embodiment, the invention relates to a compound of the general formula (I) as defined above, selected from
7-[1-methyl-2-oxo-2-(1-piperidyl)ethoxy]-4-(o-tolyl)chromen-2-one,
4-(2-chlorophenyl)-7-[1-methyl-2-oxo-2-(1-piperidyl)ethoxy]chromen-2-one,
(3S)-1-[2-[4-(o-tolyl)-2-oxo-chromen-7-yl]oxypropanoyl]piperidine-3-carboxylic acid,
2-[4-(o-tolyl)-2-oxo-chromen-7-yl]oxy-N-(2-pyridyl)propanamide,
7-(1-methyl-2-oxo-2-pyrrolidin-1-yl-ethoxy)-4-(o-tolyl)chromen-2-one,
methyl 1-[2-[4-(o-tolyl)-2-oxo-chromen-7-yl]oxypropanoyl]piperidine-3-carboxylate,
methyl 1-[2-[4-(2-chlorophenyl)-2-oxo-chromen-7-yl]oxypropanoyl]piperidine-3-carboxylate,
1-[2-[4-(o-tolyl)-2-oxo-chromen-7-yl]oxypropanoyl]piperidine-3-carboxylic acid,
1-[2-[4-(2-chlorophenyl)-2-oxo-chromen-7-yl]oxypropanoyl]piperidine-3-carboxylic acid,
1-[2-[4-(o-tolyl)-2-oxo-chromen-7-yl]oxypropanoyl]piperidine-3-sulfonic acid,
1-[2-[4-(2-chlorophenyl)-2-oxo-chromen-7-yl]oxypropanoyl]piperidine-3-sulfonic acid,
1-[2-[4-(o-tolyl)-2-oxo-chromen-7-yl]oxypropanoyl]piperidine-3-sulfonamide,
4-(2-chlorophenyl)-7-(1-methyl-2-oxo-2-pyrrolidin-1-yl-ethoxy)chromen-2-one,
(3S)-1-[(2R)-2-[4-(2-chloro-4-fluoro-phenyl)-2-oxo-chromen-7-yl]oxypropanoyl]piperidine-3-carboxylic acid,
1-[2-[4-(2-chlorophenyl)-2-oxo-chromen-7-yl]oxypropanoyl]-N-methyl-piperidine-3-carboxamide,
ethyl (3S)-1-[2-[4-(2-chlorophenyl)-2-oxo-chromen-7-yl]oxypropanoyl]piperidine-3-carboxylate,
ethyl (3S)-1-[2-[4-(o-tolyl)-2-oxo-chromen-7-yl]oxypropanoyl]piperidine-3-carboxylate,
N-methyl-1-[2-[4-(o-tolyl)-2-oxo-chromen-7-yl]oxypropanoyl]piperidine-3-sulfonamide,
N-[4-(2-hydroxyethyl)phenyl]-2-[4-(o-tolyl)-2-oxo-chromen-7-yl]oxy-propanamide,
1-[2-[4-(2-chlorophenyl)-2-oxo-chromen-7-yl]oxypropanoyl]-N-methyl-piperidine-3-sulfonamide,
N-methyl-1-[2-[4-(o-tolyl)-2-oxo-chromen-7-yl]oxypropanoyl]piperidine-3-carboxamide,
(3S)-1-[2-[4-(o-tolyl)-2-oxo-chromen-7-yl]oxypropanoyl]pyrrolidine-3-carboxylic acid,
(3S)-1-[(2R)-2-[4-(2-chlorophenyl)-2-oxo-chromen-7-yl]oxypropanoyl]piperidine-3-carboxylic acid,
1-[2-[4-(2-chlorophenyl)-2-oxo-chromen-7-yl]oxypropanoyl]piperidine-3-sulfonamide,
N-cyclopropyl-2-[4-(o-tolyl)-2-oxo-chromen-7-yl]oxy-propanamide,
2-[4-(2-chlorophenyl)-2-oxo-chromen-7-yl]oxy-N-cyclopropyl-propanamide,
(3S)-1-[(2R)-2-[4-(o-tolyl)-2-oxo-chromen-7-yl]oxypropanoyl]piperidine-3-carboxylic acid,
(3S)-1-[(2R)-2-[4-(2-chlorophenyl)-2-oxo-chromen-7-yl]oxypropanoyl]piperidine-3-carbonitrile,
(3S)-1-[2-[4-(2-chlorophenyl)-2-oxo-chromen-7-yl]oxypropanoyl]pyrrolidine-3-carboxylic acid,
7-[(1R)-1-methyl-2-oxo-2-(1-piperidyl)ethoxy]-4-(o-tolyl)chromen-2-one,
2-[4-(2-chlorophenyl)-2-oxo-chromen-7-yl]oxy-N-(2-pyridyl)propanamide,
(3S)-1-[(2R)-2-[4-(o-tolyl)-2-oxo-chromen-7-yl]oxypropanoyl]piperidine-3-carbonitrile,
(3S)-1-[2-[4-(2-chlorophenyl)-2-oxo-chromen-7-yl]oxypropanoyl]piperidine-3-carboxylic acid,
4-(2-chlorophenyl)-7-[(1R)-1-methyl-2-oxo-2-(1-piperidyl)ethoxy]chromen-2-one,
2-[4-(2-chlorophenyl)-2-oxo-chromen-7-yl]oxy-N-[4-(2-hydroxyethyl)phenyl]propanamide,
(2R)—N-isopropyl-2-[4-(o-tolyl)-2-oxo-chromen-7-yl]oxy-propanamide,
1-[2-[4-(2-chloro-4-fluoro-phenyl)-2-oxo-chromen-7-yl]oxypropanoyl]-3-methyl-piperidine-3-carboxylic acid, N,N-dimethyl-2-[4-(o-tolyl)-2-oxo-chromen-7-yl]oxy-propanamide,
4-(2-chlorophenyl)-7-[1-methyl-2-oxo-2-[3-(2H-tetrazol-5-yl)-1-piperidyl]ethoxy]chromen-2-one,
ethyl 2-[4-(2-chlorophenyl)-2-oxo-chromen-7-yl]oxypropanoate,
1-[2-[4-(o-tolyl)-2-oxo-chromen-7-yl]oxypropanoyl]piperidine-3-carbonitrile,
7-[1-methyl-2-oxo-2-[3-(2H-tetrazol-5-yl)-1-piperidyl]ethoxy]-4-(o-tolyl)chromen-2-one,
3-methyl-1-[2-[4-(o-tolyl)-2-oxo-chromen-7-yl]oxypropanoyl]piperidine-3-carboxylic acid,
(2R)—N,N-dimethyl-2-[4-(o-tolyl)-2-oxo-chromen-7-yl]oxy-propanamide,
(2R)-2-[4-(2-chlorophenyl)-2-oxo-chromen-7-yl]oxy-N,N-dimethyl-propanamide,
(3R)-1-[2-[4-(2-chlorophenyl)-2-oxo-chromen-7-yl]oxypropanoyl]piperidine-3-carboxylic acid,
(3S)-1-[2-[4-(2-chloro-4-fluoro-phenyl)-2-oxo-chromen-7-yl]oxypropanoyl]piperidine-3-carboxylic acid,
1-[2-[4-(2-chlorophenyl)-2-oxo-chromen-7-yl]oxypropanoyl]piperidine-3-carbonitrile,
2-[4-(2-chloro-3-fluoro-phenyl)-2-oxo-chromen-7-yl]oxy-N-isopropyl-propanamide,
(3S)-1-[2-[4-(2-chloro-3-fluoro-phenyl)-2-oxo-chromen-7-yl]oxypropanoyl]piperidine-3-carboxylic acid,
2-[4-(2-chlorophenyl)-2-oxo-chromen-7-yl]oxy-N-methyl-propanamide,
1-[2-[4-(2-chloro-3-fluoro-phenyl)-2-oxo-chromen-7-yl]oxypropanoyl]piperidine-3-sulfonamide,
(3R)-1-[2-[4-(o-tolyl)-2-oxo-chromen-7-yl]oxypropanoyl]piperidine-3-carboxylic acid,
1-[2-[4-(2-chlorophenyl)-2-oxo-chromen-7-yl]oxypropanoyl]-3-methyl-piperidine-3-carboxylic acid,
isopropyl (2R)-2-[4-(o-tolyl)-2-oxo-chromen-7-yl]oxy-propanoate,
(2R)-2-[4-(2-chlorophenyl)-2-oxo-chromen-7-yl]oxy-N-isopropyl-propanamide,
ethyl 2-[4-(2-chloro-3-fluoro-phenyl)-2-oxo-chromen-7-yl]oxypropanoate,
ethyl 2-[4-(o-tolyl)-2-oxo-chromen-7-yl]oxypropanoate,
2-[1-[2-[4-(2-chlorophenyl)-2-oxo-chromen-7-yl]oxypropanoyl]-4-piperidyl]acetic acid,
2-[1-[2-[4-(o-tolyl)-2-oxo-chromen-7-yl]oxypropanoyl]-4-piperidyl]acetic acid,
2-[4-(2-chloro-3-fluoro-phenyl)-2-oxo-chromen-7-yl]oxy-N-cyclopropyl-propanamide,
N-isopropyl-2-[4-(o-tolyl)-2-oxo-chromen-7-yl]oxy-propanamide,
1-[2-[4-(o-tolyl)-2-oxo-chromen-7-yl]oxypropanoyl]pyrrolidine-3-sulfonamide,
isopropyl (2R)-2-[4-(2-chlorophenyl)-2-oxo-chromen-7-yl]oxypropanoate,
2-[4-(2-chloro-4-fluoro-phenyl)-2-oxo-chromen-7-yl]oxy-N-isopropyl-propanamide,
2-[1-[2-[4-(2-chlorophenyl)-2-oxo-chromen-7-yl]oxypropanoyl]-3-piperidyl]acetic acid,
(3R)-1-[2-[4-(2-chlorophenyl)-2-oxo-chromen-7-yl]oxypropanoyl]-N,N-dimethyl-piperidine-3-carboxamide,
2-[4-(2-chloro-3-fluoro-phenyl)-2-oxo-chromen-7-yl]oxy-N-ethyl-propanamide,
1-[2-[4-(2-chloro-4-fluoro-phenyl)-2-oxo-chromen-7-yl]oxypropanoyl]piperidine-3-sulfonamide,
2-[4-(2-chlorophenyl)-2-oxo-chromen-7-yl]oxy-N-isopropyl-propanamide,
7-[2-(4,4-difluoro-1-piperidyl)-1-methyl-2-oxo-ethoxy]-4-(o-tolyl)chromen-2-one,
2-[1-[2-[4-(o-tolyl)-2-oxo-chromen-7-yl]oxypropanoyl]-3-piperidyl]acetic acid,
7-[1-methyl-2-[3-(methylsulfonimidoyl)-1-piperidyl]-2-oxo-ethoxy]-4-(o-tolyl)chromen-2-one,
4-(2-chlorophenyl)-7-[2-(4,4-difluoro-1-piperidyl)-1-methyl-2-oxo-ethoxy]chromen-2-one,
ethyl 1-[2-[4-(2-chlorophenyl)-2-oxo-chromen-7-yl]oxypropanoyl]-3-methyl-piperidine-3-carboxylate,
(3S)-1-[2-[4-(2-chlorophenyl)-2-oxo-chromen-7-yl]oxypropanoyl]-N,N-dimethyl-piperidine-3-carboxamide,
1-[2-[4-(2-chlorophenyl)-2-oxo-chromen-7-yl]oxypropanoyl]pyrrolidine-3-sulfonamide,
(3R)—N,N-dimethyl-1-[2-[4-(o-tolyl)-2-oxo-chromen-7-yl]oxypropanoyl]piperidine-3-carboxamide,
4-(2-chlorophenyl)-7-[1-methyl-2-[3-(methylsulfonimidoyl)-1-piperidyl]-2-oxo-ethoxy]chromen-2-one,
methyl -2-[1-[2-[4-(2-chlorophenyl)-2-oxo-chromen-7-yl]oxypropanoyl]-4-piperidyl]acetate,
ethyl 2-[4-(2-bromophenyl)-2-oxo-chromen-7-yl]oxypropanoate,
ethyl 2-[4-(2-chloro-4-fluoro-phenyl)-2-oxo-chromen-7-yl]oxypropanoate,
methyl -2-[1-[2-[4-(o-tolyl)-2-oxo-chromen-7-yl]oxypropanoyl]-4-piperidyl]acetate,
(3S)—N,N-dimethyl-1-[2-[4-(o-tolyl)-2-oxo-chromen-7-yl]oxypropanoyl]piperidine-3-carboxamide,
N-ethyl-2-[4-(o-tolyl)-2-oxo-chromen-7-yl]oxy-propanamide,
ethyl -2-[1-[2-[4-(2-chlorophenyl)-2-oxo-chromen-7-yl]oxypropanoyl]-3-piperidyl]acetate,
ethyl -2-[1-[2-[4-(o-tolyl)-2-oxo-chromen-7-yl]oxypropanoyl]-3-piperidyl]acetate,
ethyl 3-methyl-1-[2-[4-(o-tolyl)-2-oxo-chromen-7-yl]oxypropanoyl]piperidine-3-carboxylate,
2-[4-(2-bromophenyl)-2-oxo-chromen-7-yl]oxy-N,N-dimethyl-propanamide,
2-[4-(2-chloro-4-fluoro-phenyl)-2-oxo-chromen-7-yl]oxy-N-cyclopropyl-propanamide,
2-[4-(2-chloro-4-fluoro-phenyl)-2-oxo-chromen-7-yl]oxy-N-ethyl-propanamide,
isopropyl 2-[4-(2-bromophenyl)-2-oxo-chromen-7-yl]oxypropanoate,
2-[4-(2-chlorophenyl)-2-oxo-chromen-7-yl]oxy-N,N-dimethyl-propanamide,
2-[4-(2-chloro-3-fluoro-phenyl)-2-oxo-chromen-7-yl]oxypropanoic acid,
ethyl 1-[2-[4-(2-chloro-4-fluoro-phenyl)-2-oxo-chromen-7-yl]oxypropanoyl]-3-methyl-piperidine-3-carboxylate,
2-[4-(2-chlorophenyl)-2-oxo-chromen-7-yl]oxypropanoic acid,
2-[4-(o-tolyl)-2-oxo-chromen-7-yl]oxypropanoic acid,
2-[4-(2-chlorophenyl)-2-oxo-chromen-7-yl]oxy-N-ethyl-propanamide,
2-[4-(2-chloro-4-fluoro-phenyl)-2-oxo-chromen-7-yl]oxypropanoic acid,
methyl 2-[(3S)-1-[(2R)-2-[4-(2-chlorophenyl)-2-oxo-chromen-7-yl]oxypropanoyl]-3-piperidyl]acetate,
methyl 2-[(3R)-1-[(2R)-2-[4-(2-chlorophenyl)-2-oxo-chromen-7-yl]oxypropanoyl]-3-piperidyl]acetate,
2-[(3S)-1-[(2R)-2-[4-(2-chlorophenyl)-2-oxo-chromen-7-yl]oxypropanoyl]-3-piperidyl]acetic acid,
2-[(3R)-1-[(2R)-2-[4-(2-chlorophenyl)-2-oxo-chromen-7-yl]oxypropanoyl]-3-piperidyl]acetic acid,
methyl 2-[(3R)-1-[(2R)-2-[4-(2-chloro-4-fluoro-phenyl)-2-oxo-chromen-7-yl]oxypropanoyl]-3-piperidyl]acetate, methyl 2-[(3S)-1-[(2R)-2-[4-(2-chloro-4-fluoro-phenyl)-2-oxo-chromen-7-yl]oxypropanoyl]-3-piperidyl]acetate,
2-[(3R)-1-[(2R)-2-[4-(2-chloro-4-fluoro-phenyl)-2-oxo-chromen-7-yl]oxypropanoyl]-3-piperidyl]acetic acid,
2-[(3S)-1-[(2R)-2-[4-(2-chloro-4-fluoro-phenyl)-2-oxo-chromen-7-yl]oxypropanoyl]-3-piperidyl]acetic acid,
(3R)-1-[(2R)-2-[4-(2-chloro-4-fluoro-phenyl)-2-oxo-chromen-7-yl]oxypropanoyl]piperidine-3-carboxylic acid,
ethyl (3S)-1-[2-[4-(2-chlorophenyl)-2-oxo-chromen-7-yl]oxybutanoyl]piperidine-3-carboxylate,
(3S)-1-[2-[4-(2-chlorophenyl)-2-oxo-chromen-7-yl]oxybutanoyl]piperidine-3-carboxylic acid,
ethyl (3S)-1-[(2R)-2-[4-(2-chloro-4-fluoro-phenyl)-2-oxo-chromen-7-yl]oxypropanoyl]piperidine-3-carboxylate,
2-[4-(2-chlorophenyl)-2-oxo-chromen-7-yl]oxy-2-methyl-propanoic acid,
ethyl 2-[4-(2-chlorophenyl)-2-oxo-chromen-7-yl]oxy-2-methyl-propanoate,
2-[4-(2-chlorophenyl)-2-oxo-chromen-7-yl]oxy-N-isopropyl-2-methyl-propanamide,
N-isopropyl-2-methyl-2-[4-(o-tolyl)-2-oxo-chromen-7-yl]oxy-propanamide,
(3S)-1-[2-[4-(2-chlorophenyl)-2-oxo-chromen-7-yl]oxy-2-methyl-propanoyl]piperidine-3-carboxylic acid,
isopropyl (3S)-1-[(2R)-2-[4-(2-chloro-4-fluoro-phenyl)-2-oxo-chromen-7-yl]oxypropanoyl]piperidine-3-carboxylate,
tert-butyl (3S)-1-[(2R)-2-[4-(2-chloro-4-fluoro-phenyl)-2-oxo-chromen-7-yl]oxypropanoyl]piperidine-3-carboxylate,
2-morpholinoethyl (3S)-1-[(2R)-2-[4-(2-chloro-4-fluoro-phenyl)-2-oxo-chromen-7-yl]oxy-propanoyl]piperidine-3-carboxylate,
heptyl (3S)-1-[(2R)-2-[4-(2-chloro-4-fluoro-phenyl)-2-oxo-chromen-7-yl]oxypropanoyl]piperidine-3-carboxylate,
isopropoxycarbonyloxymethyl (3S)-1-[(2R)-2-[4-(2-chloro-4-fluoro-phenyl)-2-oxo-chromen-7-yl]oxypropanoyl]piperidine-3-carboxylate,
(3S)—N-methyl-1-[(2R)-2-[4-(2-chloro-4-fluoro-phenyl)-2-oxo-chromen-7-yl]oxypropanoyl piperidine-3-carboxamide,
isopropyl 2-[(3R)-1-[(2R)-2-[4-(2-chloro-4-fluoro-phenyl)-2-oxo-chromen-7-yl]oxypropanoyl]-3-piperidyl]acetate,
tert-butyl 2-[(3R)-1-[(2R)-2-[4-(2-chloro-4-fluoro-phenyl)-2-oxo-chromen-7-yl]oxypropanoyl]-3-piperidyl]acetate,
2-morpholinoethyl 2-[(3R)-1-[(2R)-2-[4-(2-chloro-4-fluoro-phenyl)-2-oxo-chromen-7-yl]oxypropanoyl]-3-piperidyl]acetate,
heptyl 2-[(3R)-1-[(2R)-2-[4-(2-chloro-4-fluoro-phenyl)-2-oxo-chromen-7-yl]oxypropanoyl]-3-piperidyl]acetate,
isopropoxycarbonyloxymethyl 2-[(3R)-1-[(2R)-2-[4-(2-chloro-4-fluoro-phenyl)-2-oxo-chromen-7-yl]oxypropanoyl]-3-piperidyl]acetate, and
2-[(3R)-1-[(2R)-2-[4-(2-chloro-4-fluoro-phenyl)-2-oxo-chromen-7-yl]oxypropanoyl]-3-piperidyl]-N-methyl-acetamide,
methyl 1-[(2R)-2-[4-(2-chloro-4-fluoro-phenyl)-2-oxo-chromen-7-yl]oxypropanoyl]piperidine-4-carboxylate,
(2R)-2-[4-(2-chloro-4-fluoro-phenyl)-2-oxo-chromen-7-yl]oxy-N-[4-(hydroxymethyl)phenyl]propanamide,
1-[(2R)-2-[4-(2-chloro-4-fluoro-phenyl)-2-oxo-chromen-7-yl]oxypropanoyl]piperidine-4-carboxylic acid,
(3S)-1-[(2R)-2-[4-(2-chloro-4-fluoro-phenyl)-2-oxo-chromen-7-yl]oxypropanoyl]piperidine-3-carboxamide,
2-[(3R)-1-[(2R)-2-[4-(2-chloro-4-fluoro-phenyl)-2-oxo-chromen-7-yl]oxypropanoyl]-3-piperidyl]acetamide,
(3S)-1-[(2R)-2-[4-(2-ethylphenyl)-2-oxo-chromen-7-yl]oxypropanoyl]piperidine-3-carboxylic acid,
methyl (2S)-4-[(2R)-2-[4-(2-chloro-4-fluoro-phenyl)-2-oxo-chromen-7-yl]oxypropanoyl]piperazine-2-carboxylate,
methyl (2R)-4-[(2R)-2-[4-(2-chloro-4-fluoro-phenyl)-2-oxo-chromen-7-yl]oxypropanoyl]piperazine-2-carboxylate,
methyl 1-methyl-4-[rac-(2R)-2-[4-(2-chloro-4-fluoro-phenyl)-2-oxo-chromen-7-yl]oxypropanoyl]piperazine-2-carboxylate,
(2S)-4-[(2R)-2-[4-(2-chloro-4-fluoro-phenyl)-2-oxo-chromen-7-yl]oxypropanoyl]piperazine-2-carboxylic acid,
3-[[(2R)-2-[4-(2-chloro-4-fluoro-phenyl)-2-oxo-chromen-7-yl]oxypropanoyl]amino]benzoic acid,
(2R)-2-[4-(2-chloro-4-fluoro-phenyl)-2-oxo-chromen-7-yl]oxy-N-[4-(2-methoxyethyl)phenyl]propanamide,
4-[[(2R)-2-[4-(2-chloro-4-fluoro-phenyl)-2-oxo-chromen-7-yl]oxypropanoyl]amino]benzoic acid,
methyl 2-[(3R)-1-[(2R)-2-[4-(2-chloro-4-fluoro-phenyl)-2-oxo-chromen-7-yl]oxypropanoyl]pyrrolidin-3-yl]acetate,
methyl 5-[[(2R)-2-[4-(2-chloro-4-fluoro-phenyl)-2-oxo-chromen-7-yl]oxypropanoyl]amino]pyridine-3-carboxylate,
methyl 2-[(3S)-1-[(2R)-2-[4-(2-chloro-4-fluoro-phenyl)-2-oxo-chromen-7-yl]oxypropanoyl]pyrrolidin-3-yl]acetate,
2-[(3R)-1-[(2R)-2-[4-(2-chloro-4-fluoro-phenyl)-2-oxo-chromen-7-yl]oxypropanoyl]pyrrolidin-3-yl]acetic acid,
methyl 2-[[(2R)-2-[4-(2-chloro-4-fluoro-phenyl)-2-oxo-chromen-7-yl]oxypropanoyl]amino]pyridine-4-carboxylate,
2-[(3S)-1-[(2R)-2-[4-(2-chloro-4-fluoro-phenyl)-2-oxo-chromen-7-yl]oxypropanoyl]pyrrolidin-3-yl]acetic acid,
5-[[(2R)-2-[4-(2-chloro-4-fluoro-phenyl)-2-oxo-chromen-7-yl]oxypropanoyl]amino]pyridine-3-carboxylic acid,
methyl 6-[[(2R)-2-[4-(2-chloro-4-fluoro-phenyl)-2-oxo-chromen-7-yl]oxypropanoyl]amino]pyridine-2-carboxylate,
(2R)-4-[(2R)-2-[4-(2-chloro-4-fluoro-phenyl)-2-oxo-chromen-7-yl]oxypropanoyl]piperazine-2-carboxylic acid,
6-[[(2R)-2-[4-(2-chloro-4-fluoro-phenyl)-2-oxo-chromen-7-yl]oxypropanoyl]amino]pyridine-2-carboxylic acid,
2-[[(2R)-2-[4-(2-chloro-4-fluoro-phenyl)-2-oxo-chromen-7-yl]oxypropanoyl]amino]pyridine-4-carboxylic acid,
methyl 5-[[(2R)-2-[4-(2-chloro-4-fluoro-phenyl)-2-oxo-chromen-7-yl]oxypropanoyl]amino]pyridine-2-carboxylate,
5-[[(2R)-2-[4-(2-chloro-4-fluoro-phenyl)-2-oxo-chromen-7-yl]oxypropanoyl]amino]pyridine-2-carboxylic acid, 5-[[(2R)-2-[4-(2-chloro-4-fluoro-phenyl)-2-oxo-chromen-7-yl]oxypropanoyl]amino]pyridine-2-carboxylic acid,
6-[[(2R)-2-[4-(2-chloro-4-fluoro-phenyl)-2-oxo-chromen-7-yl]oxypropanoyl]amino]pyridine-3-carboxylic acid,
methyl 4-[[(2R)-2-[4-(2-chloro-4-fluoro-phenyl)-2-oxo-chromen-7-yl]oxypropanoyl]amino]pyridine-2-carboxylate,
methyl (3S)-1-[(2R)-2-[4-(2-chloro-4-fluoro-phenyl)-2-oxo-chromen-7-yl]oxypropanoyl]pyrrolidine-3-carboxylate,
(3S)-1-[(2R)-2-[4-(4-fluoro-2-methyl-phenyl)-2-oxo-chromen-7-yl]oxypropanoyl]piperidine-3-carboxylic acid,
(3S)-1-[(2R)-2-[4-(2-chloro-4-fluoro-phenyl)-2-oxo-chromen-7-yl]oxypropanoyl]pyrrolidine-3-carboxylic acid,
4-[[(2R)-2-[4-(2-chloro-4-fluoro-phenyl)-2-oxo-chromen-7-yl]oxypropanoyl]amino]pyridine-2-carboxylic acid,
1-methyl-4-[rac-(2R)-2-[4-(2-chloro-4-fluoro-phenyl)-2-oxo-chromen-7-yl]oxypropanoyl]piperazine-2-carboxylic acid,
(3S)-1-[(2R)-2-[4-(2-cyanophenyl)-2-oxo-chromen-7-yl]oxypropanoyl]piperidine-3-carboxylic acid,
(3S)-1-[(2R)-2-[4-(2,6-dichlorophenyl)-2-oxo-chromen-7-yl]oxypropanoyl]piperidine-3-carboxylic acid,
4-(2-chloro-4-fluoro-phenyl)-7-[(1R)-1-methyl-2-oxo-2-(4-prop-2-enoylpiperazin-1-yl)ethoxy]chromen-2-one,
N-[(3S)-1-[(2R)-2-[4-(2-chloro-4-fluoro-phenyl)-2-oxo-chromen-7-yl]oxypropanoyl]-3-piperidyl]prop-2-enamide,
7-[(1R)-2-[4-(2-chloroacetyl)piperazin-1-yl]-1-methyl-2-oxo-ethoxy]-4-(2-chloro-4-fluoro-phenyl)chromen-2-one,
2-chloro-N-[(3S)-1-[(2R)-2-[4-(2-chloro-4-fluoro-phenyl)-2-oxo-chromen-7-yl]oxypropanoyl]-3-piperidyl]acetamide,
4-(2-chloro-4-fluoro-phenyl)-7-[(1R)-1-methyl-2-oxo-2-(4-propanoylpiperazin-1-yl)ethoxy]chromen-2-one,
N-[(3S)-1-[(2R)-2-[4-(2-chloro-4-fluoro-phenyl)-2-oxo-chromen-7-yl]oxypropanoyl]-3-piperidyl]propanamide,
rac-(3S)-1-[2-[4-(2-chlorophenyl)-2-oxo-pyrano[2,3-b]pyridin-7-yl]oxypropanoyl]piperidine-3-carboxylic acid,
tert-butyl rac-(3S)-1-[2-[4-(2-chlorophenyl)-2-oxo-pyrano[2,3-b]pyridin-7-yl]oxypropanoyl]piperidine-3-carboxylate,
(3S)-1-[(2R)-2-[4-(2-chlorophenyl)-2-oxo-pyrano[2,3-b]pyridin-7-yl]oxypropanoyl]piperidine-3-carboxylic acid,
(3S)-1-[(2R)-2-[4-(2-chloro-4-fluoro-phenyl)-2-oxo-pyrano[2,3-b]pyridin-7-yl]oxypropanoyl]piperidine-3-carboxylic acid,
(3S)-1-[(2R)-2-[4-(3-methyl-2-thienyl)-2-oxo-chromen-7-yl]oxypropanoyl]piperidine-3-carboxylic acid,
ethyl 2-[4-(2-fluorophenyl)-2-oxo-chromen-7-yl]oxypropanoate, and,
ethyl 2-[4-(2,6-difluorophenyl)-2-oxo-chromen-7-yl]oxypropanoate,
7-[(1R)-1-methyl-2-oxo-2-(1-piperidyl)ethoxy]-4-(3-methyl-2-thienyl)chromen-2-one,
(2R)—N-isopropyl-2-[4-(3-methyl-2-thienyl)-2-oxo-chromen-7-yl]oxy-propanamide,
(2R)—N,N-dimethyl-2-[4-(3-methyl-2-thienyl)-2-oxo-chromen-7-yl]oxy-propanamide,
ethyl 2-[(3R)-1-[(2R)-2-[4-(3-methyl-2-thienyl)-2-oxo-chromen-7-yl]oxypropanoyl]-3-piperidyl]acetate,
2-[(3R)-1-[(2R)-2-[4-(3-methyl-2-thienyl)-2-oxo-chromen-7-yl]oxypropanoyl]-3-piperidyl]acetic acid,
(3S)-1-[(2R)-2-[4-(4-methyl-3-thienyl)-2-oxo-chromen-7-yl]oxypropanoyl]piperidine-3-carboxylic acid,
7-[(1R)-1-methyl-2-oxo-2-(1-piperidyl)ethoxy]-4-(4-methyl-3-thienyl)chromen-2-one,
7-[1-methyl-2-oxo-2-(1-piperidyl)ethoxy]-4-(2-methyl-3-thienyl)chromen-2-one,
rac-(3S)-1-[2-[4-(2-methyl-3-thienyl)-2-oxo-chromen-7-yl]oxypropanoyl]piperidine-3-carboxylic acid.
or a pharmaceutically or veterinary acceptable salt, hydrate or solvate thereof.

In another aspect, the invention relates to a process for manufacturing a compound of the general formula (I) as defined above, comprising the steps of:

(a) reacting a compound of formula (A)

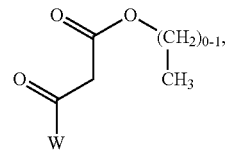

(A)

wherein W is as defined above, with resorcin or 2,6-dihydroxypyridine to obtain a compound of formula (B)

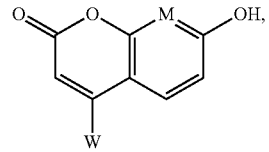

(B)

wherein W and M are as defined above,
or
(a1) reacting a compound of formula (K)

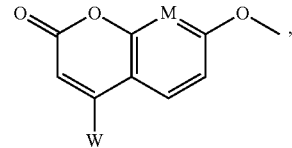

(K)

wherein W and M are as defined above,
with boron tribromide to obtain a compound of formula (B)

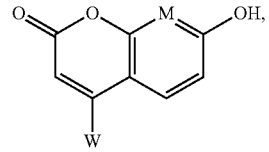

(B)

wherein W and M are as defined above, and (b) alkylating a compound of formula (B) as defined above with an alkylating agent, preferably with an alkylating agent of the formula Z—OH or Z—Br, wherein Z is the group

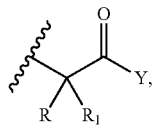

wherein R, $R_1$ and Y are as defined above, to obtain a compound of formula (C)

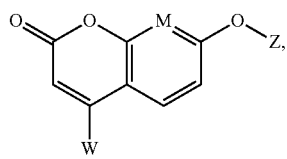

wherein W, M and Z are as defined above.

In another aspect, the invention relates to a process for manufacturing a compound as defined above, wherein Y is —$NR_3R_4$ as defined above, comprising the steps of:

(a) hydrolyzing a compound of formula (D)

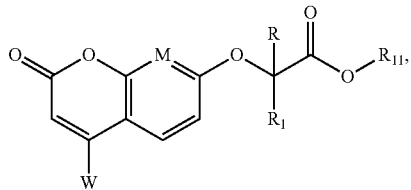

wherein W, M, R, $R_1$, and $R_{11}$ are as defined above, to obtain a compound of formula (E)

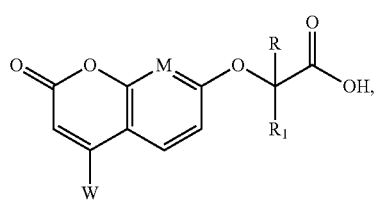

wherein W, M, R, and $R_1$ are as defined above, and (b) amidating the compound of formula (E) to obtain a compound of formula (F)

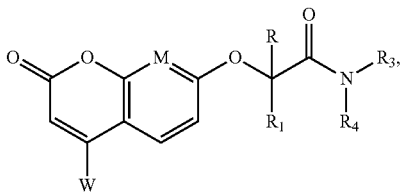

wherein W, M, R, $R_1$, $R_3$, and $R_4$, are as defined above.

In another aspect, the invention relates to a compound of the general formula (I) as defined herein for use as a medicament.

In another aspect, the invention relates to a compound of the general formula (I) as defined herein for use in the treatment of cancer, preferably melanoma, metastatic melanoma, pancreatic cancer, hepatocellular carcinoma, lymphoma, acute myeloid leukemia, breast cancer, glioblastoma, cervical cancer, renal cancer, colorectal cancer or ovarian cancer.

In another aspect, the invention relates to a compound of the general formula (I) as defined herein for use in a method for treating cancer in simultaneous, alternating or subsequent combination with another cancer therapy, preferably selected from chemotherapy, immunotherapy, hormone therapy, stem cell transplantation therapy, radiation therapy or surgery.

DETAILED DESCRIPTION OF THE INVENTION

Definitions, abbreviations and acronyms

"5- or 6-membered saturated heterocycle" represents an unsubstituted or substituted saturated or partially unsaturated ring system containing 5 or 6 ring atoms and containing in addition to C ring atoms for example one to three nitrogen atoms and/or an oxygen or a sulfur atom. In a preferred embodiment, the 5- or 6-membered saturated heterocycle contains in addition to C ring atoms one N and optionally one additional heteroatom. The additional heteroatoms are preferably selected from O, N or S. Especially preferred are heterocycles with only one N as a heteroatom. Preferably, these substituted heterocycles are single or two-fold substituted. The 5- or 6-membered saturated heterocycle may be substituted at the C atom(s), at the O atom(s), at the N atom(s) or at the S atom(s). Examples of 5- or 6-membered saturated heterocycle include, but are not limited to 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin- 5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, morpholinyl, 2-piperidinyl, 3-piperidinyl, 4-piperidinyl, 1-piperazinyl, 2-piperazinyl, 1,3-dioxan-5-yl, 2-tetrahydropyranyl, 4-tetrahydropyranyl, 2-tetrahydrothienyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl and 1,2,4-tetrahydrotriazin-3-yl, preferably piperidin-1-yl, 2-piperidinyl, 3-piperidinyl, 4-piperidinyl, 1-piperazinyl, 2-piperazinyl, 2-pyrrolidinyl, and 3-pyrrolidinyl, The 5- or 6-membered saturated heterocycle may be each optionally and independently substituted with one or more, preferably with one of the following residues:

—$C_1$-$C_4$-alkyl;
—$(CH_2)_m$—$COOR_5$ with $R_5$ is —H, —$C_2$-$C_4$-alkyl-N-morpholine or the group

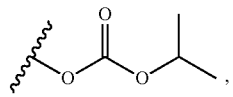 [SMILES: *OC(=O)OC(C)C]

preferably —H, -methyl, -ethyl, -isopropyl, -tert-butyl, -n-heptyl, 2-morpholinoethyl or -isopropoxycarbonyloxymethyl;
—$(CH_2)_m CONR_6R_7$ with $R_6$ and $R_7$ is independently —H, or —$C_1$-$C_4$-alkyl, preferably —H or -methyl;
—CO—($C_2$-$C_4$-alkenyl); —CO—$CH_2$—Cl; —CO—$CH_2$—$CH_3$,
—NH—CO—($C_2$-$C_4$-alkenyl); —NH—CO—$CH_2$—Cl;
—NH—CO—$CH_2$—$CH_3$;
—F;
—CN;
—$SO_3H$;
—$SO_2NR_8R_9$ with $R_8$ and $R_9$ independently are —H, or —$C_1$-$C_4$-alkyl, preferably —H or -methyl;
—$SONHR_{10}$ with $R_{10}$ is —$C_1$-$C_4$-alkyl, preferably -methyl; or

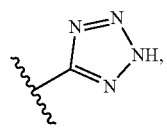

and
m=0, 1, or 2, preferably 0 or 1.

"$C_1$-$C_4$-alkyl" represents a straight-chain or branched-chain alkyl group with 1 to 4 carbon atoms. Examples of straight-chain and branched groups include, but are not limited to, methyl, ethyl, propyl, isopropyl, butyl, isobutyl, and tert.-butyl, preferably methyl and ethyl and most preferred methyl.

"$C_3$-$C_6$-cycloalkyl" represents a carbocyclic saturated ring system having 3 to 6 carbon atoms. Examples of $C_3$-$C_6$-cycloalkyl include, but are not limited cyclopropyl, cyclobutyl, cyclopentyl, or cyclohexyl, preferably cyclopentyl and cyclohexyl.

"Substitution" or "substituted" represents one or more substituents commonly known in the art, or as specifically defined herein.

"Halogen" represents fluoro, chloro, bromo or iodo, preferably represents fluoro and chloro.

"Stereoisomer(s)" as it relates to a compound of formula (I) and to its intermediate compounds represents any possible enantiomers or diastereomers of a compound of formula (I) and its salts or hydrates. In particular, the term "stereoisomer" means a single compound or a mixture of two or more compounds, wherein at least one chiral center is predominantly present in one definite isomeric form, in particular the S-enantiomer, the R-enantiomer and the racemate of a compound of formula (I). It is also possible that two or more stereogenic centers are predominantly present in one definite isomeric form of a derivative of a compound of formula (I) as defined above. In the sense of the present invention, "predominantly" has the meaning of at least 60%, preferably at least 70%, particularly preferably at least 80%, most preferably at least 90%. According to the present invention, also stereoisomers of a compound of formula (I) may be present as a salt or a hydrate.

The terms stereoisomer, salt, and hydrate may also be used in conjunction with one another. For example, a stereoisomer of a compound of formula (I) may have a salt. Combinations of these terms are considered to be within the scope of the invention.

References to compounds by number refer to the compounds as defined in Table 3.

Technical terms are used by their common sense. If a specific meaning is conveyed to certain terms, definitions of terms will be given in the following in the context of which the terms are used.

The below mentioned general or preferred residue definitions apply both to the end products of the formula (I) and also, correspondingly, to the starting materials or intermediates of formulae (A) to (J) required in each case for the preparation. These residue definitions can be combined with one another at will, i.e. including combinations between the given preferred residues. Further, individual definitions may not apply.

Novel POLRMT Inhibitors

As indicated above, there is a need for alternative novel compounds, which inhibit POLRMT and are suitable for use as a medicament. In particular, a need exists for novel compounds that can be used in the treatment of cancer, preferably melanoma, metastatic melanoma, pancreatic cancer, hepatocellular carcinoma, lymphoma, acute myeloid leukemia, breast cancer, glioblastoma, cervical cancer, renal cancer, colorectal cancer or ovarian cancer.

Further, POLRMT inhibitors are of interest, which can be used in a method for treating cancer in simultaneous, alternating or subsequent combination with another cancer therapy.

A problem of the present invention was therefore to provide novel alternative compounds having the above-mentioned desired characteristics.

In one aspect, according to the present invention there is provided a compound of the general formula (I)

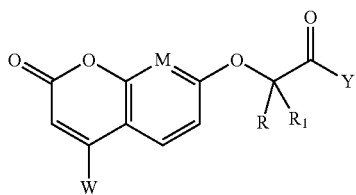

wherein
R is —$C_1$-$C_4$-alkyl, preferably -methyl or -ethyl, in particular -methyl;
$R_1$ is —H, or -methyl, preferably —H;
M is CH or N;
W is

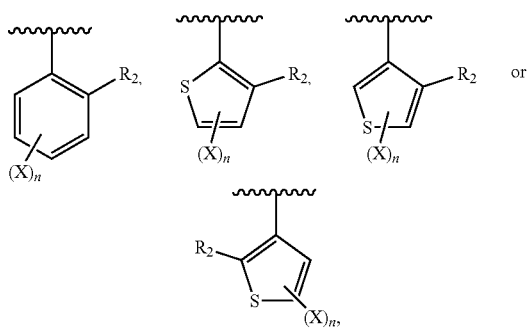

with
$R_2$ is $C_1$-$C_4$-alkyl, -halogen, —CN, preferably -methyl, -ethyl, —Cl, or —Br;
X is -halogen, or —CN, preferably —Cl, —Br, or —F, in particular —F, with n=1 or 2;
n=0, 1, or 2, preferably 0 or 1;
Y is —$NR_3R_4$ with
  $R_3$ is —H, or —$C_1$-$C_4$-alkyl, preferably —H or -methyl, and
  $R_4$ is —$C_1$-$C_4$-alkyl or —$C_3$-$C_6$-cycloalkyl, preferably -methyl, -ethyl, -isopropyl, or -cyclopropyl; or
  an unsubstituted or substituted pyridine residue; or
  an unsubstituted or substituted phenyl residue, preferably substituted at the para position;
Y is —$NR_3R_4$ with N, $R_3$ and $R_4$ forming an unsubstituted or substituted 5- or 6-membered saturated heterocycle; or
Y is —$OR_{11}$, with $R_{11}$ is —H or —$C_1$-$C_4$-alkyl, preferably —H, -methyl, -ethyl, or -isopropyl, or a pharmaceutically or veterinary acceptable salt, hydrate or solvate thereof.

In a preferred embodiment, the compounds of the general formula (I) are coumarin derivatives, wherein M is CH.

A preferred group of compounds are compounds, where Y is $OR_{11}$, with $R_{11}$ being an ethyl residue (especially compounds 40, 57, 58, 81, 82 and 113), an isopropyl residue (compounds 55, 64, 92) or —H (especially compounds 94, 96, 97, 99, 112).

Further included are pharmaceutically or veterinary acceptable salts, hydrates or solvates of the compounds of formula (I) or its intermediate compounds disclosed herein. A pharmaceutically or veterinary acceptable salt can be an anionic counterion, e.g. an acetate, a bromide, camsylate, chloride, citrate, formate, fumarate, lactate, maleate, mesylate, nitrate, oxalate, phosphate, sulfate, tartrate, thiocyanate, or tosylate, or preferably a cationic counterion, e.g. ammonium, arginine, diethylamine, ethylenediamine, piperazine, potassium, sodium, or any other counter ion disclosed in Haynes et al. (2005). Some compounds of the invention contain one or more chiral centers due to the presence of asymmetric carbon atoms, which gives rise to stereoisomers, for example to diastereoisomers with R or S stereochemistry at each chiral center. The invention includes all such stereoisomers and diastereoisomers and mixtures thereof.

As shown in the Examples, the inventors have now surprisingly and unexpectedly found that the compounds of general formula (I) or a pharmaceutically or veterinary acceptable salt, hydrate or solvate thereof, are useful as mitochondrial RNA polymerase (POLRMT) inhibitors and thereby inhibit mitochondrial DNA replication and/or mitochondrial transcription.

In the following, preferred groups of the compounds of general formula (I) of the present invention are described. The preferred groups constitute preferred embodiments of the compounds of general formula (I). Any combinations of the embodiments of the compounds of general formula (I) of the invention described herein are considered to be within the scope of the invention.

In a preferred embodiment, the invention relates to a compound of the general formula (I) as defined above, wherein
R is —$C_1$-$C_4$-alkyl, preferably -methyl or -ethyl, in particular -methyl;
$R_1$ is —H, or -methyl, preferably —H;
M is —CH;
W is

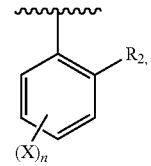

with
$R_2$ is methyl, -halogen, —CN, preferably -methyl, —Cl, or —Br;
X is -halogen, or —CN, preferably —Cl, —Br, or —F, in particular —F, with n=1 or 2;
n=0, 1, or 2, preferably 0 or 1;
Y is —$NR_3R_4$ with
$R_3$ is —H, or —$C_1$-$C_4$-alkyl, preferably —H or -methyl, and
$R_4$ is —$C_1$-$C_4$-alkyl or —$C_3$-$C_6$-cycloalkyl, preferably -methyl, -ethyl, -isopropyl, or -cyclopropyl;
or
  an unsubstituted or substituted pyridine residue; or
  an unsubstituted or substituted phenyl residue, preferably substituted at the para position;
Y is —$NR_3R_4$ with N, $R_3$ and $R_4$ form an unsubstituted or substituted 5- or 6-membered saturated heterocycle; or
Y is —$OR_{11}$, with $R_{11}$ is —H or —$C_1$-$C_4$-alkyl, preferably —H, -methyl, -ethyl, or -isopropyl.

This preferred group of compounds corresponds to the compounds of formula (IA)

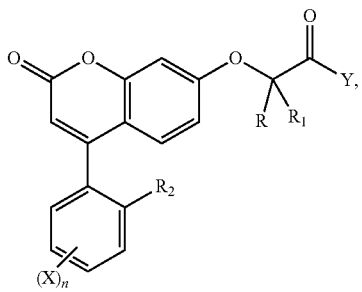

(IA)

wherein R, $R_1$, $R_2$, X, n and Y are as defined in the preferred group above.

In one embodiment, the invention relates to a compound of the general formula (I) as defined above, wherein
R is —$C_1$-$C_4$-alkyl, preferably -methyl or -ethyl, in particular -methyl;
$R_1$ is —H, or -methyl, preferably —H;
M is —CH;
W is

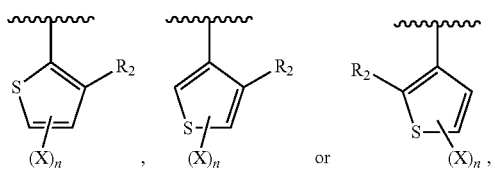

with
 $R_2$ is methyl, -halogen, —CN, preferably -methyl, —Cl, or —Br;
 X is -halogen, or —CN, preferably —Cl, —Br, or —F, in particular —F, with n=1 or 2;
 n=0, 1, or 2, preferably 0 or 1;
Y is —$NR_3R_4$ with
 $R_3$ is —H, or —$C_1$-$C_4$-alkyl, preferably —H or -methyl, and
 $R_4$ is —$C_1$-$C_4$-alkyl or —$C_3$-$C_6$-cycloalkyl, preferably -methyl, -ethyl, -isopropyl, or -cyclopropyl;
or
 an unsubstituted or substituted pyridine residue; or
 an unsubstituted or substituted phenyl residue, preferably substituted at the para position;
Y is —$NR_3R_4$ with N, $R_3$ and $R_4$ form an unsubstituted or substituted 5- or 6-membered saturated heterocycle; or
Y is —$OR_{11}$, with $R_{11}$ is —H or —$C_1$-$C_4$-alkyl, preferably —H, -methyl, -ethyl, or -isopropyl.

In one embodiment, the invention relates to a compound of the general formula (I) of the group as defined above, wherein
W is

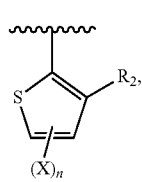

with $R_2$, X and n as defined above, especially compounds 174, 177, 178, 179, 180 and 181.

In one embodiment, the invention relates to a compound of the general formula (I) of the group as defined above, wherein
W is

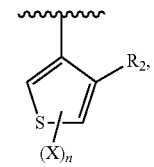

with $R_2$, X and n as defined above, especially compounds 182 and 183.

In one embodiment, the invention relates to a compound of the general formula (I) of the group as defined above, wherein
W is

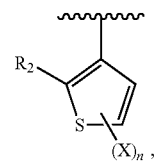

with $R_2$, X and n as defined above, especially compounds 184 and 185.

In another embodiment, the invention relates to a compound of the general formula (I) as defined above, wherein
Y is —$NR_3R_4$, with
 $R_3$ is —H, or —$C_1$-$C_4$-alkyl, preferably —H or -methyl, and
 $R_4$ is a pyridine residue; or a phenyl residue each optionally and independently substituted with —COOH; —COO—($C_1$-$C_4$-alkyl); —$(CH_2)_p$OH with p=1 or 2; or —$C_1$-$C_4$-alkyl or —$C_3$-$C_6$-cycloalkyl, preferably -methyl, -ethyl, -isopropyl or -cyclopropyl.

A group of preferred compounds have an optionally substituted phenyl residue (especially compounds (130, 139, 140 and 141). Another group of preferred compounds have a pyridine residue substituted with —COOH (especially compounds 139, 141, 148, 151, 152, 154, 155 and 160). Another group of preferred compounds have pyridine residue substituted with —COO—($C_1$-$C_4$-alkyl) (especially compounds 143, 146, 149, 153, 156).

A specific subset of the compounds of the invention as defined above are the compounds of the general formula (I), wherein Y is
—$NR_3R_4$, with
 $R_3$ is —H, or —$C_1$-$C_4$-alkyl, preferably —H or -methyl, and
 $R_4$ is a pyridine residue; or a phenyl residue substituted with —$(CH_2)_p$OH with p=1 or 2; or —$C_1$-$C_4$-alkyl or —$C_3$-$C_6$-cycloalkyl, preferably -methyl, -ethyl, -isopropyl or -cyclopropyl.

Preferred compounds are compounds with $R_3$ is H and $R_4$ is a pyridine residue (especially compounds 4 and 31) or a substituted phenyl residue (especially compounds 19 and 35) with a 2-hydroxyethyl-substitution, i.e. with p=2. Other preferred compounds are compounds with $R_3$ is H and $R_4$ is a cyclopropyl residue (especially compounds 25, 26, 61 and 90). Further preferred are compounds with $R_3$ is H and $R_4$ is —C$_1$-C$_4$-alkyl (especially compounds 36, 38, 44, 45, 49, 51, 56, 62, 65, 68, 70, 85, 89, 91, 93, 98, 114 and 115).

Another specific subset of the compounds of the invention are the compounds of the general formula (I), wherein N, R$_3$ and R$_4$ together form an unsubstituted or substituted piperidine, piperazine or pyrrolidine residue, each optionally and independently substituted with one or more, preferably with one of the following residues:
—C$_1$-C$_4$-alkyl;
—(CH$_2$)$_m$—COOR$_5$ with R$_5$ is —H, —C$_1$-C$_8$-alkyl, —C$_2$-C$_4$-alkyl-N-morpholine or the group

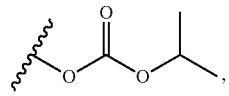

preferably —H, -methyl, -ethyl, -isopropyl, -tert-butyl, -n-heptyl, 2-morpholinoethyl or -isopropoxycarbonyloxymethyl;
—(CH$_2$)$_m$CONR$_6$R$_7$ with R$_6$ and R$_7$ is independently —H, or —C$_1$-C$_4$-alkyl, preferably —H or -methyl;
—CO—(C$_2$-C$_4$-alkenyl); —CO—CH$_2$—Cl; —CO—CH$_2$—CH$_3$,
—NH—CO—(C$_2$-C$_4$-alkenyl); —NH—CO—CH$_2$—Cl; —NH—CO—CH$_2$—CH$_3$;
—F;
—CN;
—SO$_3$H;
—SO$_2$NR$_8$R$_9$ with R$_8$ and R$_9$ independently are —H, or —C$_1$-C$_4$-alkyl, preferably —H or -methyl;
—SONHR$_{10}$ with R$_{10}$ is —C$_1$-C$_4$-alkyl, preferably -methyl; or

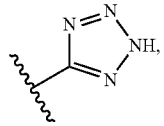

and
m=0, 1, or 2, preferably 0 or 1.

Another specific subset of the compounds of the invention are the compounds of the general formula (I), wherein N, R$_3$ and R$_4$ together form an unsubstituted or substituted piperidine or pyrrolidine residue, each optionally and independently substituted with one or more, preferably with one, of the following residues:
—C$_1$-C$_4$-alkyl;
—(CH$_2$)$_m$—COOR$_5$ with R$_5$ is —H, —C$_1$-C$_6$-alkyl, —C$_2$-C$_4$-alkyl-N-morpholine or the group

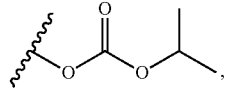 [SMILES: *OC(=O)OC(C)C]

preferably —H, -methyl, -ethyl, -isopropyl, -tert-butyl, -n-heptyl, 2-morpholinoethyl, or -isopropoxycarbonyloxymethyl;
—(CH$_2$)$_m$CONR$_6$R$_7$ with R$_6$ and R$_7$ is independently —H, or —C$_1$-C$_4$-alkyl, preferably —H or -methyl;
—F;
—CN;

—SO$_3$H;
—SO$_2$NR$_8$R$_9$ with R$_8$ and R$_9$ independently are —H, or —C$_1$-C$_4$-alkyl, preferably —H or -methyl;
—SONHR$_{10}$ with R$_{10}$ is —C$_1$-C$_4$-alkyl, preferably -methyl; or

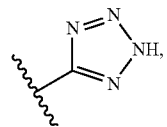 [SMILES: *c1nn[nH]n1]

and
m=0, 1, or 2, preferably 0 or 1.

A group of preferred compounds have an unsubstituted piperidine (especially compounds 1, 2, 30 and 34). Especially preferred are compounds having a substituted piperidine residue (especially compounds 3, 6, 7, 8, 9, 10, 11, 12, 14, 15, 16, 17, 18, 20, 21, 23, 24, 27, 28, 32, 33, 37, 39, 41, 42, 43, 46, 47, 48, 50, 52, 53, 54, 59, 60, 66, 67, 69, 71, 72, 73, 74, 75, 76, 78, 79, 80, 83, 84, 86, 87, 88, 95, 100, 101, 102, 103, 104, 105, 106, 107, 108, 109, 110, 111, 116, 117, 118, 119, 120, 121, 122, 123, 124, 125, 126, 127, and 128).

A more preferred subgroup are compounds having a substituted piperidine residue substituted with —COOH (especially compounds 3, 8, 9, 14, 23, 27, 33, 37, 43, 46, 47, 50, 53, 54, 108, 110, 116), or with —CH$_2$COOH (especially compounds 59, 60, 66, 72, 102, 103, 106 and 107).

Another more preferred subgroup are compounds having a substituted piperidine residue substituted with —COOR$_5$ or —CH$_2$COOR$_5$ with R$_5$ is 2-morpholinoethyl (especially compounds 119 and 125) or with R$_5$ is -isopropyl (especially compounds 117 and 123), -tertbutyl (especially compounds 118 and 124), n-heptyl (especially compounds 120 and 126), -isopropoxycarbonyloxymethyl (especially compounds 121 and 127), or with —CONHCH$_3$, —CH$_2$CONHCH$_3$ (especially compounds 15, 21, 122 and 128) or with —CON (CH$_3$)$_2$ (especially compounds 67, 76 and 78).

Another group of preferred compounds have a substituted piperidine residue substituted with —SO$_2$NR$_8$R$_9$ with R$_8$ is —H and R$_9$ is —H or -methyl (especially compounds 12, 18, 20, 24, 52 and 69).

Another group of preferred compounds are compounds having an unsubstituted pyrrolidine residue (especially compounds 5 and 13) and compounds having substituted pyrrolidine residues (especially compounds 22, 29, 63 and 77).

Another specific subset of the compounds are the compounds of the general formula (I),
wherein
R is -methyl, preferably (R)-methyl;
R$_1$ is —H;
m=0, or 1;
W is

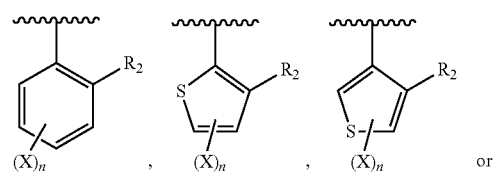

-continued

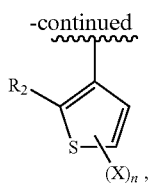

preferably

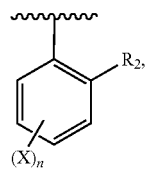

with
R$_2$ is -methyl, or —Cl;
X is —F with n=1;
Y is —NR$_3$R$_4$
  with
  R$_3$ is —H, and
  R$_4$ is a pyridine residue,
    a phenyl residue substituted at the para position, preferably substituted with —(CH$_2$)$_2$OH, or
    a cyclopropyl or isopropyl residue;
or with
  N, R$_3$ and R$_4$ are together a piperidine residue, or a pyrrolidine residue, each optionally and independently substituted with one of the following residues: —COOH, —COOCH$_3$, —COOC$_2$H$_5$, —CH$_2$COOH, —CH$_2$COOCH$_3$, —CH$_2$COOCH$_2$CH$_3$, —CONH$_2$, —CONHCH$_3$, —CON(CH$_3$)$_2$, —CH$_2$CONHCH$_3$, —SO$_2$NH$_2$, —SO$_2$NHCH$_3$, or —CN.

A more preferred group of compounds are compounds having a substituted piperidine residue where R is methyl, R$_1$ is —H, R$_2$ is -methyl or —Cl, n, m=0 or 1, X is —F with n=1 and wherein the piperidine is substituted with —COOH, —COOCH$_3$, —COOC$_2$H$_5$, —CH$_2$COOH, —CH$_2$COOCH$_3$, —CH$_2$COOCH$_2$CH$_3$, —CONH$_2$, —CONHCH$_3$, —CON(CH$_3$)$_2$, —SO$_2$NH$_2$, —SO$_2$NHCH$_3$, —CH$_2$CONHCH$_3$ or —CN (especially compounds 3, 6, 7, 8, 9, 12, 14, 15, 16, 17, 18, 20, 21, 23, 24, 27, 28, 32, 33, 41, 46, 47, 48, 50, 52, 53, 59, 60, 66, 67, 69, 72, 76, 78, 80, 83, 84, 86, 87, 100, 101, 102, 103, 104, 105, 106, 107, 108, 111, 122 and 128). An even more preferred subgroup of this group are compounds where R is (R)-methyl (especially compounds 14, 23, 27, 28, 32, 100, 101, 102, 103, 104, 105, 106, 107, 108, 111, 122 and 128).

A more preferred subgroup of this specific subset are compounds, wherein R is (R)-methyl, having a substituted piperidine residue substituted with —COOH (especially compounds 14, 23, 27 and 108), or with —CH$_2$COOH (especially compounds 102, 103, 106 and 107).

Another more preferred subgroup of this specific subset are compounds, wherein R is (R)-methyl, having a substituted piperidine residue substituted with —COOR$_5$ or —CH$_2$COOR$_5$, with R$_5$ is 2-morpholinoethyl (especially compounds 119 and 125), or with R$_5$ is -isopropyl (especially compounds 117 and 123), -tertbutyl (compounds 118 and 124), n-heptyl (especially compounds 120 and 126), -isopropoxycarbonyloxymethyl (especially compounds 121 and 127), or —CONHCH$_3$ or —CH$_2$CONHCH$_3$ (especially compounds 122 and 128).

Another more preferred subgroup are compounds having a substituted pyrrolidine residue where R is methyl, R$_1$ is —H, R$_2$ is -methyl or —Cl, n, m=0 or 1, X is —F with n=1 and wherein the pyrrolidine is substituted with —COOH, (especially compounds 22 and 29) or —SO$_2$NH$_2$ (especially compounds 63 and 77).

Another specific subset of compounds are compounds, wherein
R is (R)-methyl;
R$_1$ is —H;
W is

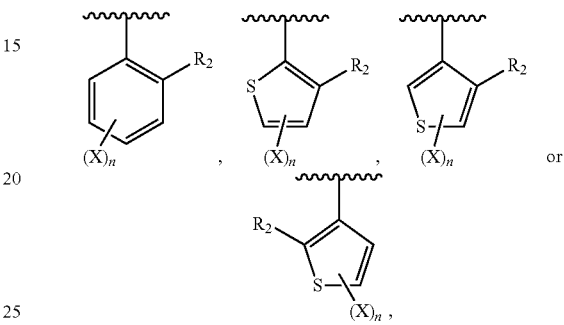

preferably

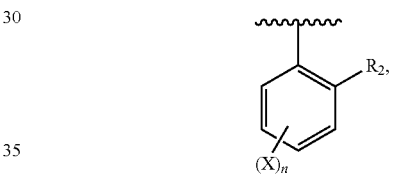

with
R$_2$ is -methyl, or —Cl, preferably —Cl;
X is —F with n=1;
Y is —NR$_3$R$_4$
  with
  N, R$_3$ and R$_4$ form a piperidine residue, or a pyrrolidine residue, each optionally and independently substituted with one of the following residues: —COOH, —CH$_2$COOH, —CONHCH$_3$, —CH$_2$CONHCH$_3$, —SO$_2$NH$_2$, —SO$_2$NHCH$_3$, or —CN, preferably —COOH, —CH$_2$COOH, —CONHCH$_3$ or —CH$_2$CONHCH$_3$, more preferably (S)—COOH, (R)—COOH, (S)—CH$_2$COOH or (R)—CH$_2$COOH, especially a piperidine residue substituted with (S)—COOH, (R)—COOH, (S)—CH$_2$COOH or (R)—CH$_2$COOH.

A more preferred group of compounds are compounds having a substituted piperidine residue where R is (R)-methyl, R$_1$ is —H, R$_2$ is -methyl or —Cl, preferably —Cl, X is —F, n=1 and wherein the piperidine is substituted with —COOH, —CH$_2$COOH, —CONHCH$_3$, —CH$_2$CONHCH$_3$, —SO$_2$NH$_2$, —SO$_2$NHCH$_3$, or —CN (especially compounds 14, 106, 107, 108, 122 and 128).

Another specific subset of compounds are compounds, wherein the piperidine residue or the pyrrolidine residue is substituted at the 3-position.

A more preferred group of compounds of this subset are compounds having any substituted piperidine or pyrrolidine residue as defined above at the 3-position (especially compounds 3, 6, 7, 8, 9, 10, 11, 12, 14, 15, 16, 17, 18, 20, 21, 22, 23, 24, 27, 28, 29, 32, 33, 37, 39, 41, 42, 43, 46, 47, 48, 50, 52, 53, 54, 63, 66, 67, 69, 72, 73, 75, 76, 77, 78, 79, 84, 86, 87, 88, 95, 100, 101, 102, 103, 104, 105, 106, 107, 108, 109, 110, 111, 116, 117, 118, 119, 120, 121, 122, 123, 124, 125, 126, 127, and 128). More preferred within this group are compounds having a substituted piperidine residue substituted with —COOH at the 3-position (especially compounds 3, 8, 9, 14, 23, 27, 33, 37, 43, 46, 47, 50, 53, 108, 110, 116), with —CH$_2$COOH at the 3-position (especially compounds 66, 72, 102, 103, 106 and 107), with —COOR$_5$ or —CH$_2$COOR$_5$ at the 3-position, with R$_5$ is 2-morpholinoethyl (especially compounds 119 and 125), or with R$_5$ is -isopropyl (compounds 117 and 123), -tertbutyl (especially compounds 118 and 124), n-heptyl (especially compounds 120 and 126), -isopropoxycarbonyloxymethyl (compounds 121 and 127), or with —CONHCH$_3$ or —CH$_2$CONHCH$_3$ at the 3-position (compounds 122 and 128).

Another group of preferred compounds of this subset have a substituted piperidine residue substituted with —SO$_2$NR$_8$R$_9$ at the 3-position with R$_8$ is —H and R$_9$ is —H or -methyl (especially compounds 12, 18, 20, 24, 52 and 69).

Another group of preferred compounds having substituted pyrrolidine residues are compounds substituted at the 3-position with —COOH (especially compounds 22, 29) or with —SO$_2$NH$_2$ (especially compounds 63 and 77).

A more preferred group of compounds are compounds having a substituted piperidine residue, wherein the substitution is at the 3-position, where R is methyl, R$_1$ is —H, R$_2$ is -methyl or —Cl, n, m=0 or 1, X is —F with n=1 and wherein the piperidine is substituted with one of the following residues: —COOH, —COOCH$_3$, —COOC$_2$H$_5$, —CH$_2$COOH, —CH$_2$COOCH$_3$, —CH$_2$COOCH$_2$CH$_3$, —CONH$_2$, —CONHCH$_3$, —CON(CH$_3$)$_2$, —CH$_2$CONHCH$_3$, —SO$_2$NH$_2$, —SO$_2$NHCH$_3$, or —CN (especially compounds 3, 6, 7, 8, 9, 12, 14, 15, 16, 17, 18, 20, 21, 23, 24, 27, 28, 32, 33, 41, 46, 47, 48, 50, 52, 53, 66, 67, 69, 72, 76, 78, 84, 86, 87, 100, 101, 102, 103, 104, 105, 106, 107, 108, 111, 122 and 128). An even more preferred subgroup of this group are compounds where R is (R)-methyl (especially compounds 14, 23, 27, 28, 32, 100, 101, 102, 103, 104, 105, 106, 107, 108, 111, 122 and 128).

A more preferred subgroup are compounds having a substituted piperidine residue substituted with —COOH at the 3-position and wherein R is (R)-methyl (especially compounds 14, 23, 27 and 108), or with —CH$_2$COOH at the 3-position and wherein R is (R)-methyl (especially compounds 102, 103, 106 and 107).

Another more preferred subgroup are compounds, wherein R is (R)-methyl and having a substituted piperidine residue, wherein the substitution is at the 3-position, substituted with —COOR$_5$ or —CH$_2$COOR$_5$, with R$_5$ is 2-morpholinoethyl (especially compounds 119 and 125), or with R$_5$ is -isopropyl (compounds 117 and 123), -tertbutyl (especially compounds 118 and 124), n-heptyl (especially compounds 120 and 126), -isopropoxycarbonyloxymethyl (especially compounds 121 and 127), or with —CONHCH$_3$ or —CH$_2$CONHCH$_3$ (especially compounds 122 and 128).

An especially preferred group of compounds are compounds having a substituted piperidine residue where R is (R)-methyl, R$_1$ is —H, R$_2$ is -methyl, or —Cl, preferably —Cl, X is —F, n=1 and wherein the piperidine is substituted with —COOH, —CH$_2$COOH, —CONHCH$_3$, —CH$_2$CONHCH$_3$, —SO$_2$NH$_2$, —SO$_2$NHCH$_3$, or —CN at the 3-position (especially compounds 14, 104, 105, 106, 107, 108, 122 and 128). An especially preferred subgroup of this group are compounds with R$_2$ is —Cl, X is —F and n=1 (especially compounds 14, 104, 105, 106, 107, 108 122 and 128).

A more preferred subgroup are compounds, wherein X is at the para-position, having a substituted piperidine residue substituted with —COOH at the 3-position and wherein R is (R)-methyl (especially compounds 14 and 108), or with —CH$_2$COOH at the 3-position and wherein R is (R)-methyl (especially compounds 106 and 107).

Another more preferred subgroup are compounds, wherein X is at the para-position, wherein R is (R)-methyl and having a substituted piperidine residue substituted with —COOR$_5$ or —CH$_2$COOR$_5$ at the 3-position, with R$_5$ is 2-morpholinoethyl (especially compounds 119 and 125), or with R$_5$ is -isopropyl (compounds 117 and 123), -tertbutyl (especially compounds 118 and 124), n-heptyl (especially compounds 120 and 126), -isopropoxycarbonyloxymethyl (especially compounds 121 and 127), or —CONHCH$_3$ or —CH$_2$CONHCH$_3$ at the 3-position (especially compounds 122 and 128).

An especially preferred group of compounds are compounds, wherein X is at the paraposition, having a substituted piperidine residue where R is (R)-methyl, R$_1$ is —H, R$_2$ is -methyl, or —Cl, preferably —Cl, X is —F, n=1 and wherein the piperidine is substituted with —COOH, —CH$_2$COOH, —CONHCH$_3$, —SO$_2$NH$_2$, —SO$_2$NHCH$_3$, or —CN at the 3-position (especially compounds 14, 106, 107, 108, 122 and 128). An especially preferred subgroup of this group concerns compounds with R$_2$ is —Cl, X is —F and n=1 (especially compounds 14, 106, 107, 108, 122 and 128).

Another specific subset of compounds concerns compounds selected from

7-[1-methyl-2-oxo-2-(1-piperidyl)ethoxy]-4-(o-tolyl)chromen-2-one, 4-(2-chlorophenyl)-7-[1-methyl-2-oxo-2-(1-piperidyl)ethoxy]chromen-2-one, (3S)-1-[2-[4-(o-tolyl)-2-oxo-chromen-7-yl]oxypropanoyl]piperidine-3-carboxylic acid, 2-[4-(o-tolyl)-2-oxo-chromen-7-yl]oxy-N-(2-pyridyl)propanamide, 7-(1-methyl-2-oxo-2-pyrrolidin-1-yl-ethoxy)-4-(o-tolyl)chromen-2-one, methyl 1-[2-[4-(o-tolyl)-2-oxo-chromen-7-yl]oxypropanoyl]piperidine-3-carboxylate, methyl 1-[2-[4-(2-chlorophenyl)-2-oxo-chromen-7-yl]oxypropanoyl]piperidine-3-carboxylate, 1-[2-[4-(o-tolyl)-2-oxo-chromen-7-yl]oxypropanoyl]piperidine-3-carboxylic acid, 1-[2-[4-(2-chlorophenyl)-2-oxo-chromen-7-yl]oxypropanoyl]piperidine-3-carboxylic acid, 1-[2-[4-(o-tolyl)-2-oxo-chromen-7-yl]oxypropanoyl]piperidine-3-sulfonic acid, 1-[2-[4-(2-chlorophenyl)-2-oxo-chromen-7-yl]oxypropanoyl]piperidine-3-sulfonic acid, 1-[2-[4-(o-tolyl)-2-oxo-chromen-7-yl]oxypropanoyl]piperidine-3-sulfonamide, 4-(2-chlorophenyl)-7-(1-methyl-2-oxo-2-pyrrolidin-1-yl-ethoxy)chromen-2-one, (3S)-1-[(2R)-2-[4-(2-chloro-4-fluoro-phenyl)-2-oxo-chromen-7-yl]oxypropanoyl]piperidine-3-carboxylic acid, 1-[2-[4-(2-chlorophenyl)-2-oxo-chromen-7-yl]oxypropanoyl]-N-methyl-piperidine-3-carboxamide, ethyl (3S)-1-[2-[4-(2-chlorophenyl)-2-oxo-chromen-7-yl]oxypropanoyl]piperidine-3-carboxylate, ethyl (3S)-1-[2-[4-(o-tolyl)-2-oxo-chromen-7-yl]oxypropanoyl]piperidine-3-carboxylate, N-methyl-1-[2-[4-(o-tolyl)-2-oxo-chromen-7-yl]oxypropanoyl]piperidine-3-sulfonamide,
N-[4-(2-hydroxyethyl)phenyl]-2-[4-(o-tolyl)-2-oxo-chromen-7-yl]oxy-propanamide,
1-[2-[4-(2-chlorophenyl)-2-oxo-chromen-7-yl]oxypropanoyl]-N-methyl-piperidine-3-sulfonamide,
N-methyl-1-[2-[4-(o-tolyl)-2-oxo-chromen-7-yl]oxypropanoyl]piperidine-3-carboxamide,
(3S)-1-[2-[4-(o-tolyl)-2-oxo-chromen-7-yl]oxypropanoyl]pyrrolidine-3-carboxylic acid,
(3S)-1-[(2R)-2-[4-(2-chlorophenyl)-2-oxo-chromen-7-yl]oxypropanoyl]piperidine-3-carboxylic acid,
1-[2-[4-(2-chlorophenyl)-2-oxo-chromen-7-yl]oxypropanoyl]piperidine-3-sulfonamide,
N-cyclopropyl-2-[4-(o-tolyl)-2-oxo-chromen-7-yl]oxy-propanamide,
2-[4-(2-chlorophenyl)-2-oxo-chromen-7-yl]oxy-N-cyclopropyl-propanamide,
(3S)-1-[(2R)-2-[4-(o-tolyl)-2-oxo-chromen-7-yl]oxypropanoyl]piperidine-3-carboxylic acid,
(3S)-1-[(2R)-2-[4-(2-chlorophenyl)-2-oxo-chromen-7-yl]oxypropanoyl]piperidine-3-carbonitrile,
(3S)-1-[2-[4-(2-chlorophenyl)-2-oxo-chromen-7-yl]oxypropanoyl]pyrrolidine-3-carboxylic acid
7-[(1R)-1-methyl-2-oxo-2-(1-piperidyl)ethoxy]-4-(o-tolyl)chromen-2-one,
2-[4-(2-chlorophenyl)-2-oxo-chromen-7-yl]oxy-N-(2-pyridyl)propanamide,
(3S)-1-[(2R)-2-[4-(o-tolyl)-2-oxo-chromen-7-yl]oxypropanoyl]piperidine-3-carbonitrile,
(3S)-1-[2-[4-(2-chlorophenyl)-2-oxo-chromen-7-yl]oxypropanoyl]piperidine-3-carboxylic acid,
4-(2-chlorophenyl)-7-[(1R)-1-methyl-2-oxo-2-(1-piperidyl)ethoxy]chromen-2-one,
2-[4-(2-chlorophenyl)-2-oxo-chromen-7-yl]oxy-N-[4-(2-hydroxyethyl)phenyl]propanamide,
(2R)—N-isopropyl-2-[4-(o-tolyl)-2-oxo-chromen-7-yl]oxy-propanamide,
1-[2-[4-(2-chloro-4-fluoro-phenyl)-2-oxo-chromen-7-yl]oxypropanoyl]-3-methyl-piperidine-3-carboxylic acid,
N, N-dimethyl-2-[4-(o-tolyl)-2-oxo-chromen-7-yl]oxypropanamide,
4-(2-chlorophenyl)-7-[1-methyl-2-oxo-2-[3-(2H-tetrazol-5-yl)-1-piperidyl]ethoxy]chromen-2-one,
ethyl 2-[4-(2-chlorophenyl)-2-oxo-chromen-7-yl]oxypropanoate,
1-[2-[4-(o-tolyl)-2-oxo-chromen-7-yl]oxypropanoyl]piperidine-3-carbonitrile,
7-[1-methyl-2-oxo-2-[3-(2H-tetrazol-5-yl)-1-piperidyl]ethoxy]-4-(o-tolyl)chromen-2-one,
3-methyl-1-[2-[4-(o-tolyl)-2-oxo-chromen-7-yl]oxypropanoyl]piperidine-3-carboxylic acid,
(2R)—N,N-dimethyl-2-[4-(o-tolyl)-2-oxo-chromen-7-yl]oxy-propanamide,
(2R)-2-[4-(2-chlorophenyl)-2-oxo-chromen-7-yl]oxy-N,N-dimethyl-propanamide,
(3R)-1-[2-[4-(2-chlorophenyl)-2-oxo-chromen-7-yl]oxypropanoyl]piperidine-3-carboxylic acid,
(3S)-1-[2-[4-(2-chloro-4-fluoro-phenyl)-2-oxo-chromen-7-yl]oxypropanoyl]piperidine-3-carboxylic acid,
1-[2-[4-(2-chlorophenyl)-2-oxo-chromen-7-yl]oxypropanoyl]piperidine-3-carbonitrile,
2-[4-(2-chloro-3-fluoro-phenyl)-2-oxo-chromen-7-yl]oxy-N-isopropyl-propanamide,
(3S)-1-[2-[4-(2-chloro-3-fluoro-phenyl)-2-oxo-chromen-7-yl]oxypropanoyl]piperidine-3-carboxylic acid,
2-[4-(2-chlorophenyl)-2-oxo-chromen-7-yl]oxy-N-methyl-propanamide,
1-[2-[4-(2-chloro-3-fluoro-phenyl)-2-oxo-chromen-7-yl]oxypropanoyl]piperidine-3-sulfonamide,
(3R)-1-[2-[4-(o-tolyl)-2-oxo-chromen-7-yl]oxypropanoyl]piperidine-3-carboxylic acid,
1-[2-[4-(2-chlorophenyl)-2-oxo-chromen-7-yl]oxypropanoyl]-3-methyl-piperidine-3-carboxylic acid,
isopropyl (2R)-2-[4-(o-tolyl)-2-oxo-chromen-7-yl]oxypropanoate,
(2R)-2-[4-(2-chlorophenyl)-2-oxo-chromen-7-yl]oxy-N-isopropyl-propanamide,
ethyl 2-[4-(2-chloro-3-fluoro-phenyl)-2-oxo-chromen-7-yl]oxypropanoate,
ethyl 2-[4-(o-tolyl)-2-oxo-chromen-7-yl]oxypropanoate,
2-[1-[2-[4-(2-chlorophenyl)-2-oxo-chromen-7-yl]oxypropanoyl]-4-piperidyl]acetic acid,
2-[1-[2-[4-(o-tolyl)-2-oxo-chromen-7-yl]oxypropanoyl]-4-piperidyl]acetic acid,
2-[4-(2-chloro-3-fluoro-phenyl)-2-oxo-chromen-7-yl]oxy-N-cyclopropyl-propanamide,
N-isopropyl-2-[4-(o-tolyl)-2-oxo-chromen-7-yl]oxy-propanamide,
1-[2-[4-(o-tolyl)-2-oxo-chromen-7-yl]oxypropanoyl]pyrrolidine-3-sulfonamide,
isopropyl (2R)-2-[4-(2-chlorophenyl)-2-oxo-chromen-7-yl]oxypropanoate,
2-[4-(2-chloro-4-fluoro-phenyl)-2-oxo-chromen-7-yl]oxy-N-isopropyl-propanamide,
2-[1-[2-[4-(2-chlorophenyl)-2-oxo-chromen-7-yl]oxypropanoyl]-3-piperidyl]acetic acid,
(3R)-1-[2-[4-(2-chlorophenyl)-2-oxo-chromen-7-yl]oxypropanoyl]-N,N-dimethyl-piperidine-3-carboxamide,
2-[4-(2-chloro-3-fluoro-phenyl)-2-oxo-chromen-7-yl]oxy-N-ethyl-propanamide,
1-[2-[4-(2-chloro-4-fluoro-phenyl)-2-oxo-chromen-7-yl]oxypropanoyl]piperidine-3-sulfonamide,
2-[4-(2-chlorophenyl)-2-oxo-chromen-7-yl]oxy-N-isopropyl-propanamide,
7-[2-(4,4-difluoro-1-piperidyl)-1-methyl-2-oxo-ethoxy]-4-(o-tolyl)chromen-2-one,
2-[1-[2-[4-(o-tolyl)-2-oxo-chromen-7-yl]oxypropanoyl]-3-piperidyl]acetic acid,
7-[1-methyl-2-[3-(methylsulfonimidoyl)-1-piperidyl]-2-oxo-ethoxy]-4-(o-tolyl)chromen-2-one,
4-(2-chlorophenyl)-7-[2-(4,4-difluoro-1-piperidyl)-1-methyl-2-oxo-ethoxy]chromen-2-one,
ethyl 1-[2-[4-(2-chlorophenyl)-2-oxo-chromen-7-yl]oxypropanoyl]-3-methyl-piperidine-3-carboxylate,
(3S)-1-[2-[4-(2-chlorophenyl)-2-oxo-chromen-7-yl]oxypropanoyl]-N,N-dimethyl-piperidine-3-carboxamide,
1-[2-[4-(2-chlorophenyl)-2-oxo-chromen-7-yl]oxypropanoyl]pyrrolidine-3-sulfonamide,
(3R)—N,N-dimethyl-1-[2-[4-(o-tolyl)-2-oxo-chromen-7-yl]oxypropanoyl]piperidine-3-carboxamide,
4-(2-chlorophenyl)-7-[1-methyl-2-[3-(methylsulfonimidoyl)-1-piperidyl]-2-oxo-ethoxy]chromen-2-one,
methyl -2-[1-[2-[4-(2-chlorophenyl)-2-oxo-chromen-7-yl]oxypropanoyl]-4-piperidyl]acetate,
ethyl 2-[4-(2-bromophenyl)-2-oxo-chromen-7-yl]oxypropanoate,
ethyl 2-[4-(2-chloro-4-fluoro-phenyl)-2-oxo-chromen-7-yl]oxypropanoate,
methyl -2-[1-[2-[4-(o-tolyl)-2-oxo-chromen-7-yl]oxypropanoyl]-4-piperidyl]acetate,
(3S)—N,N-dimethyl-1-[2-[4-(o-tolyl)-2-oxo-chromen-7-yl]oxypropanoyl]piperidine-3-carboxamide, N-ethyl-2-[4-(o-tolyl)-2-oxo-chromen-7-yl]oxy-propanamide,
ethyl 2-[1-[2-[4-(2-chlorophenyl)-2-oxo-chromen-7-yl]oxypropanoyl]-3-piperidyl]acetate,
ethyl 2-[1-[2-[4-(o-tolyl)-2-oxo-chromen-7-yl]oxypropanoyl]-3-piperidyl]acetate,
ethyl 3-methyl-1-[2-[4-(o-tolyl)-2-oxo-chromen-7-yl]oxypropanoyl]piperidine-3-carboxylate,
2-[4-(2-bromophenyl)-2-oxo-chromen-7-yl]oxy-N,N-dimethyl-propanamide,
2-[4-(2-chloro-4-fluoro-phenyl)-2-oxo-chromen-7-yl]oxy-N-cyclopropyl-propanamide,
2-[4-(2-chloro-4-fluoro-phenyl)-2-oxo-chromen-7-yl]oxy-N-ethyl-propanamide,
isopropyl 2-[4-(2-bromophenyl)-2-oxo-chromen-7-yl]oxypropanoate,
2-[4-(2-chlorophenyl)-2-oxo-chromen-7-yl]oxy-N,N-dimethyl-propanamide,
2-[4-(2-chloro-3-fluoro-phenyl)-2-oxo-chromen-7-yl]oxypropanoic acid,
ethyl 1-[2-[4-(2-chloro-4-fluoro-phenyl)-2-oxo-chromen-7-yl]oxypropanoyl]-3-methyl-piperidine-3-carboxylate,
2-[4-(2-chlorophenyl)-2-oxo-chromen-7-yl]oxypropanoic acid,
2-[4-(o-tolyl)-2-oxo-chromen-7-yl]oxypropanoic acid,
2-[4-(2-chlorophenyl)-2-oxo-chromen-7-yl]oxy-N-ethyl-propanamide,
2-[4-(2-chloro-4-fluoro-phenyl)-2-oxo-chromen-7-yl]oxypropanoic acid,
methyl 2-[(3S)-1-[(2R)-2-[4-(2-chlorophenyl)-2-oxo-chromen-7-yl]oxypropanoyl]-3-piperidyl]acetate,
methyl 2-[(3R)-1-[(2R)-2-[4-(2-chlorophenyl)-2-oxo-chromen-7-yl]oxypropanoyl]-3-piperidyl]acetate,
2-[(3S)-1-[(2R)-2-[4-(2-chlorophenyl)-2-oxo-chromen-7-yl]oxypropanoyl]-3-piperidyl]acetic acid,
2-[(3R)-1-[(2R)-2-[4-(2-chlorophenyl)-2-oxo-chromen-7-yl]oxypropanoyl]-3-piperidyl]acetic acid,
methyl 2-[(3R)-1-[(2R)-2-[4-(2-chloro-4-fluoro-phenyl)-2-oxo-chromen-7-yl]oxypropanoyl]-3-piperidyl]acetate,
methyl 2-[(3S)-1-[(2R)-2-[4-(2-chloro-4-fluoro-phenyl)-2-oxo-chromen-7-yl]oxypropanoyl]-3-piperidyl]acetate,
2-[(3R)-1-[(2R)-2-[4-(2-chloro-4-fluoro-phenyl)-2-oxo-chromen-7-yl]oxypropanoyl]-3-piperidyl]acetic acid,
2-[(3S)-1-[(2R)-2-[4-(2-chloro-4-fluoro-phenyl)-2-oxo-chromen-7-yl]oxypropanoyl]-3-piperidyl]acetic acid,
(3R)-1-[(2R)-2-[4-(2-chloro-4-fluoro-phenyl)-2-oxo-chromen-7-yl]oxypropanoyl]piperidine-3-carboxylic acid,
ethyl (3S)-1-[2-[4-(2-chlorophenyl)-2-oxo-chromen-7-yl]oxybutanoyl]piperidine-3-carboxylate,
(3S)-1-[2-[4-(2-chlorophenyl)-2-oxo-chromen-7-yl]oxybutanoyl]piperidine-3-carboxylic acid,
ethyl (3S)-1-[(2R)-2-[4-(2-chloro-4-fluoro-phenyl)-2-oxo-chromen-7-yl]oxypropanoyl]piperidine-3-carboxylate,
2-[4-(2-chlorophenyl)-2-oxo-chromen-7-yl]oxy-2-methyl-propanoic acid,
ethyl 2-[4-(2-chlorophenyl)-2-oxo-chromen-7-yl]oxy-2-methyl-propanoate,
2-[4-(2-chlorophenyl)-2-oxo-chromen-7-yl]oxy-N-isopropyl-2-methyl-propanamide,
N-isopropyl-2-methyl-2-[4-(o-tolyl)-2-oxo-chromen-7-yl]oxy-propanamide,
(3S)-1-[2-[4-(2-chlorophenyl)-2-oxo-chromen-7-yl]oxy-2-methyl-propanoyl]piperidine-3-carboxylic acid,
isopropyl (3S)-1-[(2R)-2-[4-(2-chloro-4-fluoro-phenyl)-2-oxo-chromen-7-yl]oxypropanoyl]piperidine-3-carboxylate,
tert-butyl (3S)-1-[(2R)-2-[4-(2-chloro-4-fluoro-phenyl)-2-oxo-chromen-7-yl]oxypropanoyl]piperidine-3-carboxylate,
2-morpholinoethyl (3S)-1-[(2R)-2-[4-(2-chloro-4-fluoro-phenyl)-2-oxo-chromen-7-yl]oxypropanoyl]piperidine-3-carboxylate,
heptyl (3S)-1-[(2R)-2-[4-(2-chloro-4-fluoro-phenyl)-2-oxo-chromen-7-yl]oxypropanoyl]piperidine-3-carboxylate,
isopropoxycarbonyloxymethyl (3S)-1-[(2R)-2-[4-(2-chloro-4-fluoro-phenyl)-2-oxo-chromen-7-yl]oxypropanoyl]piperidine-3-carboxylate,
(3S)—N-methyl-1-[(2R)-2-[4-(2-chloro-4-fluoro-phenyl)-2-oxo-chromen-7-yl]oxypropanoyl piperidine-3-carboxamide,
isopropyl 2-[(3R)-1-[(2R)-2-[4-(2-chloro-4-fluoro-phenyl)-2-oxo-chromen-7-yl]oxypropanoyl]-3-piperidyl]acetate,
tert-butyl 2-[(3R)-1-[(2R)-2-[4-(2-chloro-4-fluoro-phenyl)-2-oxo-chromen-7-yl]oxypropanoyl]-3-piperidyl]acetate,
2-morpholinoethyl 2-[(3R)-1-[(2R)-2-[4-(2-chloro-4-fluoro-phenyl)-2-oxo-chromen-7-yl]oxy-propanoyl]-3-piperidyl]acetate,
heptyl 2-[(3R)-1-[(2R)-2-[4-(2-chloro-4-fluoro-phenyl)-2-oxo-chromen-7-yl]oxypropanoyl]-3-piperidyl]acetate,
isopropoxycarbonyloxymethyl 2-[(3R)-1-[(2R)-2-[4-(2-chloro-4-fluoro-phenyl)-2-oxo-chromen-7-yl]oxypropanoyl]-3-piperidyl]acetate,
2-[(3R)-1-[(2R)-2-[4-(2-chloro-4-fluoro-phenyl)-2-oxo-chromen-7-yl]oxypropanoyl]-3-piperidyl]-N-methyl-acetamide,
methyl 1-[(2R)-2-[4-(2-chloro-4-fluoro-phenyl)-2-oxo-chromen-7-yl]oxypropanoyl]piperidine-4-carboxylate,
(2R)-2-[4-(2-chloro-4-fluoro-phenyl)-2-oxo-chromen-7-yl]oxy-N-[4-(hydroxymethyl)phenyl]propanamide,
1-[(2R)-2-[4-(2-chloro-4-fluoro-phenyl)-2-oxo-chromen-7-yl]oxypropanoyl]piperidine-4-carboxylic acid,
(3S)-1-[(2R)-2-[4-(2-chloro-4-fluoro-phenyl)-2-oxo-chromen-7-yl]oxypropanoyl]piperidine-3-carboxamide,
2-[(3R)-1-[(2R)-2-[4-(2-chloro-4-fluoro-phenyl)-2-oxo-chromen-7-yl]oxypropanoyl]-3-piperidyl]acetamide,
(3S)-1-[(2R)-2-[4-(2-ethylphenyl)-2-oxo-chromen-7-yl]oxypropanoyl]piperidine-3-carboxylic acid,
methyl (2S)-4-[(2R)-2-[4-(2-chloro-4-fluoro-phenyl)-2-oxo-chromen-7-yl]oxypropanoyl]piperazine-2-carboxylate,
methyl (2R)-4-[(2R)-2-[4-(2-chloro-4-fluoro-phenyl)-2-oxo-chromen-7-yl]oxypropanoyl]piperazine-2-carboxylate,
methyl 1-methyl-4-[rac-(2R)-2-[4-(2-chloro-4-fluoro-phenyl)-2-oxo-chromen-7-yl]oxypropanoyl]piperazine-2-carboxylate,
(2S)-4-[(2R)-2-[4-(2-chloro-4-fluoro-phenyl)-2-oxo-chromen-7-yl]oxypropanoyl]piperazine-2-carboxylic acid,
3-[[(2R)-2-[4-(2-chloro-4-fluoro-phenyl)-2-oxo-chromen-7-yl]oxypropanoyl]amino]benzoic acid,
(2R)-2-[4-(2-chloro-4-fluoro-phenyl)-2-oxo-chromen-7-yl]oxy-N-[4-(2-methoxyethyl)phenyl]propanamide,
4-[[(2R)-2-[4-(2-chloro-4-fluoro-phenyl)-2-oxo-chromen-7-yl]oxypropanoyl]amino]benzoic acid,
methyl 2-[(3R)-1-[(2R)-2-[4-(2-chloro-4-fluoro-phenyl)-2-oxo-chromen-7-yl]oxypropanoyl]pyrrolidin-3-yl]acetate,
methyl 5-[[(2R)-2-[4-(2-chloro-4-fluoro-phenyl)-2-oxo-chromen-7-yl]oxypropanoyl]amino]pyridine-3-carboxylate,
methyl 2-[(3S)-1-[(2R)-2-[4-(2-chloro-4-fluoro-phenyl)-2-oxo-chromen-7-yl]oxypropanoyl]pyrrolidin-3-yl]acetate,
2-[(3R)-1-[(2R)-2-[4-(2-chloro-4-fluoro-phenyl)-2-oxo-chromen-7-yl]oxypropanoyl]pyrrolidin-3-yl]acetic acid, methyl 2-[[(2R)-2-[4-(2-chloro-4-fluoro-phenyl)-2-oxo-chromen-7-yl]oxypropanoyl]amino]pyridine-4-carboxylate,
2-[(3S)-1-[(2R)-2-[4-(2-chloro-4-fluoro-phenyl)-2-oxo-chromen-7-yl]oxypropanoyl]pyrrolidin-3-yl]acetic acid,
5-[[(2R)-2-[4-(2-chloro-4-fluoro-phenyl)-2-oxo-chromen-7-yl]oxypropanoyl]amino]pyridine-3-carboxylic acid,
methyl 6-[[(2R)-2-[4-(2-chloro-4-fluoro-phenyl)-2-oxo-chromen-7-yl]oxypropanoyl]amino]pyridine-2-carboxylate,
(2R)-4-[(2R)-2-[4-(2-chloro-4-fluoro-phenyl)-2-oxo-chromen-7-yl]oxypropanoyl]piperazine-2-carboxylic acid,
6-[[(2R)-2-[4-(2-chloro-4-fluoro-phenyl)-2-oxo-chromen-7-yl]oxypropanoyl]amino]pyridine-2-carboxylic acid,
2-[[(2R)-2-[4-(2-chloro-4-fluoro-phenyl)-2-oxo-chromen-7-yl]oxypropanoyl]amino]pyridine-4-carboxylic acid,
methyl 5-[[(2R)-2-[4-(2-chloro-4-fluoro-phenyl)-2-oxo-chromen-7-yl]oxypropanoyl]amino]pyridine-2-carboxylate,
5-[[(2R)-2-[4-(2-chloro-4-fluoro-phenyl)-2-oxo-chromen-7-yl]oxypropanoyl]amino]pyridine-2-carboxylic acid,
5-[[(2R)-2-[4-(2-chloro-4-fluoro-phenyl)-2-oxo-chromen-7-yl]oxypropanoyl]amino]pyridine-2-carboxylic acid,
6-[[(2R)-2-[4-(2-chloro-4-fluoro-phenyl)-2-oxo-chromen-7-yl]oxypropanoyl]amino]pyridine-3-carboxylic acid,
methyl 4-[[(2R)-2-[4-(2-chloro-4-fluoro-phenyl)-2-oxo-chromen-7-yl]oxypropanoyl]amino]pyridine-2-carboxylate,
methyl (3S)-1-[(2R)-2-[4-(2-chloro-4-fluoro-phenyl)-2-oxo-chromen-7-yl]oxypropanoyl]pyrrolidine-3-carboxylate,
(3S)-1-[(2R)-2-[4-(4-fluoro-2-methyl-phenyl)-2-oxo-chromen-7-yl]oxypropanoyl]piperidine-3-carboxylic acid,
(3S)-1-[(2R)-2-[4-(2-chloro-4-fluoro-phenyl)-2-oxo-chromen-7-yl]oxypropanoyl]pyrrolidine-3-carboxylic acid,
4-[[(2R)-2-[4-(2-chloro-4-fluoro-phenyl)-2-oxo-chromen-7-yl]oxypropanoyl]amino]pyridine-2-carboxylic acid,
1-methyl-4-[rac-(2R)-2-[4-(2-chloro-4-fluoro-phenyl)-2-oxo-chromen-7-yl]oxypropanoyl]piperazine-2-carboxylic acid,
(3S)-1-[(2R)-2-[4-(2-cyanophenyl)-2-oxo-chromen-7-yl]oxypropanoyl]piperidine-3-carboxylic acid,
(3S)-1-[(2R)-2-[4-(2,6-dichlorophenyl)-2-oxo-chromen-7-yl]oxypropanoyl]piperidine-3-carboxylic acid,
4-(2-chloro-4-fluoro-phenyl)-7-[(1R)-1-methyl-2-oxo-2-(4-prop-2-enoylpiperazin-1-yl)ethoxy]chromen-2-one,
N-[(3S)-1-[(2R)-2-[4-(2-chloro-4-fluoro-phenyl)-2-oxo-chromen-7-yl]oxypropanoyl]-3-piperidyl]prop-2-enamide,
7-[(1R)-2-[4-(2-chloroacetyl)piperazin-1-yl]-1-methyl-2-oxo-ethoxy]-4-(2-chloro-4-fluoro-phenyl)chromen-2-one,
2-chloro-N-[(3S)-1-[(2R)-2-[4-(2-chloro-4-fluoro-phenyl)-2-oxo-chromen-7-yl]oxypropanoyl]-3-piperidyl]acetamide,
4-(2-chloro-4-fluoro-phenyl)-7-[(1R)-1-methyl-2-oxo-2-(4-propanoylpiperazin-1-yl)ethoxy]chromen-2-one,
N-[(3S)-1-[(2R)-2-[4-(2-chloro-4-fluoro-phenyl)-2-oxo-chromen-7-yl]oxypropanoyl]-3-piperidyl]propanamide,
rac-(3S)-1-[2-[4-(2-chlorophenyl)-2-oxo-pyrano[2,3-b]pyridin-7-yl]oxypropanoyl]piperidine-3-carboxylic acid,
tert-butyl rac-(3S)-1-[2-[4-(2-chlorophenyl)-2-oxo-pyrano[2,3-b]pyridin-7-yl]oxypropanoyl]piperidine-3-carboxylate,
(3S)-1-[(2R)-2-[4-(2-chlorophenyl)-2-oxo-pyrano[2,3-b]pyridin-7-yl]oxypropanoyl]piperidine-3-carboxylic acid,
(3S)-1-[(2R)-2-[4-(2-chloro-4-fluoro-phenyl)-2-oxo-pyrano[2,3-b]pyridin-7-yl]oxypropanoyl]piperidine-3-carboxylic acid,
(3S)-1-[(2R)-2-[4-(3-methyl-2-thienyl)-2-oxo-chromen-7-yl]oxypropanoyl]piperidine-3-carboxylic acid,
ethyl 2-[4-(2-fluorophenyl)-2-oxo-chromen-7-yl]oxypropanoate,
ethyl 2-[4-(2,6-difluorophenyl)-2-oxo-chromen-7-yl]oxypropanoate,
7-[(1R)-1-methyl-2-oxo-2-(1-piperidyl)ethoxy]-4-(3-methyl-2-thienyl)chromen-2-one
(2R)—N-isopropyl-2-[4-(3-methyl-2-thienyl)-2-oxo-chromen-7-yl]oxy-propanamide
(2R)—N,N-dimethyl-2-[4-(3-methyl-2-thienyl)-2-oxo-chromen-7-yl]oxy-propanamide
ethyl 2-[(3R)-1-[(2R)-2-[4-(3-methyl-2-thienyl)-2-oxo-chromen-7-yl]oxypropanoyl]-3-piperidyl]acetate, and
2-[(3R)-1-[(2R)-2-[4-(3-methyl-2-thienyl)-2-oxo-chromen-7-yl]oxypropanoyl]-3-piperidyl]acetic acid,
(3S)-1-[(2R)-2-[4-(4-methyl-3-thienyl)-2-oxo-chromen-7-yl]oxypropanoyl]piperidine-3-carboxylic acid,
7-[(1R)-1-methyl-2-oxo-2-(1-piperidyl)ethoxy]-4-(4-methyl-3-thienyl)chromen-2-one,
7-[1-methyl-2-oxo-2-(1-piperidyl)ethoxy]-4-(2-methyl-3-thienyl)chromen-2-one,
rac-(3S)-1-[2-[4-(2-methyl-3-thienyl)-2-oxo-chromen-7-yl]oxypropanoyl]piperidine-3-carboxylic acid or a pharmaceutically or veterinary acceptable salt, hydrate or solvate thereof.

Processes for the Preparation of Compounds of the General Formula (I)

In another aspect, the present invention provides novel processes for the preparation of compounds of the general formula (I).

In one aspect, the present invention relates to a process for the preparation of a compound of the general formula (I) comprising the steps of:

(a) reacting a compound of formula (A)
wherein W is as defined above,

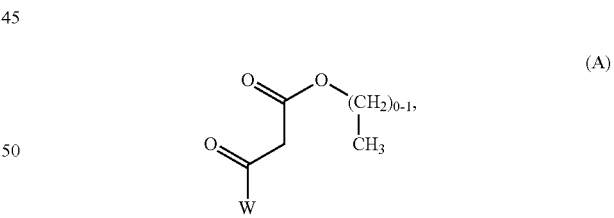

(A)

with resorcin or 2,6-dihydroxypyridine to obtain a compound of formula (B)

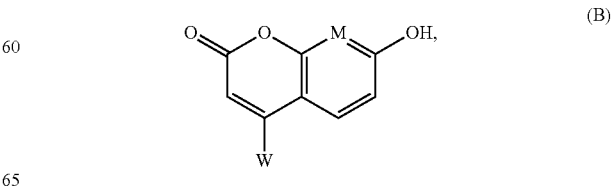

(B)

wherein W and M are as defined above, or
(a1) reacting a compound of formula (K)

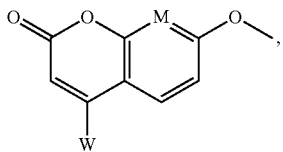
(K)

wherein W and M are as defined above,
with boron tribromide to obtain a compound of formula (B)

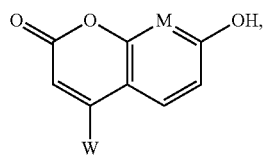
(B)

wherein W and M are as defined above,
and
(b) alkylating a compound of formula (B) as defined above with an alkylating agent, preferably with an alkylating agent of the formula Z—OH or Z—Br, wherein Z is the group

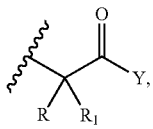

wherein R, $R_1$ and Y are as defined above,
to obtain a compound of formula (C)

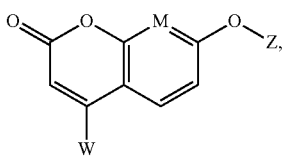
(C)

wherein W, M and Z are as defined above.
The compounds of formula (C) correspond to compounds of formula (I) as defined above

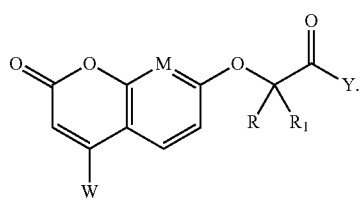
(I)

The compounds of formula (A) and (K) used as a starting material in process steps (a) and (a1) are either commercially available or can be prepared in similar manners as described in literature procedures or in the specific examples. For example, the compounds of formula (K) may be obtained as shown in Scheme 1 in the Examples by reacting a commercially available coumarin derivative with a compound of the formula W—B(OH)$_2$, wherein W and M are as defined above. In one embodiment, M is CH as shown below.

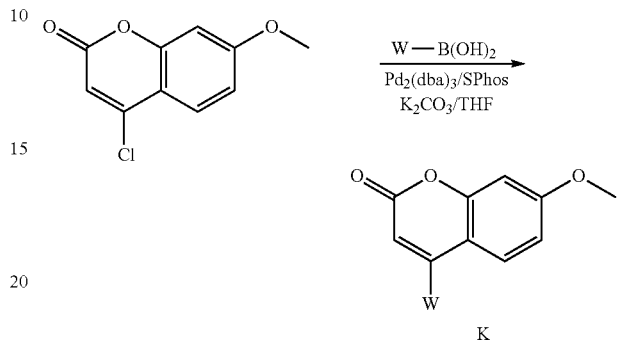
K

The compounds of formula W—B(OH)$_2$ may be prepared as described in literature procedures.

Resorcin, 2,6-dihydroxypyridine and boron tribromide used as a starting material in process steps (a) and (a1), respectively are commercially available or can be obtained by standard procedures known to the skilled person.

The desired coumarin and 8-aza-coumarin compounds of formula (B) may be prepared according to process step (a) from the corresponding β-ketoesters of formula (A) and the required resorcinol through a Pechmann cyclisation such as the one described by Leonetti et al. (2004) or Gosselin et al. (2010). Further literature examples include publications such as Tasler et al., WO 2016/146,583A1, p.49—Scheme 1, or Sharma et al. (2013).

In process step (b), alkylation of the compounds of formula (B) can be carried out with any suitable alkylating agent under standard alkylation conditions, e.g. with an alkylbromide (Z—Br), or with an alcohol (Z—OH) according to the Mitsunobu reaction (Mitsunobu et al. 1967).

Process steps (a), (a1) and (b) can be carried out according to standard procedures known in the art, whereas further guidance can be found in the reaction schemes and examples disclosed below.

In one aspect, the invention relates to an intermediate compound of formula (B) or a compound of formula (K) as defined above.

In a preferred embodiment, the present invention relates to a process for manufacturing a compound of the invention of formula (IA) as defined above comprising the steps of:
(a) reacting a compound of formula (A)

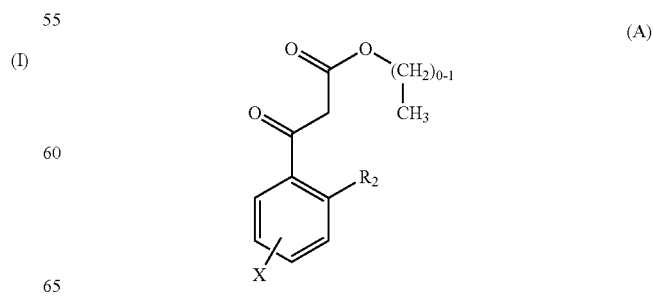
(A)

wherein $R_2$, and X are as defined above;

with resorcin to obtain a compound of formula (B)

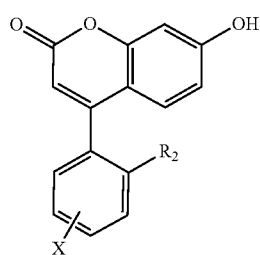

with $R_2$ and X as defined above,
and (b) alkylating the compound of formula (B) to obtain a compound of formula (C)

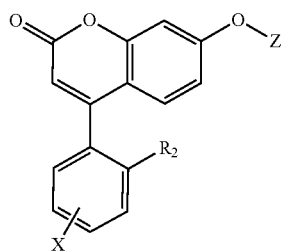

wherein $R_2$ and X are as defined above, and
Z is the group

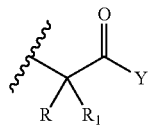

wherein R, $R_1$ and Y are as defined above.

The compounds of formula (A) used as a starting material in process step (a) are either commercially available or can be prepared in similar manners as described in literature procedures or in the specific examples. Resorcin used as a starting material in process step (a) is commercially available or can be obtained by standard procedures known to the skilled person.

The alkylation of the compound of formula (B) can be carried out with any suitable alkylation agent, e.g. with an alkylbromide (Z—Br), or with an alcohol (Z—OH) according to the Mitsunobu reaction (Mitsunobu and Yamada, 1967). Both reaction steps can be carried out according to standard procedures known in the art, whereas further guidance can be found in the reaction schemes and examples disclosed below.

In another aspect, the present invention relates to a process for the preparation of a compound of formula (I) of the invention, wherein Y is —$NR_3R_4$ as defined above corresponding to a compound of formula (F), comprising the steps of:

(a) hydrolyzing a compound of formula (D)

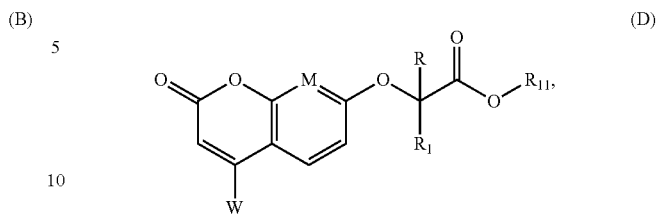

wherein W, M, R, $R_1$, and $R_{11}$ are as defined above,
to obtain a compound of formula (E)

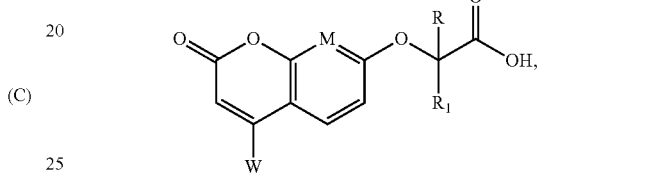

wherein W, M, R, and $R_1$ are as defined above,
and (b) amidating the compound of formula (E) to obtain a compound of formula (F)

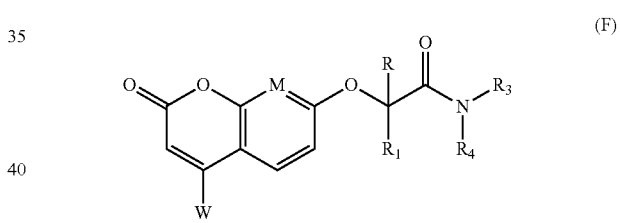

wherein W, M, R, $R_1$, $R_3$, and $R_4$, are as defined above.

The compounds of formula (D) used as starting material in process step (a) correspond to compound of formula (I), wherein Y=—$OR_{11}$, and can be obtained for example by the process for the preparation of compounds of formula (I) as described above.

The optionally substituted amines used as starting materials in process step (b) are commercially available or can be prepared by standard procedures.

In one aspect, the invention relates to an intermediate compound of formula (D) or to an intermediate compound of formula (E) as defined above.

Again, both reaction steps can be carried out according to standard procedures known in the art, whereas further guidance can be found in the reaction schemes and examples disclosed below. For example, step (b) can be carried out with an optionally substituted amine according to known standard procedures.

In another preferred embodiment, the present invention relates to a process for manufacturing a compound of formula (IA) of the invention, wherein Y is —$NR_3R_4$ as defined above, comprising the steps of:

(a) hydrolyzing a compound of formula (D)

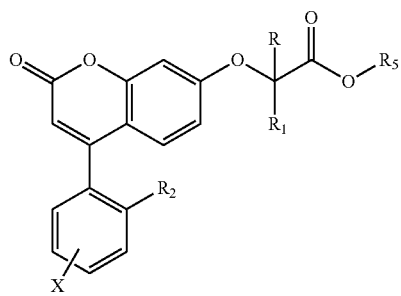
(D)

wherein R, R$_1$, R$_2$, R$_5$ and X are as defined above,
to obtain a compound of formula (E)

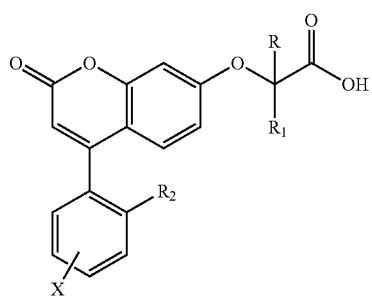
(E)

wherein X, R, R$_1$ and R$_2$ are as defined above,
and
(b) amidating the compound of formula (E) to obtain a compound of formula (F)

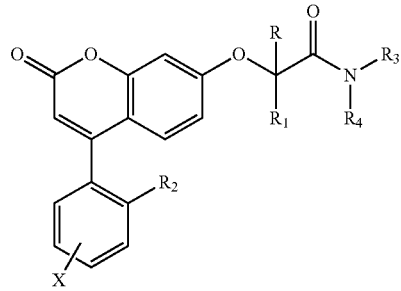
(F)

wherein X, R, R$_1$, R$_2$, R$_3$ and R$_4$ are as defined above.

In another aspect, the present invention relates to a process for manufacturing compounds of the invention, wherein Y is —NR$_3$R$_4$ and N, R$_3$ and R$_4$ form a substituted 5- or 6-membered saturated heterocycle as defined herein, comprising the steps of:

(a) hydrolyzing a compound of formula (G)

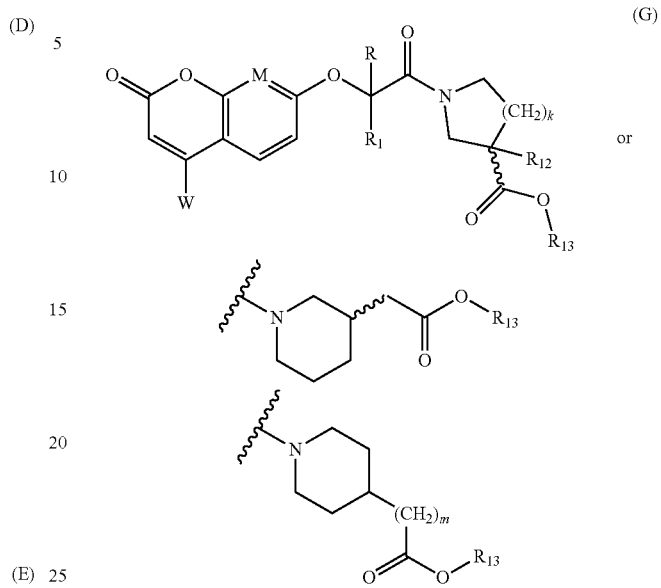
(G)

wherein W, M, R, R$_1$, and m are as defined above, k=1 or 2, R$_{12}$ is defined as —H or —C$_1$-C$_4$-alkyl and R$_{13}$ is defined as —C$_1$-C$_4$-alkyl,
to obtain a compound of formula (H)

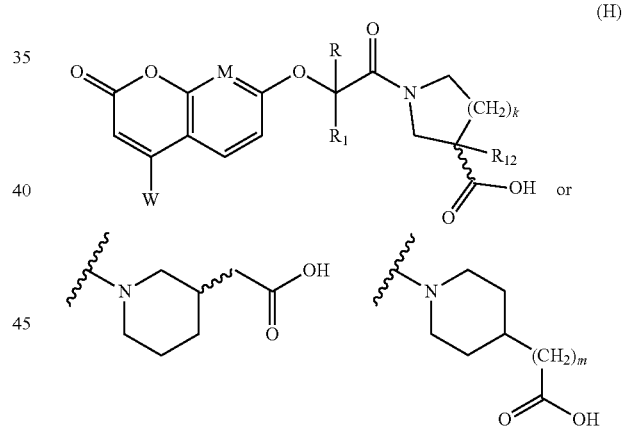
(H)

wherein W, M, R, R$_1$, and m are as defined above, k=1 or 2, and R$_{12}$ is defined as —H or —C$_1$-C$_4$-alkyl,
and
(b) esterifying the compound of formula (H) to obtain a compound of formula (J)

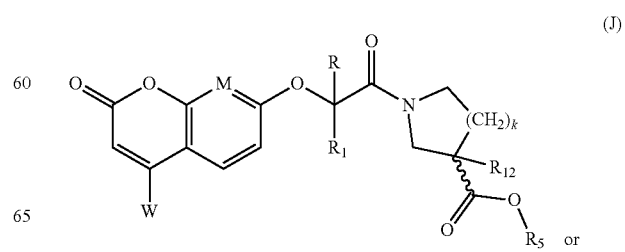
(J)

-continued

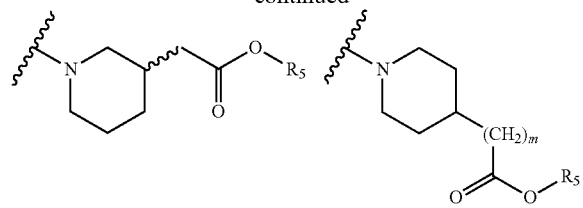

wherein W, M, R, $R_1$, and m are as defined above, k=1 or 2, $R_{12}$ is defined as —H or —$C_1$-$C_4$-alkyl, and $R_5$ is as defined above, provided that $R_5$ is not hydrogen.

In another preferred embodiment, the present invention relates to a process for manufacturing compounds of formula (IA) of the invention, wherein Y is —$NR_3R_4$ and N, $R_3$ and $R_4$ form a substituted 5- or 6-membered saturated heterocycle as defined herein, comprising the steps of:

(a) hydrolyzing a compound of formula (G)

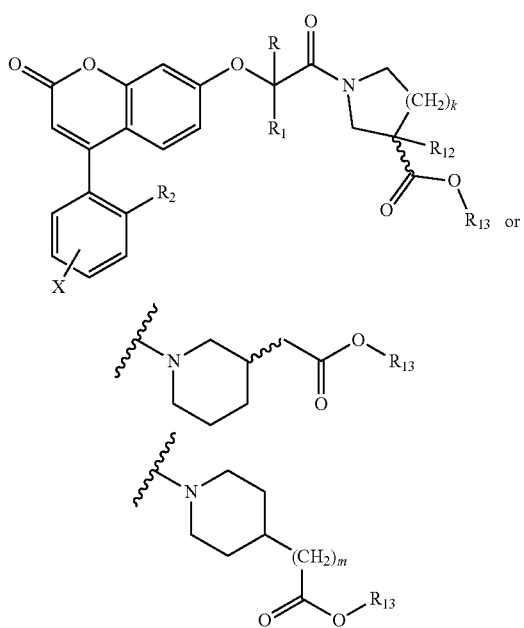

(G)

wherein R, $R_1$, $R_2$, X, and m as defined above, k=1 or 2, $R_{12}$ is defined as —H or —$C_1$-$C_4$-alkyl and $R_{13}$ is defined as —$C_1$-$C_4$-alkyl, to obtain a compound of formula (H)

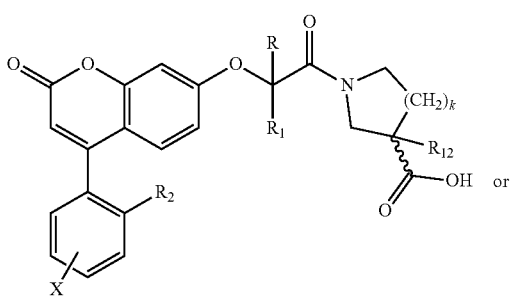

(H)

wherein R, $R_1$, $R_2$, X, and m are as defined above, k=1 or 2, and $R_{12}$ is defined as —H or —$C_1$-$C_4$-alkyl, and (b) esterifying the compound of formula (H) to obtain a compound of formula (J)

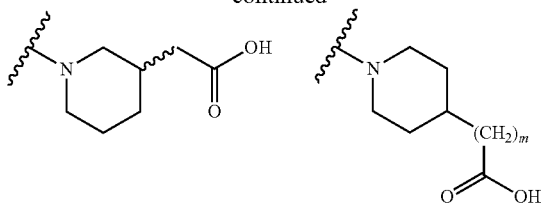

(J)

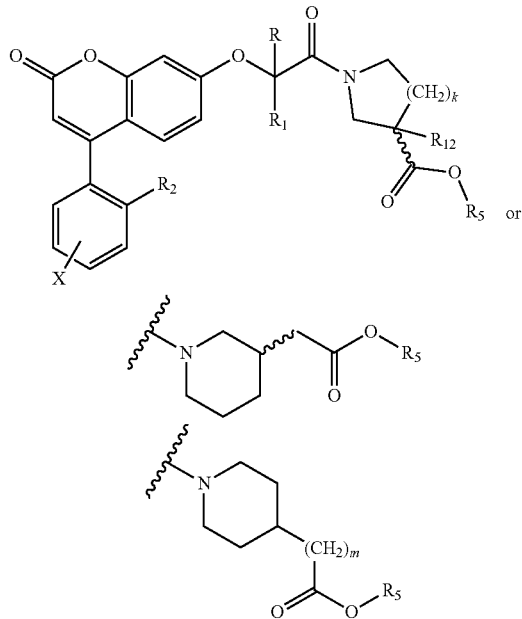

with R, $R_1$, $R_2$, X, and m as defined above, k=1 or 2, $R_{12}$ is defined as —H or —$C_1$-$C_4$-alkyl, and $R_5$ is as defined above, provided that $R_5$ is not hydrogen.

The compounds of formula (C), compounds of formula (F), compounds of formula (H) and compounds of formula (J) are compounds of the general formula (I).

Also these reaction steps can be carried out according to standard procedures known in the art, whereas further guidance can be found in the reaction schemes and in the Examples disclosed below.

Scheme 1.1 shows the preparation of a compound of formula (C) corresponding to compounds of formula (I) as defined above. As mentioned above, the starting materials are either commercially available or are prepared in similar manners as described in literature procedures or in the specific examples. The desired coumarins of formula (B) were commercially available or were prepared from the corresponding β-ketoesters of formula (A), wherein X is defined as above, and the required resorcinol through a Pechmann cyclisation such as the one described by Leonetti et al. (2004) or Gosselin et al. (2010). Further literature examples include publications such as Tasler et al., WO 2016/146,583A1, p.49—Scheme 1, or Sharma et al. (2013).

The coumarins of formula (B) can be further alkylated with a commercial alkylbromide (Z—Br) or subjected to a Mitsunobu (Z—OH) reaction with a commercial alcohol to produce compounds of formula (C).

It is apparent to the skilled person that the sequence of the synthetic steps is dependent on the starting materials' availability and functional group compatibility and could vary from compound to compound.

Scheme 1.1: Exemplary preparation of a compound of formula (C)

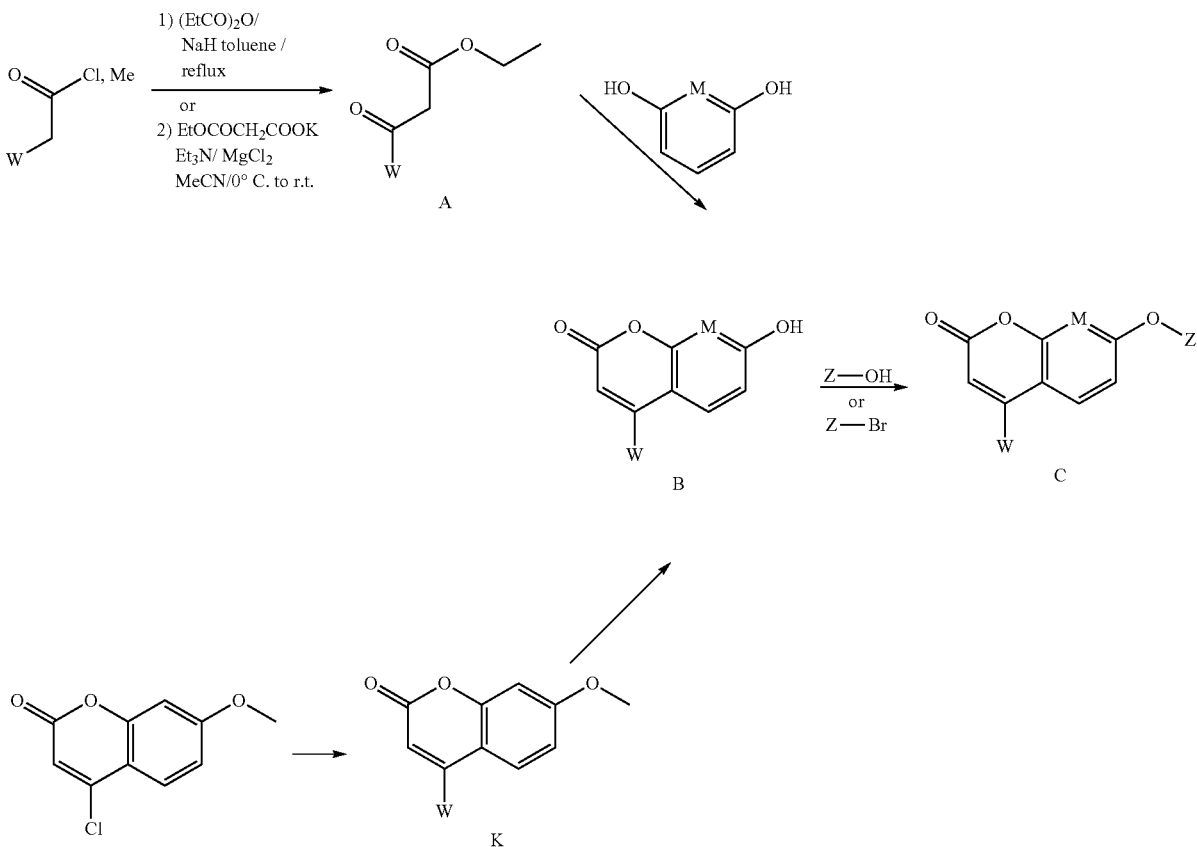

Scheme 1.2 shows the preparation of a preferred embodiment of a compound of formula (C) corresponding to compounds of formula (I) as defined above.

Scheme 1.2: Exemplary preparation of a compound of formula (C)

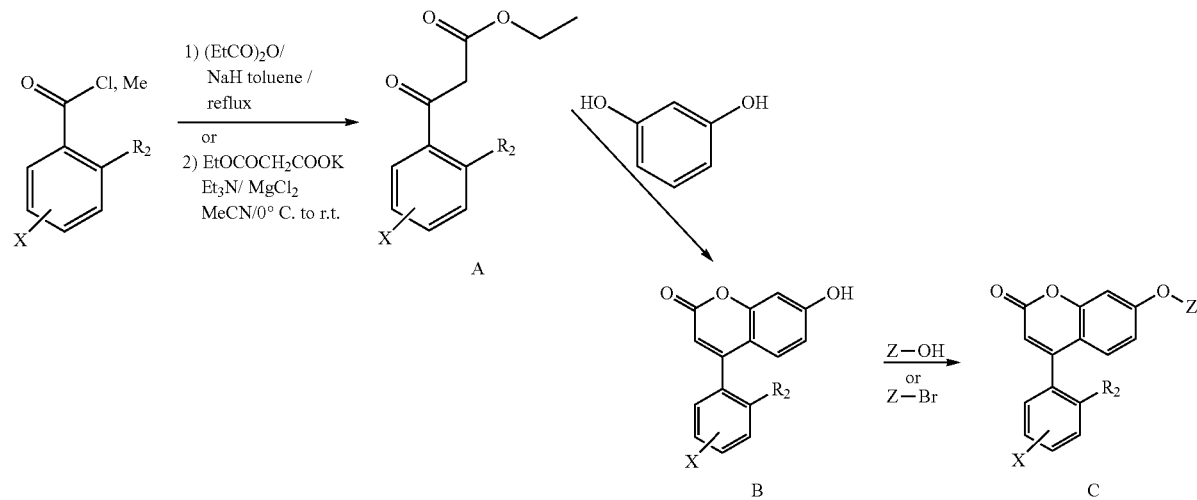

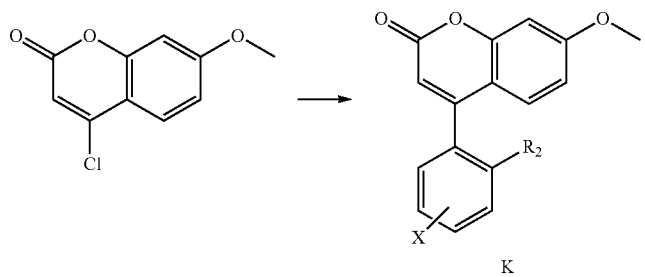

Use of the Novel Compounds of Formula (I) as a Medicament

Furthermore, it has been found that the compounds of formula (I) are suitable for use as a medicament. Specifically, it has been found that the compounds of formula (I) can be used in the treatment of cancer, preferably in the treatment of melanoma, metastatic melanoma, pancreatic cancer, hepatocellular carcinoma, lymphoma, acute myeloid leukemia, breast cancer, glioblastoma, cervical cancer, renal cancer, colorectal cancer or ovarian cancer.

POLRMT inhibitors previously have been described to trigger the death of AML cells allegedly through rather unspecific inhibition of mitochondrial transcription confirms this rational (Bralha et al., 2015). As described in the examples below compounds of the invention were surprisingly and unexpectedly shown to have cytostatic activity on a number of tumor cells and tumor models both in vitro and in vivo.

Accordingly, the compounds of formula (I) of the invention and their pharmaceutically or veterinary acceptable salts, hydrates or solvates, exhibit valuable pharmacological properties and are therefore useful as a medicament or pharmaceutical. The medicament or pharmaceutical can be further formulated with additional pharmaceutically or veterinary acceptable carriers and/or excipients, e.g. for oral administrations in the form of tablets. Tablets may contain suitable binders, lubricants, disintegrating agents, coloring agents, flavoring agents, flow-inducing agents and/or melting agents, generally known in the art.

Thus, in one aspect, the invention relates to a compound of the general formula (I) as defined herein for use as a medicament.

Compounds of the invention exhibit a marked and selective inhibitory effect on the POLRMT. This can be determined for example in the Homogeneous TR-FRET assay (see example 4) or the Quantitative real time-PCR assay (see example 5). The skilled person however may use different assays to determine the direct or indirect inhibition of POLRMT.

As mentioned above, it has been found that the compounds of the invention are useful in the treatment of cancer. There is evidence that in melanoma and especially in metastatic melanoma OXPHOS plays a major role in cancer cells and that inhibition of mitochondria in general may lead to superior treatment success. For example it was shown that $H_3K4$-demethylase (JARID1B) and OXPHOS dependent drug resistance play a role in metastatic melanoma (Roesch et al., 2013). Haq et al. (2013) describe that the standard of care (SoC) treatment with MEK inhibitors in melanoma leads to PGC1-a-dependent increase in OXPHOS as a drug-resistance escape route. It was also shown that the inhibition of mutated BRAF by vemurafenib increases OXPHOS dependency of BRAF mutated melanoma cells (Schöckel et al., 2015). And further, enhanced OXPHOS, glutaminolysis and β-oxidation constitute the metastatic phenotype of melanoma cells (Rodrigues et al., 2016).

For pancreatic cancer selective killing of OXPHOS-dependent Panc-1 cells has been described for treatment with arctigenin (Brecht et al., 2017). In hepatocellular carcinoma, standard of care (SoC) treatment with MEK inhibitor is leading to PGC1-a-dependent increase in OXPHOS as a drug-resistance escape route (Bhat et al., 2013, Ling et al., 2017). For lymphoma it has been demonstrated that OXPHOS is dependent on mt-complex III inhibitor antimycinA (Dörr et al., 2013). As described above acute myeloid leukemia, POLRMT inhibitors previously have been described to trigger the death of AML cells allegedly through rather unspecific inhibition of mitochondrial transcription (Bralha et al., 2015).

Also breast cancer should be a suitable cancer indication as overexpression of progesterone receptor is present in more than 50% of all breast cancer patients, whereas progesterone is stimulating mitochondrial activity with subsequent inhibition of apoptosis (Nadji et al., 2005, Behera et al., 2009). Further, the inhibition of mTOR leads to a shift towards OXPHOS-dependence and there is a glucose-dependent effect of mTOR inhibitors in combination with metformin (Pelicano et al., 2014, Ariaans et al., 2017). Additionally, it is described that mitochondrial dysfunction caused by metformin prevents tumor growth in breast cancer (Sanchez-Alvarez et al., 2013).

For glioblastoma it is known that malignant repopulation is dependent on OXPHOS (Yeung et al., 2014). With respect to cervical cancer, POLRTM inhibitors inhibit free fatty acid oxidation (data not shown), which otherwise promote cervical cancer cell proliferation (Rodriguez-Enriquez et al., 2015). In renal cancer there is evidence that Birt-Hogg-Dubé renal tumors are associated with up-regulation of mitochondrial gene expression (Klomp et al., 2010). In colon carcinoma the rational is based on the finding that 5-fluorouracil resistant colorectal/colon cancer cells are addicted to OXPHOS to survive and enhance stem-like traits (Denise et al., 2015). Further, the in vivo efficacy demonstrated in the DLD-1 tumor model (see example 8) supports this rational. In vivo efficacy has further been demonstrated in an ovary carcinoma model in single treatment (see example 7).

Accordingly, in another aspect, the invention relates to compounds of formula (I) of the invention as defined herein for use in the treatment of cancer, preferably melanoma, metastatic melanoma, pancreatic cancer, hepatocellular carcinoma, lymphoma, acute myeloid leukemia, breast cancer, glioblastoma, cervical cancer, renal cancer, colorectal cancer or ovarian cancer.

The compounds of the invention are preferably useful in a method for treating cancer in simultaneous, alternating or subsequent combination with another cancer therapy, preferably selected from chemotherapy, immunotherapy, hormone therapy, stem cell transplantation therapy, radiation therapy or surgery. It is likely that the cytostatic activity of the POLRMT inhibitors on tumor cells can be further enhanced by combining the treatment with the respective standard of care in order to get improved/additive treatment results. In this context simultaneous, alternating or subsequent application of the various treatments is envisaged. Any of the standard classes of cancer therapy, chemotherapy, immunotherapy, hormone therapy, stem cell transplantation therapy, radiation therapy or surgery, appears to be feasible for combination with the POLRMT inhibitors of this invention.

Thus, in another aspect, the invention relates to a compound of the general formula (I) as defined herein for use in a method for treating cancer in simultaneous, alternating or subsequent combination with another cancer therapy, preferably selected from chemotherapy, immunotherapy, hormone therapy, stem cell transplantation therapy, radiation therapy or surgery.

The present invention also concerns a method for treating a patient suffering from cancer, which comprises the step of administering a therapeutically effective amount of a compound as described above, preferably in simultaneous, alternating or subsequent combination with another cancer therapy as e.g. disclosed above.

FIGURES

FIG. 1: Therapeutic effect of compound 14 on human A2780 ovary carcinoma xenograft in nude mouse.

Diamonds=vehicle control up to day 28 post transplantation;

Squares=30 mg/kg of compound 14 up to day 21 post transplantation;

Triangles=100 mg/kg of compound 14 up to day 28 post transplantation;

Circles=200 mg/kg of compound 14 up to day 28 post transplantation.

A: Mean tumor volume±standard deviation in cm$^3$ in dependence of time post transplantation in days.

B: Mean body weight±standard deviation in g in dependence of time post transplantation in days.

Figure 2:
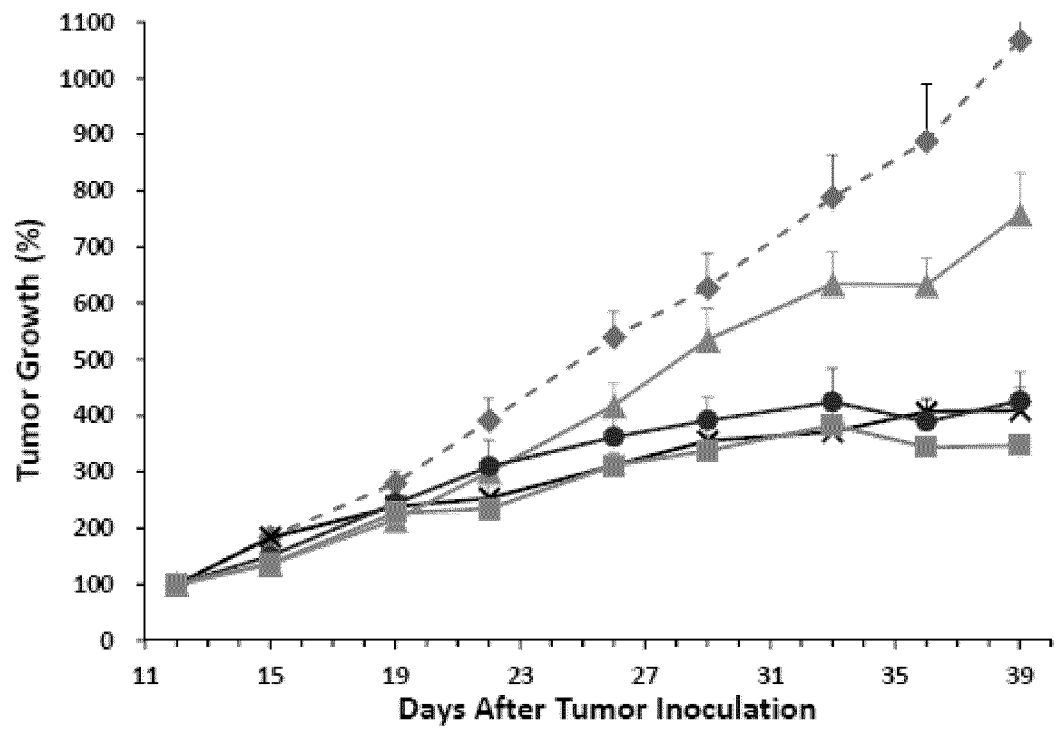
Figure 2:
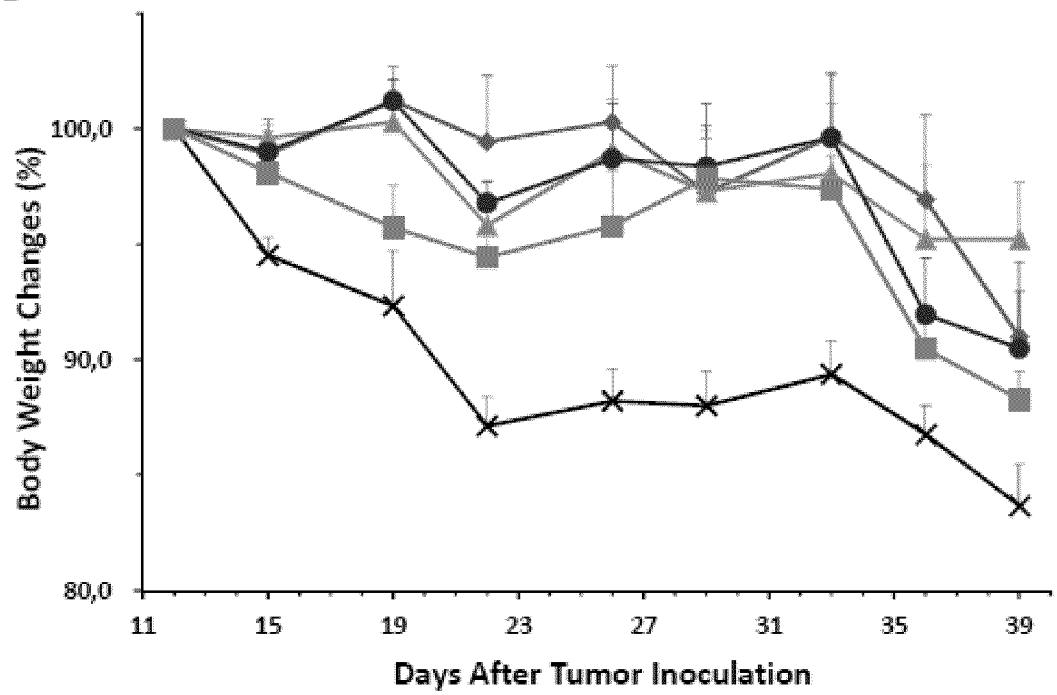

FIG. 2: Therapeutic effect of compound 14 on human DLD-1 colon carcinoma xenograft in nude mice.

Diamonds=Group-1: Control up to day 28 post transplantation;

X=Group-2: 30 mg/kg Sorafenib of up to day 28 Squares

Triangles=Group-3: 30 mg/kg of compound 14 up to day 28 post transplantation;

Circles=Group-4: 100 mg/kg of compound 14 up to day 28 post transplantation;

Squares=Group-5: 200 mg/kg of compound 14 up to day 28 post transplantation.

A: Tumor growth in % in dependence of time post tumor inoculation in days.

B: Mean body changes in % in dependence of time post tumor inoculation in days.

EXAMPLES

Abbreviations and Acronyms

Abbreviations and Acronyms used in the description of the chemistry and in the Examples that follow are:

Abs Absolute configuration (at least one stereocenter)
aq. aqueous
BB building block
BBr$_3$ boron tribromide
br. broad
Bu$_3$SnN$_3$ tributyltin azide
CDCl$_3$ deuterated chloroform
CD$_3$OD deuterated methanol
CHCl$_3$ chloroform
cHex cyclohexane
Cs$_2$CO$_3$ cesium carbonate
CuI copper(I) iodide
d doublet
DCM dichloromethane
DIAD diisopropylazodicarboxylate
DIPEA Diisopropylethylamine
DMAP 4-N,N-Dimethylaminopyridine
DMF dimethylformamide
DMSO dimethylsulfoxide
DMSO-d$_6$ deuterated dimethylsulphoxide
EDC 1-Ethyl-3-(3-dimethylaminopropyl)carbodiimide
ES electrospray
Et$_3$N triethylamine
Et$_2$NH diethylamine
Et$_2$O diethylether
EtOAc ethyl acetate
EtOH ethanol
h hour
HATU O-(7-Azabenzotriazol-1-yl)—N,N,N',N'-tetramethyluronium-hexafluorphosphate
HBTU 3-[Bis(dimethylamino)methyliumyl]-3H-benzotriazol-1-oxide hexafluorophosphate
HCl hydrochloric acid
H$_2$O water
HOBt 1H-benzo[d][1,2,3]triazol-1-ol
K$_2$OC$_3$ potassium carbonate
m multiplet
MeCN acetonitrile
MeOH methanol
MeI methyl iodide
min minutes
MS mass spectrometry
NaHCO$_3$ sodium hydrogencarbonate
NaCl sodium chloride
NaH sodium hydride
NH$_4$Cl ammonium chloride
NMR nuclear magnetic resonance
Pd(PPh$_3$)$_4$ Tetrakis(triphenylphosphine)palladium(0)
PPh$_3$ triphenylphosphine
PBu$_3$ tributylphosphine
p.o. per os—oral adiministration
q quartet
QD quaqua die, once per day
quint quintet
rt room temperature
s singlet
sat. saturated
sept septet S.D. standard deviation
SPhos 2-Dicyclohexylphosphino-2',6'-dimethoxybiphenyl
t triplet
THF tetrahydrofuran 1. Methods of Making the Compounds of Formula (I) of the Present Invention In general, the compounds of formula (I) used of the invention might be prepared by standard techniques known in the art, by known processes analogous thereto, and/or by the processes described herein, using starting materials which are either commercially available or producible according to conventional chemical methods. The particular processes to be utilised in the preparation of the compounds of formula (I) of this invention depends upon the specific compound desired. Such factors as the type of substitution at various locations of the molecule and the commercial availability of the starting materials play a role in the path to be followed and in the chosen reaction conditions for the preparation of the specific compounds of formula (I) of this invention. Those factors are readily recognised by one of ordinary skill in the art.

The following preparative methods are presented to aid the reader in the synthesis of the compounds of the present invention.

2. Experimental Procedures

LC-MS Method

HPLC—electrospray mass spectra (HPLC ES-MS) were obtained using a Waters Acquity Ultra Performance Liquid Chromatography (UPLC) equipped SQ 3100 Mass detector spectrometer.
   Column: Acquity UPLC BEH C18 1.7 µm, 2.1×50 mm
   Flow: 0.500 mL/min
   Eluents: A: $H_2O$ with 0.05% formic acid and B: MeCN with 0.05% formic acid.
   Gradient: elution from 5% to 100% B over 3.5 min with an initial hold of 0.5 min and a final hold at 100% B of 0.5 min. Total run time: 5 min.
   The gradient described could be altered in function of the physico-chemical properties of the compound analyzed and is in no way restrictive.

Preparative HPLC Method

Preparative HPLC was performed using a Waters System consisting of a Waters 2767 Sample Manager, a Waters 2545 Binary Gradient Module, a Waters SFO (System Fluidics Organizer), a Waters 3100 Mass Detector, and a Waters 2498 UV/Visible Detector.
   Column: XBridge® Prep C18 5 µm OBD™, 19×150 mm
   Flow: 20 mL/min
   Eluents: A: $H_2O$ with 0.1% TFA and B: MeCN with 0.1% TFA.
   General Gradient: elution from X % to Y % B over 20 min with an initial hold of 2 min and a final increase to 100% B over 2 min and hold at 100% B of 2 min followed by a 1 min gradient back to the initial composition. Total run time: 26 min. X=Y−30% where Y=concentration of elution on the above described LC-MS method.
   The gradient described could be altered in function of the physicochemical properties of the compound analysed and is in no way restrictive.

Chiral LC-MS Method

Chiral HPLC—electrospray mass spectra (HPLC ES-MS) were obtained using a Waters Acquity Ultra Performance Liquid Chromatography (UPLC) equipped SQ 3100 Mass detector spectrometer.
   Column: Lux 5u Cellulose-2; 150×4.6 mm
   Flow: 0.500 mL/min-1.000 mL/min
   Eluents: A: $H_2O$ with 0.05% formic acid and B: MeCN with 0.05% formic acid.
   Gradient: elution from X % to Y % B over 15 min with an initial hold of 0.5 min and a return to 100% B and final hold at of 2.5 min. Total run time: 18 min. Example for compound 47: X=55%; Y=65%
   The gradient could be altered in function of the physico-chemical properties of the compound analyzed and is in no way restrictive.

Chiral Preparative HPLC Method

Preparative HPLC was performed using a Waters System consisting of a Waters 2767 Sample Manager, a Waters 2545 Binary Gradient Module, a Waters SFO (System Fluidics Organizer), a Waters 3100 Mass Detector, and a Waters 2498 UVNisible Detector.
   Column: Lux 5u Cellulose-2, 150×21.2 mm (Phenomenex)
   Flow: 20 mL/min-30 mL/min
   Eluents: A: $H_2O$ with 0.1% TFA and B: MeCN with 0.1% TFA.
   Gradient example for compound 108: elution from 30% to 50% B over 30 min with an initial hold of 3 min and a final hold at 100% B of 6 min. Total run time: 39 min.
   The gradient could be altered in function of the physico-chemical properties of the compound analysed and is in no way restrictive.

GC-MS Method

Gas Chromatography—Mass spectra were obtained using Agilent 7820A GC with 5977E MSD
   Column: HP-5MS 30 m, 0.25 mm ID, 0.25 µm
   Flow: 2 mL/min. He
   Injection: 100 µl/s, 250° C.; Split Flow: 20 mL/min. Split Ratio: 10
   Detection: Agilent 5977E
   Gradient: 0 min 50° C.; 0.5 min 50° C.; 7.6 min 300° C.; 9.6 min 300° C.
   The gradient described could be altered in function of the physico-chemical properties of the compound analyzed and is in no way restrictive.

NMR Methods

Proton ($^1$H) nuclear magnetic resonance (NMR) spectra were measured with an Oxford Varian 400/54 (400 MHz) spectrometer or a Bruker Avance II (300 MHz) spectrometer with residual protonated solvent ($CHCl_3$ δ 7.26; MeOH δ 3.30; DMSO δ 2.49) as standard. The NMR data of the synthesized examples, are in agreement with their corresponding structural assignments.

Synthetic Methods

The general synthesis of a compound of this invention is described below in Schemes 1-3. The starting materials are either commercially available or are prepared in similar manners as described in literature procedures or in the specific examples. The desired coumarins were prepared from the corresponding β-ketoesters and the required resorcinol or 2,6-dihydroxypyridine through a Pechmann cyclisation such as the one described by Leonetti et al. (2004) or Gosselin et al. (2010). Alternatively, the phenylcoumarins B, were synthesized from 4-Chloro-7-methoxy-2H-chromen-2-one through a Suzuki Coupling to obtain compounds K, followed by demethylation with $BBr_3$.

When the β-ketoesters could not be purchased, they were synthesized from the required benzoylchlorides and diethylcarbonate or acetophenones and ethyl potassium malonate under basic conditions in a similar manner as indicated in Scheme 1.

It should be apparent to those skilled in the art that the sequence of the synthetic steps is dependent on starting materials availability and functional group compatibility and could vary from compound to compound.

Scheme 1: Exemplary preparation of a compound of formula (C)

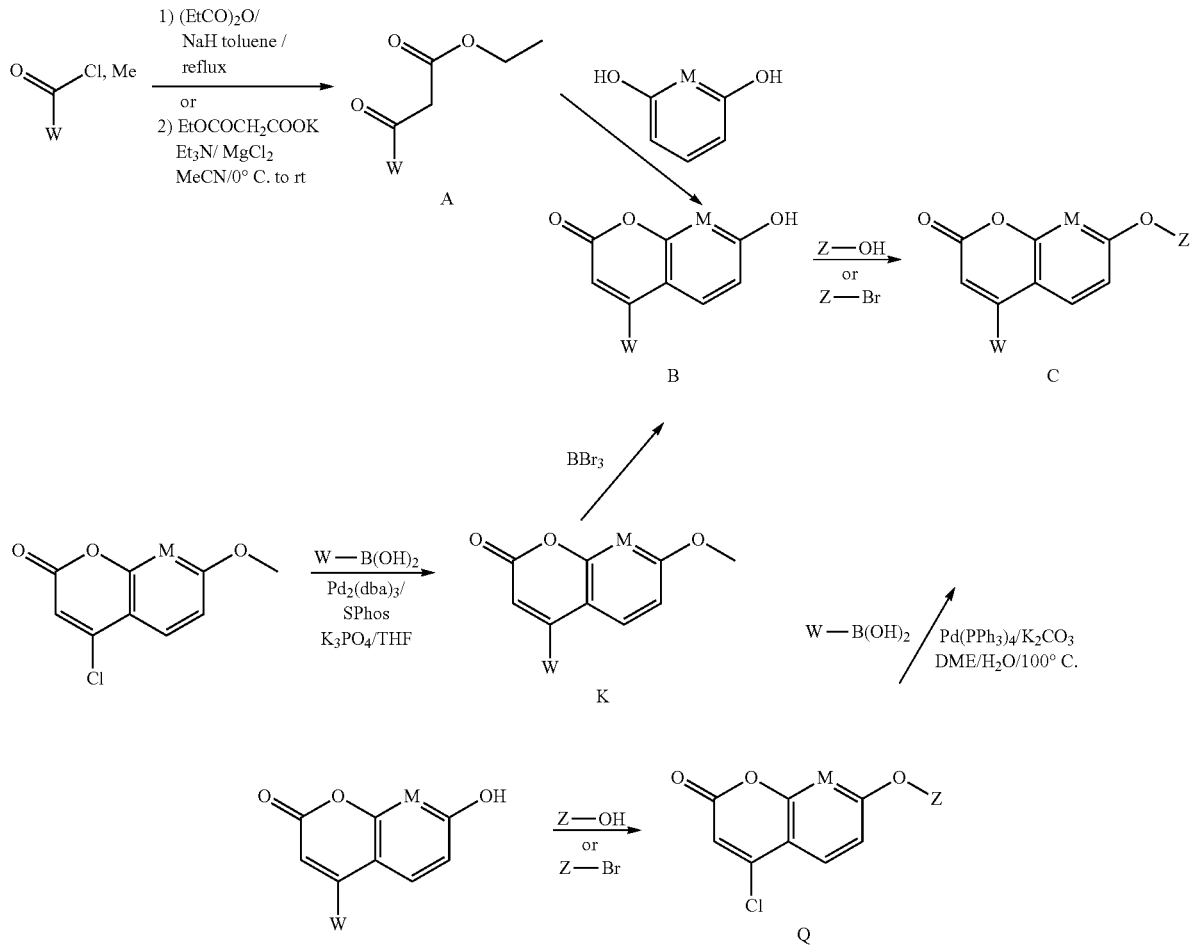

It should be apparent to those skilled in the art that the sequence of the synthetic steps is dependent on starting materials availability and functional group compatibility and could vary from compound to compound. In particular, and for the purpose of rapid diversification, the Mitsunobu/alkylation reaction step (B to C) and the Suzuki Coupling step (K to B), could be reversed. This was applied, for example, to the synthesis of different thiophene-containing intermediates ((R)-16D, (R)-16E, 17D, and 17E). Conditions for the Suzuki Coupling of intermediates Q is described in method M3d.

The coumarin can be further alkylated with a commercial alkylbromide (Z—Br) or subjected to a Mitsunobu (Z—OH) reaction with a commercial alcohol to produce compounds of formula C.

For the examples described in this patent, Z was a potentially substituted alkyl acetate group; this was usually further modified by hydrolysis to the corresponding carboxylic acid (E), followed by coupling with a commercially available, optionally substituted amine, according to standard procedures known in the art, and as described in Scheme 2, to produce structure F. Alternatively, the Mitsunobu reaction could be carried out with a suitable, synthesized or commercially available 2-hydroxyacetamide L to obtain a compound of structure F directly. The specific procedures are listed below.

Scheme 2: Exemplary preparation of a compound of formula (F)

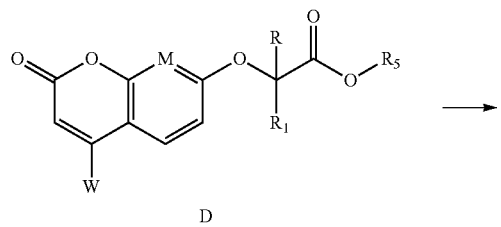

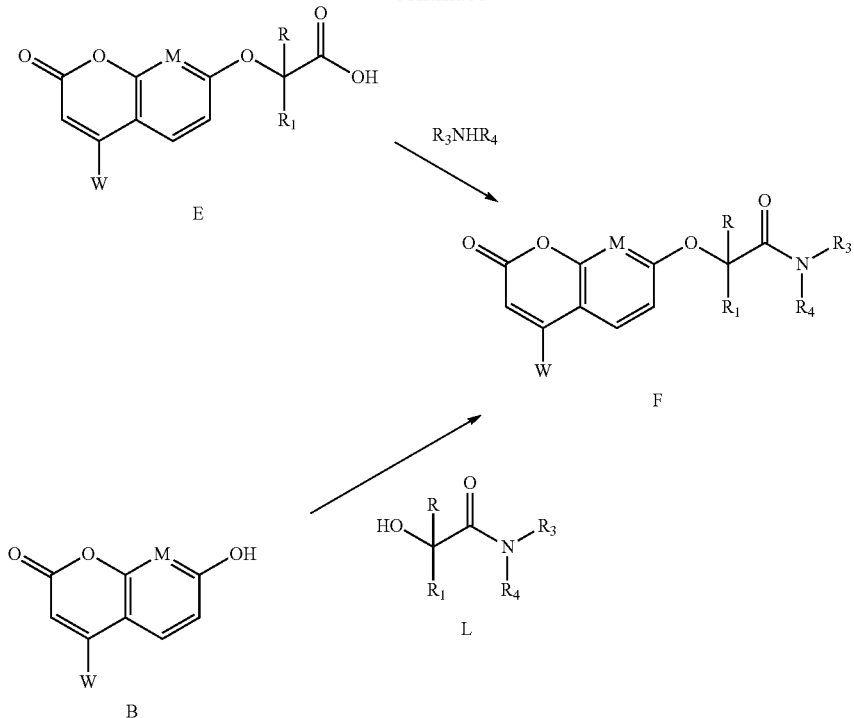

When $R_3$ and $R_4$ form an optionally substituted cyclic amide, this amide can carry an ester moiety or a carbamate moiety, as highlighted in formulas G and M, which can be further hydrolyzed to obtain compounds of substructure H or N. Examples are outlined in Scheme 3. When the commercially available ester building blocks were racemic, or intermediate D was prepared according to method M4, the coupling reaction was sometimes followed by chiral preparative HPLC to allow separation of the diastereomers.

In case of non-commercially available ester building blocks, the synthesis of compounds J required further derivatization of compound H, in a way that is described in methods 10 or 11. Amines N could also be further modified using methods known in the art, to obtain amides of formula P. An example of such modification is described in method M12 for compound 166.

Scheme 3: Exemplary preparation of a compound of formula (H), (J), (N) and (P)

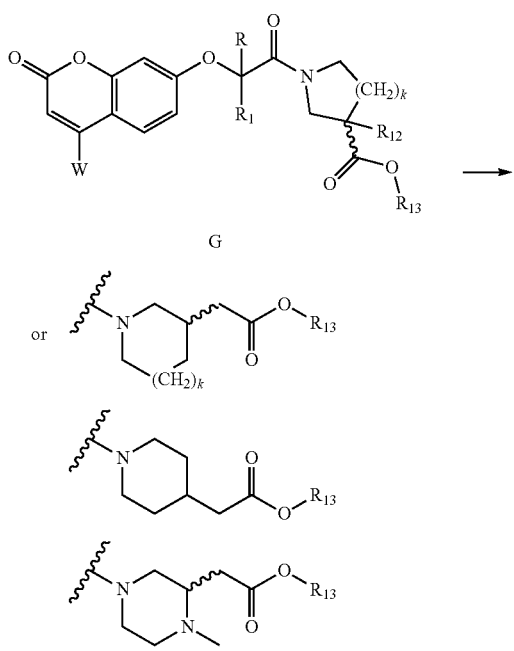

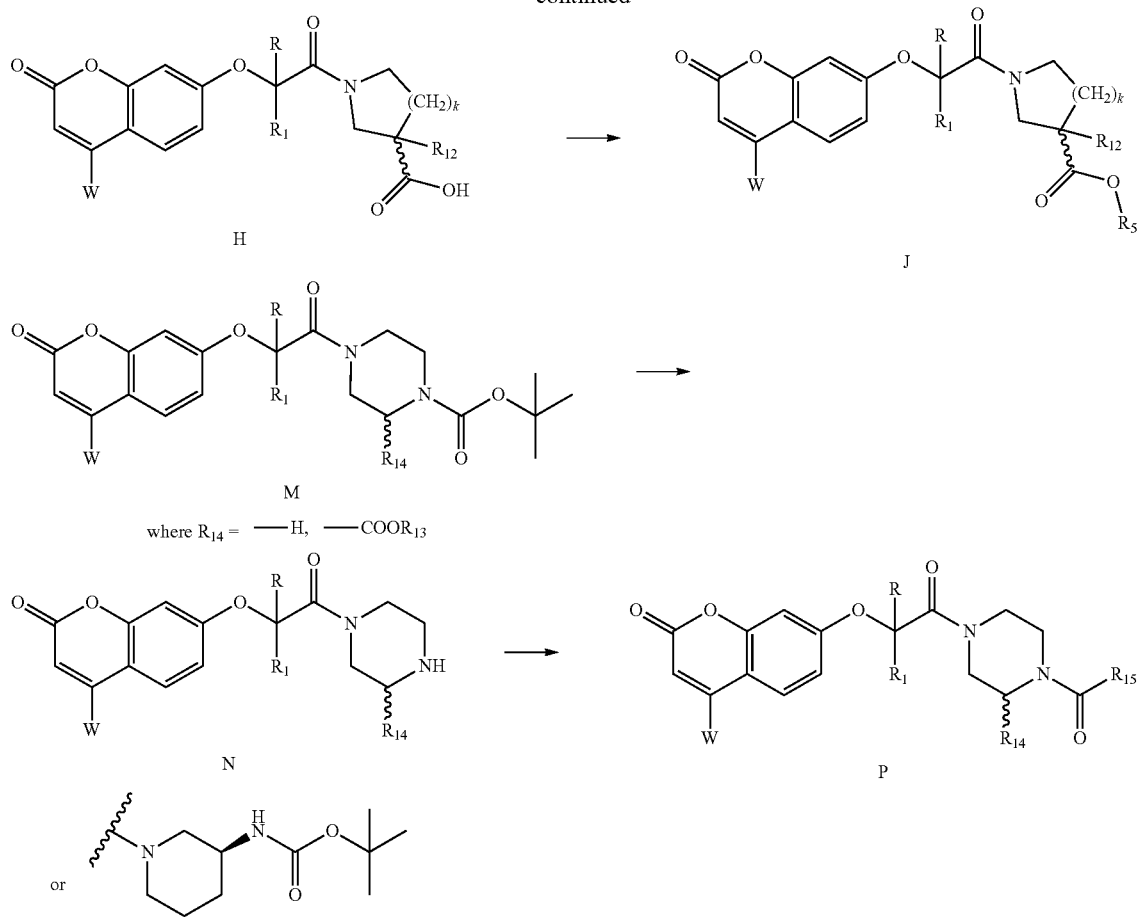

The compounds of formula (C), compounds of formula (F), compounds of formula (H), compounds of formula (J) and compounds of formula (P) are compounds of the general formula (I) of the invention.

3. Experimental Examples of the Invention

The following specific examples are presented to illustrate the invention, but they should not be construed as limiting the scope of the invention in any way. In the tables listing the intermediates, the compounds might have characterization such as $(M+H)^+$ mass spectrometry data, HPLC purity and/or NMR. Those that have no characterization are commercially available, and a CAS number is given.

3.1 Preparation of Intermediates for the Preparation of Compounds of Formula (I)

3.1.1 Synthesis of Substituted β-Ketoesters of Formula (A)

The non-commercial substituted β-ketoesters A intermediates required for the Pechmann condensation reaction are prepared from the corresponding acetophenone or from the corresponding acid chloride as described in by E. J. Hanan et al. (2012), and as illustrated in Scheme 1. The methods are exemplified by intermediates 1A and 2A.

At least one intermediate example per method is described below:

Intermediate 1A—Synthesis According to Method 1 (M1)

Ethyl 3-(2-chloro-4-fluorophenyl)-3-oxopropanoate

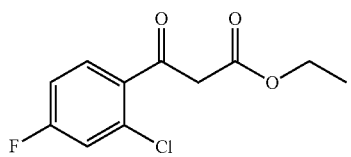 [SMILES: CCOC(=O)CC(=O)c1ccc(F)cc1Cl]

60% NaH in mineral oil (4.86 g, 121.7 mmol) was washed with pentane and dried under a flow of nitrogen. Dry toluene (350 mL) was added and the suspension was cooled to 0° C. Diethyl carbonate (27.4 g, 231.8 mmol) was added dropwise over a period of 25 min, followed by 2-Chloro-4-fluoroacetophenone (10 g, 57.9 mmol) over a period of 20 min. The cooling bath was removed, and the reaction heated to 50° C. and stirred for 18 h. The reaction mixture was allowed to cool to rt and was poured into ice cold water (500 mL).The aqueous layer was acidified to pH 2 with 10% aq. HCl and extracted with $Et_2O$. The combined organic phases were dried over $MgSO_4$, filtered and evaporated in vacuo to yield the desired product 1A (6.0 g, 42%) as a mixture of tautomers, which was used in the following step without further purification.

$^1$H NMR (300 MHz, $CDCl_3$) δ 7.63 (dd, 1H), 7.14-6.93 (m, 2H), 4.12 (q, 2H), 3.96 (s, 2H), 1.18 (t, 3H)—tautomer 1, ethyl 3-(2-chloro-4-fluorophenyl)-3-oxopropanoate ¹H NMR (300 MHz, CDCl₃) δ 12.43 (s, 1H), 7.52 (dd, 1H), 7.14-6.93 (m, 2H), 5.48 (s, 1H), 4.21 (q, 2H), 1.27 (t, 3H)—tautomer 2, (Z)-ethyl 3-(2-chloro-4-fluorophenyl)-3-hydroxyacrylate MS (ES) C₁₁H₁₀ClFO₃ requires: 244/246, found: 245/247 (M+H)⁺, 65%

Intermediate 2A—Synthesis According to Method 2 (M2)
Ethyl 3-(2-bromophenyl)-3-oxopropanoate

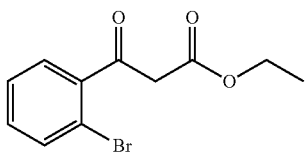

Ethyl potassium malonate (1.39 g, 8.2 mmol) was suspended in dry MeCN (22 mL) under a flow of nitrogen, and the mixture was cooled to 10° C. Et₃N (1.2 mL, 8.6 mmol) and MgCl₂ (935 mg, 9.84 mmol) were added and the reaction was stirred at rt for 2 h 30 min. The reaction was once again cooled to 10° C. and 2-bromobenzoyl chloride (900 mg, 4.1 mmol) followed by further Et₃N (114 µl, 0.82 mmol) were added. The mixture was stirred at rt overnight. The reaction was quenched with a saturated NH₄Cl solution and extracted with EtOAc. The combined organic layers were dried over MgSO₄, filtered and evaporated in vacuo. The crude product was purified by flash chromatography on silica gel using a gradient of EtOAc in cHex to yield the desired product 2A (379 mg, 34%) as a mixture of tautomers, which was used in the following step without further purification.

¹H NMR (400 MHz, CDCl₃) δ 7.63-7.58 (m, 1H), 7.39-7.21 (m, 2H), 4.16 (q, 2H), 3.99 (s, 2H), 1.22 (t, 3H)—tautomer 1, ethyl 3-(2-bromophenyl)-3-oxopropanoate ¹H NMR (400 MHz, CDCl₃) δ 12.40 (s, 1H), 7.52-7.45 (m, 1H), 7.39-7.21 (m, 2H), 5.43 (s, 1H), 4.25 (q, 2H), 3.99 (s, 1H), 1.31 (t, 3H)—tautomer 2, (Z)-ethyl 3-(2-bromophenyl)-3-hydroxyacrylate MS (ES) C₁₁H₁₁BrO₃ requires: 270/272, found: 271/273 (M+H)⁺, ~100%

3.1.2 Preparation of Intermediate Compounds of Formula (B)
Intermediate 1B—Synthesis According to Method 3a (M3a)
4-(2-Chloro-4-fluorophenyl)-7-hydroxy-2H-chromen-2-one (1B)

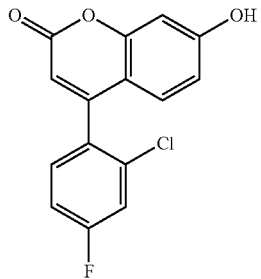 [SMILES: O=c1cc(-c2ccc(F)cc2Cl)c2ccc(O)cc2o1]

Intermediate 1A (2 g, 8.18 mmol) was dissolved in methansulfonic acid (12.41 g, 25 mL, 129.1 mmol) and resorcinol (851 mg, 7.72 mmol) was added. The mixture was stirred at 45° C. for 2 h, upon which the reaction was allowed to cool to rt. EtOH (30 mL) was added dropwise, followed by water (100 mL). The suspension was extracted with EtOAc and washed with brine. The combined organic layers were dried over MgSO₄ filtered and evaporated in vacuo. The crude product was purified by column chromatography using a gradient of EtOAc in cHex to yield the desired product 1B (1.896 g, 80%) as a pink solid.

¹H NMR (300 MHz, DMSO-d₆) δ 10.70 (br. s, 1H), 7.69 (dd, 1H), 7.50-7.53 (m, 1H), 7.42 (td, 1H), 6.87 (d, 1H), 6.81 (d, 1H), 6.74 (dd, 1H), 6.21 (s, 1H).

MS (ES) C₁₅H₈ClFO₃ requires: 290/292, found: 291/293 (M+H)⁺, 95%

3.1.3 Preparation of Intermediate Compounds of Formula (K)
Intermediate 8B—Synthesis According to Method 3b (M3b)
2-(7-methoxy-2-oxo-2H-chromen-4-yl)benzonitrile (1K)

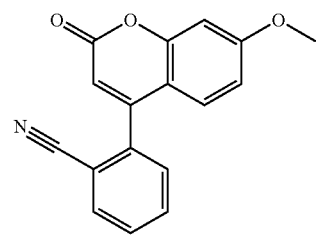 [SMILES: COc1ccc2c(-c3ccccc3C#N)cc(=O)oc2c1]

4-Chloro-7-methoxy-2H-chromen-2-one (500 mg, 2.37 mmol), 2-cyanophenylboronic acid (384 mg, 2.61 mmol), Pd₂(dba)₃ (109 mg, 0.12 mmol), SPhos (146 mg, 0.36 mmol) and K₃PO₄ (1.01 g, 4.76 mmol) were put in a 20 mL microwave vial, the vial was conditioned with 3 cycles vacuum/N₂, then dry THF (10 mL) was added and the reaction was heated to 60° C. and stirred for 20 h. The mixture was allowed to cool to rt, and the solid was filtered off and washed with acetone. The crude was purified by column chromatography using a gradient of EtOAc in cHex to yield the desired product 1K (336 mg, 56%) as a white solid.

¹H NMR (300 MHz, CDCl₃) δ 7.79 (d, 1H), 7.75-7.63 (m, 1H), 7.57 (t, 1H), 7.41 (d, 1H), 6.97-6.81 (m, 2H), 6.72 (dd, 1H), 6.20 (s, 1H), 3.82 (s, 3H).

MS (ES) C₁₇H₁₁NO₃ requires: 277, found: 278 (M+H)⁺, 100%

2-(7-hydroxy-2-oxo-2H-chromen-4-yl)benzonitrile (8B)

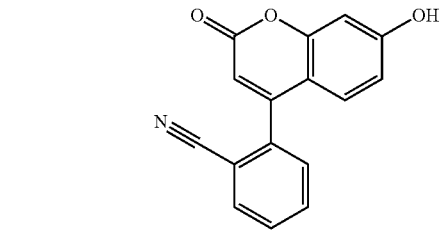 [SMILES: N#Cc1ccccc1-c1cc(=O)oc2cc(O)ccc12]

Compound 1K (150 mg, 0.541 mol) was dissolved in DCM (9 mL), and then mixture was cooled down to −20° C. and BBr₃ (150 mg, 58 µL) was added in DCM (5 mL). The reaction was allowed to slowly warm up to rt overnight. Small aliquots of BBr₃ in DCM were added until full consumption of the starting material. The reaction was poured onto ice-water (20 mL) and extracted with DCM (3×10 mL). The combined organic layers were washed with water (10 mL) and brine (5 mL), dried over MgSO₄, filtered and evaporated in vacuo to yield the desired product 8B (68 mg, 48%) as a pink solid.

¹H NMR (300 MHz, CDCl₃) δ 7.84-7.75 (m, 1H), 7.70 (td, 1H), 7.57 (td, 1H), 7.47-7.38 (m, 1H), 6.91 (d, 1H), 6.82 (d, 1H), 6.68 (dd, 1H), 6.20 (s, 1H).

MS (ES) C$_{16}$H$_9$NO$_3$ requires: 263, found: 264 (M+H)$^+$, 100%

Intermediate 11B—Synthesis According to Method 3c (M3c) 4-(2-chloro-4-fluorophenyl)-7-hydroxy-2H-pyrano[2,3-b]ipyridin-2-one (11B)

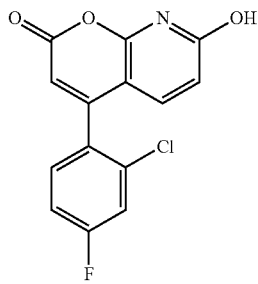 [SMILES: O=c1cc(-c2ccc(F)cc2Cl)c2ccc(O)nc2o1]

Intermediate 1A (1.211 g, 5 mmol) was dissolved in NMP (0.5 mL) and 2,6-dihydroxypyridine (500 mg, 4.5 mmol) was added. The mixture was stirred at 170° C. in a sealed tube for 3 h, upon which the reaction was allowed to cool to 90° C. and diluted with dioxane (50 ml). The crude was transferred to a flask containing hydromatrix, and the dioxane was removed. The crude was purified by column chromatography using a gradient of EtOAc in cHex to yield the desired product 11B (224 mg, 17%) as a red brick solid.

¹H NMR (400 MHz, DMSO-d$_6$) δ 12.30 (s, 1H), 7.68 (dd, 1H), 7.53 (dd, 1H), 7.42 (td, 1H), 7.32 (d, 1H), 6.58 (d, 1H), 6.30 (s, 1H).

MS (ES) C$_{14}$H$_7$ClFNO$_3$ requires: 291/293, found: 292/294 (M+H))$^+$, ~92%

The following coumarin intermediates were synthesized in a similar manner as for intermediate 1B, 8B or 11B (see Table 1).

TABLE 1

| | Hydroxy-Coumarins of formula (B) | |
|---|---|---|
| Intermediate | Structure | (M + H)$^+$, purity |
| 2B | ![structure] | MS (ES) C$_{15}$H$_9$BrO$_3$ requires: 316/318, found 317/319 (M + H)$^+$, 100% |
| 3B | ![structure] | MS (ES) C$_{16}$H$_{12}$O$_3$ requires: 252, found 253 (M + H)$^+$, 98% |
| 4B | ![structure] | MS (ES) C$_{15}$H$_9$ClO$_3$ requires: 272/274, found 273/275 (M + H)$^+$, 95% |
| 5B | ![structure] | MS (ES) C$_{15}$H$_8$ClFO$_3$ requires: 290/292, found 291/293 (M + H)$^+$, 95% |

TABLE 1-continued

Hydroxy-Coumarins of formula (B)

| Intermediate | Structure | (M + H)+, purity |
|---|---|---|
| 6B | (4-(2-ethylphenyl)-7-hydroxy-2H-chromen-2-one) | MS (ES) C17H14O3: requires: 266, found 267 (M + H)+, 92% |
| 7B | (4-(4-fluoro-2-methylphenyl)-7-hydroxy-2H-chromen-2-one) | MS (ES) C16H11FO3: requires: 270, found 271 (M + H)+, 95% |
| 9B | (4-(2,6-dichlorophenyl)-7-hydroxy-2H-chromen-2-one) | MS (ES) C15H8Cl2O3: requires: 306, found 307 (M + H)+, 97% |
| 10B | (7-hydroxy-4-(3-methylthiophen-2-yl)-2H-chromen-2-one) | MS (ES) C14H10O3S: requires: 258, found 259 (M + H)+, 95% |
| 12B | (4-(2-chlorophenyl)-7-hydroxy-2H-pyrano[2,3-b]pyridin-2-one) | MS (ES) C14H8ClNO3 requires: 273/275, found 274/276 (M + H)+, 96% |

TABLE 1-continued

Hydroxy-Coumarins of formula (B)

| Intermediate | Structure | (M + H)+, purity |
|---|---|---|
| 13B | (structure shown) | MS (ES) C15H9FO3 requires: 256, found 257 (M + H)+, 98% |
| 14B | (structure shown) | MS (ES) C15H8F2O3 requires: 274, found 275 (M + H)+, 100% |

3.1.4 Preparation of Intermediate Compounds of Formula (D)

Intermediate 1D—Synthesis According to Method 4 (M4) Ethyl 2-((4-(2-chloro-4-fluorophenyl)-2-oxo-2H-chromen-7-yl)oxy)propanoate (1D -82)

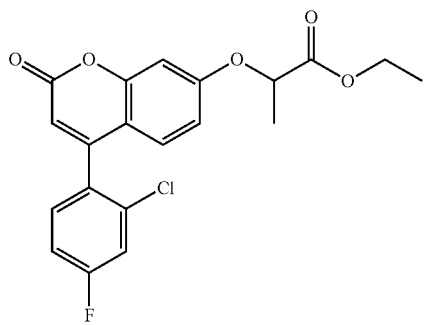 [SMILES: CCOC(=O)C(C)Oc1ccc2c(-c3ccc(F)cc3Cl)cc(=O)oc2c1]

Intermediate 1B (3.8 g, 13.1 mmol) was dissolved in DMF (18 mL) and Cs$_2$CO$_3$ (11 g, 33.8 mmol), followed by ethyl 2-bromopropanoate (3.5 g, 19.5 mmol) were added. The reaction was stirred at rt for 3 h. The mixture was diluted with water and extracted with EtOAc. The organic layer was washed with water and brine, dried over MgSO$_4$, filtered and evaporated in vacuo. The solid was further triturated with Et$_2$O to yield the desired product 1 D (3.00 g, 59%) as an off-white solid.

$^1$H NMR (300 MHz, CDCl$_3$) δ 7.26-7.16 (m, 2H), 7.12-7.01 (m, 1H), 6.94-6.86 (m, 1H), 6.79-6.63 (m, 2H), 6.13 (s, 1H), 4.73 (q, 1H), 4.17 (q, 2H), 1.59 (d, 3H), 1.22 (t, 3H).

MS (ES) C$_{20}$H$_{16}$ClFO$_5$ requires: 390/392, found: 391/393 (M+H)$^+$, 95%

Intermediate (R)-1D—Synthesis According to Method 5 (M5) (R)-Ethyl 2-((4-(2-chloro-4-fluorophenyl)-2-oxo-2H-chromen-7-yl)oxy)propanoate ((R)-1D)

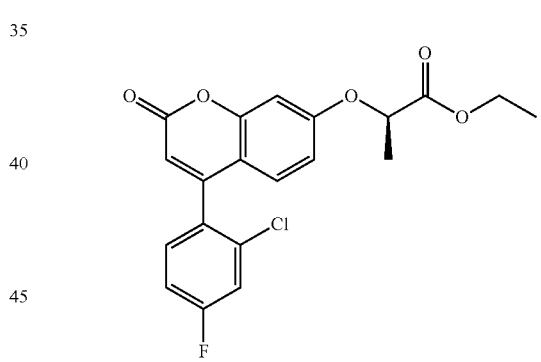

Intermediate 1B (200 mg, 0.69 mmol) and PPh$_3$ (198 mg, 0.76 mmol) were dissolved in THF (7 mL), and (−)-Ethyl (S)-2-hydroxypropionate (117 µl, 1.03 mmol) was added. The reaction was cooled to 0° C. and DIAD (149 µl, 0.76 mmol) was added dropwise. The reaction was then stirred at rt for 4 h. The mixture was diluted with EtOAc and washed with a sat. Na—HCO$_3$ solution, a sat. NH$_4$Cl solution, and water. The organic layer was dried over MgSO$_4$, filtered and evaporated in vacuo. The crude product was purified by flash chromatography on silica gel using a gradient of EtOAc in cHex to yield the desired product (R)-1D (203 mg, 75%) as a colorless glue.

$^1$H NMR (400 MHz, DMSO-d$_6$) δ 7.73-7.67 (m, 1H), 7.60-7.54 (m, 1H), 7.47-7.40 (m, 1H), 7.02 (dd, 1H), 6.98-6.93 (m, 1H), 6.90-6.85 (m, 1H), 6.33 (s, 1H), 5.18 (q, 1H), 4.16 (q, 2H), 1.54 (d, 3H), 1.19 (t, 3H).

MS (ES) C$_{20}$H$_{16}$ClFO$_5$ requires: 390/392, found: 391/393 (M+H)$^+$, 100%

3.1.4.1 Preparation of Intermediate Compounds of Formula (D) Through Intermediate (Q)

Intermediate 1Q—Synthesis According to Method 5 (M5) (R)-tert-butyl 2-((4-chloro-2-oxo-2H-chromen-7-yl)oxy)propanoate 1Q

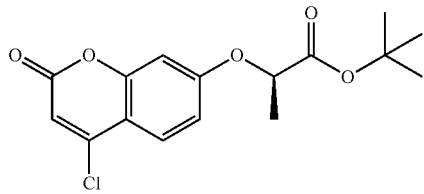 [SMILES: C[C@@H](Oc1ccc2c(Cl)cc(=O)oc2c1)C(=O)OC(C)(C)C]

4-Chloro-7-methoxy-2H-chromen-2-one (72 mg, 0.37 mmol) and PPh$_3$ (119 mg, 0.40 mmol) were dissolved in dry THF (3 mL), and tert-butyl (2S)-2-hydroxypropanoate (80 mg, 0.55 mmol) was added. The reaction was cooled to 0° C. and DIAD (79 µl, 0.40 mmol) was added dropwise in dry THF (1 mL). The reaction was then stirred at rt for 2 h. The mixture was diluted with EtOAc and washed with a sat. NaHCO$_3$ solution, a sat. NH$_4$Cl solution, and water. The organic layer was dried over MgSO$_4$, filtered and evaporated in vacuo. The crude product was purified by flash chromatography on silica gel using a gradient of EtOAc in cHex to yield the desired product 1Q (33 mg, 28%) as a colorless glue.

$^1$H NMR (400 MHz, CDCl$_3$) δ 7.76 (d, 1H), 6.92 (dd, 1H), 6.75 (d, 1H), 6.44 (s, 1H), 4.69 (q, 1H), 1.64 (d, 3H), 1.46 (s, 9H).

MS (ES) C$_{16}$H$_{17}$ClO$_5$ requires: 324/326, found: 325/327 (M+H)$^+$, 95%

Intermediate (R)-16D—Synthesis According to Method 3d (M3d) (R)tert-butyl 2-((4-(4-methylthiophen-3-yl)-2-oxo-2H-chromen-7-yl)oxy)propanoate ((R)-16D)

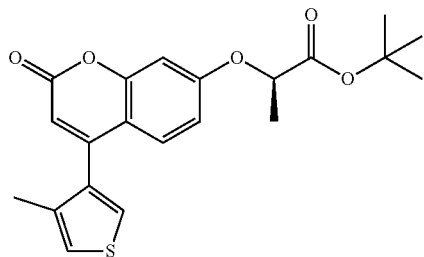 [SMILES: Cc1cscc1-c1cc(=O)oc2cc(O[C@H](C)C(=O)OC(C)(C)C)ccc12]

Intermediate 1C$^1$ (31 mg, 0.095 mmol), 4-methyl-3-thiopheneboronic acid (18 mg, 0.123 mmol), Pd(PPh$_3$)$_3$ (4.4 mg, 0.004 mmol), and K$_2$OC$_3$ (26 mg, 0.191 mmol) were put in a 4 mL microwave vial, the vial was conditioned with 3 cycles vacuum/N$_2$, then a 2:1 mixture of DME:H$_2$O (2 mL) was added and the reaction was heated to 100° C. and stirred for 2 h. The mixture was diluted with EtOAc and washed with water and brine. The organic layer was dried over MgSO$_4$, filtered over celite, and the filtrate evaporated in vacuo. The crude was purified by column chromatography using a gradient of EtOAc in cHex to yield the desired product (R)-16D (30 mg, 81%) as a white solid.

$^1$H NMR (400 MHz, DMSO-d$_6$) δ 7.69 (dt, 1H), 7.43 (ddt, 1H), 7.16 (d, 1H), 6.95 (d, 1H), 6.89 (ddd, 1H), 6.21 (d, 1H), 5.01 (q, 1H), 2.07 (dt, 3H), 1.52 (dd, 3H), 1.40 (d, 9H).

MS (ES) C$_{21}$H$_{22}$O$_5$S requires: 386, found: 387 (M+H)$^+$, 100%

3.1.5 Preparation of Intermediate Compounds of Formula (E)

Intermediate 1E—Synthesis According to Method 6a (M6a) 2-((4-(2-chloro-4-fluorophenyl)-2-oxo-2H-chromen-7-yl)oxy)propanoic acid (1E -99)

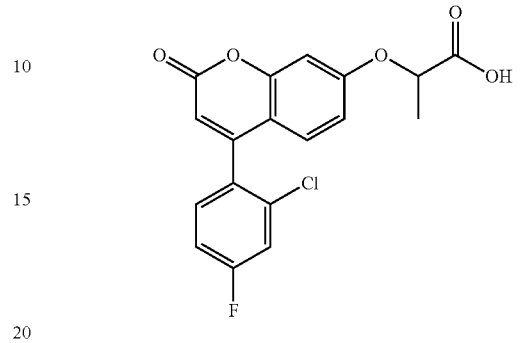

Intermediate 1D (3 g, 7.67 mmol) was dissolved in THF (53 mL) and 0.5 M NaOH aq. solution (32 mL) was added. The reaction was stirred at rt for 3 h, upon which further 0.5 M NaOH aq. solution (7 mL) was added and the reaction stirred for 3 h 30 min. The mixture was extracted with EtOAc, then the aqueous phase was acidified with 10% aq. HCl to pH2 and extracted with DCM. The combined DCM layers were dried over MgSO$_4$, filtered, and evaporated in vacuo to yield the desired product 1E (2.8 g, 100%) as a white solid.

$^1$H NMR (300 MHz, CDCl$_3$) δ 7.27-7.19 (m, 2H), 7.08 (td, 1H), 7.93 (d, 1H), 6.82-6.69 (m, 2H), 6.15 (s, 1H), 4.80 (q, 1H), 1.66 (d, 3H).

MS (ES) C$_{18}$H$_{12}$ClFO$_5$ requires: 362/364, found: 363/365 (M+H)$^+$, 98%

Intermediate 14E—Synthesis According to Method 6c (M6c) 2-((4-(2-chloro-4-fluorophenyl)-2-oxo-2H-pyrano[2,3-b]pyridin-7-yl)oxy)propanoic acid (14E)

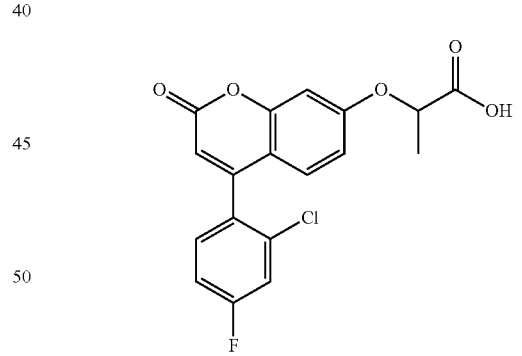

Intermediate 14D (200 mg, 0.5 mmol) was dissolved in a 4:1 DCM:TFA solution (5 ml) and the reaction was stirred at rt for 2 h. The solvents were evaporated in vacuo to yield the desired product 14E (213 mg, 93%) as a brown foam (TFA salt).

$^1$H NMR (400 MHz, DMSO-d$_6$) δ 7.69 (ddd, 1H), 7.55 (td, 1H), 7.43 (tt, 2H), 6.87 (d, 1H), 6.43 (d, 1H), 5.25 (qd, 1H), 1.53 (d, 3H).

MS (ES) C$_{17}$H$_{11}$ClFNO$_5$ requires: 365/367, found: 364/366 (M–H)$^+$, 94%

The ethyl esters and carboxylic acids intermediates shown in Table 2 were synthesized in a similar manner as for intermediates 1D, (R)-1D, 1E, 14E or (R)-16D.

TABLE 2

Ethyl esters and carboxylic acids intermediates

| Intermediates | Structure | (M + H)+, purity |
|---|---|---|
| (R)-1E | 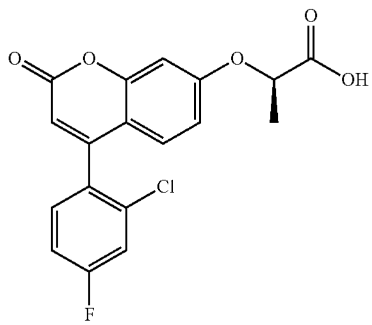 [SMILES: C[C@@H](Oc1ccc2c(-c3ccc(F)cc3Cl)cc(=O)oc2c1)C(=O)O] | (R)-1E: MS (ES) $C_{18}H_{12}ClFO_5$ requires: 362/364, found 363/365 (M + H)+, 100% |
| 2D | 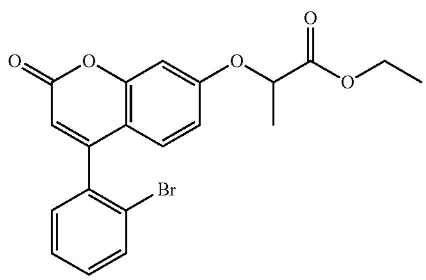 [SMILES: CCOC(=O)C(C)Oc1ccc2c(-c3ccccc3Br)cc(=O)oc2c1] | 2D: MS (ES) $C_{20}H_{17}BrO_5$ requires: 416/418, found 417/419 (M + H)+, 97% |
| 3D: $R_5$ = Et<br>3E: $R_5$ = H | 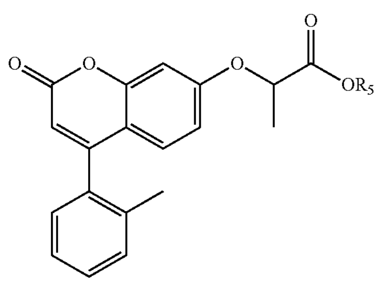 | 3D: MS (ES) $C_{21}H_{20}O_5$ requires: 352, found 353(M + H)+, 100%<br>3E: MS (ES) $C_{19}H_{16}O_5$ requires: 324, found 325 (M+ H)+, 98% |
| (R)-3D: $R_5$ = Et<br>(R)-3E: $R_5$ = H | 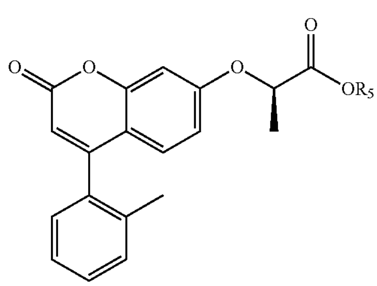 | (R)-3D: MS (ES) $C_{21}H_{20}O_5$ requires: 352, found 353 (M + H)+, 99%<br>(R)-3E: MS (ES) $C_{19}H_{16}O_5$ requires: 324, found 325 (M + H)+, 100% |
| 4D: $R_5$ = Et<br>4E: $R_5$ = H | 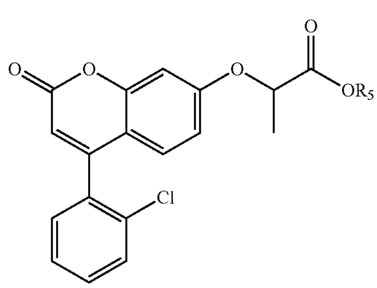 | 4D: MS (ES) $C_{20}H_{17}ClO_5$ requires: 372/374 found 373/375 (M + H)+, 96%<br>4E: MS (ES) $C_{18}H_{13}ClO_5$ requires: 344/346, found 345/347 (M + H)+, 98% |

TABLE 2-continued

Ethyl esters and carboxylic acids intermediates

| Intermediates | Structure | (M + H)+, purity |
|---|---|---|
| (R)-4D: R$_5$ = Et<br>(R)-4E: R$_5$ = H | 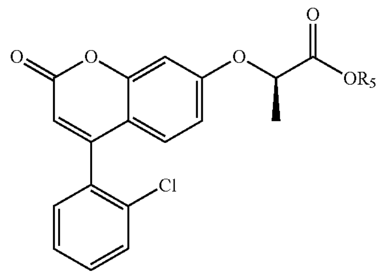 | (R)-4D: MS (ES)<br>C$_{20}$H$_{17}$ClO$_5$ requires: 372/374<br>found 373/374 (M + H)+, 99%,<br>100%ee<br>(R)-4E: MS (ES)<br>C$_{18}$H$_{13}$ClO$_5$ requires: 344/346,<br>found 345/347 (M + H)+, 96% |
| 5D: R$_5$ = Et<br>5E: R$_5$ = H | 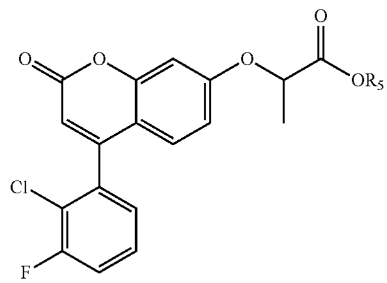 | 5D: MS (ES) C$_{20}$H$_{16}$ClFO$_5$ requires: 390/392 found 391/393<br>(M + H)+, 99%<br>5E: MS (ES) C$_{18}$H$_{12}$ClFO$_5$ requires: 362/364 found 363/365<br>(M + H)+, 99% |
| 6D R$_5$ = Et<br>6E R$_5$ = H | 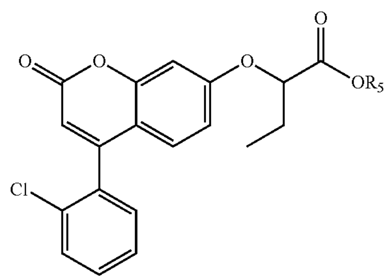 | 6D: MS (ES) C$_{21}$H$_{19}$ClO$_5$ requires:<br>386/389 found 387/390 (M + H)+,<br>99%<br>6E: MS (ES) C$_{21}$H$_{19}$ClO$_5$ requires:<br>358/360 found 359/361 (M + H)+,<br>99% |
| 7D R$_5$ = Et<br>7E R$_5$ = H | 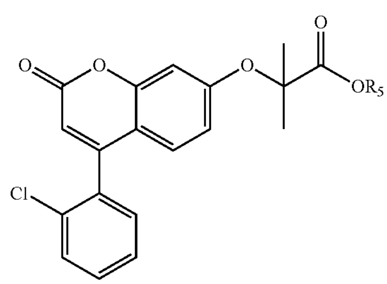 | 7D: MS (ES) C$_{21}$H$_{19}$ClO$_5$ requires:<br>386/389 found 387/390 (M + H)+,<br>100%<br>7E: MS (ES) C$_{19}$H$_{15}$ClO$_5$ requires:<br>358/360 found 359/361 (M + H)+,<br>100% |
| 8D R$_5$ = Et<br>8E R$_5$ = H | 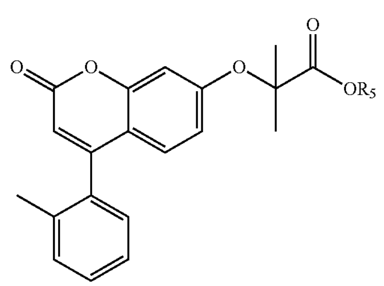 | 8D: MS (ES) C$_{21}$H$_{19}$ClO$_5$ requires:<br>386/389 found 387/390 (M + H)+,<br>99%<br>8E: MS (ES) C$_{21}$H$_{19}$ClO$_5$ requires:<br>358/360 found 359/361 (M + H)+,<br>99% |

TABLE 2-continued

| Ethyl esters and carboxylic acids intermediates | | |
|---|---|---|
| Intermediates | Structure | (M + H)+, purity |
| (R)-13D R₅ = Et<br>(R)-13E R₅ = H | | 13D: MS (ES) C19H18O5S requires: 358 found 359 (M + H)+, 98%<br>13E: MS (ES) C17H14O5S requires: 330 found 331 (M + H)+, 96% |
| 14D: R₅ = tBu<br>14E: R₅ = H | | 14D: MS (ES) C21H19ClFNO5 requires: 419/421, found 420/422 (M + H)+, 97%<br>14E: see description |
| 15D: R₅ = tBu<br>15E: R₅ = H | | 14D: MS (ES) C21H20ClNO5 requires: 401/403, found 402/404 (M + H)+, 93%<br>14E: MS (ES) C17H12ClNO5 requires: 345/347, found 346/348 (M + H)+, 96% |
| (R)-16D R₅ = tBu<br>(R)-16E R₅ = H | | 16D: MS (ES) C21H22O5S requires: 386 found 387 (M + H)+, 100%<br>16E: MS (ES) C17H14O5S requires: 330 found 331 (M + H)+, 98% |
| 17D R₅ = tBu<br>17E R₅ = H | | 17D: MS (ES) C21H22O5S requires: 386 found 387 (M + H)+, 100%<br>17E: MS (ES) C17H14O5S requires: 330 found 331 (M + H)+, 98% |

3.1.6 Preparation of Intermediate Compounds of Formula (G)
Intermediate 1G—Synthesis According to Method 7a (M7a) (3S)-ethyl 1-(2-((4-(2-chloro-4-fluorophenyl)-2-oxo-2H-chromen-7-yl)oxy)propanoyl)piperidine-3-carboxylate (1G)

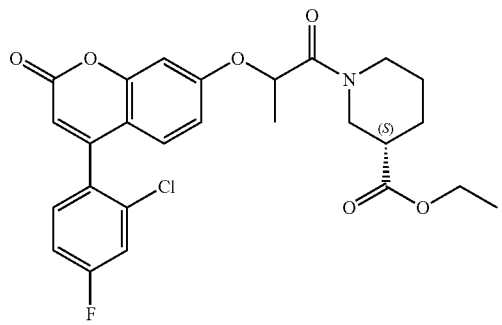

Intermediate 1E (1.37 g, 3.78 mmol), EDC.HCl (1.09 g, 5.67 mmol), and HOBt.xH$_2$O (765 mg, 5.67 mmol) were dissolved in DMF (57 mL) and (S)-piperidine-3-carboxylic acid ethyl ester; (2R,3R)-2,3-dihydroxybutanedioate (1:1) (3.48 g, 11.33 mmol) was added slowly. Et$_3$N (1.6 mL, 11.33 mmol) was added, and the mixture was stirred at 40° C. for 2 h 30 min. The reaction was diluted with EtOAc and washed with water, a sat. NaHCO$_3$ solution, a sat. NH$_4$Cl solution, and again with water. The organic phase was dried over MgSO$_4$, filtered and evaporated in vacuo. The crude product was purified by flash chromatography on silica gel using a gradient of EtOAc in cHex to yield the desired product 1G (806 mg, 42%) as a colorless glue.

$^1$H NMR (400 MHz, DMSO-d$_6$) δ 7.73-7.67 (m, 1H), 7.58-7.51 (m, 1H), 7.49-7.38 (m, 1H), 7.08-6.73 (m, 3H), 6.31 (s, 1H), 5.63-5.35 (m, 1H), 4.26-3.89 (m, 3H), 3.88-3.53 (m, 1H), 3.28-2.91 (m, 1H), 2.50-2.30 (m, 1H), 2.08-1.83 (m, 1H), 1.83-1.00 (m, 10H).

MS (ES) C$_{26}$H$_{25}$ClFNO$_6$ requires: 501/503, found: 502/504 (M+H)$^+$, 100%

3.1.6.1 Preparation of Intermediate Compound(S,S)-1L for the Direct Synthesis of Intermediates of Formula (G)
Intermediate (S,S)-1L—Synthesis According to Method 7c (M7c) (S)-ethyl 1-((S)-2-hydroxypropanoyl)piperidine-3-carboxylate ((S,S)-1L)

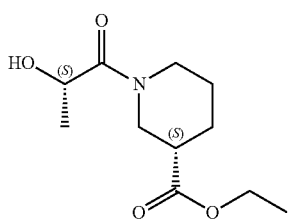

L-(+)-Lactic acid (10 g, 111 mmol) and (S)-(+)—Nipecotic acid ethyl ester (17.5 g, 111 mmol) were dissolved in dry DMF (15 mL), and the flask was conditioned with 3 cycles of vacuum/N$_2$. Dry DIPEA (14.35 g, 19.3 mL) was added, followed by HATU (50.6 g, 133 mmol) portionwise (exothermic reaction). The reaction was stirred overnight at rt. The reaction mixture was poured into water (500 mL) and extracted with EtOAc. The combined organic layers were washed with water and brine. The organic layer was dried over MgSO$_4$, and evaporated in vacuo. The crude compound was purified by flash chromatography using a gradient of MeOH in DCM to yield the desired product (S,S)-1 L (12.7 g, 50% as an off-white solid.

$^1$H-NMR (300 MHz, CDCl$_3$) δ 4.59-4.40 (m, 2H), 4.20-4.09 (m, 2H), 3.84-3.62 (m, 2H), 3.15-2.70 (m, 2H), 2.50-2.40 (m, 1H), 2.21-2.08 (m, 1H), 1.80-1.51 (m, 3H), 1.32-1.25 (m, 6H). GC-MS C$_{11}$H$_{19}$NO$_4$ requires: 229, found: 229 (M$^+$), 93%.

3.1.7 Preparation of Intermediate Compounds of Formula (M)
Intermediate 1 M—Synthesis According to Method 7b (M7b) (R)-tert-butyl 4-(2-((4-(2-chloro-4-fluorophenyl)-2-oxo-2H-chromen-7-yl)oxy)propanoyl)piperazine-1-carboxylate (1 M)

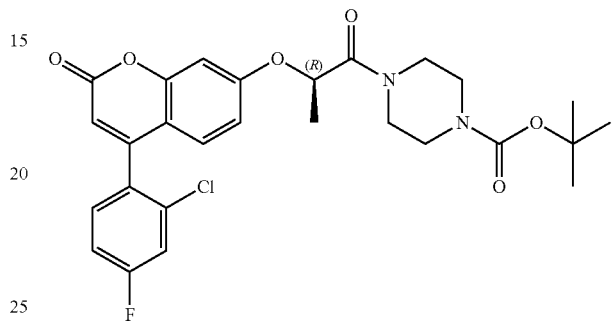

Intermediate (R)-1E (150.0 mg, 0.414 mmol), tert-butyl piperazine-1-carboxylate (154.0 mg, 0.827 mmol), and DIPEA (141 μL, 0.827 mmol) were dissolved in dry DMF (2 mL) and HATU (235.8 mg, 0.620 mmol) was added at ambient temperature. The resulting reaction mixture was stirred overnight. The reaction was then diluted with EtOAc and washed with water, a sat. NaHCO$_3$ solution and brine. The organic phase was dried over MgSO$_4$, filtered and evaporated in vacuo. The crude product was purified by flash chromatography on silica gel using a gradient of EtOAc in cHex to yield the desired product 1 M after lyophilization (171.8 mg, 78%) as a white fluffy solid.

$^1$H NMR (400 MHz, DMSO-d$_6$) δ 7.73-7.67 (m, 1H), 7.58-7.53 (m, 1H), 7.46-7.40 (m, 1H), 6.98-6.94 (m, 2H), 6.85-6.78 (m, 1H), 6.31 (s, 1H), 5.51-5.40 (m, 1H), 3.68-3.57 (m, 1H), 3.56-3.45 (m, 2H), 3.43-3.20 (m, 5H), 1.46 (d, 3H), 1.41 (s, 9H).

MS (ES) C$_{27}$H$_{28}$ClFN$_2$O$_6$ requires: 530/532, found: 531/533 (M+H)$^+$, 100%

3.1.8 Preparation of Intermediate Compounds of Formula (N)
Intermediate 1N—Synthesis According to Method 6c (M6c) (R)-4-(2-chloro-4-fluorophenyl)-7-((1-oxo-1-(piperazin-1-yl)propan-2-yl)oxy)-2H-chromen-2-one TFA salt (1N)

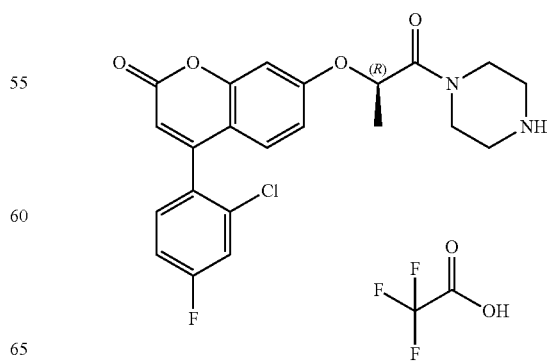

Intermediate 1 M (162.5 mg, 0.306 mmol) was reacted according to method 6c to yield the desired product 1N after lyophilization (162.5 mg, 97%) as a white fluffy solid after.

$^1$H NMR (400 MHz, DMSO-$d_6$) δ 8.96 (br. s, 2H), 7.73-7.67 (m, 1H), 7.59-7.52 (m, 1H), 7.47-7.40 (m, 1H), 7.02 (d, 1H), 6.95 (d, 1H), 6.88-6.81 (m, 1H), 6.33 (s, 1H), 5.54-5.44 (m, 1H), 3.89-3.58 (m, 4H), 3.25-3.04 (m, 4H), 1.47 (d, 3H).

MS (ES) $C_{22}H_{20}ClFN_2O_4$ requires: 430/432, found: 431/433 (M+H)$^+$, 100%

3.2. Preparation of Compounds of Formula (I) of the Invention

Compound 47—Synthesis According to Method 6b (M6b) (3S)-1-(2-((4-(2-chloro-4-fluorophenyl)-2-oxo-2H-chromen-7-yl)oxy)propanoyl)piperidine-3-carboxylic acid (47)

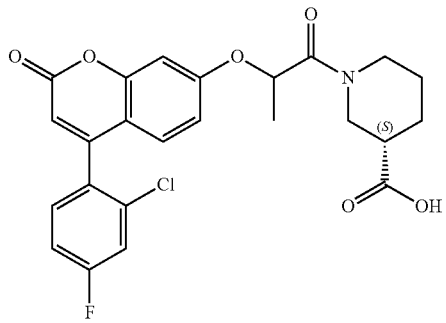

Intermediate 1G (805 mg, 1.60 mmol) was dissolved in THF (24 mL) and 2 M NaOH aq. solution (12 mL) was added. A few drops of MeOH were added until the mixture was homogeneous. The reaction was stirred at rt for 1 h, neutralized with 2 M HCl, and stirred for a further 30 min. The mixture was extracted with EtOAc and the combined organic phases were washed with water, dried over MgSO$_4$, filtered and evaporated in vacuo. The crude product was purified by flash chromatography on silica gel using a gradient of MeOH in DCM to yield the desired product 47 (726 mg, 95%) as a white solid.

$^1$H NMR (400 MHz, DMSO-$d_6$) δ 12.41 (1H, m), 7.68 (dd, 1H), 7.58-7.51 (m, 1H), 7.42 (td, 1H), 6.99-6.87 (m, 2H), 6.87-6.74(m, 1H), 6.29 (s, 1H), 5.55-5.36 (m, 1H), 4.34-3.90 (m, 1H), 3.89-3.46 (m, 1H), 3.23-3.06 (m, 1H), 2.92-2.70 (m, 1H), 2.33-2.19 (m, 1H), 2.04-1.84 (m, 1H), 1.81-1.67 (m, 1H), 1.66-1.48 (m, 1H), 1.47-1.39 (m, 3H), 1.39-1.26 (m, 1H).

MS (ES) $C_{24}H_{21}ClFNO_6$ requires: 473/475, found: 474/476 (M+H)$^+$, 100%

The tetrazole derivatives 39 and 42 described in Table 3 were synthesized from the corresponding nitriles according to Method 8:

Compound 42—Synthesis According to Method 8 (M8) 7-((1-(3-(2H-tetrazol-5-yl)piperidin-1-yl)-1-oxopropan-2-yl)oxy)-4-(o-tolyl)-2H-chromen-2-one (42)

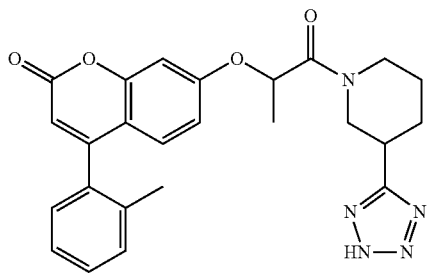 [SMILES: Cc1ccccc1-c1cc(=O)oc2cc(OC(C)C(=O)N3CCCC(c4nn[nH]n4)C3)ccc12]

Compound 41 (26 mg, 0.063 mmol) was dissolved in o-dichlorobenzene (600 µl) and Bu$_3$SnN$_3$ was added in a sealed tube. The reaction was stirred at 125° C. for 1 h 30 min. The mixture was allowed to cool to rt, filtered through a plug of silica and washed with DCM (40 mL) and 20% MeOH in DCM (400 mL). The latest fraction was evaporated in vacuo, resuspended in EtOAc, and extracted with a 20:1 sat. NaHCO$_3$/1 M NaOH solution. The combined aq. phases were re-acidified to pH 1 and extracted with EtOAc. The combined organic phases were dried over MgSO$_4$, filtered, and evaporated in vacuo. The crude product was purified by flash chromatography on silica gel using a gradient of MeOH in EtOAc to yield the desired product 42 (12 mg, 42%) as an off-white solid.

$^1$H NMR (400 MHz, DMSO-$d_6$) δ 7.45-7.29 (m, 3H), 7.26-7.19 (m, 1H), 6.98-6.70 (m, 3H), 6.17 (s, 1H), 5.55-5.38 (m, 1H), 4.52-3.87 (m, 2H), 3.65-2.92 (m, 2H), 2.23-2.05 (m, 4H), 1.91-1.60 (m, 3H), 1.55-1.38 (m, 4H).

MS (ES) $C_{25}H_{25}N_6O_4$ requires: 459, found: 460 (M+H)$^+$, 99%

The isopropylic ester 55 was synthesized from precursor (R)-3E as described below:

Compound 55—Synthesis According to Method 9 (M9) (R)-isopropyl 2-((2-oxo-4-(o-tolyl)-2H-chromen-7-yl)oxy)propanoate (55)

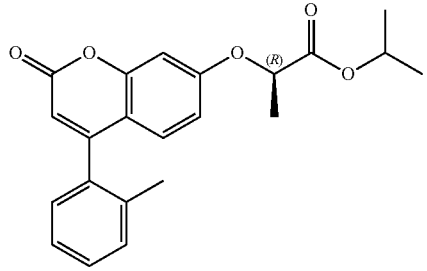

Intermediate (R)-3E (10 mg, 0.031 mmol) was dissolved in 5 M HCl in isopropanol (2 mL) and the mixture was stirred at rt overnight. The reaction mixture was diluted with EtOAc and washed with water, a 1:1 sat. NaHCO$_3$/H$_2$O solution, and again with water. The combined organic phases were dried over MgSO$_4$, filtered, and evaporated in vacuo. The crude product was purified by flash chromatography on silica gel using a gradient of EtOAc in cHex to yield the desired product 55 (9.4 mg, 83%) as a colorless glue.

$^1$H NMR (400 MHz, CDCl$_3$) δ 7.41-7.36 (m, 1H), 7.34-7.27 (m, 2H), 7.16 (d, 1H), 6.95 (d, 1H), 6.80 (d, 1H), 6.74 (dt, 1H), 6.16 (s, 1H), 5.08 (sept, 1H), 4.75 (q, 1H), 2.15 (s, 3H), 1.64 (d, 3H), 1.30 (dd, 3H), 1.22 (dd, 3H).

MS (ES) $C_{22}H_{22}O_5$ requires: 366, found: 367 (M+H)$^+$, 95%

Compound 125—Synthesis According to Method 10 (M10) 2-morpholinoethyl 2-((R)-4((R)-2-((4-(2-chloro-4-fluorophenyl)-2-oxo-2H-chromen-7-yl)oxy)propanoyl)piperidin-3-yl)acetate (125)

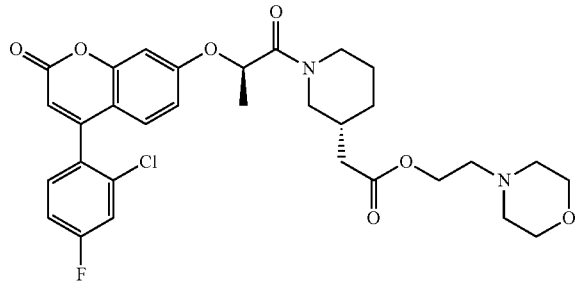 [SMILES: C[C@@H](Oc1ccc2c(-c3ccc(F)cc3Cl)cc(=O)oc2c1)C(=O)N1CCC[C@H](CC(=O)OCCN2CCOCC2)C1]

Compound 106 (40 mg, 0.082 mmol) was dissolved in DMF (0.8 mL) and EDC·HCl (24 mg, 0.123 mmol), DMAP (1 mg, 0.008 mmol) and 4-(2—Hydroxyethyl)morpholine (54 mg, 0.410 mmol) were added. The mixture was stirred at rt for 4 h. The reaction mixture was diluted with EtOAc and washed with sat. NaHCO₃ solution followed by water. The organic phases were dried over MgSO₄, filtered, and evaporated in vacuo. The crude was purified by flash chromatography on silica gel using a gradient of MeOH in DCM to yield the desired product 125 (37 mg, 75%) as a white powder.

$^1$H NMR (400 MHz, DMSO-$d_6$) δ 7.70 (dd, 1H), 7.59-7.52 (m, 1H), 7.46-7.40 (m, 1H), 6.98-6.89 (m, 2H), 6.85-6.79 (m, 1H), 6.31 (s, 1H), 5.51-5.35 (m, 1H), 4.20-4.05 (m, 3H), 3.99-3.77 (m, 1H), 3.57-3.44 (m, 4H), 3.15-3.04 (m, 1H), 2.99-2.88 (m, 1H), 2.71-2.53 (m, 1H), 2.42-2.13 (m, 6H), 1.88-1.71 (m, 2H), 1.71-1.58 (m, 1H), 1.55-1.40 (m, 4H), 1.33-1.19 (m, 2H).

MS (ES) $C_{31}H_{34}ClFN_2O_7$ requires: 600/601, found: 601/602 (M+H)⁺, 98%

Compound 121—Synthesis According to Method 11 (M11) (S)-((isopropoxycarbonyl)oxy)methyl 1-((R)-2-((4-(2-chloro-4-fluorophenyl)-2-oxo-2H-chromen-7-yl)oxy)propanoyl)piperidine-3-carboxylate (121)

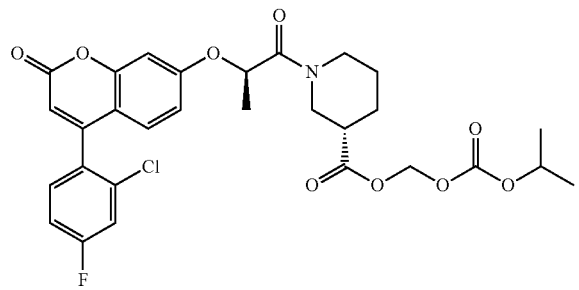 [SMILES: CC(C)OC(=O)OCOC(=O)[C@H]1CCCN(C(=O)[C@@H](C)Oc2ccc3c(-c4ccc(F)cc4Cl)cc(=O)oc3c2)C1]

Compound 14 (50 mg, 0.106 mmol) was dissolved in DMF (1 mL) and chloromethyl propan 2-yl carbonate (24 mg, 0.158 mmol) and K₂CO₃ (22 mg, 0.158 mmol) were added. The mixture was stirred at 50° C. for 30 min. The reaction mixture was diluted with EtOAc and washed with water. The combined organic phases were dried over MgSO₄, filtered, and evaporated in vacuo. The crude was purified by flash chromatography on silica gel using a gradient of EtOAc in cHex to yield the desired product 121 (58 mg, 93%) as a white powder.

$^1$H NMR (400 MHz, DMSO-$d_6$) δ 7.70 (dd, 1H), 7.59-7.52 (m, 1H), 7.46-7.40 (m, 1H), 7.01-6.90 (m, 2H), 6.87-6.75 (m, 1H), 6.31 (s, 1H), 5.82-5.64 (m, 2H), 5.52-5.42 (m, 1H), 4.84-4.73 (m, 1H), 4.20-3.50 (m, 2H), 3.28-3.02 (m, 2H), 2.72-2.53 (m, 1H), 2.02-1.88 (m, 1H), 1.82-1.36 (m, 6H), 1.28-1.20 (m, 6H).

MS (ES) $C_{29}H_{29}ClFNO_9$ requires: 589/591, found: 590/592 (M+H)⁺, 99%

Compound 166—Synthesis According to Method 12 (M12) (R)-4-(2-chloro-4-fluorophenyl)-7-((1-(4-(2-chloroacetyl)piperazin-1-yl)-1-oxopropan-2-yl)oxy)-2H-chromen-2-one (166)

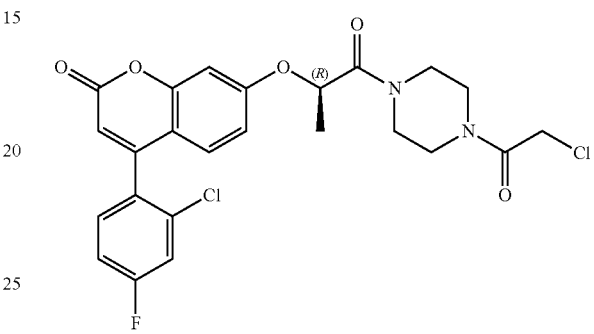

To an ice-cold solution of chloroacetyl chloride (6.4 μL, 80.8 μmol) in dry DCM (1 mL) was added dropwise a solution of intermediate 1N (40.0 mg, 73.4 μmol) and Et₃N (24.4 μL, 176.2 μmol) in dry DCM (1 mL). The resulting mixture was stirred at 0° C. for 30 min followed by 1 h at rt. The reaction was then diluted with EtOAc and washed with water, a sat. NaHCO₃ solution and brine. The organic phase was dried over MgSO₄, filtered and evaporated in vacuo. The crude product was purified by flash chromatography on silica gel using a gradient of EtOAc in cHex to yield the desired product 166 after lyophilization (25.5 mg, 68%) as a white fluffy solid.

$^1$H NMR (400 MHz, CDCl₃) δ 7.32-7.26 (m, 2H), 7.18-7.12 (m, 1H), 7.02-6.96 (m, 1H), 6.89-6.83 (m, 1H), 6.82-6.76 (m, 1H), 6.22 (s, 1H), 5.04 (q, 1H), 4.06 (s, 2H), 3.84-3.29 (m, 8H), 1.67 (d, 3H).

MS (ES) $C_{24}H_{21}Cl_2FN_2O_5$ requires: 506/508, found: 507/509 (M+H)⁺, 100%

The compounds exemplifying the invention are described in Table 3.

When not otherwise specified, it should be assumed that method 7a, 7b or 7c, optionally followed by methods 6a, 6b, 6c or 8, were used to yield the target compound. Compounds 44 and 45 were synthesized in a similar manner as for intermediate (R)-1D (method 5), except for the use of PBu₃ instead of PPh₃. Occasionally, a variation of method 7b was used, in which the coupling agent HBTU was used instead of HATU. This procedure was used, for instance, to obtain compounds 129, 130, and 139, as well as the precursors (formulas M) of compounds 135/138 and 136/150. When the piperidine ring carries an ester moiety (compounds J), the ester can sometimes be synthesized from carboxylic acid precursor H according to methods 9, 10 or 11. Piperazines or piperidine-amines carbamates M could also be further modified according to method 6c to obtain amines N followed by methods 7a, 7b, 7c or 12 to yield amides of formula P. It should be apparent to a person skilled in the art that reaction conditions such as temperature, dilution, reaction time or work-up procedures, including pH adjustment, are dependent on reaction partners and functional group compatibility and could vary from compound to compound.

Generally, enantiomeric excess (ee) of intermediates (esters (D) and (G), acids (H)) was not measured, and was assumed equal to the value determined by chiral HPLC for the final compounds (amides (F), acids (H) or esters (J)). Chiral separation of the diastereomeric mixture was occasionally required to improve ee, particularly when any of the hydroxy-coumarins was alkylated via method 4.

TABLE 3

Compounds of formula (I) of the invention

| Ex | Structure | BB | $^1$H-NMR | LC purity %ee |
|---|---|---|---|---|
| 1 | 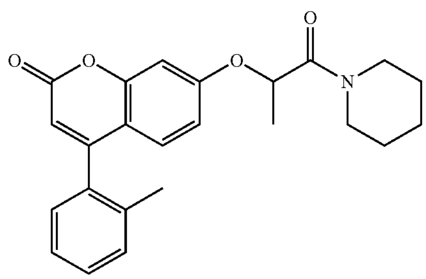 [SMILES: Cc1ccccc1-c1cc(=O)oc2cc(OC(C)C(=O)N3CCCCC3)ccc12] | 3E | (400 MHz, DMSO-d$_6$) δ 7.44-7.36 (m, 2H), 7.36-7.30 (m, 1H), 7.24-7.20 (m, 1H), 6.92-6.88 (m, 1H), 6.88-6.84 (m, 1H), 6.81-6.76 (m, 1H), 6.17 (s, 1H), 5.42 (quint, 1H), 3.61-3.32 (m, 4H), 2.10 (s, 3H), 1.66-1.51 (m, 3H), 1.51-1.34 (m, 6H). | 90% |
| 2 | 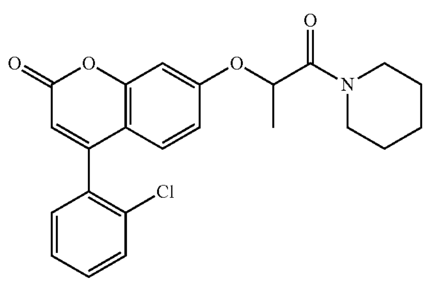 [SMILES: CC(Oc1ccc2c(-c3ccccc3Cl)cc(=O)oc2c1)C(=O)N1CCCCC1] | 4E | (400 MHz, DMSO-d$_6$) δ 7.65 (dd, 1H), 7.59-7.45 (m, 3H), 6.92-6.87 (m, 2H), 6.83-6.78 (m, 1H), 6.28 (s, 1H), 5.43 (quint, 1H), 3.61-3.26 (m, 4H), 1.46-1.51 (m, 3H), 1.50-1.33 (m, 6H). | 90% |
| 3 | 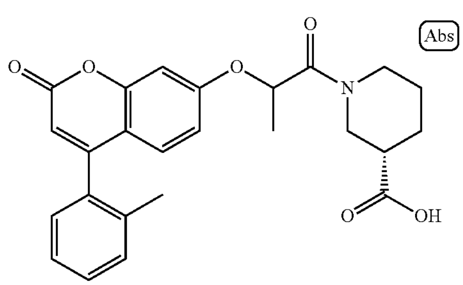 [SMILES: Cc1ccccc1-c1cc(=O)oc2cc(OC(C)C(=O)N3CCC[C@H](C(=O)O)C3)ccc12] | 3E, 17 | (400 MHz, DMSO-d$_6$) δ 12.42 (br. s, 1H), 7.46-7.36 (m, 2H), 7.36-7.30 (m, 1H), 7.26-7.20 (m, 1H), 6.98-6.75 (m, 3H), 6.17 (s, 1H), 5.55-5.35 (m, 1H), 4.33-3.88 (m, 1H), 3.88-3.47 (m, 1H), 3.29-2.70 (m, 2H), 2.33-2.20 (m, 1H), 2.10 (s, 3H), 2.03-1.48 (m, 4H), 1.48-1.38 (m, 3H). | 97% |
| 4 | 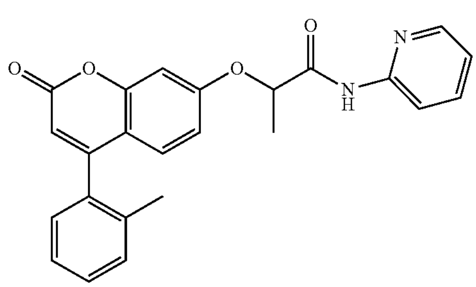 [SMILES: Cc1ccccc1-c1cc(=O)oc2cc(OC(C)C(=O)Nc3ccccn3)ccc12] | 3E | (400 MHz, DMSO-d$_6$) δ 10.80 (d, 1H), 8.35-8.32 (m, 1H), 8.00 (d, 1H), 7.77 (td, 1H), 7.43-7.28 (m, 3H), 7.20 (d, 1H), 7.15-7.11 (m, 1H), 7.04-7.00 (m, 1H), 6.91-6.84 (m, 2H), 6.17 (s, 1H), 5.20 (q, 1H), 2.09 (s, 3H), 1.57 (d, 3H). | 95% |

TABLE 3-continued

Compounds of formula (I) of the invention

| Ex | Structure | BB | ¹H-NMR | LC purity %ee |
|----|-----------|----|--------|---------------|
| 5 | 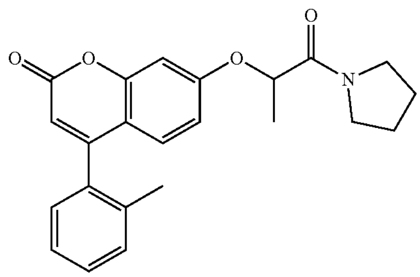 [SMILES: Cc1ccccc1-c1cc(=O)oc2cc(OC(C)C(=O)N3CCCC3)ccc12] | 3E | (400 MHz, DMSO-d$_6$) δ 7.45-7.36 (m, 2H), 7.36-7.30 (m, 1H), 7.24-7.20 (m, 1H), 6.92-6.89 (m, 1H), 6.89-6.84 (m, 1H), 6.81-6.75 (m, 1H), 6.17 (s, 1H), 5.16 (q, 1H), 3.45-3.21 (m, 4H), 2.10 (s, 3H), 1.99-1.82 (m, 2H), 1.82-1.68 (m, 2H), 1.43 (d, 3H). | 95% |
| 6 | 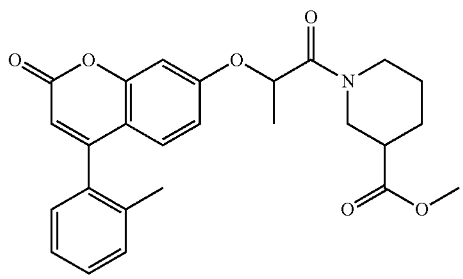 [SMILES: COC(=O)C1CCCN(C(=O)C(C)Oc2ccc3c(-c4ccccc4C)cc(=O)oc3c2)C1] | 3E | (400 MHz, DMSO-d$_6$) δ 7.46-7.38 (m, 2H), 7.38-7.32 (m, 1H), 7.26-7.21 (m, 1H), 7.01-6.75 (m, 3H), 6.21-6.16 (m, 1H), 5.54-5.37 (m, 1H), 4.25-3.93 (m, 1H), 3.88-3.61 (m, 1H), 3.70-3.54 (m, 3H), 3.27-2.75 (m, 2H), 2.65-2.39 (m, 1H), 2.11 (s, 3H), 2.05-1.87 (m, 1H), 1.85-1.59 (m, 2H), 1.58-1.32 (m, 1H), 1.48-1.41 (m, 3H). | 90% |
| 7 | 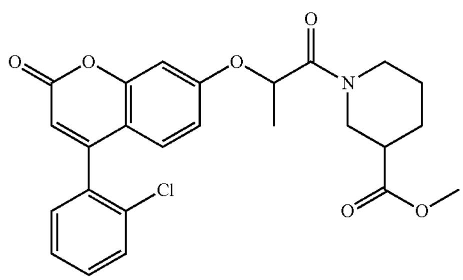 [SMILES: COC(=O)C1CCCN(C(=O)C(C)Oc2ccc3c(-c4ccccc4Cl)cc(=O)oc3c2)C1] | 4E | (400 MHz, DMSO-d$_6$) δ 7.66 (d, 1H), 7.60-7.49 (m, 2H), 7.49-7.43 (m, 1H), 7.02-6.75 (m, 3H), 6.28 (s, 1H), 5.54-5.37 (m, 1H), 4.23-3.70 (m, 1H), 3.70-3.52 (m, 4H), 3.33-2.56 (m, 2H), 2.45-2.36 (m, 1H), 2.03-1.85 (m, 1H), 1.85-1.48 (m, 2H), 1.48-1.29 (m, 4H). | 90% |
| 8 | 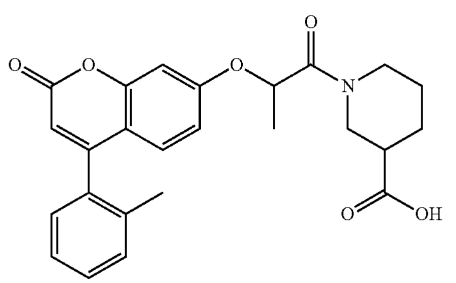 | 3E, 6 | (400 MHz, DMSO-d$_6$) δ 12.42 (br. s, 1H), 7.45-7.30 (m, 3H), 7.25-7.19 (m, 1H), 6.97-6.77 (m, 3H), 6.17 (s, 1H), 5.54-5.35 (m, 1H), 4.33-3.04 (m, 3H), 2.90-2.09 (m, 2H), 2.10 (s, 3H), 2.03-1.82 (m, 1H), 1.82-1.48 (m, 2H), 1.48-1.38 (m, 4H). | 93% |
| 9 | 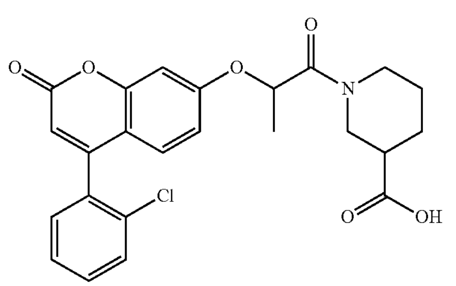 | 4E, 7 | (400 MHz, DMSO-d$_6$) δ 12.43 (br. s, 1H), 7.66 (d, 1H), 7.60-7.43 (m, 3H), 6.99-6.75 (m, 3H), 6.28 (s, 1H), 5.55-5.37 (m, 1H), 4.35-3.06 (m, 3H), 2.90-2.19 (m, 1H), 2.04-1.83 (m, 1H), 1.79-1.67 (m, 1H), 1.67-1.39 (m, 6H). | 93% |

TABLE 3-continued

Compounds of formula (I) of the invention

| Ex | Structure | BB | ¹H-NMR | LC purity %ee |
|---|---|---|---|---|
| 10 | 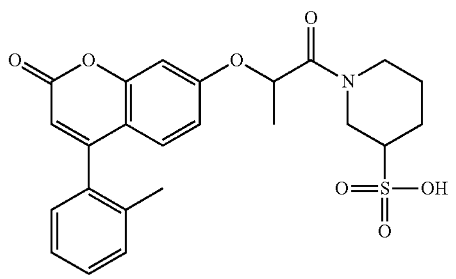 [SMILES: Cc1ccccc1-c1cc(=O)oc2cc(OC(C)C(=O)N3CCCC(S(=O)(=O)O)C3)ccc12] | 3E | (400 MHz, DMSO-d₆) δ 7.45-7.30 (m, 3H), 7.25-7.20 (m, 1H), 6.97-6.73 (m, 3H), 6.18-6.13 (m, 1H), 5.47-5.29 (m, 1H), 4.70-3.86 (m, 2H), 3.29-2.83 (m, 1H), 2.55-2.14 (m, 2H), 2.10 (s, 3H), 2.10-1.92 (m, 2H), 1.77-1.66 (m, 1H), 1.66-1.14 (m, 4H). | 97% |
| 11 | 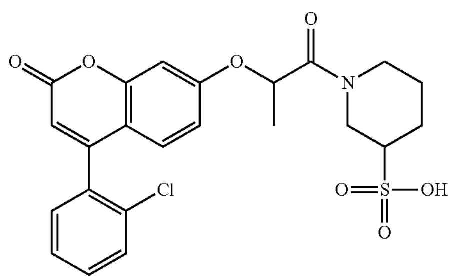 [SMILES: CC(Oc1ccc2c(-c3ccccc3Cl)cc(=O)oc2c1)C(=O)N1CCCC(S(=O)(=O)O)C1] | 4E | (400 MHz, DMSO-d₆) δ 7.65 (d, 1H), 7.59-7.45 (m, 3H), 6.98-6.86 (m, 2H), 6.86-6.74 (m, 1H), 6.28-6.24 (m, 1H), 5.49-5.23 (m, 1H), 4.17-4.83 (m, 2H), 3.31-2.83 (m, 1H), 2.77-2.14 (m, 2H), 2.12-1.94 (m, 1H), 1.77-1.66 (m, 1H), 1.66-1.14 (m, 5H). | 98% |
| 12 | 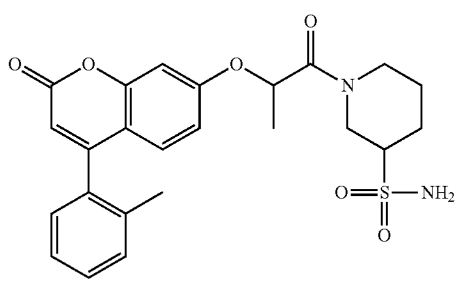 [SMILES: Cc1ccccc1-c1cc(=O)oc2cc(OC(C)C(=O)N3CCCC(S(N)(=O)=O)C3)ccc12] | 3E | (400 MHz, DMSO-d₆) δ 7.44-7.36 (m, 2H), 7.33 (td, 1H), 7.22 (d, 1H), 6.99-6.74 (m, 5H), 6.18-6.16 (m, 1H), 5.50-5.28 (m, 1H), 4.73 (br. d, 1H), 4.01-3.91 (m, 1H), 3.35-2.78 (m, 2H), 2.73-2.58 (m, 1H), 2.20-2.08 (m, 1H), 2.10 (s, 3H), 1.85-1.74 (m, 1H), 1.71-1.42 (m, 2H), 1.49-1.42 (m, 3H). | 90% |
| 13 | 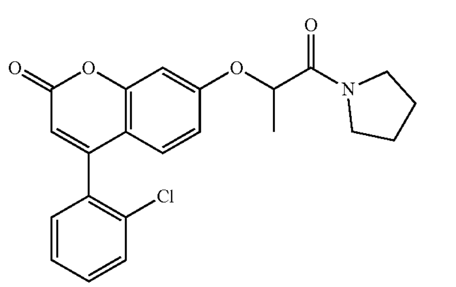 | 4E | (400 MHz, DMSO-d₆) δ 7.68-7.63 (m, 1H), 7.59-7.49 (m, 2H), 7.49-7.44 (m, 1H), 6.93-6.86 (m, 2H), 6.83-6.77 (m, 1H), 6.28 (s, 1H), 5.21-5.13 (m, 1H), 3.72-3.59 (m, 1H), 3.44-3.34 (m, 1H), 3.34-3.22 (m, 2H), 1.96-1.83 (m, 2H), 1.83-1.69 (m, 2H), 1.44 (d, 3H). | 97% |
| 14 | 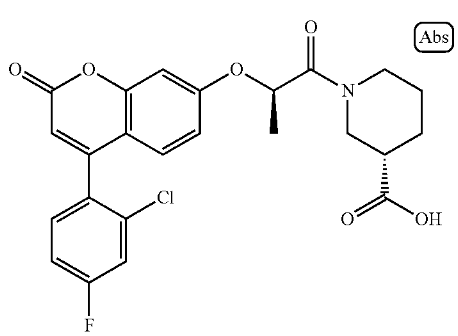 [SMILES: C[C@@H](Oc1ccc2c(-c3ccc(F)cc3Cl)cc(=O)oc2c1)C(=O)N1CCC[C@H](C(=O)O)C1] | (R)-1E | ¹H NMR (400 MHz, DMSO-d₆) δ 12.52 (1H, m), 7.70 (dd, 1H), 7.61-7.53 (m, 1H), 7.44 (td, 1H), 7.02-6.89 (m, 2H), 6.87-6.76 (m, 1H), 6.31 (s, 1H), 5.61-5.42 (m, 1H), 4.34-4.25 (m, 0.5H), 3.91-3.75 (m, 1H), 3.70-3.48 (m, 1H), 3.26-3.06 (m, 2H), 2.89-2.78 (m, 0.5H), 2.03-1.85 (m, 1H), 1.83-1.69 (m, 1H), 1.69-1.32 (m, 5H). | 96% ee 91-100% |

TABLE 3-continued

Compounds of formula (I) of the invention

| Ex | Structure | BB | ¹H-NMR | LC purity %ee |
|---|---|---|---|---|
| 15 | 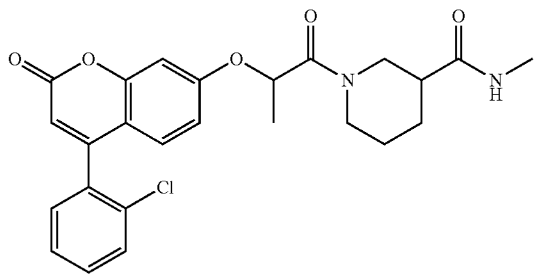 [SMILES: CNC(=O)C1CCCN(C(=O)C(C)Oc2ccc3c(-c4ccccc4Cl)cc(=O)oc3c2)C1] | 4E | (400 MHz, DMSO-d₆) δ 7.92-7.77 (br m, 1H), 7.67 (d, 1H), 7.61-7.46 (m, 3H), 6.98-6.80 (m, 3H), 6.31-6.27 (m, 1H), 5.55-5.38 (m, 1H), 4.34-3.35 (m, 3H), 3.18-2.92 (m, 1H); 2.75-2.58 (m, 1H); 2.58-2.08 (m, 4H); 1.92-1.21 (m, 6H). | 95% |
| 16 | [Abs] | 4E | (400 MHz, DMSO-d₆) δ 7.67 (dd, 1H), 7.58 (td, 1H), 7.53 (td, 1H), 7.50-7.45 (m, 1H), 7.04-6.79 (m, 3H), 6.29 (s, 1H), 5.56-5.39 (m, 1H), 4.20-4.16 (m, 1H), 4.13-3.89 (m, 3H), 3.85-3.71 (m, 1H), 3.69-2.73 (m, 2H), 2.62-2.38 (m, 1H), 2.03-1.86 (m, 1H), 1.83-1.58 (m, 2H), 1.47-1.41 (m, 3H), 1.20-1.06 (m, 3H). | 90% |
| 17 | [Abs] | 3E | (400 MHz, DMSO-d₆) δ 7.43-7.37 (m, 2H), 7.33 (t, 1H), 7.24-7.19 (m, 1H), 7.03-6.74 (m, 3H), 6.22-6.15 (m, 1H), 5.52-5.39 (m, 1H), 4.20-3.97 (m, 4H), 3.82-3.71 (m, 2H), 3.23-2.71 (m, 1H), 2.60-2.35 (m, 1H), 2.10 (s, 3H), 1.99-1.86 (m, 1H), 1.78-1.58 (m, 2H), 1.46-1.41 (m, 3H), 1.18-1.04 (m, 3H). | 90% |
| 18 | 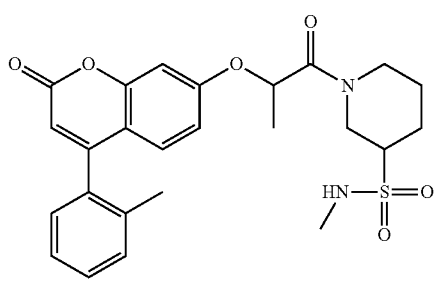 [SMILES: CNS(=O)(=O)C1CCCN(C(=O)C(C)Oc2ccc3c(-c4ccccc4C)cc(=O)oc3c2)C1] | 3E | (400 MHz, DMSO-d₆) δ 7.46-7.37 (m, 2H), 7.34 (t, 1H), 7.23 (d, 1H), 7.15-7.02 (m, 1H), 7.00-6.75 (m, 3H), 6.19 (s, 1H), 5.50-5.33 (m, 1H), 4.62 (d, 1H), 4.26-4.12 (m, 3H), 3.94 (br. d, 1H), 3.39-2.70 (m, 2H), 2.62-2.55 (m, 2H), 2.15-2.02 (m, 1H), 2.11 (s, 3H), 1.87-1.75 (m, 1H), 1.73-1.62 (m, 1H), 1.50-1.43 (m, 3H). | 90% |
| 19 | 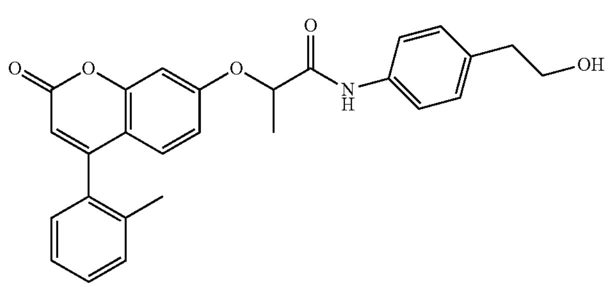 [SMILES: Cc1ccccc1-c1cc(=O)oc2cc(OC(C)C(=O)Nc3ccc(CCO)cc3)ccc12] | 3E | (400 MHz, DMSO-d₆) δ 10.12 (d, 1H), 7.52-7.46 (m, 2H), 7.43-7.34 (m, 2H), 7.34-7.28 (m, 1H), 7.21 (d, 1H), 7.13 (d, 2H), 7.04-7.00 (m, 1H), 6.94-6.84 (m, 2H), 6.17 (s, 1H), 5.02 (q, 1H), 4.57 (t, 1H), 3.54 (q, 2H), 2.64 (t, 2H), 2.09 (s, 3H), 1.56 (d, 3H). | 92% |

TABLE 3-continued

Compounds of formula (I) of the invention

| Ex | Structure | BB | ¹H-NMR | LC purity %ee |
|---|---|---|---|---|
| 20 | 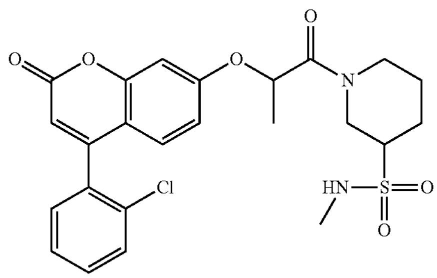 | 4E | (400 MHz, DMSO-d₆) δ 7.66 (dd, 1H), 7.56 (td, 1H), 7.52 (td, 1H), 7.49-7.44 (m, 1H), 7.13-6.76 (m, 4H), 6.28 (s, 1H), 5.51-5.32 (m, 1H), 4.68-4.04 (m, 4H), 3.37-2.98 (m, 2H), 2.79-2.67 (m, 1H), 2.60-2.54 (m, 2H), 2.13-2.00 (m, 1H), 1.86-1.72 (m, 1H), 1.72-1.57 (m, 1H), 1.49-1.42 (m, 3H). | 90% |
| 21 | 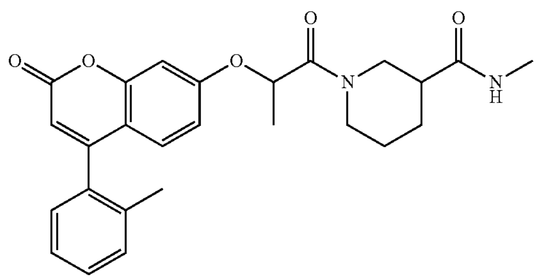 [SMILES: CNC(=O)C1CCCN(C(=O)C(C)Oc2ccc3c(-c4ccccc4C)cc(=O)oc3c2)C1] | 3E | (400 MHz, DMSO-d₆) δ 7.91-7.77 (m, 1H), 7.46-7.38 (m, 2H), 7.35 (t, 1H), 7.28-7.21 (m, 1H), 7.17-6.77 (m, 3H), 6.20-6.16 (m, 1H), 5.52-5.38 (m, 1H), 4.34-3.78 (m, 2H), 3.48-2.88 (m, 2H), 2.64-2.52 (m, 3H), 2.11 (s, 3H), 1.92-1.40 (m, 4H), 1.48-1.40 (m, 3H), 1.36-1.22 (m, 1H). | 90% |
| 22 | 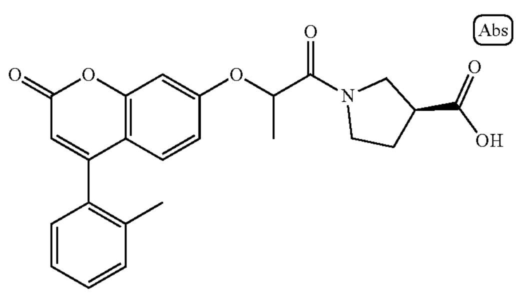 [SMILES: Cc1ccccc1-c1cc(=O)oc2cc(OC(C)C(=O)N3CC[C@H](C(=O)O)C3)ccc12] | 3E | (400 MHz, DMSO-d₆) δ 12.51 (br. s, 1H), 7.46-7.37 (m, 1H), 7.35 (t, 1H), 7.23 (d, 1H), 6.97-6.91 (m, 1H), 6.88-6.84 (m, 1H), 6.83-6.75 (m, 1H), 6.83-6.76 (m, 1H), 6.19-6.17 (m, 1H), 5.25-5.14 (m, 1H), 3.95-3.59 (m, 2H), 3.41-2.99 (m, 3H), 2.24-1.92 (m, 2H), 2.11 (s, 3H), 1.48-1.42 (m, 3H). | 92% |
| 23 | 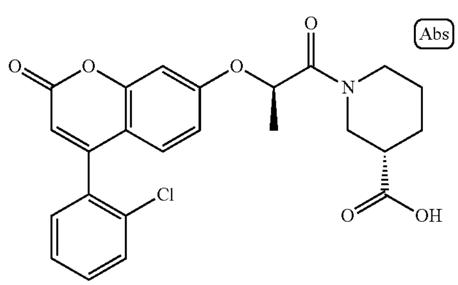 [SMILES: C[C@@H](Oc1ccc2c(-c3ccccc3Cl)cc(=O)oc2c1)C(=O)N1CCC[C@H](C(=O)O)C1] | (R)-4E | (400 MHz, DMSO-d₆) δ 12.48 (br. s, 1H), 7.66 (dd, 1H), 7.57 (td, 1H), 7.52 (td, 1H), 7.49-7.44 (m, 1H), 6.97-6.76 (m, 3H), 6.29-6.26 (m, 1H), 5.52-5.43 (m, 1H), 4.33-4.22 (m, 0.5H), 3.87-3.74 (m, 1H), 3.65-3.49 (m, 1H), 3.24-3.07 (m, 1H), 2.86-2.79 (m, 0.5H), 2.45-2.22 (m, 1H), 2.01-1.83 (m, 1H), 1.79-1.66 (m, 1H), 1.62-1.46 (m, 2H), 1.46-1.41 (m, 3H). | 90% |
| 24 | 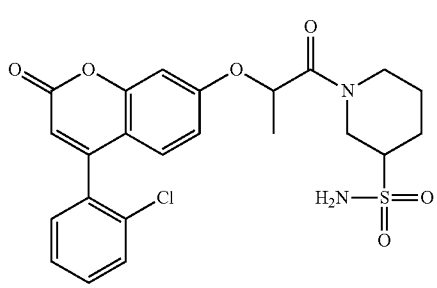 [SMILES: CC(Oc1ccc2c(-c3ccccc3Cl)cc(=O)oc2c1)C(=O)N1CCCC(S(N)(=O)=O)C1] | 4E | (400 MHz, DMSO-d₆) δ 7.66 (dd, 1H), 7.56 (td, 1H), 7.52 (td, 1H), 7.49-7.44 (m, 1H), 6.99-6.86 (m, 4H), 6.85-6.75 (m, 1H), 6.29-6.27 (m, 1H), 5.52-5.29 (m, 1H), 4.73-3.92 (m, 2H), 3.26-2.91 (m, 2H), 2.87-2.54 (m, 2H), 2.21-2.08 (m, 1H), 1.87-1.73 (m, 1H), 1.71-1.41 (m, 4H). | 98% |

TABLE 3-continued

Compounds of formula (I) of the invention

| Ex | Structure | BB | ¹H-NMR | LC purity %ee |
|---|---|---|---|---|
| 25 | 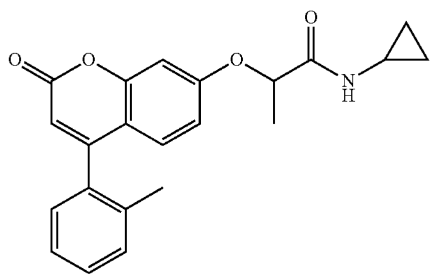 [SMILES: Cc1ccccc1-c1cc(=O)oc2cc(OC(C)C(=O)NC3CC3)ccc12] | 3E | (400 MHz, CDCl₃) δ 7.42-7.36 (m, 1H), 7.35-7.28 (m, 2H), 7.16 (d, 1H), 6.98 (d, 1H), 6.91-6.88 (m, 1H), 6.72 (dt, 1H), 6.37 (br. s, 1H), 6.19 (s, 1H), 4.72 (q, 1H), 2.77-2.69 (m, 1H), 2.15 (s, 3H), 1.58 (d, 3H), 0.84-0.77 (m, 2H), 0.52-0.46 (m, 2H). | 99% |
| 26 | 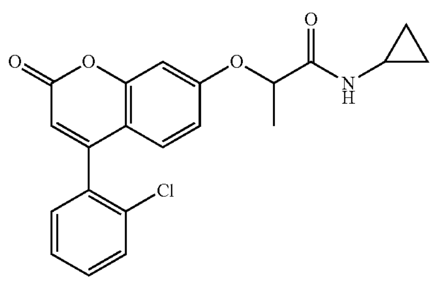 [SMILES: CC(Oc1ccc2c(-c3ccccc3Cl)cc(=O)oc2c1)C(=O)NC1CC1] | 4E | (400 MHz, CDCl₃) δ 7.49-7.46 (m, 1H), 7.42-7.32 (m, 2H), 7.24-7.21 (m, 1H), 6.94 (d, 1H), 6.82 (d, 1H), 6.67 (dd, 1H), 6.30 (br. s, 1H), 6.17 (s, 1H), 4.69-4.62 (m, 1H), 2.70-2.61 (m, 1H), 1.52 (d, 3H), 0.76-0.70 (m, 2H), 0.44-0.39 (m, 2H). | 99% |
| 27 | 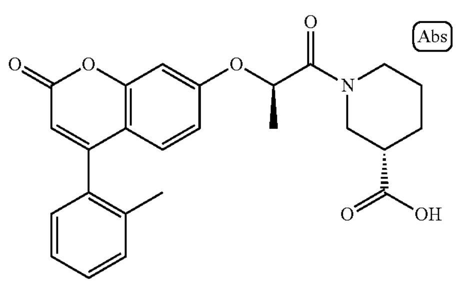 [SMILES: Cc1ccccc1-c1cc(=O)oc2cc(O[C@H](C)C(=O)N3CCC[C@H](C(=O)O)C3)ccc12] | (R)-3E | (400 MHz, DMSO-d₆) δ 12.48 (br. s, 1H), 7.46-7.38 (m, 2H), 7.35 (td, 1H), 7.27-7.21 (m, 1H), 6.99-6.76 (m, 3H), 6.18 (s, 1H), 5.52-5.43 (m, 1H), 4.29 (d, 0.5H), 3.89-3.74 (m, 1H), 3.68-3.49 (m, 1H), 3.26-3.07 (m, 1H), 2.85 (t, 0.5H), 2.47-2.26 (m, 1H), 2.11 (s, 3H), 2.03-1.85 (m, 1H), 1.82-1.67 (m, 1H), 1.64-1.40 (m, 2H), 1.47-1.42 (m, 3H). | 90% |
| 28 | 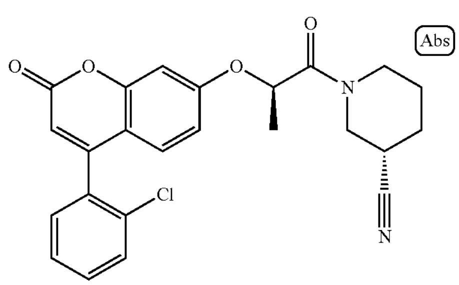 | (R)-4E | (400 MHz, DMSO-d₆) δ 7.65 (d, 1H), 7.62-7.43 (m, 3H), 7.04-6.65 (m, 3H), 6.28 (s, 1H), 5.55-5.43 (m, 1H), 3.99-3.79 (m, 1H), 3.79-3.60 (m, 1H), 3.54-3.00 (m, 3H), 2.02-1.79 (m, 2H), 1.79-1.50 (m, 2H), 1.50-1.40 (m, 3H). | 95% |
| 29 | 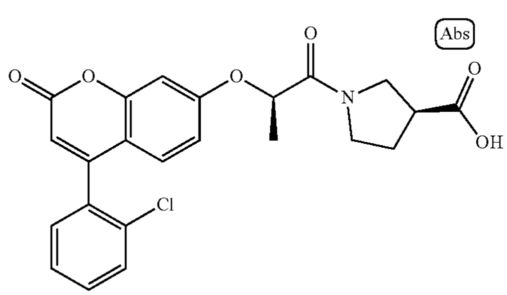 | 4E | (400 MHz, DMSO-d₆) δ 12.51 (br. s, 1H), 7.68-7.64 (m, 1H), 7.59-7.54 (td, 1H), 7.54-7.49 (td, 1H), 7.49-7.44 (m, 1H), 6.96-6.91 (m, 1H), 6.90-6.86 (m, 1H), 6.83-6.75 (m, 1H), 6.29-6.27 (m, 1H), 5.23-5.15 (m, 1H), 3.93-3.65 (m, 1H), 3.60-3.54 (m, 1H), 3.22-2.97 (m, 1H), 2.56-2.52 (m, 1H), 2.22-1.92 (m, 3H), 1.47-1.40 (m, 3H). | 98% |

TABLE 3-continued

Compounds of formula (I) of the invention

| Ex | Structure | BB | ¹H-NMR | LC purity %ee |
|---|---|---|---|---|
| 30 | 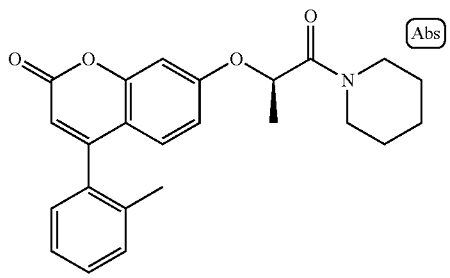 | (R)-3E | (400 MHz, DMSO-d₆) δ 7.44-7.30 (m, 3H), 7.22 (d, 1H), 6.92-6.83 (m, 2H), 6.82-6.76 (m, 1H), 6.16 (s, 1H), 5.46-5.37 (m, 1H), 3.60-3.31 (m, 4H), 2.10 (s, 3H), 1.66-1.36 (m, 6H), 1.42 (d, 3H). | 97% |
| 31 | 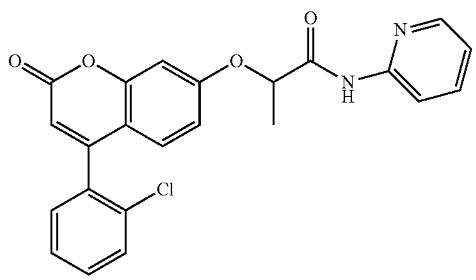 [SMILES: CC(Oc1ccc2c(-c3ccccc3Cl)cc(=O)oc2c1)C(=O)Nc1ccccn1] | 4E | (400 MHz, DMSO-d₆) δ 10.80 (s, 1H), 8.36-8.32 (m, 1H), 8.00 (d, 1H), 7.80-7.73 (m, 1H), 7.67-7.61 (m, 1H), 7.59-7.42 (m, 3H), 7.16-7.10 (m, 1H), 7.03 (s, 1H), 6.95-6.86 (m, 2H), 6.28 (d, 1H), 5.21 (q, 1H), 1.56 (d, 3H). | 96% |
| 32 | 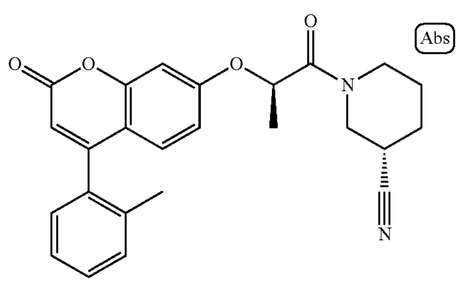 | (R)-3E | (400 MHz, DMSO-d₆) δ 7.46-7.29 (m, 3H), 7.26-7.18 (m, 1H), 7.03-6.90 (m, 1H), 6.90-6.76 (m, 2H), 6.18-6.15 (m, 1H), 5.53-5.42 (m, 1H), 4.01-3.80 (m, 1H), 3.78-3.60 (m, 1H), 3.55-3.00 (m, 3H), 2.10 (s, 3H), 2.01-1.79 (m, 2H), 1.76-1.51 (m, 2H), 1.51-1.39 (m, 3H). | 95% |
| 33 | 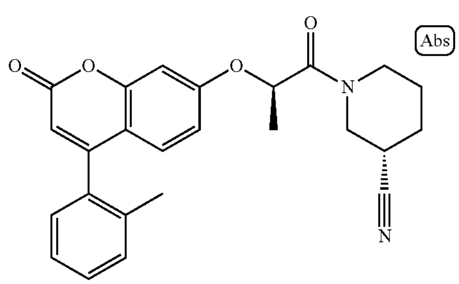 | 4E, 16 | (400 MHz, DMSO-d₆) δ 12.43 (br. s, 1H), 7.67 (d, 1H), 7.58 (td, 1H), 7.53 (td, 1H), 7.50-7.46 (m, 1H), 7.00-6.78 (m, 3H), 6.31-6.27 (m, 1H), 5.55-5.40 (m, 1H), 4.35-3.92 (m, 1H), 3.89-3.49 (m, 1H), 3.27-3.09 (m, 1H), 2.91-2.73 (m, 1H), 2.58-2.23 (m, 1H), 2.04-1.86 (m, 1H), 1.82-1.69 (m, 1H), 1.67-1.32 (m, 2H), 1.48-1.42 (m, 3H). | 90% |
| 34 | 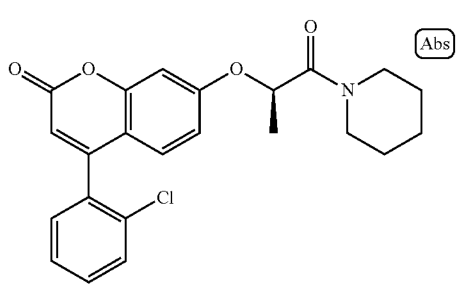 | (R)-4E | (400 MHz, DMSO-d₆) δ 7.69-7.63 (m, 1H), 7.60-7.43 (m, 3H), 6.93-6.86 (m, 2H), 6.83-6.78 (m, 1H), 6.27 (s, 1H), 5.43 (quint, 1H), 3.60-3.29 (m, 4H), 1.68-1.33 (m, 6H), 1.42 (d, 3H). | 98% |

TABLE 3-continued

Compounds of formula (I) of the invention

| Ex | Structure | BB | ¹H-NMR | LC purity %ee |
|---|---|---|---|---|
| 35 | 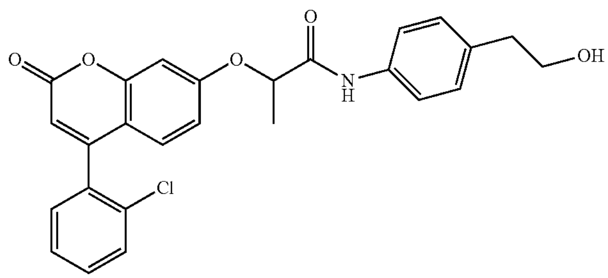 [SMILES: CC(Oc1ccc2c(-c3ccccc3Cl)cc(=O)oc2c1)C(=O)Nc1ccc(CCO)cc1] | 4E | (400 MHz, DMSO-d₆) δ 10.12 (s, 1H), 7.67-7.62 (m, 1H), 7.59-7.43 (m, 5H), 7.13 (d, 2H), 7.04-7.00 (m, 1H), 6.95-6.89 (m, 2H), 6.28 (s, 1H), 5.06-4.98 (m, 1H), 4.57 (t, 1H), 3.54 (q, 2H), 2.64 (t, 2H), 1.56 (d, 3H). | 92% |
| 36 | 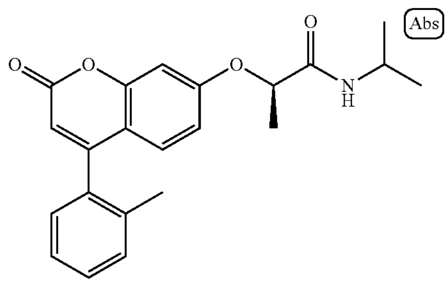 [SMILES: Cc1ccccc1-c1cc(=O)oc2cc(O[C@H](C)C(=O)NC(C)C)ccc12] | (R)-3E | (400 MHz, DMSO-d₆) δ 8.01 (d, 1H), 7.44-7.29 (m, 3H), 7.25-7.19 (m, 1H), 6.97-6.92 (m, 1H), 6.90-6.81 (m, 2H), 6.17 (s, 1H), 4.79 (q, 1H), 3.91-3.75 (m, 1H), 2.09 (d, 3H), 1.41 (d, 3H), 1.04 (dd, 6H). | 98% |
| 37 | 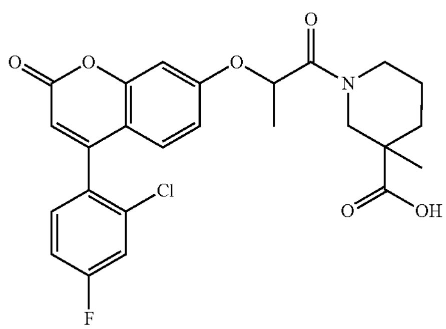 [SMILES: CC(Oc1ccc2c(-c3ccc(F)cc3Cl)cc(=O)oc2c1)C(=O)N1CCCC(C)(C(=O)O)C1] | 1E | (400 MHz, DMSO-d₆) δ 12.35 (br. s, 1H), 7.72-7.66 (m, 1H), 7.58-7.51 (m, 1H), 7.41 (td, 1H), 7.00-6.74 (m, 3H), 6.31-6.25 (m, 1H), 5.59-5.36 (m, 1H), 4.17-3.35 (m, 2H), 3.21-3.06 (m, 1H), 2.63-2.42 (m, 1H), 2.01-1.82 (m, 1H), 1.65-1.34 (m, 3H), 1.47-1.43 (m, 3H), 1.17-0.96 (m, 3H). | 95% |
| 38 | 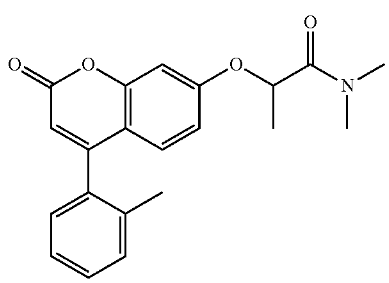 [SMILES: Cc1ccccc1-c1cc(=O)oc2cc(OC(C)C(=O)N(C)C)ccc12] | 3B | (400 MHz, CDCl₃) δ 7.34-7.28 (m, 1H), 7.28-7.20 (m, 2H), 7.11-7.05 (m, 1H), 6.88 (d, 1H), 6.73-6.66 (m, 2H), 6.09 (s, 1H), 5.01-4.94 (m, 1H), 3.07 (d, 3H), 2.92 (d, 3H), 2.09 (d, 3H), 1.57 (d, 3H). | 95% |
| 39 | 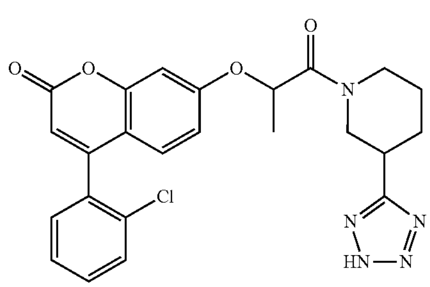 | 4E, 48 | (400 MHz, DMSO-d₆) δ 7.65 (d, 1H), 7.60-7.41 (m, 3H), 7.00-6.72 (m, 3H), 6.28 (s, 1H), 5.58-5.39 (m, 1H), 4.53-4.12 (m, 1H), 4.05-2.63 (m, 4H), 2.24-2.08 (m, 1H), 1.90-1.60 (m, 2H), 1.54-1.37 (m, 4H). | 95% |

TABLE 3-continued

Compounds of formula (I) of the invention

| Ex | Structure | BB | ¹H-NMR | LC purity %ee |
|---|---|---|---|---|
| 40 (4D) | 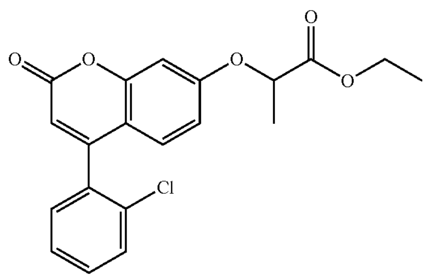 [SMILES: CCOC(=O)C(C)Oc1ccc2c(-c3ccccc3Cl)cc(=O)oc2c1] | 4B | (400 MHz, CDCl₃) δ 7.46 (d, 1H), 7.49-7.29 (m, 2H), 7.24-7.18 (m, 1H), 6.91 (d, 1H), 6.77-6.66 (m, 2H), 6.14 (s, 1H), 4.72 (q, 1H), 4.17 (q, 2H), 1.59 (d, 3H), 1.24-1.19 (m, 3H). | 99% |
| 41 | 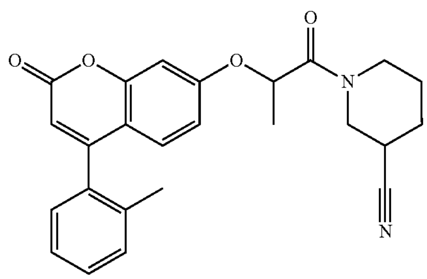 [SMILES: Cc1ccccc1-c1cc(=O)oc2cc(OC(C)C(=O)N3CCCC(C#N)C3)ccc12] | 3E | (400 MHz, DMSO-d₆) δ 7.45-7.30 (m, 3H), 7.26-7.19 (m, 1H), 7.02-6.89 (m, 1H), 6.89-6.76 (m, 2H), 6.16 (s, 1H), 5.54-5.42 (m, 1H), 4.03-3.60 (m, 2H), 3.55-3.00 (m, 3H), 2.09 (s, 3H), 2.01-1.51 (m, 4H), 1.51-1.39 (m, 4H). | 95% |
| 42 | 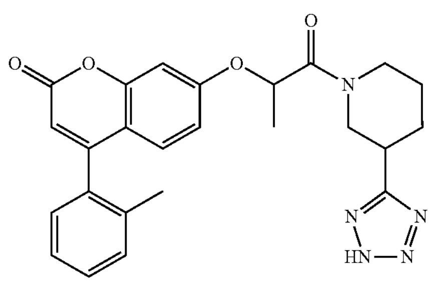 [SMILES: Cc1ccccc1-c1cc(=O)oc2cc(OC(C)C(=O)N3CCCC(c4nn[nH]n4)C3)ccc12] | 3E, 41 | (400 MHz, DMSO-d₆) δ 7.45-7.29 (m, 3H), 7.26-7.19 (m, 1H), 6.98-6.70 (m, 3H), 6.17 (s, 1H), 5.55-5.38 (m, 1H), 4.52-3.87 (m, 2H), 3.65-2.92 (m, 2H), 2.23-2.05 (m, 4H), 1.91-1.60 (m, 3H), 1.55-1.38 (m, 4H). | 99% |
| 43 | 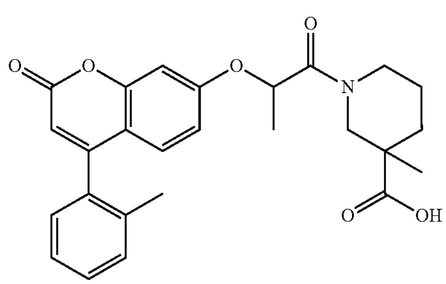 [SMILES: Cc1ccccc1-c1cc(=O)oc2cc(OC(C)C(=O)N3CCCC(C)(C(=O)O)C3)ccc12] | 3E, 88 | (400 MHz, DMSO-d₆) δ 12.48 (br. s, 1H), 7.45-7.39 (m, 2H), 7.35 (t, 1H), 7.24 (d, 1H), 7.02-6.75 (m, 3H), 6.20-6.15 (m, 1H), 5.59-5.38 (m, 1H), 4.18-3.37 (m, 2H), 3.15-3.07 (m, 1H), 2.59-2.44 (m, 1H), 2.12 (s, 3H), 2.03-1.84 (m, 1H), 1.65-1.36 (m, 3H), 1.48-1.45 (m, 3H), 1.18-0.97 (m, 3H). | 95% |
| 44 | 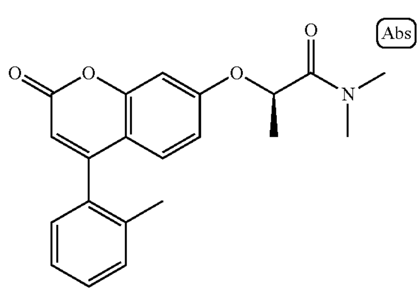 [SMILES: Cc1ccccc1-c1cc(=O)oc2cc(O[C@H](C)C(=O)N(C)C)ccc12] | 3B | (400 MHz, DMSO-d₆) δ 7.44-7.30 (m, 3H), 7.22 (d, 1H), 6.88 (t, 1H), 6.87-6.83 (m, 1H), 6.81-6.76 (m, 1H), 6.17 (s, 1H), 5.43-5.35 (m, 1H), 3.08 (d, 3H), 2.83 (s, 3H), 2.10 (s, 3H), 1.43 (d, 3H). | 94% |

TABLE 3-continued
Compounds of formula (I) of the invention
| Ex | Structure | BB | ¹H-NMR | LC purity %ee |
|----|-----------|----|--------|---------------|
| 45 | 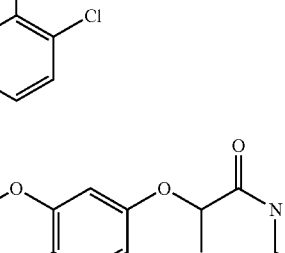 | 4B | (400 MHz, DMSO-d$_6$) δ 7.68-7.63 (m, 1H), 7.59-7.44 (m, 3H), 6.92-6.95 (m, 2H), 6.84-6.76 (m, 1H), 6.28 (s, 1H), 5.45-5.35 (m, 1H), 3.08 (d, 3H), 2.83 (s, 3H), 1.43 (d, 3H). | 98% |
| 46 | 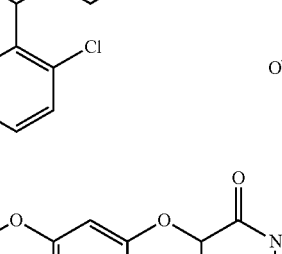 | 4E | (400 MHz, DMSO-d$_6$) δ 12.42 (br. s, 1H), 7.67 (d, 1H), 7.58 (td, 1H), 7.53 (td, 1H), 7.50-7.46 (m, 1H), 7.00-6.77 (m, 3H), 6.30-6.28 (m, 1H), 5.55-5.40 (m, 1H), 4.35-4.25 (m, 0.5H), 4.06-3.51 (m, 2H), 3.26-3.09 (m, 1H), 2.91-2.73 (m, 1H), 2.30-2.23 (m, 0.5H), 2.03-1.87 (m, 1H), 1.80-1.32 (m, 6H). | 92% |
| 47 | 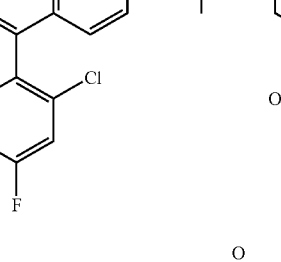 | 1G | (400 MHz, DMSO-d$_6$) δ 12.41 (1H, br. s), 7.68 (dd, 1H), 7.58-7.51 (m, 1H), 7.42 (td, 1H), 6.99-6.87 (m, 2H), 6.87-6.74 (m, 1H), 6.29 (s, 1H), 5.55-5.36 (m, 1H), 4.34-3.90 (m, 1H), 3.89-3.46 (m, 1H), 3.23-3.06 (m, 1H), 2.92-2.70 (m, 1H), 2.33-2.19 (m, 1H), 2.04-1.84 (m, 1H), 1.81-1.67 (m, 1H), 1.66-1.48 (m, 1H), 1.47-1.39 (m, 3H), 1.39-1.26 (m, 1H). | 99% |
| 48 | 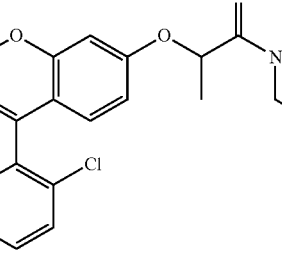 | 4E | (400 MHz, DMSO-d$_6$) δ 7.65 (d, 1H), 7.59-7.42 (m, 3H), 7.04-6.76 (m, 3H), 6.28 (s, 1H), 5.56-5.48 (m, 1H), 3.97-3.61 (m, 2H), 3.54-2.98 (m, 3H), 1.95-1.78 (m, 2H), 1.78-1.51 (m, 2H), 1.51-1.38 (m, 3H). | 90% |
| 49 | 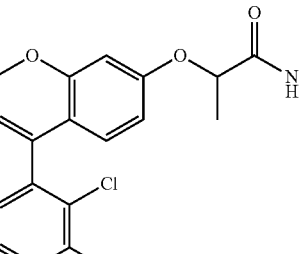 | 5E | (400 MHz, DMSO-d$_6$) δ 8.01 (d, 1H), 7.63-7.53 (m, 2H), 7.33 (d, 1H), 6.99-6.94 (m, 2H), 6.86 (dt, 1H), 6.34 (s, 1H), 4.80 (q, 1H), 3.89-3.79 (m, 1H), 1.43 (d, 3H), 1.06 (d, 3H), 1.02 (dd, 3H). | 99% |

TABLE 3-continued

Compounds of formula (I) of the invention

| Ex | Structure | BB | ¹H-NMR | LC purity %ee |
|---|---|---|---|---|
| 50 | [Abs] | 5E | (400 MHz, DMSO-d₆) δ 12.41 (br. s, 1H), 7.64-7.55 (m, 2H), 7.37-7.33 (m, 1H), 7.00-6.78 (m, 3H), 6.36-6.33 (m, 1H), 5.55-5.41 (m, 1H), 4.36-4.25 (m, 0.5H), 4.07-3.47 (m, 2H), 3.26-3.09 (m, 1H), 2.90-2.72 (m, 1H), 2.31-2.24 (m, 0.5H), 2.03-1.86 (m, 1H), 1.80-1.38 (m, 3H), 1.48-1.43 (m, 3H). | 93% |
| 51 | 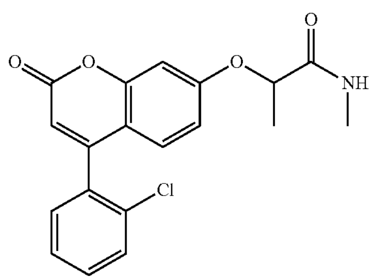 [SMILES: CNC(=O)C(C)Oc1ccc2c(-c3ccccc3Cl)cc(=O)oc2c1] | 4E | (400 MHz, CDCL₃) δ 7.50-7.45 (m, 1H), 7.42-7.32 (m, 2H), 7.22 (dd, 1H), 6.95 (d, 1H), 6.84 (d, 1H), 6.69 (dd, 1H), 6.28 (br. s, 1H), 6.17 (s, 1H), 4.70 (q, 1H), 2.78 (d, 3H), 1.55 (d, 3H). | 93% |
| 52 | 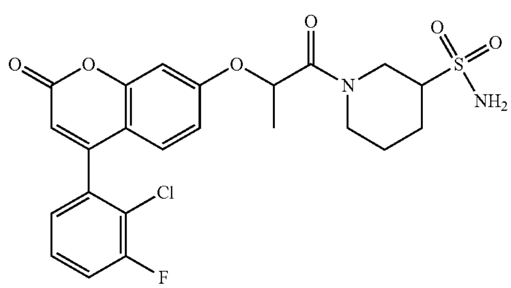 [SMILES: CC(Oc1ccc2c(-c3cccc(F)c3Cl)cc(=O)oc2c1)C(=O)N1CCCC(S(N)(=O)=O)C1] | 5E | (400 MHz, DMSO-d₆) δ 7.65-7.55 (m, 2H), 7.38-7.32 (m, 1H), 7.03-6.90 (m, 4H), 6.87-6.76 (m, 1H), 6.35 (s, 1H), 5.54-5.30 (m, 1H), 4.78-4.70 (br. d, 0.5H), 4.36-3.92 (m, 1H), 3.32-2.92 (m, 2H), 2.89-2.79 (m, 0.5H), 2.75-2.57 (m, 1H), 2.23-2.09 (m, 1H), 1.90-1.75 (m, 1H), 1.73-1.33 (m, 2H), 1.52-1.43 (m, 3H). | 95% |
| 53 | [Abs] | 3E | (400 MHz, DMSO-d₆) δ 12.43 (br. s, 1H), 7.45-7.39 (m, 2H), 7.35 (t, 1H), 7.24 (d, 1H), 6.97-6.77 (m, 3H), 6.19-6.17 (m, 1H), 5.54-5.38 (m, 1H), 4.34-3.92 (m, 1H), 3.89-3.45 (m, 1H), 3.26-3.08 (m, 1H), 2.91-2.23 (m, 1H), 2.11 (s, 3H), 2.03-1.85 (m, 1H), 1.81-1.34 (m, 4H), 1.47-1.42 (m, 3H). | 95% |
| 54 | 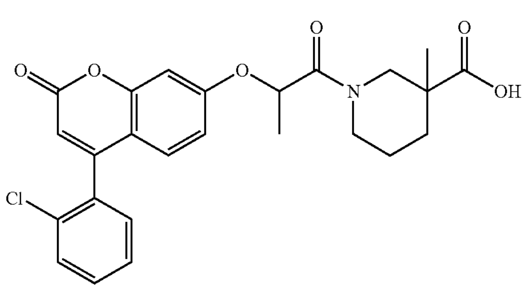 [SMILES: CC(Oc1ccc2c(-c3ccccc3Cl)cc(=O)oc2c1)C(=O)N1CCCC(C)(C(=O)O)C1] | 4E, 75 | (400 MHz, DMSO-d₆) δ 7.71-7.65 (m, 1H), 7.62-7.47 (m, 3H), 7.02-6.76 (m, 3H), 6.31-6.25 (m, 1H), 5.62-5.36 (m, 1H), 4.21-3.82 (m, 1H), 3.78-3.36 (m, 2H), 3.29-3.14 (m, 2H), 2.04-1.81 (m, 1H), 1.69-1.33 (m, 6H), 1.20-1.12 (m, 2H). | 98% |

TABLE 3-continued

Compounds of formula (I) of the invention

| Ex | Structure | BB | ¹H-NMR | LC purity %ee |
|---|---|---|---|---|
| 55 | 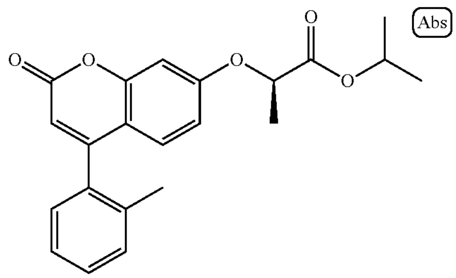 [SMILES: Cc1ccccc1-c1cc(=O)oc2cc(O[C@H](C)C(=O)OC(C)C)ccc12] | (R)-3E | (400 MHz, CDCl₃) δ 7.41-7.36 (m, 1H), 7.34-7.27 (m, 2H), 7.16 (d, 1H), 6.95 (d, 1H), 6.80 (d, 1H), 6.74 (dt, 1H), 6.16 (s, 1H), 5.08 (sept, 1H), 4.75 (q, 1H), 2.15 (s, 3H), 1.64 (d, 3H), 1.30 (dd, 3H), 1.22 (dd, 3H). | 95% |
| 56 | 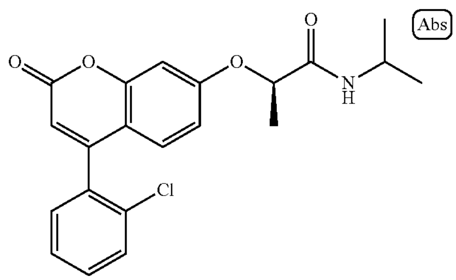 [SMILES: CC(C)NC(=O)[C@@H](C)Oc1ccc2c(-c3ccccc3Cl)cc(=O)oc2c1] | (R)-4E | (400 MHz, DMSO-d₆) δ 8.02 (d, 1H), 7.66 (d, 1H), 7.60-7.44 (m, 3H), 6.95 (dd, 1H), 6.92-6.83 (m, 2H), 6.28 (s, 1H), 4.83-4.76 (m, 1H), 3.92-3.78 (m, 1H), 1.43 (d, 3H), 1.06 (d, 3H), 1.02 (dd, 3H). | 98% |
| 57 (5D) | 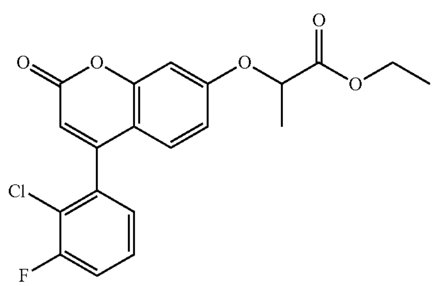 [SMILES: CCOC(=O)C(C)Oc1ccc2c(-c3cccc(F)c3Cl)cc(=O)oc2c1] | 5B | (300 MHz, CDCl₃) δ 7.38-7.17 (m, 2H), 7.08-6.99 (m, 1H), 6.94-6.85 (m, 1H), 6.79-6.64 (m, 2H), 6.14 (s, 1H), 4.73 (q, 1H), 4.17 (q, 2H), 1.59 (d, 3H), 1.21 (td, 3H). | 99% |
| 58 (3D) | 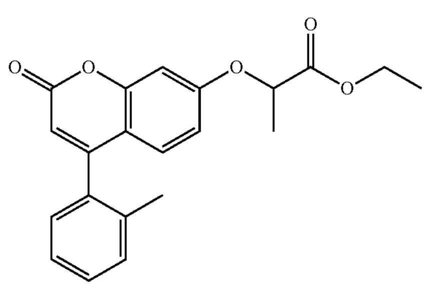 [SMILES: CCOC(=O)C(C)Oc1ccc2c(-c3ccccc3C)cc(=O)oc2c1] | 3B | (400 MHz, CDCl₃) δ 7.42-7.35 (m, 1H), 7.34-7.27 (m, 2H), 7.16 (d, 1H), 6.96 (d, 1H), 6.82-6.79 (m, 1H), 6.77-6.72 (m, 1H), 6.16 (s, 1H), 4.79 (q, 1H), 4.24 (q, 2H), 2.15 (s, 3H), 1.66 (d, 3H), 1.29 (td, 3H). | 97% |
| 59 | 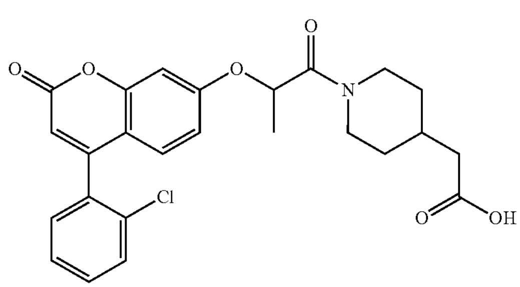 [SMILES: CC(Oc1ccc2c(-c3ccccc3Cl)cc(=O)oc2c1)C(=O)N1CCC(CC(=O)O)CC1] | 4E, 80 | (400 MHz, DMSO-d₆) δ 12.13 (br. s, 1H), 7.67 (dd, 1H), 7.58 (td, 1H), 7.53 (td, 1H), 7.51-7.46 (m, 1H), 6.98-6.79 (m, 3H), 6.29 (s, 1H), 5.51-5.38 (m, 1H), 4.29 (br. d, 1H), 3.97 (br. d, 1H), 3.19-3.02 (m, 1H), 2.69-2.56 (m, 1H), 2.16 (q, 2H), 2.01-1.85 (m, 1H), 1.79-1.65 (m, 2H), 1.44 (t, 3H), 1.31-0.9 (m, 2H). | 96% |

TABLE 3-continued

Compounds of formula (I) of the invention

| Ex | Structure | BB | ¹H-NMR | LC purity %ee |
|---|---|---|---|---|
| 60 | 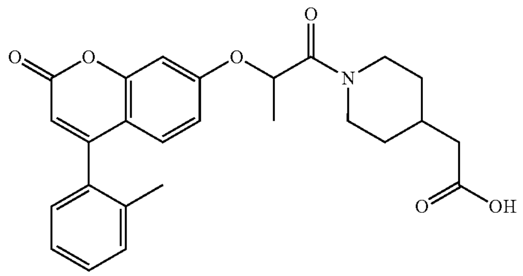 [SMILES: Cc1ccccc1-c1cc(=O)oc2cc(OC(C)C(=O)N3CCC(CC(=O)O)CC3)ccc12] | 3E | (400 MHz, DMSO-d₆) δ 12.10 (br. s, 1H), 7.45-7.33 (m, 3H), 7.24 (d, 1H), 6.96-6.77 (m, 3H), 6.18 (d, 1H), 5.49-5.37 (m, 1H), 4.29 (br. d, 1H), 3.97 (br. d, 1H), 3.20-3.00 (m, 1H), 2.65-2.55 (m, 1H), 2.16 (q, 2H), 2.11 (s, 3H), 1.98-1.86 (m, 1H), 1.78-1.65 (m, 2H), 1.44 (t, 3H), 1.27-0.92 (m, 2H). | 95% |
| 61 | 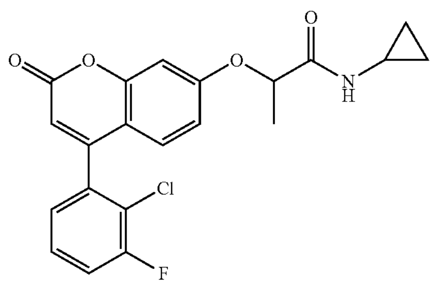 [SMILES: CC(Oc1ccc2c(-c3cccc(F)c3Cl)cc(=O)oc2c1)C(=O)NC1CC1] | 5E | (400 MHz, DMSO-d₆) δ 7.84 (d, 1H), 7.24-7.14 (m, 2H), 6.96-6.92 (m, 1H), 6.59-6.54 (m, 2H), 6.46 (dt, 1H), 5.95 (s, 1H), 4.40 (q, 1H), 2.28-2.19 (m, 1H), 1.04 (d, 3H), 0.25-0.18 (m, 2H), 0.05-0.01 (m, 2H). | 98% |
| 62 | 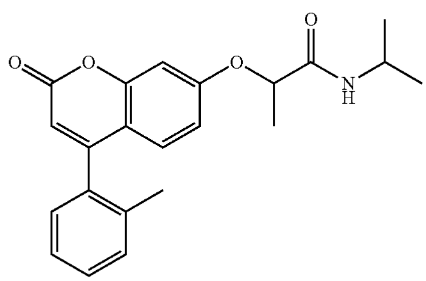 [SMILES: Cc1ccccc1-c1cc(=O)oc2cc(OC(C)C(=O)NC(C)C)ccc12] | 3E | (400 MHz, CDCl₃) δ 7.35-7.30 (m, 1H), 7.28-7.21 (m, 2H), 7.12-7.07 (m, 1H), 6.92 (d, 1H), 6.85 (t, 1H), 6.67 (dd, 1H), 6.12 (s, 1H), 6.01 (br. t, 1H), 4.63 (q, 1H), 4.09-3.97 (m, 1H), 2.09 (d, 3H), 1.53 (d, 3H), 1.11 (d, 3H), 1.02 (dd, 3H). | 98% |
| 63 | 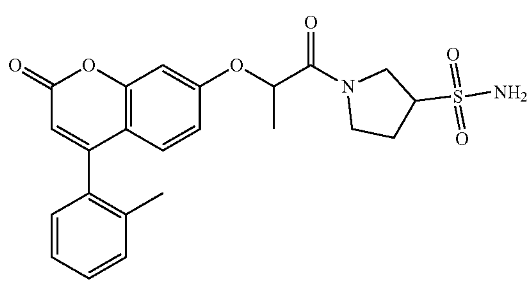 [SMILES: Cc1ccccc1-c1cc(=O)oc2cc(OC(C)C(=O)N3CCC(S(N)(=O)=O)C3)ccc12] | 3E | (400 MHz, DMSO-d₆) δ 7.45-7.38 (m, 2H), 7.35 (t, 1H), 7.23 (d, 1H), 7.11-7.03 (m, 2H), 6.98-6.93 (m, 1H), 6.88-6.75 (m, 2H), 6.21-6.18 (m, 1H), 5.26-5.15 (m, 1H), 4.12-3.33 (m, 5H), 2.38-2.16 (m, 2H), 2.11 (m, 3H), 1.52-1.42 (m, 3H). | 93% |
| 64 | 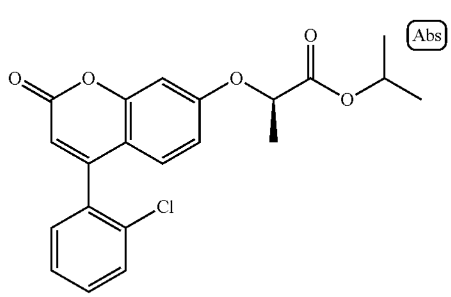 [SMILES: CC(C)OC(=O)[C@@H](C)Oc1ccc2c(-c3ccccc3Cl)cc(=O)oc2c1] | (R)-4E | (400 MHz, CDCl₃) δ 7.56-7.51 (m, 1H), 7.48-7.37 (m, 2H), 7.29 (dd, 1H), 6.98 (d, 1H), 6.83-6.73 (m, 2H), 6.21 (s, 1H), 5.09 (sept, 1H), 4.76 (q, 1H), 1.64 (d, 3H), 1.30 (dd, 3H), 1.22 (dd, 3H). | 95% |

TABLE 3-continued

Compounds of formula (I) of the invention

| Ex | Structure | BB | ¹H-NMR | LC purity %ee |
|---|---|---|---|---|
| 65 | 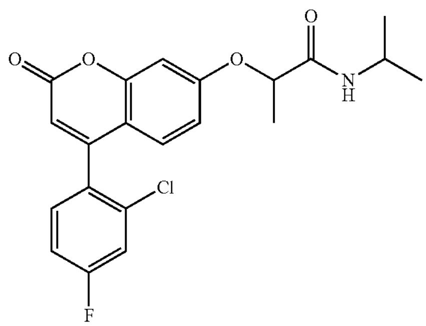 [SMILES: CC(C)NC(=O)C(C)Oc1ccc2c(-c3ccc(F)cc3Cl)cc(=O)oc2c1] | 1E | (400 MHz, DMSO-d₆) δ 8.02 (d, 1H), 7.68 (dd, 1H), 7.57-7.51 (m, 1H), 7.45-7.38 (m, 1H), 6.98-6.91 (m, 2H), 6.88-6.84 (m, 1H), 6.29 (s, 1H), 4.80 (q, 1H), 3.90-3.78 (m, 1H), 1.42 (d, 3H), 1.06 (d, 3H), 1.01 (dd, 3H). | 98% |
| 66 | 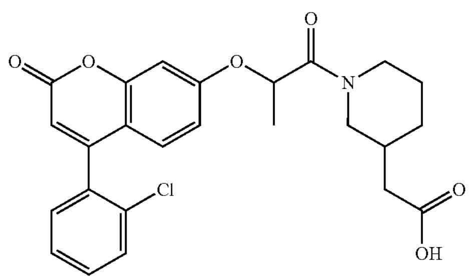 [SMILES: CC(Oc1ccc2c(-c3ccccc3Cl)cc(=O)oc2c1)C(=O)N1CCCC(CC(=O)O)C1] | 4E | (400 MHz, DMSO-d₆) δ 12.16 (br. s, 1H), 7.67 (dd, 1H), 7.58 (td, 1H), 7.53 (td, 1H), 7.50-7.46 (m, 1H), 6.96-6.79 (m, 3H), 6.29 (s, 1H), 5.49-5.36 (m, 1H), 4.24-3.79 (m, 2H), 3.21-3.03 (m, 1H), 2.92-2.42 (m, 1H), 2.26-2.06 (m, 2H), 1.86-1.61 (m, 3H), 1.53-1.42 (m, 3H), 1.40-1.16 (m, 2H). | 95% |
| 67 | 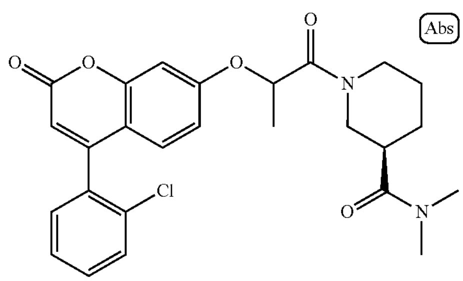 [SMILES: CC(Oc1ccc2c(-c3ccccc3Cl)cc(=O)oc2c1)C(=O)N1CCC[C@@H](C(=O)N(C)C)C1] | 46, then M7 | (400 MHz, DMSO-d₆) δ 7.67 (d, 1H), 7.60-7.51 (m, 2H), 7.50-7.46 (m, 1H), 7.04-6.79 (m, 3H), 6.29 (s, 1H), 5.57-5.39 (m, 1H), 4.36-4.24 (m, 1H), 3.96-3.84 (m, 1H), 3.34-3.04 (m, 1H), 3.03-2.93 (m, 3H), 2.84-2.75 (m, 3H), 2.74-2.54 (m, 2H), 1.95-1.32 (m, 4H), 1.47-1.41 (q, 3H). | 98% |
| 68 | 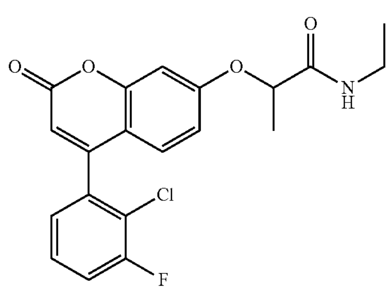 [SMILES: CCNC(=O)C(C)Oc1ccc2c(-c3cccc(F)c3Cl)cc(=O)oc2c1] | 5E | (400 MHz, DMSO-d₆) δ 8.17 (br. t, 1H), 7.64-7.53 (m, 2H), 7.36-7.31 (m, 1H), 7.00-6.94 (m, 2H), 6.90-6.85 (m, 1H), 6.34 (s, 1H), 4.83 (q, 1H), 3.14-3.03 (m, 2H), 1.44 (d, 3H), 0.99 (td, 3H). | 94% |
| 69 | 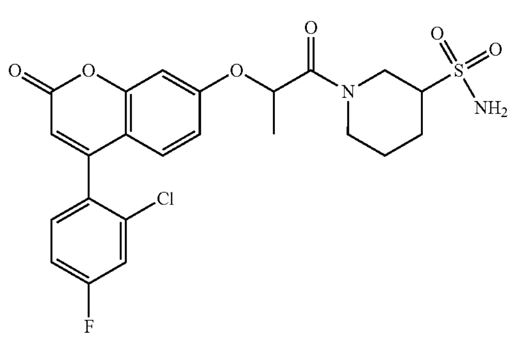 [SMILES: CC(Oc1ccc2c(-c3ccc(F)cc3Cl)cc(=O)oc2c1)C(=O)N1CCCC(S(N)(=O)=O)C1] | 1E | (400 MHz, DMSO-d₆) δ 7.70 (dd, 1H), 7.59-7.53 (m, 1H), 7.43 (td, 1H), 7.00-6.90 (m, 4H), 6.87-6.76 (m, 1H), 6.31 (m, 1H), 5.54-5.29 (m, 1H), 4.74 (br. d, 1H), 4.35-3.96 (m, 1H), 3.38-3.07 (m, 1H), 3.05-2.78 (m, 1H), 2.77-2.58 (m, 1H), 2.23-2.10 (m, 1H), 1.90-1.75 (m, 1H), 1.73-1.38 (m, 2H), 1.52-1.42 (m, 3H). | 98% |

TABLE 3-continued

Compounds of formula (I) of the invention

| Ex | Structure | BB | ¹H-NMR | LC purity %ee |
|---|---|---|---|---|
| 70 | 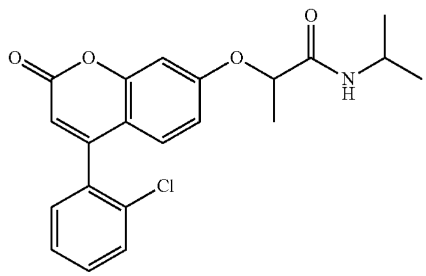 | 4E | (400 MHz, CDCl₃) δ 7.47 (d, 1H), 7.42-7.31 (m, 2H), 7.23 (dt, 1H), 6.95 (d, 1H), 6.85 (d, 1H), 6.69 (dd, 1H), 6.17 (s, 1H), 6.01 (br. t, 1H), 4.64 (qd, 1H), 4.09-3.97 (m, 1H), 1.53 (d, 3H), 1.11 (d, 3H), 1.02 (dd, 3H). | 98% |
| 71 | 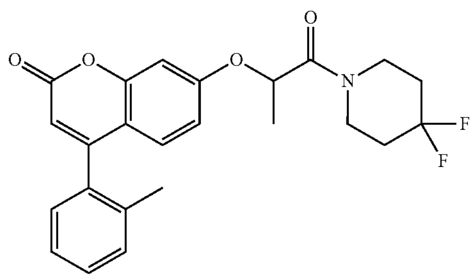 [SMILES: Cc1ccccc1-c1cc(=O)oc2cc(OC(C)C(=O)N3CCC(F)(F)CC3)ccc12] | 3E | (400 MHz, DMSO-d₆) δ 7.45-7.30 (m, 3H), 7.26-7.20 (m, 1H), 6.97 (t, 1H), 6.87 (d, 1H), 6.83-6.77 (m, 1H), 6.18 (d, 1H), 5.53-5.44 (m, 1H), 3.76-3.60 (m, 4H), 2.14-1.84 (m, 4H), 2.10 (d, 3H), 1.45 (d, 3H). | 92% |
| 72 | 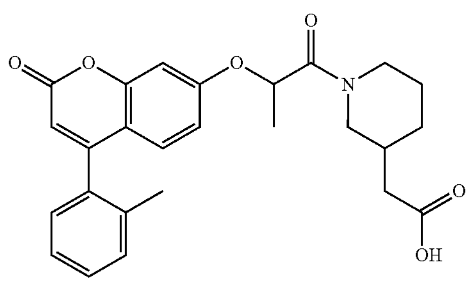 [SMILES: Cc1ccccc1-c1cc(=O)oc2cc(OC(C)C(=O)N3CCCC(CC(=O)O)C3)ccc12] | 3E, 87 | (400 MHz, DMSO-d₆) δ 12.16 (br. s, 1H), 7.45-7.38 (m, 2H), 7.35 (t, 1H), 7.25-7.23 (d, 1H), 6.94-6.78 (m, 3H), 6.20-6.17 (m, 1H), 5.49-5.31 (m, 1H), 4.24-4.09 (m, 1H), 4.03-3.79 (m, 1H), 3.21-3.03 (m, 1H), 2.85-2.55 (m, 1H), 2.23-2.04 (m, 2H), 2.11 (s, 3H), 1.89-1.59 (m, 3H), 1.53-1.42 (m, 3H), 1.33-1.15 (m, 2H). | 95% |
| 73 | 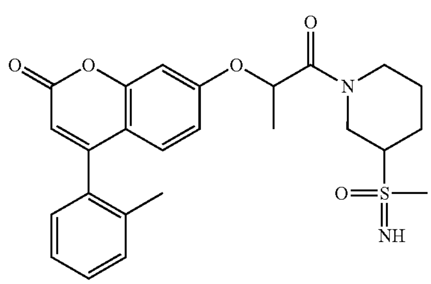 | 3E | (400 MHz, DMSO-d₆) δ 7.48-7.31 (m, 3H), 7.24 (d, 1H), 7.07-6.75 (m, 3H), 6.20 (s, 1H), 5.56-5.40 (m, 1H), 4.70 (br. d, 0.5H), 4.40-4.14 (m, 1H), 4.05-3.70 (m, 2H), 3.24-2.90 (m, 2.5H), 2.90-2.70 (m, 3H), 2.25-2.06 (m, 1H), 2.11 (s, 3H), 1.96-1.61 (m, 2H), 1.52-1.40 (m, 3H). | 95% |
| 74 | 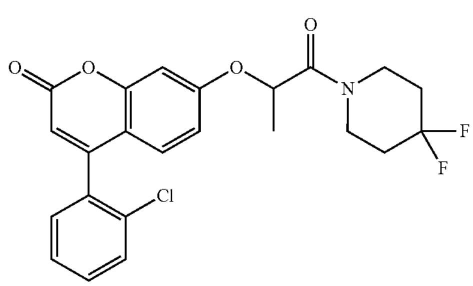 [SMILES: CC(Oc1ccc2c(-c3ccccc3Cl)cc(=O)oc2c1)C(=O)N1CCC(F)(F)CC1] | 4E | (400 MHz, DMSO-d₆) δ 7.68-7.64 (m, 1H), 7.60-7.43 (m, 3H), 7.00-6.96 (m, 1H), 6.91 (dd, 1H), 6.85-6.78 (m, 1H), 6.28 (s, 1H), 5.54-5.45 (m, 1H), 3.76-3.43 (m, 4H), 2.16-2.09 (m, 4H), 1.45 (d, 3H). | 96% |

TABLE 3-continued

Compounds of formula (I) of the invention

| Ex | Structure | BB | ¹H-NMR | LC purity %ee |
|---|---|---|---|---|
| 75 | 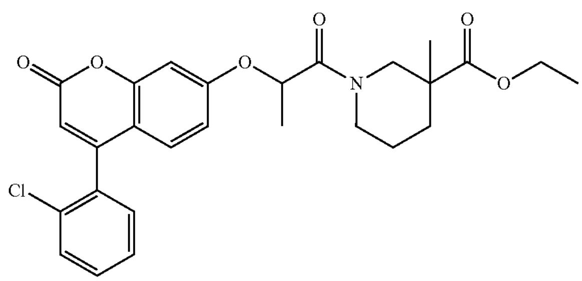 [SMILES: CCOC(=O)C1(C)CCCN(C(=O)C(C)Oc2ccc3c(-c4ccccc4Cl)cc(=O)oc3c2)C1] | 4E | (400 MHz, DMSO-d₆) δ 7.70-7.65 (m, 1H), 7.62-7.51 (m, 2H), 7.50-7.44 (m, 1H), 7.04-6.74 (m, 3H), 6.32-6.26 (m, 1H), 5.58-5.40 (m, 1H), 4.44-3.47 (m, 2H), 3.10-2.94 (m, 1H), 2.08-1.92 (m, 1H), 1.72-1.53 (m, 2H), 1.53-1.38 (m, 6H), 1.25-1.10 (m, 4H), 1.10-0.97 (m, 3H). | 100% |
| 76 | [Abs] | 4E | (400 MHz, DMSO-d₆) δ 7.67 (d, 1H), 7.60-7.51 (m, 2H), 7.50-7.45 (m, 1H), 7.04-6.87 (m, 2H), 6.87-6.78 (m, 1H), 6.29 (s, 1H), 5.57-5.38 (m, 1H), 4.35-4.13 (m, 1H), 3.87 (m, 1H-signal under H₂O peak), 3.33-3.05 (m, 1H), 3.02-2.90 (m, 3H), 2.86-2.75 (m, 3H), 2.74-2.54 (m, 2H), 1.96-1.31 (m, 4H), 1.47-1.42 (m, 3H). | 95% |
| 77 | 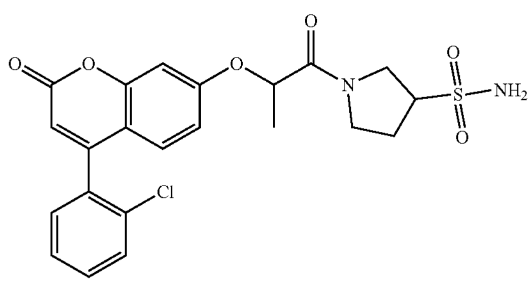 [SMILES: CC(Oc1ccc2c(-c3ccccc3Cl)cc(=O)oc2c1)C(=O)N1CCC(S(N)(=O)=O)C1] | 4E | (400 MHz, DMSO-d₆) δ 7.67 (dd, 1H), 7.58 (td, 1H), 7.53 (t, 1H), 7.50-7.45 (m, 1H), 7.07 (d, 2H), 7.00-6.94 (m, 1H), 6.91-6.76 (m, 2H), 6.31-6.28 (m, 1H), 5.28-5.15 (m, 1H), 4.15-3.71 (m, 3H), 3.57-3.32 (m, 2H), 2.40-2.14 (m, 2H), 1.52-1.41 (m, 3H). | 97% |
| 78 | [Abs] | 3E | (400 MHz, DMSO-d₆) δ 7.45-7.38 (m, 2H), 7.35 (t, 1H), 7.23 (d, 1H), 7.02-6.91 (m, 1H), 6.90-6.77 (m, 2H), 6.18 (s, 1H), 5.56-5.38 (m, 1H), 4.36-4.13 (m, 1H), 3.99-3.86 (m, 1H), 3.33-3.04 (m, 1H), 3.02-2.94 (m, 3H), 2.84-2.75 (m, 3H), 2.73-2.54 (m, 2H), 2.11 (s, 3H), 1.95-1.34 (m, 4H), 1.48-1.42 (m, 3H). | 98% |
| 79 | 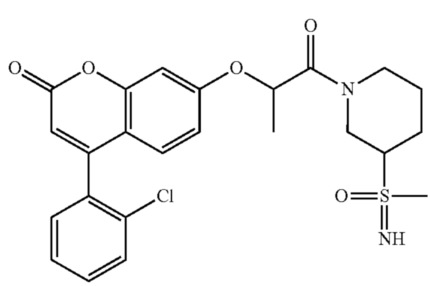 [SMILES: CC(Oc1ccc2c(-c3ccccc3Cl)cc(=O)oc2c1)C(=O)N1CCCC(S(C)(=N)=O)C1] | 4E | (400 MHz, DMSO-d₆) δ 7.70-7.64 (m, 1H), 7.62-7.45 (m, 3H), 7.08-6.77 (m, 3H), 6.31 (s, 1H), 5.58-5.40 (m, 1H), 4.76-4.62 (m, 1H), 4.41-4.14 (m, 1H), 4.04-3.85 (m, 1H), 3.82-3.71 (m, 1H), 3.15-2.92 (m, 2H), 2.89-2.76 (m, 3H), 2.23-2.10 (m, 1H), 1.92-1.64 (m, 2H), 1.50-1.44 (m, 3H). | 90% |

TABLE 3-continued

Compounds of formula (I) of the invention

| Ex | Structure | BB | ¹H-NMR | LC purity %ee |
|---|---|---|---|---|
| 80 | 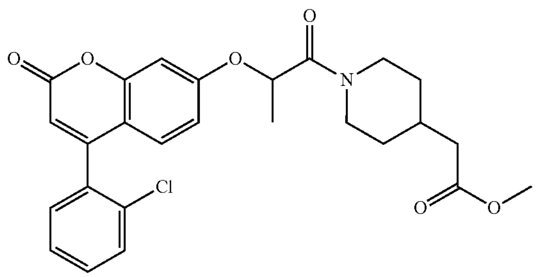 | 4E | (400 MHz, DMSO-d₆) δ 7.67 (dd, 1H), 7.58 (td, 1H), 7.53 (td, 1H), 7.50-7.46 (m, 1H), 6.97-6.88 (m, 2H), 6.84-6.78 (m, 1H), 6.29 (s, 1H), 5.51-5.37 (m, 1H), 4.29 (br. d, 1H), 3.97 (br. d, 1H), 3.58 (s, 3H), 3.21-3.01 (m, 1H), 2.69-2.55 (m, 1H), 2.30 (d, 1H), 2.25 (d, 1H), 1.98-1.89 (m, 1H), 1.76-1.63 (m, 2H), 1.45-1.42 (t, 3H), 1.32-0.92 (m, 2H). | 95% |
| 81 (2D) | 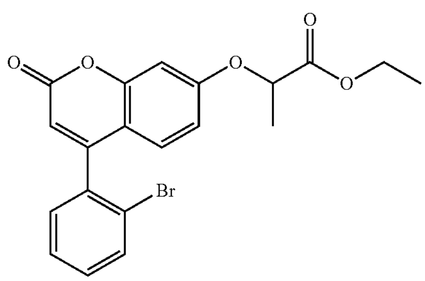 [SMILES: CCOC(=O)C(C)Oc1ccc2c(-c3ccccc3Br)cc(=O)oc2c1] | 2B | (400 MHz, CDCl₃) δ 7.65 (d, 1H), 7.41-7.35 (m, 1H), 7.32-7.26 (m, 1H), 7.22-7.19 (m, 1H), 6.90 (d, 1H), 6.77-6.64 (m, 2H), 6.13 (s, 1H), 4.73 (q, 1H), 4.17 (q, 2H), 1.59 (d, 3H), 1.22 (td, 3H). | 97% |
| 82 | 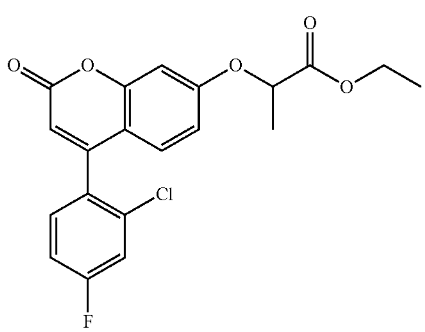 [SMILES: CCOC(=O)C(C)Oc1ccc2c(-c3ccc(F)cc3Cl)cc(=O)oc2c1] | 1B | (300 MHz, CDCl₃) δ 7.26-7.16 (m, 2H), 7.12-7.01 (m, 1H), 6.94-6.86 (m, 1H), 6.79-6.63 (m, 2H), 6.13 (s, 1H), 4.73 (q, 1H), 4.17 (q, 2H), 1.59 (d, 3H), 1.22 (t, 3H). | 95% |
| 83 | 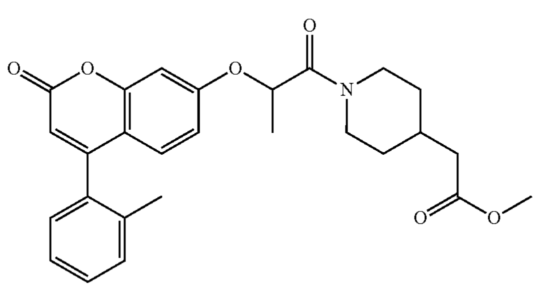 [SMILES: COC(=O)CC1CCN(C(=O)C(C)Oc2ccc3c(-c4ccccc4C)cc(=O)oc3c2)CC1] | 3E | (400 MHz, DMSO-d₆) δ 7.45-7.38 (m, 2H), 7.35 (t, 1H), 7.24 (d, 1H), 6.96-6.84 (m, 2H), 6.82-6.77 (m, 1H), 6.18 (d, 1H), 5.49-5.37 (m, 1H), 4.29 (br. d, 1H), 4.01-3.91 (m, 1H), 3.58 (s, 3H), 3.20-3.01 (m, 1H), 2.66-2.55 (m, 1H), 2.29 (d, 1H), 2.25 (d, 1H), 2.11 (s, 3H), 2.01-1.89 (m, 1H), 1.76-1.62 (m, 2H), 1.45-1.42 (t, 3H), 1.31-0.92 (m, 2H). | 95% |
| 84 | 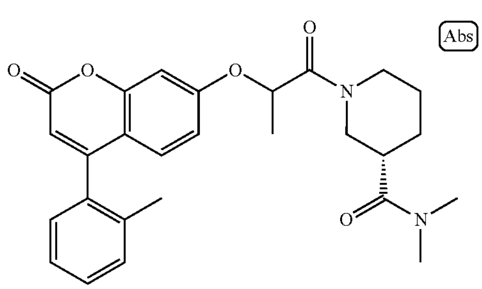 [SMILES: Cc1ccccc1-c1cc(=O)oc2cc(OC(C)C(=O)N3CCC[C@H](C(=O)N(C)C)C3)ccc12] | 3E | (400 MHz, DMSO-d₆) δ 7.46-7.33 (m, 3H), 7.23 (d, 1H), 7.03-6.77 (m, 3H), 6.18 (s, 1H), 5.55-5.38 (m, 1H), 4.35-4.14 (m, 1H), 3.89-3.85 (m, 1H), 3.21-3.05 (m, 1H), 3.02-2.92 (m, 3H), 2.85-2.75 (m, 3H), 2.74-2.54 (m, 2H), 2.11 (s, 3H), 1.94-1.39 (m, 4H), 1.48-1.41 (m, 3H). | 95% |

TABLE 3-continued

Compounds of formula (I) of the invention

| Ex | Structure | BB | ¹H-NMR | LC purity %ee |
|---|---|---|---|---|
| 85 | 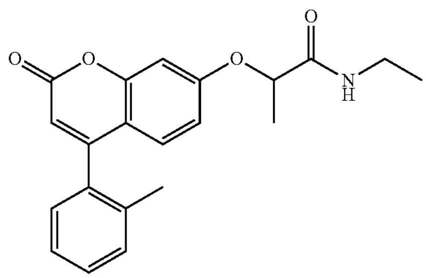 [SMILES: CCNC(=O)C(C)Oc1ccc2c(-c3ccccc3C)cc(=O)oc2c1] | 3E | (400 MHz, CDCl$_3$) δ 7.42-7.37 (m, 1H), 7.35-7.28 (m, 2H), 7.16 (d, 1H), 6.99 (d, 1H), 6.92 (br. t, 1H), 6.74 (dt, 1H), 6.30 (br. s, 1H), 6.19 (s, 1H), 4.74 (q, 1H), 3.40-3.28 (m, 2H), 2.15 (s, 3H), 1.61 (d, 3H), 1.13 (td, 3H). | 95% |
| 86 | 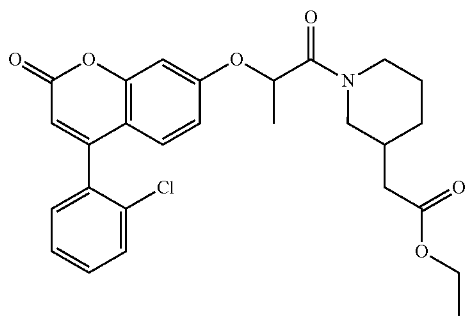 [SMILES: CCOC(=O)CC1CCCN(C(=O)C(C)Oc2ccc3c(-c4ccccc4Cl)cc(=O)oc3c2)C1] | 4E | (400 MHz, DMSO-d$_6$) δ 7.67 (dd, 1H), 7.58 (td, 1H), 7.54 (td, 1H), 7.50-7.46 (m, 1H), 6.95-6.87 (m, 2H), 6.86-6.79 (m, 1H), 6.29 (s, 1H), 5.50-5.35 (m, 1H), 4.27-3.99 (m, 3H), 3.98-3.77 (m, 1H), 3.22-2.76 (m, 1H), 2.64-2.46 (m, 1H), 2.31-2.12 (m, 2H), 1.86-1.59 (m, 3H), 1.52-1.42 (m, 3H), 1.32-1.21 (m, 2H), 1.20-1.12 (m, 3H). | 98% |
| 87 | 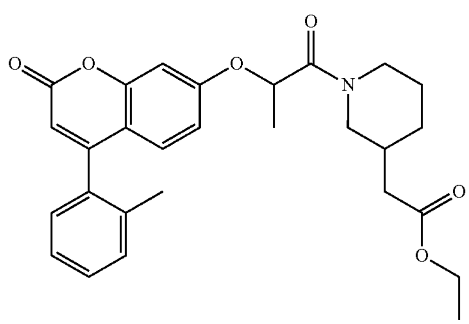 [SMILES: CCOC(=O)CC1CCCN(C(=O)C(C)Oc2ccc3c(-c4ccccc4C)cc(=O)oc3c2)C1] | 3E | (400 MHz, DMSO-d$_6$) δ 7.47-7.31 (m, 3H), 7.27-7.20 (m, 2H), 6.99-6.76 (m, 3H), 6.20-6.17 (m, 1H), 5.49-5.33 (m, 1H), 4.29-3.75 (m, 4H), 3.26-3.04 (m, 1H), 2.97-2.58 (m, 1H), 2.34-2.15 (m, 2H), 2.14-2.05 (m, 3H), 2.02-1.58 (m, 3H), 1.51-1.41 (m, 3H), 1.32-1.20 (m, 1H), 1.18-1.10 (m, 3H). | 99% |
| 88 | 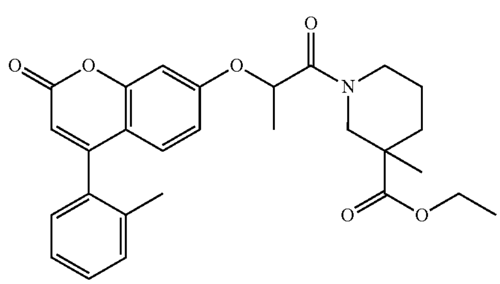 [SMILES: CCOC(=O)C1(C)CCCN(C(=O)C(C)Oc2ccc3c(-c4ccccc4C)cc(=O)oc3c2)C1] | 3E | (400 MHz, DMSO-d$_6$) δ 7.43-7.37 (m, 2H), 7.33 (t, 1H), 7.21 (d, 1H), 7.01-6.71 (m, 3H), 6.19-6.12 (m, 1H), 5.56-5.37 (m, 1H), 4.42-3.81 (m, 3H), 3.75-3.54 (m, 1H), 3.25-2.93 (m, 2H), 2.14-2.07 (m, 3H), 2.03-1.91 (m, 1H), 1.67-1.38 (m, 3H), 1.46-1.41 (m, 3H), 1.20-1.08 (m, 3H), 1.07-0.95 (m, 3H). | 90% |
| 89 | 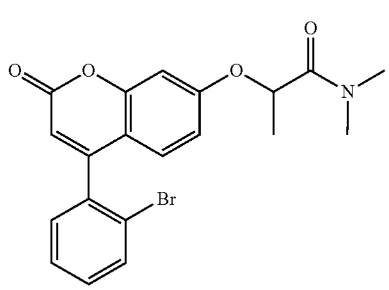 [SMILES: CC(Oc1ccc2c(-c3ccccc3Br)cc(=O)oc2c1)C(=O)N(C)C] | 2B | (400 MHz, CDCl$_3$) δ 7.67-7.63 (m, 1H), 7.41-7.35 (m, 1H), 7.32-7.26 (m, 1H), 7.21-7.17 (m, 1H), 6.89 (d, 1H), 6.76-6.65 (m, 2H), 6.12 (s, 1H), 5.02-4.93 (m, 1H), 3.07 (d, 3H), 2.92 (d, 3H), 1.57 (d, 3H). | 92% |

TABLE 3-continued

Compounds of formula (I) of the invention

| Ex | Structure | BB | ¹H-NMR | LC purity %ee |
|---|---|---|---|---|
| 90 | (structure: 4-(2-chloro-4-fluorophenyl)-7-[(1-(cyclopropylamino)-1-oxopropan-2-yl)oxy]-2H-chromen-2-one) | 1E | (400 MHz, DMSO-d₆) δ 7.84 (d, 1H), 7.28 (dd, 1H), 7.17-7.11 (m, 1H), 7.02 (td, 1H), 6.58-6.52 (m, 2H), 6.45 (dt, 1H), 5.90 (s, 1H), 4.38 (q, 1H), 2.27-2.18 (m, 1H), 1.03 (d, 3H), 0.25-0.17 (m, 2H), 0.05-0.02 (m, 2H). | 96% |
| 91 | (structure: 4-(2-chloro-4-fluorophenyl)-7-[(1-(ethylamino)-1-oxopropan-2-yl)oxy]-2H-chromen-2-one) | 1E | (400 MHz, DMSO-d₆) δ 8.17 (br. t, 1H), 7.68 (dd, 1H), 7.57-7.51 (m, 1H), 7.45-7.38 (m, 1H), 7.00-6.91 (m, 2H), 6.90-6.85 (m, 1H), 6.30 (s, 1H), 4.87-4.79 (m, 1H), 3.15-3.02 (m, 2H), 1.44 (d, 3H), 0.99 (td, 3H). | 95% |
| 92 | (structure: 4-(2-bromophenyl)-7-[(1-isopropoxy-1-oxopropan-2-yl)oxy]-2H-chromen-2-one) | 2B | (400 MHz, DMSO-d₆) δ 7.65 (d, 1H), 7.38 (tt, 1H), 7.32-7.27 (m, 1H), 7.22-7.17 (m, 1H), 6.89 (d, 1H), 6.77-6.65 (m, 2H), 6.12 (s, 1H), 5.07-4.96 (m, 1H), 4.72-4.65 (m, 1H), 1.57 (d, 3H), 1.23 (dd, 3H), 1.15 (d, 3H). | 93% |
| 93 | (structure: 4-(2-chlorophenyl)-7-[(1-(dimethylamino)-1-oxopropan-2-yl)oxy]-2H-chromen-2-one) | 4B | (400 MHz, CDCl₃) δ 7.46 (dd, 1H), 7.40-7.30 (m, 2H), 7.23-7.19 (m, 1H), 6.91 (d, 1H), 6.76-6.66 (m, 2H), 6.14 (s, 1H), 5.01-4.93 (m, 1H), 3.07 (d, 3H), 2.92 (d, 3H), 1.57 (d, 3H). | 99% |
| 94 (5E) | (structure: 2-{[4-(2-chloro-3-fluorophenyl)-2-oxo-2H-chromen-7-yl]oxy}propanoic acid) | 5D | (300 MHz, CD₃OD) δ 7.47-7.27 (m, 2H), 7.19-7.10 (m, 1H), 6.94-6.71 (m, 3H), 6.14 (s, 1H), 4.94-4.80 (m, 1H), 1.53 (d, 3H). | 100% |

TABLE 3-continued

Compounds of formula (I) of the invention

| Ex | Structure | BB | ¹H-NMR | LC purity %ee |
|---|---|---|---|---|
| 95 | 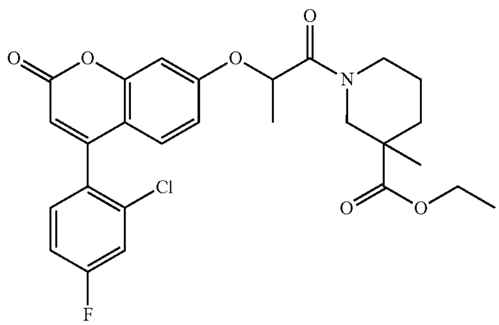 [SMILES: CCOC(=O)C1(C)CCCN(C(=O)C(C)Oc2ccc3c(-c4ccc(F)cc4Cl)cc(=O)oc3c2)C1] | 1E | (400 MHz, DMSO-d₆) δ 7.68 (dd, 1H), 7.57-7.51 (m, 1H), 7.45-7.38 (m, 1H), 7.03-6.74 (m, 3H), 6.31-6.25 (m, 1H), 5.58-5.38 (m, 1H), 4.43-3.53 (m, 4H), 3.18-2.93 (m, 1H), 2.61-2.14 (m, 1H), 2.03-1.91 (m, 1H), 1.67-1.37 (m, 3H), 1.47-1.40 (m, 3H), 1.20-1.08 (m, 3H), 1.06-0.96 (m, 3H). | 90% |
| 96 (4E) | 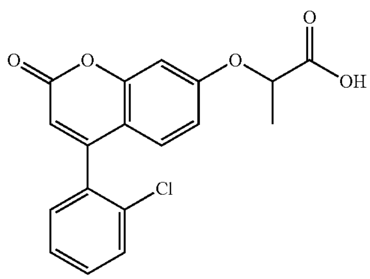 [SMILES: CC(Oc1ccc2c(-c3ccccc3Cl)cc(=O)oc2c1)C(=O)O] | 4D | (400 MHz, DMSO-d₆) δ 13.17 (br. s, 1H), 7.67-7.64 (m, 1H), 7.59-7.45 (m, 3H), 6.99-6.95 (m, 1H), 6.91-6.83 (m, 2H), 6.28 (s, 1H), 5.08-5.00 (m, 1H), 1.52 (d, 3H). | 98% |
| 97 (3E) | 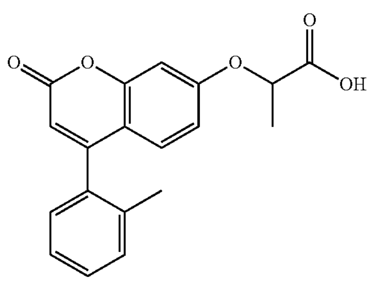 [SMILES: Cc1ccccc1-c1cc(=O)oc2cc(OC(C)C(=O)O)ccc12] | 3D | (400 MHz, DMSO-d₆) δ 7.44-7.29 (m, 3H), 7.20 (d, 1H), 6.97 (d, 1H), 6.93-6.90 (m, 1H), 6.86-6.81 (m, 1H), 6.13 (s, 1H), 4.96 (q, 1H), 2.15 (s, 3H), 1.62 (d, 3H). | 95% |
| 98 | 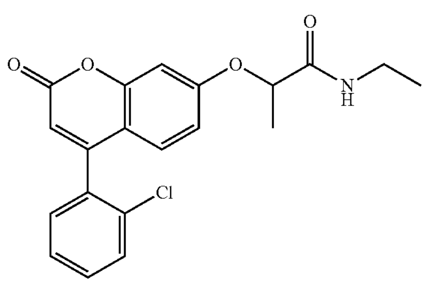 [SMILES: CCNC(=O)C(C)Oc1ccc2c(-c3ccccc3Cl)cc(=O)oc2c1] | 4E | (400 MHz, CDCl₃) δ 7.49-7.46 (m, 1H), 7.42-7.32 (m, 2H), 7.25-7.21 (m, 1H), 6.94 (d, 1H), 6.85 (d, 1H), 6.71-6.67 (m, 1H), 6.23 (br. s, 1H), 6.17 (s, 1H), 4.71-4.62 (m, 1H), 3.22-3.19 (m, 2H), 1.54 (d, 3H), 1.06 (td, 3H). | 100% |
| 99 (1E) | 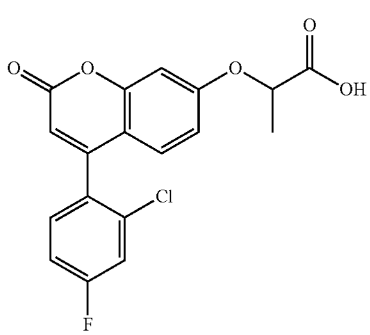 [SMILES: CC(Oc1ccc2c(-c3ccc(F)cc3Cl)cc(=O)oc2c1)C(=O)O] | 1D | (300 MHz, CDCl₃) δ 7.27-7.19 (m, 2H), 7.08 (td, 1H), 7.93 (d, 1H), 6.82-6.69 (m, 2H), 6.15 (s, 1H), 4.80 (q, 1H), 1.66 (d, 3H). | 90% |

TABLE 3-continued

Compounds of formula (I) of the invention

| Ex | Structure | BB | ¹H-NMR | LC purity %ee |
|---|---|---|---|---|
| 100 | 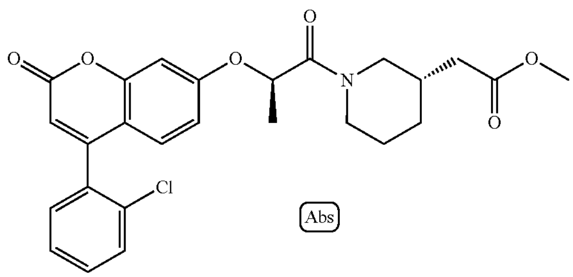 [SMILES: COC(=O)C[C@@H]1CCCN(C(=O)[C@@H](C)Oc2ccc3c(-c4ccccc4Cl)cc(=O)oc3c2)C1] | (R)-4E | (300 MHz, DMSO-d₆) δ 7.70-7.64 (m, 1H), 7.62-7.45 (m, 3H), 6.97-6.86 (m, 2H), 6.86-6.78 (m, 1H), 6.30 (s, 1H), 5.53-5.36 (m, 1H), 4.25-4.06 (m, 1H), 4.00-3.77 (m, 1H), 3.61-3.55 (m, 3H), 3.17-2.84 (m, 1H), 2.68-2.55 (m, 1H), 2.35-2.12 (m, 2H), 1.86-1.58 (m, 3H), 1.56-1.39 (m, 3H), 1.30-1.20 (m, 2H). | 91% ee 100% (see 102) |
| 101 | 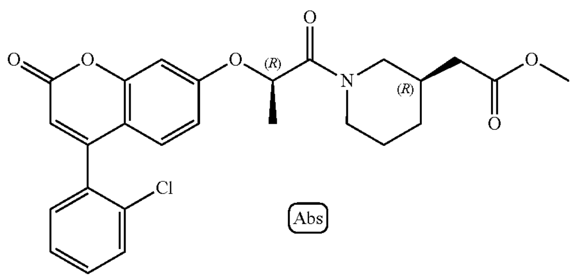 | (R)-4E | (300 MHz, DMSO-d₆) δ 7.68 (dd, 1H), 7.61-7.46 (m, 3H), 6.97-6.78 (m, 3H), 6.30 (s, 1H), 5.52-5.36 (m, 1H), 4.25-4.05 (m, 1H), 4.00-3.76 (m, 1H), 3.64-3.52 (m, 3H), 3.17-2.83 (m, 1H), 2.68-2.54 (m, 1H), 2.34-2.12 (m, 2H), 1.89-1.58 (m, 3H), 1.53-1.40 (m, 3H), 1.31-1.20 (m, 2H). | 90% ee 100% (see 103) |
| 102 | 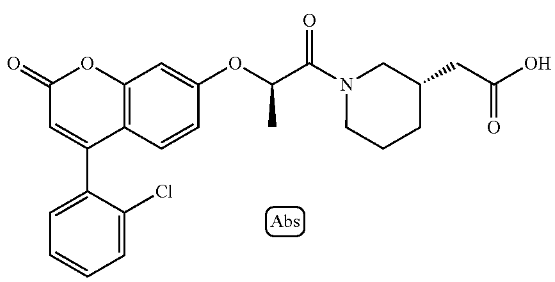 [SMILES: C[C@@H](Oc1ccc2c(-c3ccccc3Cl)cc(=O)oc2c1)C(=O)N1CCC[C@@H](CC(=O)O)C1] | (R)-4E, 100 | (300 MHz, DMSO-d₆) δ 12.20 (br. s, 1H), 7.70-7.64 (m, 1H), 7.62-7.44 (m, 3H), 6.97-6.77 (m, 3H), 6.29 (s, 1H), 5.54-5.27 (m, 1H), 4.25-4.11 (m, 1H), 4.05-3.77 (m, 1H), 3.14-2.82 (m, 1H), 2.68-2.53 (m, 1H), 2.24-2.08 (m, 2H), 1.87-1.58 (m, 3H), 1.50-1.43 (m, 3H), 1.32-1.13 (m, 2H). | 97% ee 100% |
| 103 | 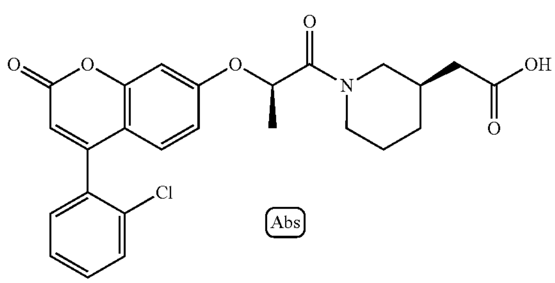 [SMILES: C[C@@H](Oc1ccc2c(-c3ccccc3Cl)cc(=O)oc2c1)C(=O)N1CCC[C@H](CC(=O)O)C1] | (R)-4E, 101 | (300 MHz, DMSO-d₆) δ 12.20 (br. s, 1H), 7.70-7.63 (m, 1H), 7.62-7.43 (m, 3H), 6.97-6.78 (m, 3H), 6.30 (s, 1H), 5.54-5.30 (m, 1H), 4.26-4.11 (m, 1H), 4.05-3.77 (m, 1H), 3.14-2.83 (m, 1H), 2.68-2.54 (m, 1H), 2.24-2.09 (m, 2H), 1.87-1.60 (m, 3H), 1.57-1.38 (m, 3H), 1.33-1.13 (m, 2H). | 97% ee 100% |
| 104 | 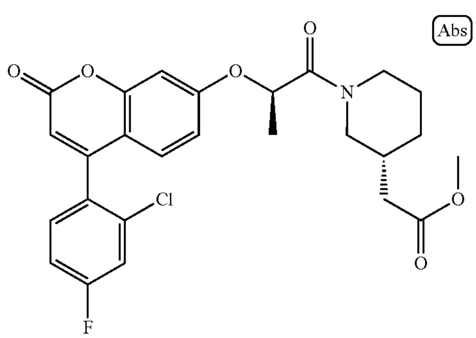 [SMILES: COC(=O)C[C@H]1CCCN(C(=O)[C@@H](C)Oc2ccc3c(-c4ccc(F)cc4Cl)cc(=O)oc3c2)C1] | (R)-1E | (300 MHz, DMSO-d₆) δ 7.71 (dd, 1H), 7.61-7.51 (m, 1H), 7.44 (td, 1H), 7.00-6.87 (m, 2H), 6.86-6.77 (m, 1H), 6.32 (s, 1H), 5.54-5.30 (m, 1H), 4.25-4.07 (m, 1H), 4.00-3.76 (m, 1H), 3.64-3.51 (m, 3H), 3.17-2.83 (m, 1H), 2.69-2.53 (m, 1H), 2.35-2.13 (m, 2H), 1.87-1.58 (m, 3H), 1.54-1.39 (m, 3H), 1.32-1.16 (m, 2H). | 96% ee 99% (see 106) |

TABLE 3-continued

Compounds of formula (I) of the invention

| Ex | Structure | BB | ¹H-NMR | LC purity %ee |
|---|---|---|---|---|
| 105 | [Structure: 4-(2-chloro-4-fluorophenyl)-7-[(R)-1-oxo-1-(3-(methoxycarbonylmethyl)piperidin-1-yl)propan-2-yloxy]-2H-chromen-2-one] | (R)-1E | (300 MHz, DMSO-d₆) δ 7.71 (dd, 1H), 7.61-7.52 (m, 1H), 7.44 (dt, 1H), 6.99-6.88 (m, 2H), 6.86-6.78 (m, 1H), 6.32 (s, 1H), 5.54-5.31 (m, 1H), 4.25-4.06 (m, 1H), 4.01-3.74 (m, 1H), 3.63-3.54 (m, 3H), 3.17-2.83 (m, 1H), 2.69-2.54 (m, 1H), 2.35-2.18 (m, 2H), 1.86-1.59 (m, 3H), 1.53-1.40 (m, 3H), 1.29-1.20 (m, 2H). | 92% ee 99% (see 107) |
| 106 | [Structure: corresponding carboxylic acid analog] | (R)-1E, 104 | (300 MHz, DMSO-d₆) δ 12.24 (br. s, 1H), 7.71 (dd, 1H), 7.60-7.51 (m, 1H), 7.43 (td, 1H), 7.00-6.87 (m, 2H), 6.85-6.77 (m, 1H), 6.31 (s, 1H), 5.54-5.30 (m, 1H), 4.25-4.10 (m, 1H), 4.05-3.77 (m, 1H), 3.14-2.83 (m, 1H), 2.68-2.45 (m, 1H), 2.24-2.08 (m, 2H), 1.87-1.59 (m, 3H), 1.53-1.38 (m, 3H), 1.32-1.13 (m, 2H). | 96% ee 99% |
| 107 | [Structure: corresponding carboxylic acid analog] | (R)-1E, 105 | (300 MHz, DMSO-d₆) δ 12.27 (br. s, 1H), 7.70 (dd, 1H), 7.61-7.51 (m, 1H), 7.43 (td, 1H), 7.00-6.87 (m, 2H), 6.86-6.76 (m, 1H), 6.31 (s, 1H), 5.55-5.29 (m, 1H), 4.28-4.09 (m, 1H), 4.06-3.76 (m, 1H), 3.14-2.82 (m, 1H), 2.68-2.45 (m, 1H), 2.25-2.08 (m, 2H), 1.88-1.58 (m, 3H), 1.54-1.39 (m, 3H), 1.33-1.13 (m, 2H). | 95% ee 99% |
| 108 | [Structure: 3-carboxypiperidinyl analog] | (R)-1E | (300 MHz, DMSO-d₆) δ 12.45 (br. s, 1H), 7.71 (dd, 1H), 7.60-7.51 (m, 1H), 7.44 (td, 1H), 7.02-6.89 (m, 2H), 6.86-6.78 (m, 1H), 6.32 (s, 1H), 5.59-5.39 (m, 1H), 4.37-3.83 (m, 2H), 3.30-3.10 (m, 1H), 2.94-2.71 (m, 1H), 2.34-2.19 (m, 1H), 2.06-1.88 (m, 1H), 1.83-1.52 (m, 2H), 1.49-1.29 (m, 1H), 1.45 (d, 3H). | 97% ee 100% |

TABLE 3-continued

Compounds of formula (I) of the invention

| Ex | Structure | BB | ¹H-NMR | LC purity %ee |
|---|---|---|---|---|
| 109 | [structure with coumarin, 2-Cl-phenyl, O-CH(Et)-C(O)-N-piperidine-3-C(O)O-ethyl, Abs] | 6E | (300 MHz, DMSO-d$_6$) δ 7.70-7.64 (m, 1H), 7.62-7.44 (m, 3H), 7.02-6.75 (m, 3H), 6.30 (s, 1H), 5.39-5.18 (m, 1H), 4.27-3.94 (m, 3H), 3.92-3.53 (m, 1H), 3.28-3.00 (m, 2H), 2.61-2.33 (m, 1H), 2.04-1.30 (m, 6H), 1.20-1.08 (m, 3H), 1.04-0.92 (m, 3H). | 99% ee 94% (see 110) |
| 110 | [structure with coumarin, 2-Cl-phenyl, O-CH(Et)-C(O)-N-piperidine-3-COOH, Abs] | 6E, 109 | (300 MHz, DMSO-d$_6$) δ 12.52 (br. s, 1H), 7.71-7.64 (m, 1H), 7.62-7.45 (m, 3H), 6.99-6.75 (m, 3H), 6.29 (s, 1H), 5.38-5.18 (m, 1H), 4.38-3.99 (m, 1H), 3.97-3.75 (m, 1H), 3.70-3.52 (m, 1H), 3.24-2.80 (m, 2H), 2.05-1.45 (m, 5H), 1.42-1.28 (m, 1H), 0.99 (t, 3H). | 99% ee 94% |
| 111 | [structure with coumarin, 2-Cl-4-F-phenyl, O-CH(Me)-C(O)-N-piperidine-3-C(O)O-ethyl, Abs] | (R)-1E | (400 MHz, DMSO-d$_6$) δ 7.73-7.67 (m, 1H), 7.60-7.53 (m, 1H), 7.47-7.40 (m, 1H), 7.01-6.89 (m, 2H), 6.88-6.76 (m, 1H), 6.31 (s, 1H), 5.53-5.43 (m, 1H) 4.25-4.00 (m, 2.5H), 3.87-3.74 (m, 1H), 3.69-3.53 (m, 1H), 3.27-3.17 (m, 1H), 3.06-2.95 (m, 0.5H), 2.64-2.36 (m, 1H), 2.02-1.41 (m, 7H), 1.22-1.13 (m, 3H). | 99% ee 100% (see 14) |
| 112 | [structure with coumarin, 2-Cl-phenyl, O-C(Me)$_2$-COOH] | 7D (113) | (400 MHz, DMSO-d$_6$) δ 7.67 (dd, 1H), 7.60-7.48 (m, 3H), 6.93 (d, 1H), 6.79-6.74 (m, 2H), 6.33 (s, 1H), 1.58 (s, 6H). | 100% |
| 113 | [structure with coumarin, 2-Cl-phenyl, O-C(Me)$_2$-C(O)O-ethyl] | 7B | (400 MHz, DMSO-d$_6$) δ 13.31 (br. s, 1H), 7.65 (dd, 1H), 7.58-7.45 (m, 3H), 6.91 (d, 1H), 6.78-6.76 (m, 2H), 6.29 (s, 1H), 4.19 (q, 3H), 1.61 (s, 6H), 1.16 (t, 2H). | 100% |

TABLE 3-continued

Compounds of formula (I) of the invention

| Ex | Structure | BB | ¹H-NMR | LC purity %ee |
|---|---|---|---|---|
| 114 | 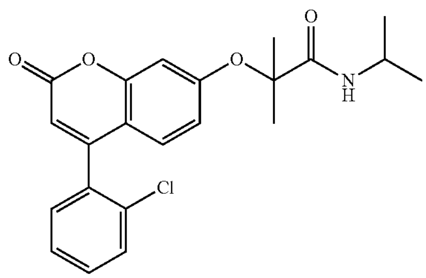 [SMILES: CC(C)NC(=O)C(C)(C)Oc1ccc2c(-c3ccccc3Cl)cc(=O)oc2c1] | 7E (112) | (400 MHz, DMSO-d₆) δ 7.90 (d, 1H), 7.69-7.65 (m, 1H), 7.60-7.47 (m, 3H), 6.94-6.90 (m, 1H), 6.84-6.78 (m, 2H), 6.31 (s, 1H), 3.98-3.87 (m, 1H), 1.51 (s, 6H), 1.02 (dd, 6H). | 96% |
| 115 | 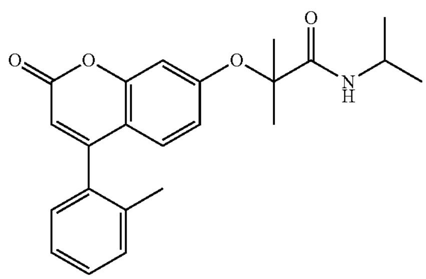 [SMILES: Cc1ccccc1-c1cc(=O)oc2cc(OC(C)(C)C(=O)NC(C)C)ccc12] | 8E | (400 MHz, DMSO-d₆) δ 7.87 (d, 1H), 7.44-7.30 (m, 3H), 7.24-7.21 (m, 1H), 6.87 (d, 1H), 6.84 (d, 1H), 6.77 (dd, 1H), 6.19 (s, 1H), 3.96-3.84 (m, 1H), 2.09 (s, 3H), 1.49 (s, 6H), 1.00 (dd, 6H). | 96% |
| 116 | 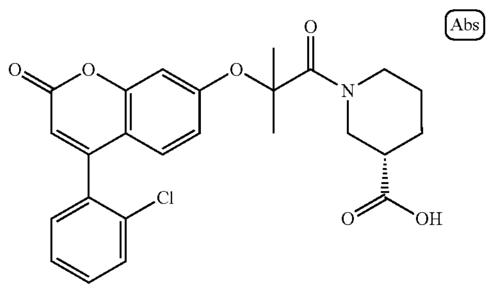 [SMILES: CC(C)(Oc1ccc2c(-c3ccccc3Cl)cc(=O)oc2c1)C(=O)N1CCC[C@H](C(=O)O)C1] | 7E (112) | (400 MHz, DMSO-d₆) δ 7.66-7.64 (m, 1H), 7.58-7.46 (m, 3H), 6.93 (d, 1H), 6.81-6.74 (m, 2H), 6.31 (s, 1H), 4.61-4.05 (m, 2H), 3.08-2.69 (m, 2H), 2.24-2.09 (m, 1H), 1.88-1.38 (m, 4H), 1.59 (d, 6H). | 100% |
| 117 | 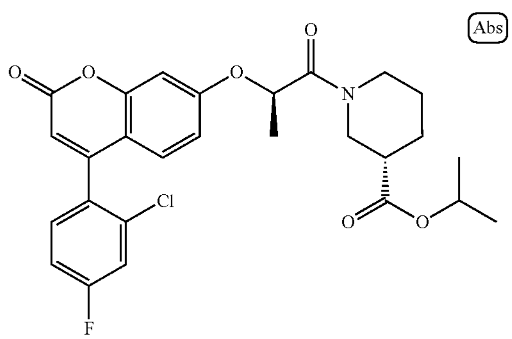 [SMILES: CC(C)OC(=O)[C@H]1CCCN(C(=O)[C@@H](C)Oc2ccc3c(-c4ccc(F)cc4Cl)cc(=O)oc3c2)C1] | (R)-1E | (400MHz, DMSO-d₆) δ 7.73-7.68 (m, 1H), 7.60-7.53 (m, 1H), 7.47-7.40 (m, 1H), 7.09-6.76 (m, 3H), 6.31 (s, 1H), 5.56-5.42 (m, 1H), 5.07-4.79 (m, 1H), 4.19-4.09 (m, 0.5H), 3.84-3.72 (m, 1H), 3.68-3.51 (m, 1H), 3.27-3.17 (m, 1H), 3.08-2.98 (m, 0.5H), 2.42-2.31 (m, 1H), 2.03-1.33 (m, 4H), 1.49-1.41 (m, 3H), 1.21-1.13 (m, 6H). | 99% ee 94% |
| 118 | 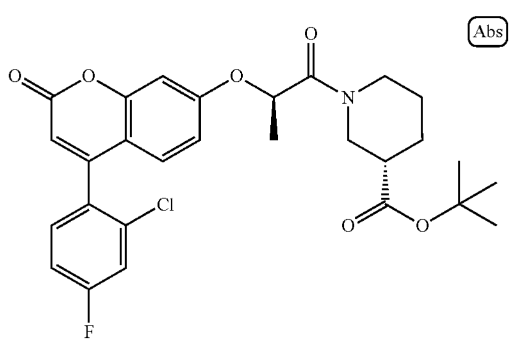 [SMILES: C[C@@H](Oc1ccc2c(-c3ccc(F)cc3Cl)cc(=O)oc2c1)C(=O)N1CCC[C@H](C(=O)OC(C)(C)C)C1] | (R)-1E | (400 MHz, DMSO-d₆) δ 7.70 (dd, 1H), 7.59-7.52 (m, 1H), 7.43 (td, 1H), 7.10-6.76 (m, 3H), 6.33-6.29 (m, 1H), 5.56-5.42 (m, 1H), 4.10-4.03 (m, 0.5H), 3.81-3.68 (m, 1H), 3.65-3.46 (m, 1H), 3.29-3.19 (m, 1H), 3.11-3.03 (m, 0.5H), 2.48-2.26 (m, 1H), 1.94-1.82 (m, 1H), 1.81-1.27 (m, 15H). | 98% ee 100% |

TABLE 3-continued
Compounds of formula (I) of the invention
| Ex | Structure | BB | $^1$H-NMR | LC purity %ee |
|----|-----------|----|-----------|---------------|
| 119 | 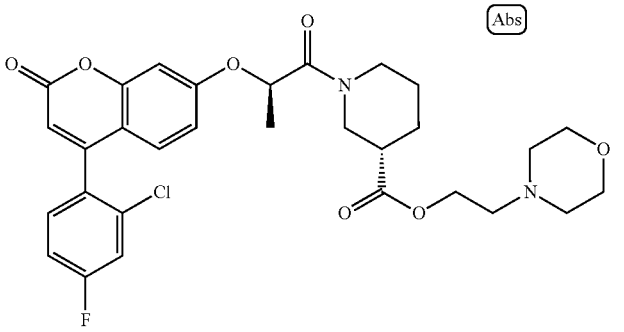 [SMILES: C[C@@H](Oc1ccc2c(-c3ccc(F)cc3Cl)cc(=O)oc2c1)C(=O)N1CCC[C@H](C(=O)OCCN2CCOCC2)C1] | 14, M10 | (400MHz, DMSO-d$_6$) δ 7.70 (dd, 1H), 7.60-7.52 (m, 1H), 7.47-7.40 (m, 1H), 7.05-6.76 (m, 3H), 6.31 (s, 1H), 5.53-5.42 (m, 1H), 4.37-4.19 (m, 1H), 4.18-4.02 (m, 2H), 3.85-3.71 (m, 1H), 3.67-3.45 (m, 5H), 3.21-2.90 (m, 2H), 2.65-2.28 (m, 6H), 2.03-1.33 (m, 4H), 1.49-1.42 (m, 3H). | 98% ee 90% |
| 120 | 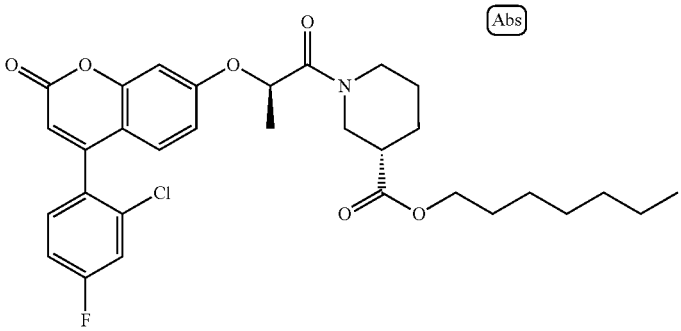 [SMILES: CCCCCCCOC(=O)[C@H]1CCCN(C(=O)[C@@H](C)Oc2ccc3c(-c4ccc(F)cc4Cl)cc(=O)oc3c2)C1] | (R)-1E | (400 MHz, DMSO-d$_6$) δ 7.70 (dd, 1H), 7.59-7.52 (m, 1H), 7.43 (tt, 1H), 7.01-6.88 (m, 2H), 6.87-6.76 (m, 1H), 6.31 (s, 1H), 5.53-5.42 (m, 1H), 4.23-4.10 (m, 1H), 4.08-3.91 (m, 1.5H), 3.85-3.74 (m, 1H), 3.67-3.53 (m, 1H), 3.28-3.15 (m, 1H), 3.04-2.95 (m, 0.5H), 2.64-2.36 (m, 1H), 2.03-1.75 (m, 2H), 1.75-1.50 (m, 4H), 1.50-1.39 (m, 4H), 1.32-1.24 (m, 7H), 0.91-0.80 (m, 3H). | 99% ee 90% |
| 121 | 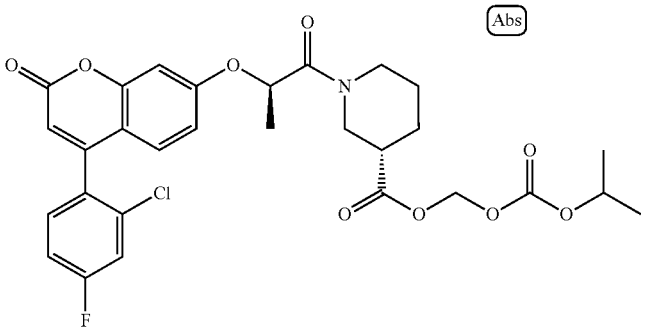 [SMILES: CC(C)OC(=O)OCOC(=O)[C@H]1CCCN(C(=O)[C@@H](C)Oc2ccc3c(-c4ccc(F)cc4Cl)cc(=O)oc3c2)C1] | 14, M11 | (400 MHz, DMSO-d$_6$) δ 7.70 (dd, 1H), 7.59-7.52 (m, 1H), 7.46-7.40 (m, 1H), 7.01-6.90 (m, 2H), 6.87-6.75 (m, 1H), 6.31 (s, 1H), 5.82-5.64 (m, 2H), 5.52-5.42 (m, 1H), 4.84-4.73 (m, 1H), 4.20-3.50 (m, 2H), 3.28-3.02 (m, 2H), 2.72-2.53 (m, 1H), 2.02-1.88 (m, 1H), 1.82-1.36 (m, 6H), 1.28-1.20 (m, 6H). | 99% ee 90% |
| 122 | 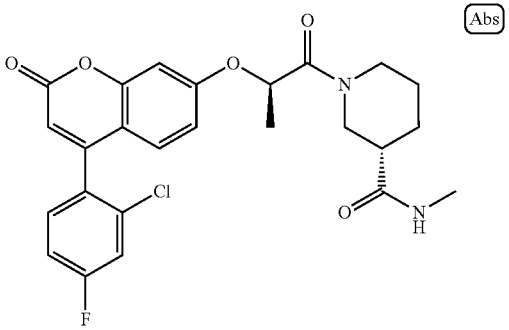 [SMILES: CNC(=O)[C@H]1CCCN(C(=O)[C@@H](C)Oc2ccc3c(-c4ccc(F)cc4Cl)cc(=O)oc3c2)C1] | (R)-1E | (400 MHz, DMSO-d$_6$) δ 7.89-7.77 (m, 1H), 7.73-7.67 (m, 1H), 7.60-7.52 (m, 1H), 7.43 (t, 1H), 6.94 (d, 2H), 6.86-6.78 (m, 1H), 6.31 (s, 1H), 5.56-5.38 (m, 1H), 4.31-4.20 (m, 1H), 3.98-3.86 (m, 1H), 3.19-3.07 (m, 1H), 2.76-2.67 (m, 0.5H), 2.62-2.35 (m, 4H), 2.19-2.09 (m, 0.5H), 1.94-1.53 (m, 3H), 1.45 (t, 3H), 1.40-1.27 (m, 1H). | 97% ee 97% |

TABLE 3-continued

Compounds of formula (I) of the invention

| Ex | Structure | BB | ¹H-NMR | LC purity %ee |
|---|---|---|---|---|
| 123 | 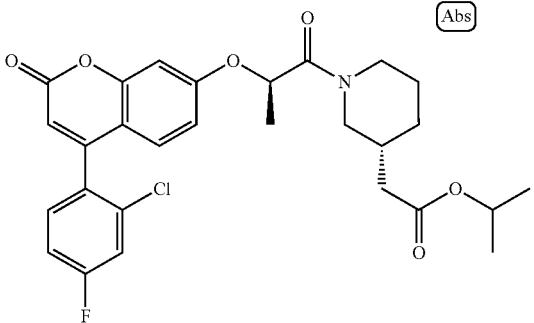 [SMILES: CC(C)OC(=O)C[C@H]1CCCN(C(=O)[C@@H](C)Oc2ccc3c(-c4ccc(F)cc4Cl)cc(=O)oc3c2)C1] [Abs] | 106 (chiral prep HPLC) | (400 MHz, DMSO-d$_6$) δ 7.70 (d, 1H), 7.60-7.52 (m, 1H), 7.43 (td, 1H), 6.98-6.89 (m, 2H), 6.86-6.78 (m, 1H), 6.31 (s, 1H), 5.50-5.34 (m, 1H), 4.95-4.81 (m, 1H), 4.20-4.09 (m, 1H), 3.98-3.78 (m, 1H), 3.23-3.04 (m, 1H), 2.97-2.88 (m, 0.5H), 2.70-2.52 (m, 1H), 2.30-2.09 (m, 2.5H), 1.86-1.71 (m, 2H), 1.71-1.58 (m, 1H), 1.58-1.41 (m, 4H), 1.20-1.13 (m, 6H). | 98% ee 98% |
| 124 | 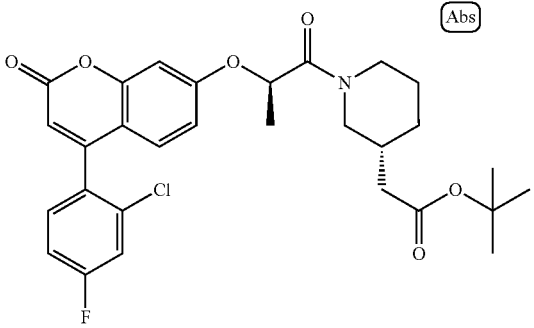 [SMILES: C[C@@H](Oc1ccc2c(-c3ccc(F)cc3Cl)cc(=O)oc2c1)C(=O)N1CCC[C@H](CC(=O)OC(C)(C)C)C1] [Abs] | 106 (chiral prep HPLC) | (400 MHz, DMSO-d$_6$) δ 7.70 (dd, 1H), 7.59-7.52 (m, 1H), 7.43 (td, 1H), 6.98-6.89 (m, 2H), 6.86-6.78 (m, 1H), 6.31 (s, 1H), 5.51-5.32 (m, 1H), 4.15 (d, 1H), 3.94-3.79 (m, 1H), 3.13-2.86 (m, 1H), 2.71-2.62 (m, 0.5H), 2.26-1.96 (m, 2.5H), 1.84-1.59 (m, 3H), 1.56-1.42 (m, 4H) 1.40-1.35 (m, 10H). | 98% ee 100% |
| 125 | 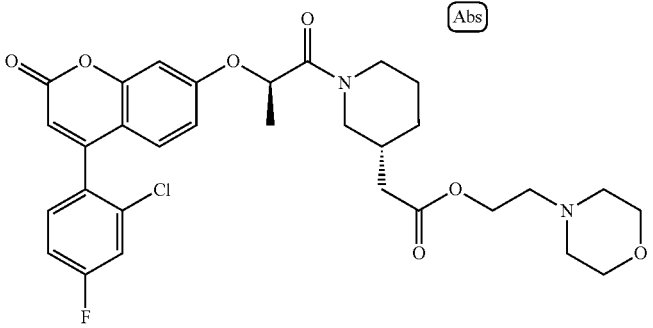 [SMILES: C[C@@H](Oc1ccc2c(-c3ccc(F)cc3Cl)cc(=O)oc2c1)C(=O)N1CCC[C@H](CC(=O)OCCN2CCOCC2)C1] [Abs] | 106, M10 | (400 MHz, DMSO-d$_6$) δ 7.70 (dd, 1H), 7.59-7.52 (m, 1H), 7.46-7.40 (m, 1H), 6.98-6.89 (m, 2H), 6.85-6.79 (m, 1H), 6.31 (s, 1H), 5.51-5.35 (m, 1H), 4.20-4.05 (m, 3H), 3.99-3.77 (m, 1H), 3.57-3.44 (m, 4H), 3.15-3.04 (m, 1H), 2.99-2.88 (m, 1H), 2.71-2.53 (m, 1H), 2.42-2.13 (m, 6H), 1.88-1.71 (m, 2H), 1.71-1.58 (m, 1H), 1.55-1.40 (m, 4H), 1.33-1.19 (m, 2H). | 98% ee 98% |
| 126 | 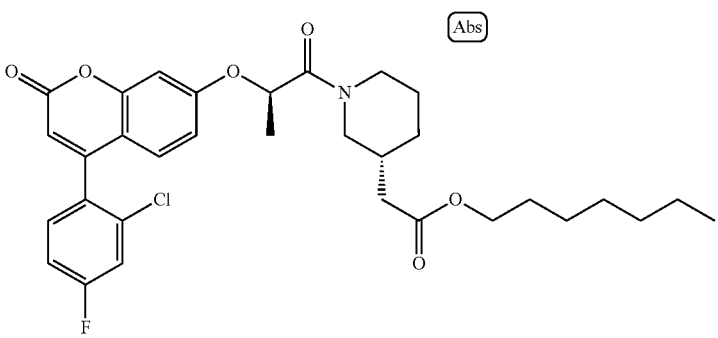 [SMILES: CCCCCCCOC(=O)C[C@H]1CCCN(C(=O)[C@@H](C)Oc2ccc3c(-c4ccc(F)cc4Cl)cc(=O)oc3c2)C1] [Abs] | 106 (chiral prep HPLC) | (400 MHz, DMSO-d$_6$) δ 7.70 (dd, 1H), 7.59-7.52 (m, 1H), 7.46-7.40 (m, 1H), 6.98-6.89 (m, 2H), 6.85-6.78 (m, 1H), 6.31 (s, 1H), 5.51-5.31 (m, 1H), 4.20-4.08 (m, 1H), 4.03-3.78 (m, 3H), 3.14-2.88 (m, 1H), 2.72-2.52 (m, 1H), 2.36-2.10 (m, 2H), 1.85-1.71 (m, 2H), 1.70-1.59 (m, 1H), 1.57-1.50 (m, 2H), 1.50-1.42 (m, 3H), 1.29-1.18 (m, 10H), 0.88-0.80 (m, 3H). | 99% ee 98% |

TABLE 3-continued
Compounds of formula (I) of the invention
| Ex | Structure | BB | ¹H-NMR | LC purity %ee |
|---|---|---|---|---|
| 127 | 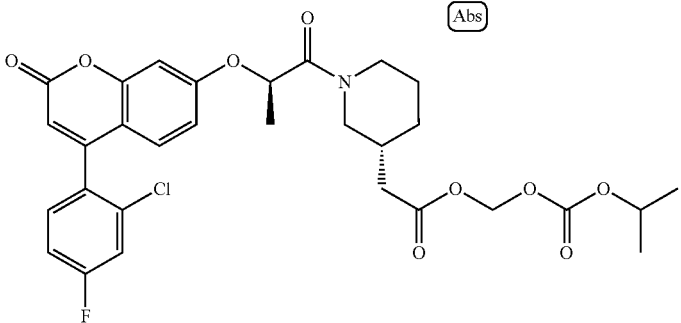 [SMILES: CC(C)OC(=O)OCOC(=O)C[C@H]1CCCN(C(=O)[C@@H](C)Oc2ccc3c(-c4ccc(F)cc4Cl)cc(=O)oc3c2)C1] | 106, M11 | (400 MHz, DMSO-d₆) δ 7.70 (dd, 1H), 7.59-7.53 (m, 1H), 7.47-7.40 (m, 1H), 6.98-6.88 (m, 2H), 6.85-6.78 (m, 1H), 6.31 (s, 1H), 5.68 (dd, 2H), 5.51-5.34 (m, 1H), 4.84-4.73 (m, 1H), 4.24-4.09 (m, 1H), 4.01-3.78 (m, 1H), 3.14-2.88 (m, 1H), 2.69-2.22 (m, 3H), 1.86-1.58 (m, 3H), 1.54-1.41 (m, 3H), 1.31-1.19 (m, 8H). | 98% ee 96% |
| 128 | 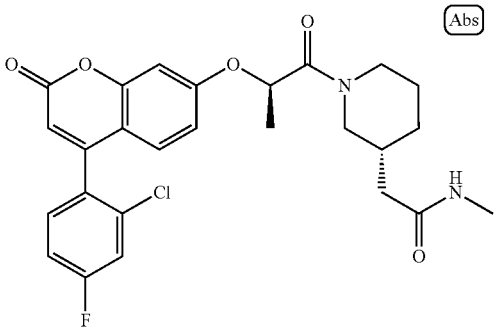 [SMILES: CNC(=O)C[C@H]1CCCN(C(=O)[C@@H](C)Oc2ccc3c(-c4ccc(F)cc4Cl)cc(=O)oc3c2)C1] | 106, M7 | (400 MHz, DMSO-d₆) δ 7.81-7.72 (m, 1H), 7.70 (dd, 1H), 7.60-7.53 (m, 1H), 7.43 (td, 1H), 6.99-6.89 (m, 2H), 6.85-6.78 (m, 1H), 6.31 (s, 1H), 5.52-5.35 (m, 1H), 4.21-4.06 (m, 1H), 3.88 (d, 1H), 3.08-2.85 (m, 1H), 2.76-2.35 (m, 4H), 2.06-2.02 (m, 1H), 2.02-1.90 (m, 1H), 1.87-1.57 (m, 3H), 1.55-1.40 (m, 4H) 1.33-1.12 (m, 1H). | 99% ee 100% |
| 129 | 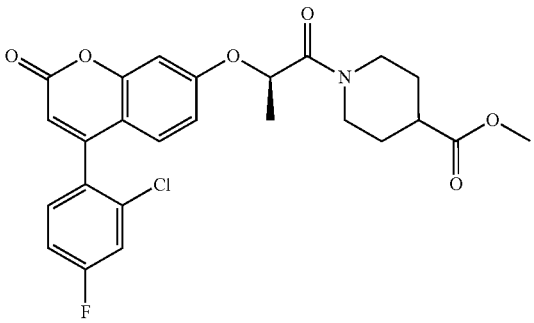 [SMILES: COC(=O)C1CCN(C(=O)[C@@H](C)Oc2ccc3c(-c4ccc(F)cc4Cl)cc(=O)oc3c2)CC1] | (R)-1E | (400 MHz, CDCl₃) δ 7.31-7.26 (m, 2H), 7.14 (ddd, 1H), 6.96 (d, 1H), 6.90-6.73 (m, 2H), 6.19 (s, 1H), 5.03 (q, 1H), 4.40-4.24 (m, 1H), 4.05 (d, 1H), 3.69 (d, 3H), 3.21 (dt, 1H), 2.90 (q, 1H), 2.62-2.49 (m, 1H), 1.95 (d, 2H), 1.74 (dt, 1H), 1.64 (d, 3H), 1.57-1.48 (m, 1H). | 99% |
| 130 | 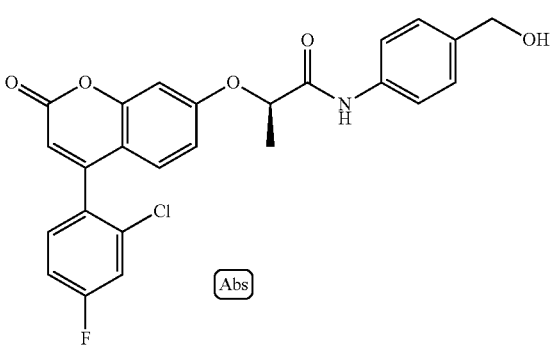 [SMILES: C[C@@H](Oc1ccc2c(-c3ccc(F)cc3Cl)cc(=O)oc2c1)C(=O)Nc1ccc(CO)cc1] | (R)-1E | (400 MHz, CDCl₃) δ 7.97 (s, 1H), 7.50-7.43 (m, 2H), 7.31-7.17 (m, 5H), 7.08 (ddt, 1H), 6.99-6.89 (m, 2H), 6.78 (dt, 1H), 6.17 (s, 1H), 4.81 (q, 1H), 4.59 (s, 2H), 1.64 (d, 3H). | 95% |

TABLE 3-continued

Compounds of formula (I) of the invention

| Ex | Structure | BB | ¹H-NMR | LC purity %ee |
|---|---|---|---|---|
| 131 | 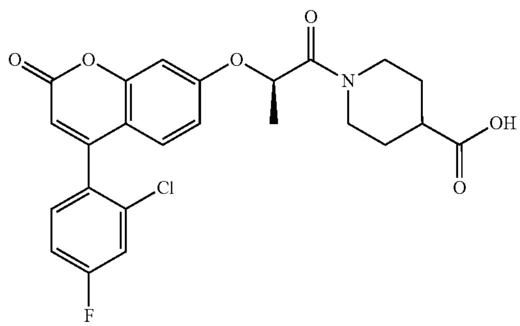 [SMILES: C[C@@H](Oc1ccc2c(-c3ccc(F)cc3Cl)cc(=O)oc2c1)C(=O)N1CCC(C(=O)O)CC1] | (R)-1E | (300 MHz, DMSO-d₆) δ 12.36 (s, 1H), 7.70 (dd, 1H), 7.56 (ddd, 1H), 7.43 (td, 1H), 7.02-6.89 (m, 2H), 6.82 (dt, 1H), 6.32 (s, 1H), 5.47 (dt, 1H), 4.16 (s, 1H), 3.93 (d, 1H), 3.15 (t, 1H), 2.95-2.69 (m, 1H), 1.86 (s, 2H), 1.73-1.14 (m, 6H). | 100% |
| 132 | 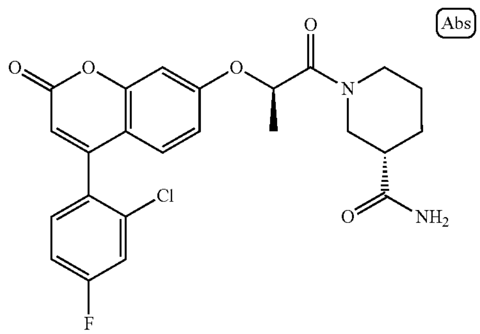 [SMILES: C[C@@H](Oc1ccc2c(-c3ccc(F)cc3Cl)cc(=O)oc2c1)C(=O)N1CCC[C@H](C(N)=O)C1] | (R)-1E | (400 MHz, DMSO-d₆) δ 7.70 (dd, 1H), 7.61-7.53 (m, 1H), 7.47-7.32 (m, 2H), 7.00-6.78 (m, 4H), 6.34-6.28 (m, 1H), 5.52 (p, 1H), 4.39-3.76 (m, 2H), 3.43-2.97 (m, 1H), 2.96-2.57 (m, 1H), 2.36-2.12 (m, 1H), 1.94-1.39 (m, 7H). | 100% |
| 133 | 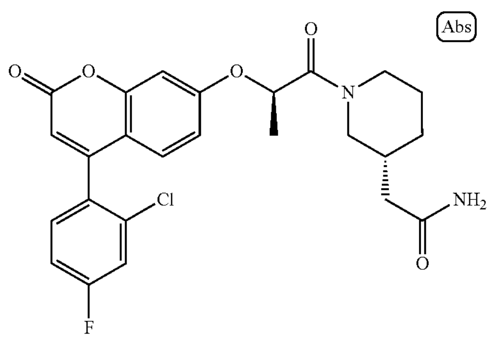 [SMILES: C[C@@H](Oc1ccc2c(-c3ccc(F)cc3Cl)cc(=O)oc2c1)C(=O)N1CCC[C@H](CC(N)=O)C1] | (R)-1E | (400 MHz, DMSO-d₆) δ 7.70 (dd, 1H), 7.56 (ddd, 1H), 7.43 (td, 1H), 7.30 (d, 1H), 7.02-6.89 (m, 2H), 6.87-6.71 (m, 2H), 6.30 (d, 1H), 5.55-5.32 (m, 1H), 4.16 (dd, 1H), 3.91 (t, 1H), 3.10-2.85 (m, 1H), 2.76-2.65 (m, 1H), 2.45-2.31 (m, 1H), 2.07-1.90 (m, 2H), 1.86-1.59 (m, 3H), 1.46 (dd, 4H). | 100% |
| 134 | 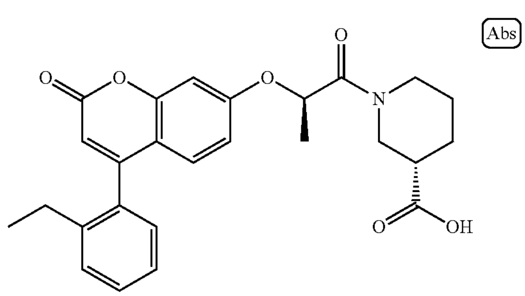 [SMILES: CCc1ccccc1-c1cc(=O)oc2cc(O[C@H](C)C(=O)N3CCC[C@H](C(=O)O)C3)ccc12] | 6B | (300 MHz, CD₃OD) δ 7.41-7.26 (m, 2H), 7.22 (td, 1H), 7.11-6.99 (m, 1H), 6.98-6.66 (m, 3H), 6.05 (d, 1H), 5.49-5.22 (m, 1H), 4.30-3.54 (m, 3H), 3.33-2.96 (m, 1H), 2.56-2.22 (m, 3H), 2.06-1.53 (m, 3H), 1.54-1.33 (m, 4H), 0.98 (t, 3H). | 99% |

TABLE 3-continued
Compounds of formula (I) of the invention
| Ex | Structure | BB | ¹H-NMR | LC purity %ee |
|---|---|---|---|---|
| 135 | 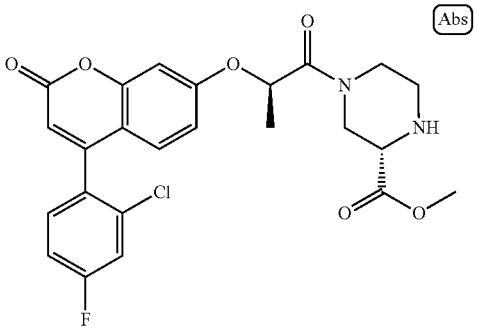 [SMILES: COC(=O)[C@@H]1CN(C(=O)[C@@H](C)Oc2ccc3c(-c4ccc(F)cc4Cl)cc(=O)oc3c2)CCN1] | (R)-1E | (400 MHz, CDCl₃) δ 7.31 (dd, 2H), 7.14 (td, 1H), 7.01 (d, 1H), 6.88 (d, 1H), 6.84-6.71 (m, 1H), 6.23 (s, 1H), 5.17-4.98 (m, 1H), 4.76-4.25 (m, 1H), 4.15-3.38 (m, 8H), 3.23-2.83 (m, 1H), 1.73-1.60 (m, 3H). | 98% |
| 136 | 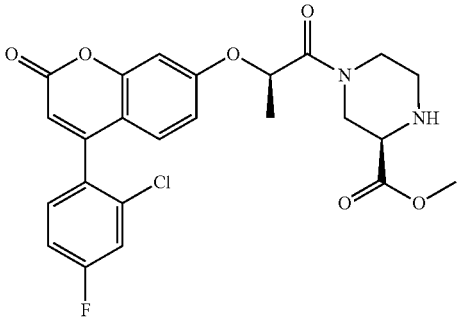 [SMILES: COC(=O)[C@H]1CN(C(=O)[C@@H](C)Oc2ccc3c(-c4ccc(F)cc4Cl)cc(=O)oc3c2)CCN1] | (R)-1E | (400 MHz, CDCl₃) δ 7.27-7.19 (m, 2H), 7.11-7.04 (m, 1H), 6.98-6.92 (m, 1H), 6.90-6.81 (d, 1H), 6.75-6.66 (m, 1H), 6.16 (s, 1H), 5.09-4.91 (m, 1H), 4.76-3.86 (m, 2H), 3.79-3.37 (m, 6H), 3.36-2.59 (m, 2H), 1.60 (d, 3H). | 100% |
| 137 | 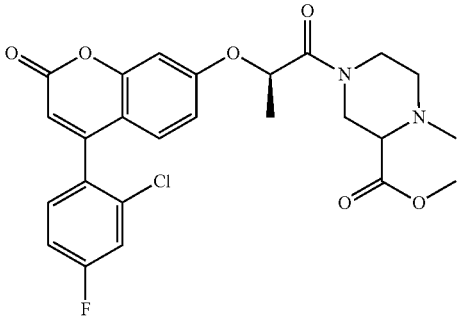 [SMILES: COC(=O)C1CN(C(=O)[C@@H](C)Oc2ccc3c(-c4ccc(F)cc4Cl)cc(=O)oc3c2)CCN1C] | (R)-1E | (400 MHz, CDCl₃) δ 7.33-7.26 (m, 2H), 7.18-7.10 (m, 1H), 7.00-6.94 (m, 1H), 6.90-6.73 (m, 2H), 6.23-6.17 (m, 1H), 5.14-4.95 (m, 1H), 4.15-3.38 (m, 7H), 3.29-2.85 (m, 2H), 2.45-2.09 (m, 4H), 1.65 (dd, 3H). | 98% |
| 138 | 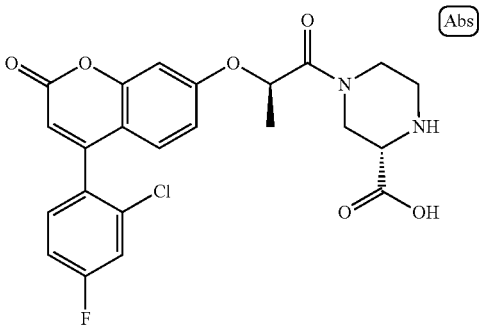 [SMILES: C[C@@H](Oc1ccc2c(-c3ccc(F)cc3Cl)cc(=O)oc2c1)C(=O)N1CCN[C@H](C(=O)O)C1] | (R)-1E | (400 MHz, DMSO-d₆) δ 7.70 (dd, 1H), 7.61-7.51 (m, 1H), 7.44 (td, 1H), 7.03 (d, 1H), 6.98-6.79 (m, 2H), 6.32 (s, 1H), 5.60-5.42 (m, 1H), 4.53-2.88 (m, 7H), 1.54-1.42 (m, 3H). | 98% |

TABLE 3-continued
Compounds of formula (I) of the invention
| Ex | Structure | BB | ¹H-NMR | LC purity %ee |
|---|---|---|---|---|
| 139 | 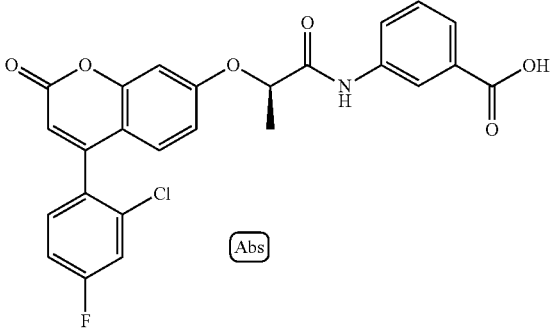 [SMILES: C[C@@H](Oc1ccc2c(-c3ccc(F)cc3Cl)cc(=O)oc2c1)C(=O)Nc1cccc(C(=O)O)c1] | (R)-1E | (300 MHz, DMSO-d₆) δ 13.02 (s, 1H), 10.42 (s, 1H), 8.25 (d, 1H), 7.91-7.80 (m, 1H), 7.75-7.60 (m, 2H), 7.55 (dd, 1H), 7.50-7.37 (m, 2H), 7.07 (dd, 1H), 7.03-6.90 (m, 2H), 6.32 (d, 1H), 5.08 (dd, 1H), 1.60 (d, 3H). | 100% ee 100% |
| 140 | 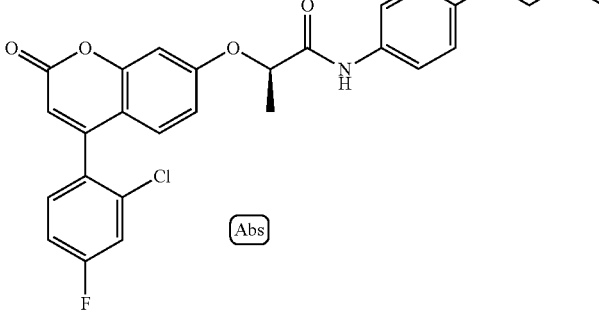 | (R)-1E | (400 MHz, CDCl₃) δ 7.95 (s, 1H), 7.47-7.42 (m, 2H), 7.33-7.26 (m, 2H), 7.22-7.10 (m, 3H), 7.04-6.97 (m, 2H), 6.84 (dt, 1H), 6.23 (s, 1H), 4.86 (q, 1H), 3.60-3.52 (m, 2H), 3.33 (d, 3H), 2.84 (t, 2H), 1.70 (dd, 3H). | 99% |
| 141 | 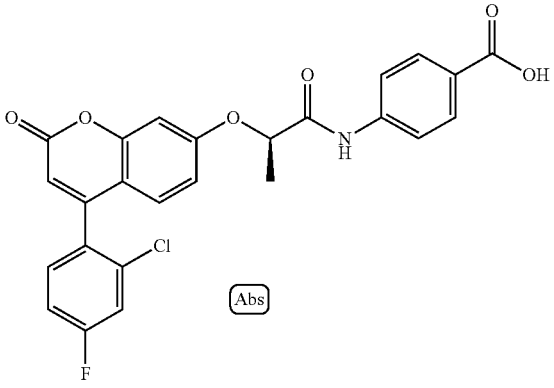 [SMILES: C[C@@H](Oc1ccc2c(-c3ccc(F)cc3Cl)cc(=O)oc2c1)C(=O)Nc1ccc(C(=O)O)cc1] | (R)-1E | (300 MHz, DMSO-d₆) δ 12.79 (s, 1H), 10.55 (s, 1H), 7.90 (d, 2H), 7.81-7.66 (m, 3H), 7.55 (dd, 1H), 7.43 (tt, 1H), 7.06 (dd, 1H), 7.03-6.90 (m, 2H), 6.33 (d, 1H), 5.19-5.03 (m, 1H), 1.60 (d, 3H). | 100% ee 89% |
| 142 | 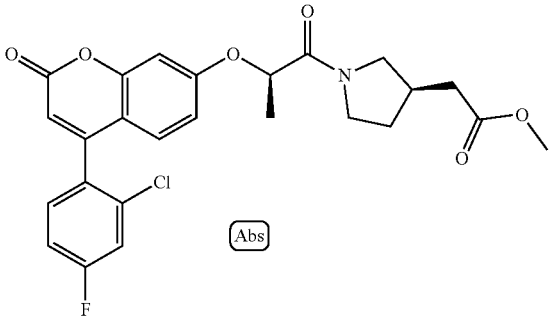 [SMILES: COC(=O)C[C@H]1CCN(C(=O)[C@@H](C)Oc2ccc3c(-c4ccc(F)cc4Cl)cc(=O)oc3c2)C1] | (R)-1E | (400 MHz, CDCl₃) δ 7.33-7.26 (m, 2H), 7.17-7.10 (m, 1H), 7.00-6.93 (m, 1H), 6.84-6.72 (m, 2H), 6.21-6.17 (m, 1H), 4.95-4.83 (m, 1H), 3.89-3.37 (m, 6H), 3.36-3.04 (m, 1H), 2.71-1.99 (m, 4H), 1.74-1.55 (m, 4H). | 100% |

TABLE 3-continued
Compounds of formula (I) of the invention
| Ex | Structure | BB | ¹H-NMR | LC purity %ee |
|----|-----------|-----|--------|---------------|
| 143 | 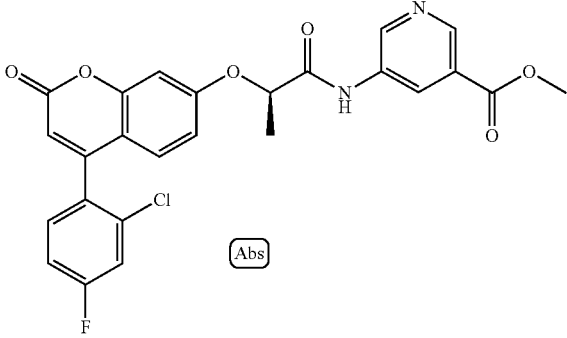 [SMILES: COC(=O)c1cncc(NC(=O)[C@@H](C)Oc2ccc3c(-c4ccc(F)cc4Cl)cc(=O)oc3c2)c1] | (R)-1E | (400 MHz, CDCl$_3$) δ 9.02-8.95 (m, 2H), 8.71 (ddd, 1H), 8.46 (d, 1H), 7.34-7.26 (m, 2H), 7.15 (ddt, 1H), 7.07-7.01 (m, 2H), 6.87 (ddd, 1H), 6.24 (s, 1H), 4.97 (qd, 1H), 3.96 (d, 3H), 1.73 (d, 3H). | 98% |
| 144 | 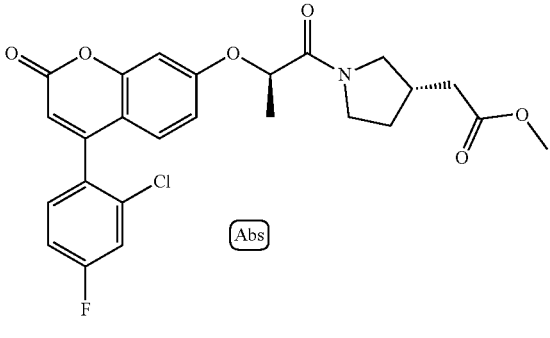 [SMILES: COC(=O)C[C@@H]1CCN(C(=O)[C@@H](C)Oc2ccc3c(-c4ccc(F)cc4Cl)cc(=O)oc3c2)C1] | (R)-1E | (400 MHz, CDCl$_3$) δ 7.33-7.25 (m, 3H), 7.18-7.10 (m, 1H), 6.96 (d, 1H), 6.83-6.73 (m, 2H), 6.19 (s, 1H), 4.93-4.84 (m, 1H), 3.99-3.59 (m, 5H), 3.54-3.33 (m, 1H), 3.16-3.05 (m, 1H), 2.77-2.29 (m, 3H), 2.26-2.05 (m, 1H), 1.79-1.47 (m, 4H). | 99% |
| 145 | 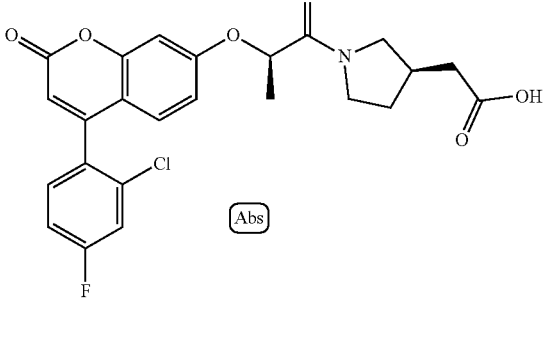 | (R)-1E | (400 MHz, DMSO-d$_6$) δ 12.18 (s, 1H), 7.70 (dd, 1H), 7.56 (dtd, 1H), 7.43 (td, 1H), 6.97-6.91 (m, 2H), 6.85-6.76 (m, 1H), 6.31 (s, 1H), 5.22-5.10 (m, 1H), 3.72-3.42 (m, 2H), 3.29-2.87 (m, 1H), 2.46-2.29 (m, 3H), 2.16-1.92 (m, 1H), 1.68-1.41 (m, 5H). | 100% |
| 146 | 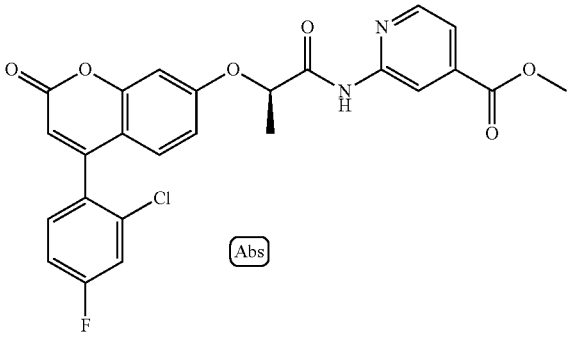 [SMILES: COC(=O)c1ccnc(NC(=O)[C@@H](C)Oc2ccc3c(-c4ccc(F)cc4Cl)cc(=O)oc3c2)c1] | (R)-1E | (400 MHz, CDCl$_3$) δ 8.82 (s, 1H), 8.78 (ddd, 1H), 8.41 (dt, 1H), 7.65 (ddd, 1H), 7.30 (dddd, 2H), 7.14 (dddd, 1H), 7.04-6.97 (1H), 4.92 (q, 1H), 3.97 (d, 3H), 1.73 (d, 3H). | 100% |

TABLE 3-continued

Compounds of formula (I) of the invention

| Ex | Structure | BB | ¹H-NMR | LC purity %ee |
|----|-----------|----|--------|---------------|
| 147 | 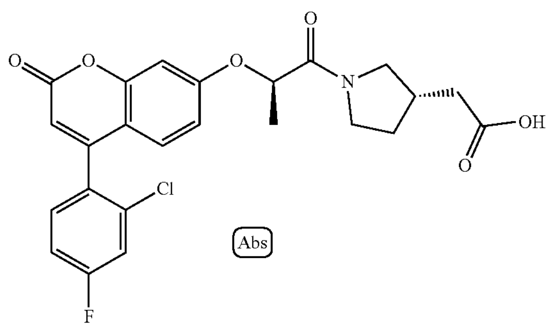 [SMILES: C[C@@H](Oc1ccc2c(-c3ccc(F)cc3Cl)cc(=O)oc2c1)C(=O)N1CC[C@@H](CC(=O)O)C1] | (R)-1E | (300 MHz, DMSO-d₆) δ 12.26 (s, 1H), 7.71 (dd, 1H), 7.56 (td, 1H), 7.43 (td, 1H), 6.93 (t, 2H), 6.82 (td, 1H), 6.32 (s, 1H), 5.46-5.01 (m, 1H), 4.00-3.43 (m, 2H), 3.15-2.87 (m, 1H), 2.35 (d, 2H), 2.07 (s, 1H), 1.66 (s, 1H), 1.45 (dd, 3H). | 100% ee 100% |
| 148 | 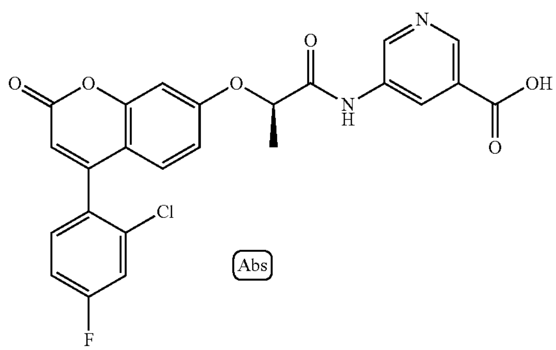 [SMILES: C[C@@H](Oc1ccc2c(-c3ccc(F)cc3Cl)cc(=O)oc2c1)C(=O)Nc1cncc(C(=O)O)c1] | (R)-1E | (400 MHz, DMSO-d₆) δ 10.61 (s, 1H), 8.96 (d, 1H), 8.78 (dd, 1H), 8.59 (ddd, 1H), 7.69 (dt, 1H), 7.55 (dd, 1H), 7.42 (tdd, 1H), 7.13-7.06 (m, 1H), 7.02-6.92 (m, 2H), 6.32 (d, , 1H), 5.18-5.08 (m, 1H), 1.67-1.53 (m, 3H). | 100% |
| 149 | 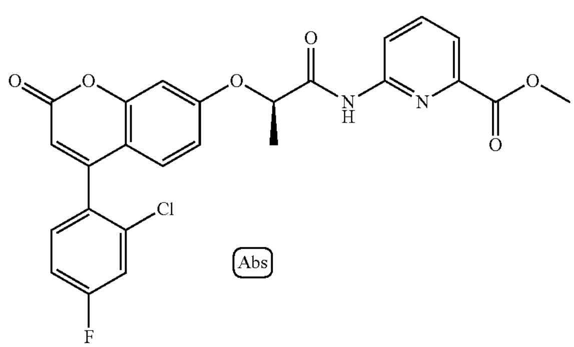 [SMILES: COC(=O)c1cccc(NC(=O)[C@@H](C)Oc2ccc3c(-c4ccc(F)cc4Cl)cc(=O)oc3c2)n1] | (R)-1E | (400 MHz, CDCl₃) δ 8.92 (s, 1H), 8.56-8.47 (m, 1H), 7.94-7.87 (m, 2H), 7.34-7.26 (m, 2H), 7.14 (dddd, 1H), 7.05-6.95 (m, 2H), 6.88 (ddd, 1H), 6.23 (s, 1H), 4.88 (qd, 1H), 3.99 (d, 3H), 1.71 (d, 3H). | 100% |
| 150 | 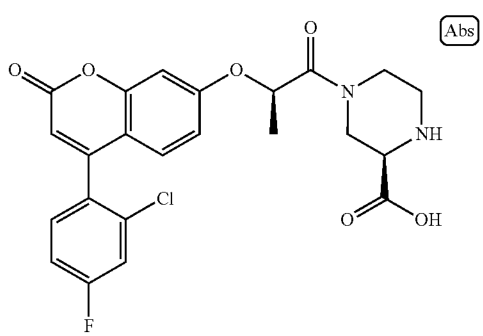 [SMILES: C[C@@H](Oc1ccc2c(-c3ccc(F)cc3Cl)cc(=O)oc2c1)C(=O)N1CCN[C@@H](C(=O)O)C1] | (R)-1E | (400 MHz, DMSO-d₆) δ 7.70 (dd, 1H), 7.56 (ddd, 1H), 7.44 (td, 1H), 7.12-6.80 (m, 3H), 6.33 s, 1H), 5.58-5.40 (m, 1H), 4.56-3.82 (m, 2H), 3.61-2.89 (m, 5H), 1.48 (d, 3H). | 98% |

TABLE 3-continued
Compounds of formula (I) of the invention
| Ex | Structure | BB | ¹H-NMR | LC purity %ee |
|---|---|---|---|---|
| 151 | 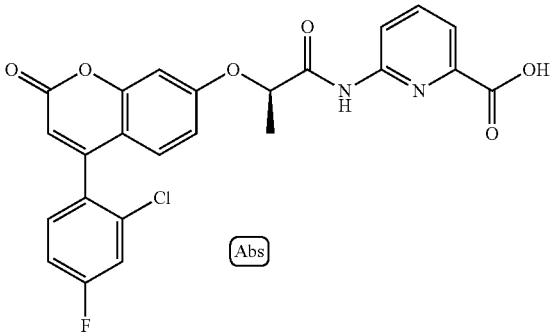 [SMILES: C[C@@H](Oc1ccc2c(-c3ccc(F)cc3Cl)cc(=O)oc2c1)C(=O)Nc1cccc(C(=O)O)n1] | (R)-1E | (400 MHz, DMSO-d₆) δ 13.28 (br. s, 1H), 11.19 (d, 1H), 8.23 (d, 1H), 7.96 (ddd, 1H), 7.79 (dt, 1H), 7.68 (ddd, 1H), 7.54 (ddd, 1H), 7.41 (tdd, 1H), 7.09-6.84 (m, 3H), 6.31 (d, 1H), 5.28 (q, 1H), 1.59 (d, 3H). | 97% |
| 152 | 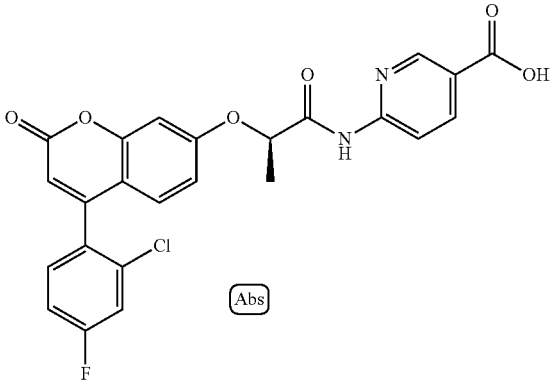 [SMILES: C[C@@H](Oc1ccc2c(-c3ccc(F)cc3Cl)cc(=O)oc2c1)C(=O)Nc1ccc(C(=O)O)cn1] | (R)-1E | (400 MHz, CD₃OD) δ 8.67-8.61 (m, 1H), 8.46 (dt, 1H), 7.65 (ddd, 1H), 7.44 (ddt, 2H), 7.32-7.21 (m, 1H), 7.10-7.00 (m, 2H), 6.98 (ddd, 1H), 6.22 (d, 1H), 5.17-5.07 (m, 1H), 1.71 (d, 3H). | 98% |
| 153 | 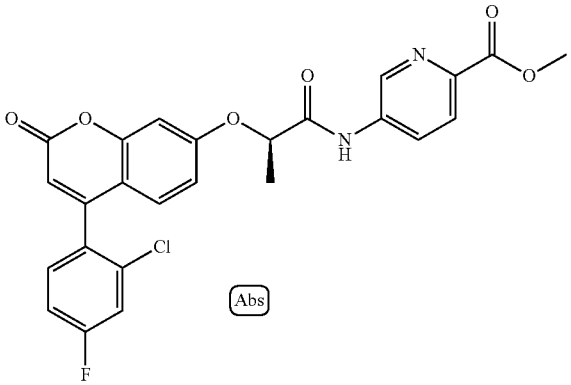 [SMILES: COC(=O)c1ccc(NC(=O)[C@@H](C)Oc2ccc3c(-c4ccc(F)cc4Cl)cc(=O)oc3c2)cn1] | (R)-1E | (400 MHz, DMSO-d₆) δ 10.74 (s, 1H), 8.86 (dd, 1H), 8.26 (dd, 1H), 8.04 (ddd, 1H), 7.67 (dt, 1H), 7.53 (dd, 1H), 7.40 (tdd, 1H), 7.07 (dd, 1H), 7.01-6.89 (m, 2H), 6.33-6.28 (m, 1H), 5.18-5.08 (m, 1H), 3.83 (s, 3H), 1.60 (d, 3H). | 100% |
| 154 | 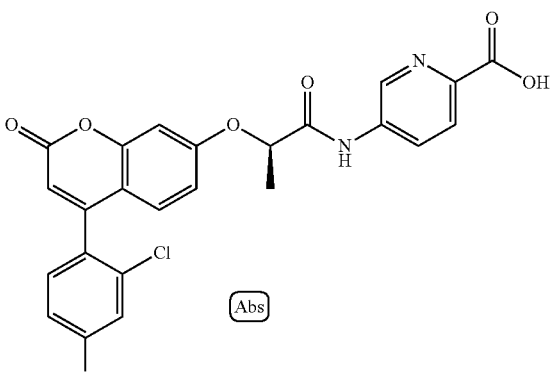 | (R)-1E | (400 MHz, DMSO-d₆) δ 10.78 (s, 1H), 8.90 (d, 1H), 8.23 (dd, 1H), 8.03 (d, 1H), 7.69 (dt, 1H), 7.55 (dd, 1H), 7.42 (tdd, 1H), 7.09 (dd, 1H), 6.98 (s, 1H), 7.03-6.87 (m, 1H), 6.33 (d, 1H), 5.17 (tt, 1H), 4.03 (s, 1H), 1.62 (d, 3H). | 100% |

TABLE 3-continued

Compounds of formula (I) of the invention

| Ex | Structure | BB | ¹H-NMR | LC purity %ee |
|---|---|---|---|---|
| 155 | 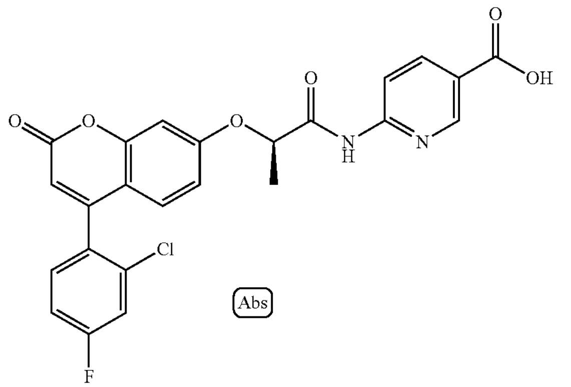 [SMILES: C[C@@H](Oc1ccc2c(-c3ccc(F)cc3Cl)cc(=O)oc2c1)C(=O)Nc1ccc(C(=O)O)cn1] | (R)-1E | (400 MHz, DMSO-d$_6$) δ 11.25 (s, 1H), 8.87 (d, 1H), 8.27 (dt, 1H), 8.14 (d, 1H), 7.70 (dt, 1H), 7.55 (ddd, 1H), 7.48-7.38 (m, 1H), 7.06 (t, 1H), 7.01-6.87 (m, 2H), 6.33 (d, 1H), 5.26 (q, 1H), 1.60 (d, 3H). | 100% |
| 156 | 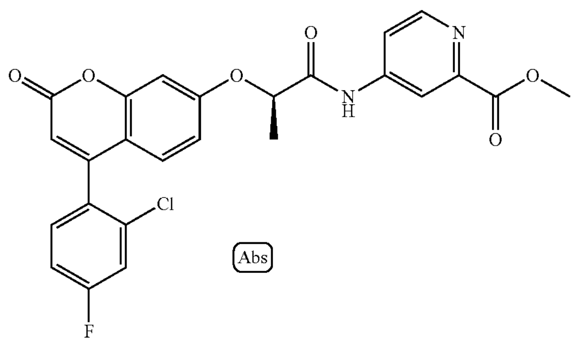 [SMILES: COC(=O)c1cc(NC(=O)[C@@H](C)Oc2ccc3c(-c4ccc(F)cc4Cl)cc(=O)oc3c2)ccn1] | (R)-1E | (400 MHz, CDCl$_3$) δ 8.71-8.64 (m, 1H), 8.40 (s, 1H), 8.08 (ddd, 1H), 8.01 (ddd, 1H), 7.35-7.26 (m, 2H), 7.15 (dddd, 1H), 7.09-6.97 (m, 2H), 6.86 (ddd, 1H), 6.26 (s, 1H), 4.93 (q, 1H), 4.00 (s, 3H), 1.72 (d, 3H). | 100% |
| 157 | 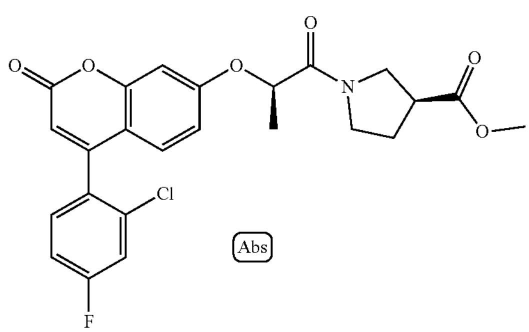 [SMILES: COC(=O)[C@H]1CCN(C(=O)[C@@H](C)Oc2ccc3c(-c4ccc(F)cc4Cl)cc(=O)oc3c2)C1] | (R)-1E | (400 MHz, CDCl$_3$) δ 7.32-7.25 (m, 2H), 7.17-7.10 (m, 1H), 6.97 (d, 1H), 6.86-6.71 (m, 2H), 6.19 (s, 1H), 4.90 (p, 1H), 4.07-3.44 (m, 7H), 3.25-2.97 (m, 1H), 2.33-2.07 (m, 2H), 1.68-1.58 (m, 3H). | 100% |
| 158 | 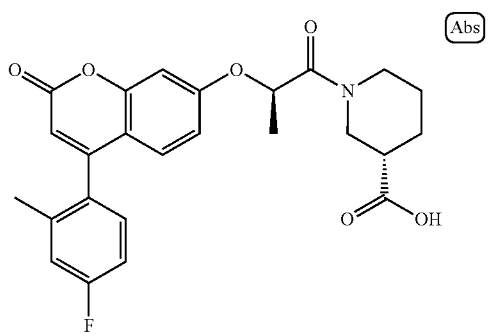 [SMILES: Cc1cc(F)ccc1-c1cc(=O)oc2cc(O[C@H](C)C(=O)N3CCC[C@H](C(=O)O)C3)ccc12] | 7B | (300 MHz, CD$_3$OD) δ 7.14 (dd, 1H), 7.04 (dd, 1H), 7.04-6.92 (m, 1H), 6.98-6.78 (m, 2H), 6.84-6.68 (m, 1H), 6.05 (d, 1H), 5.49-5.20 (m, 1H), 4.34-3.53 (m, 3H), 3.32-2.94 (m, 1H), 2.58-2.29 (m, 1H), 2.05 (s, 3H), 2.00-1.73 (m, 2H), 1.48 (t, 4H), 1.17 (dd, 1H). | 95% |

TABLE 3-continued
Compounds of formula (I) of the invention
| Ex | Structure | BB | ¹H-NMR | LC purity %ee |
|---|---|---|---|---|
| 159 | 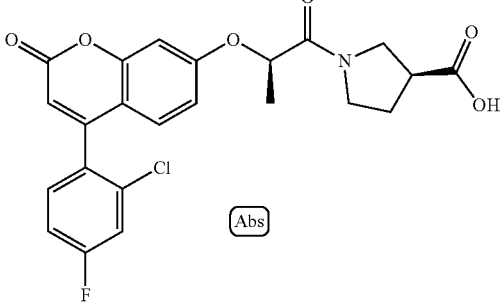 | (R)-1E | (400 MHz, DMSO-d$_6$) δ 12.55 (s, 1H), 7.70 (dd, 1H), 7.56 (ddt, 1H), 7.43 (td, 1H), 7.02-6.88 (m, 2H), 6.88-6.76 (m, 1H), 6.31 (d, 1H), 5.27-5.15 (m, 1H), 3.81-3.33 (m, 4H), 3.11 (ddt, 1H), 2.31-1.93 (m, 2H), 1.45 (dd, 3H). | 100% |
| 160 | 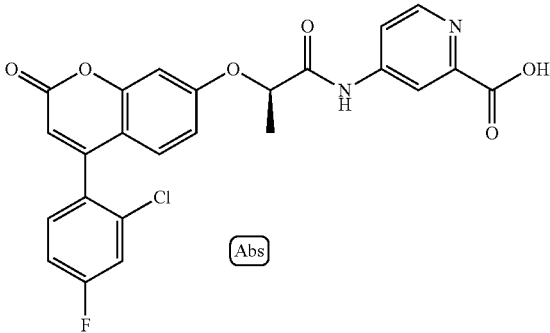 [SMILES: C[C@@H](Oc1ccc2c(-c3ccc(F)cc3Cl)cc(=O)oc2c1)C(=O)Nc1ccnc(C(=O)O)c1] | (R)-1E | (400 MHz, DMSO-d$_6$) δ 10.86-10.74 (m, 1H), 8.56 (dt, 1H), 8.33 (dd, 1H), 7.85 (dd, 1H), 7.69 (dt, 1H), 7.55 (dd, 1H), 7.42 (tdd, 1H), 7.14-7.03 (m, 1H), 7.02-6.89 (m, 2H), 6.33 (d, 1H), 5.21-5.06 (m, 1H), 1.65-1.57 (m, 3H). | 98% |
| 161 | 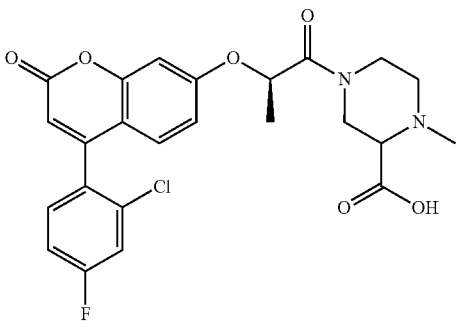 [SMILES: C[C@@H](Oc1ccc2c(-c3ccc(F)cc3Cl)cc(=O)oc2c1)C(=O)N1CCN(C)C(C(=O)O)C1] | (R)-1E | (400 MHz, DMSO-d$_6$) δ 7.70 (dd, 1H), 7.56 (ddd, 1H), 7.43 (td, 1H), 7.04-6.75 (m, 3H), 6.32 (s, 1H), 5.47 (dq, 1H), 4.02-2.84 (m, 6H), 2.48-2.28 (m, 4H), 1.60-1.40 (m, 3H). | 98% |
| 162 | 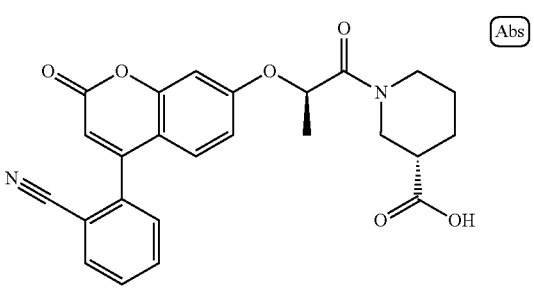 [SMILES: C[C@@H](Oc1ccc2c(-c3ccccc3C#N)cc(=O)oc2c1)C(=O)N1CCC[C@H](C(=O)O)C1] | 8B | (300 MHz, CD$_3$OD) δ 7.90-7.80 (m, 1H), 7.81-7.69 (m, 1H), 7.62 (dd, 1H), 7.51 (d, 1H), 7.05-6.70 (m, 3H), 6.22 (t, 1H), 5.51-5.24 (m, 1H), 4.29-3.54 (m, 3H), 3.36-2.96 (m, 2H), 2.59-2.28 (m, 1H), 2.06-1.14 (t, 6H). | 98% |

TABLE 3-continued
Compounds of formula (I) of the invention
| Ex | Structure | BB | ¹H-NMR | LC purity %ee |
|---|---|---|---|---|
| 163 | 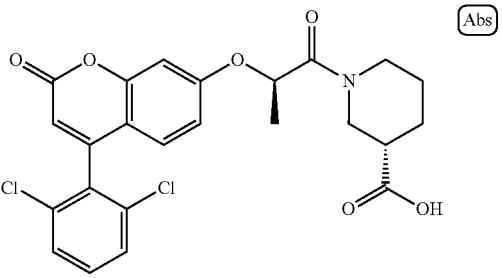 [SMILES: C[C@@H](Oc1ccc2c(-c3c(Cl)cccc3Cl)cc(=O)oc2c1)C(=O)N1CCC[C@H](C(=O)O)C1] [Abs] | 9B | (300 MHz, CD$_3$OD) δ 8.00 (ddd, 1H), 7.53-7.36 (m, 3H), 7.14-6.83 (m, 2H), 6.31 (dd, 1H), 5.53-5.28 (m, 1H), 4.28-3.59 (m, 2H), 3.53-3.37 (m, 1H), 3.22-2.87 (m, 1H), 2.51-2.27 (m, 1H), 2.03-1.79 (m, 2H), 1.79-1.34 (m, 5H). | 99% |
| 164 | 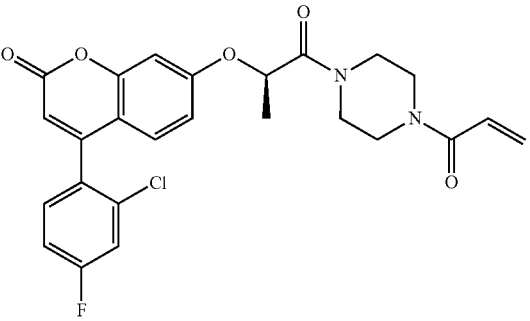 [SMILES: C=CC(=O)N1CCN(C(=O)[C@@H](C)Oc2ccc3c(-c4ccc(F)cc4Cl)cc(=O)oc3c2)CC1] | (R)-1E | (400 MHz, CDCl$_3$) δ 7.30 (ddd, 2H), 7.14 (tddd, 1H), 6.98 (d, 1H), 6.86 (dd, 1H), 6.79 (ddd, 1H), 6.52 (dd, 1H), 6.35-6.26 (m, 1H), 6.21 (s, 1H), 5.74 (dd, 1H), 5.04 (q, 1H), 3.84-3.31 (m, 8H), 1.67 (d, 3H). | 100% |
| 165 | 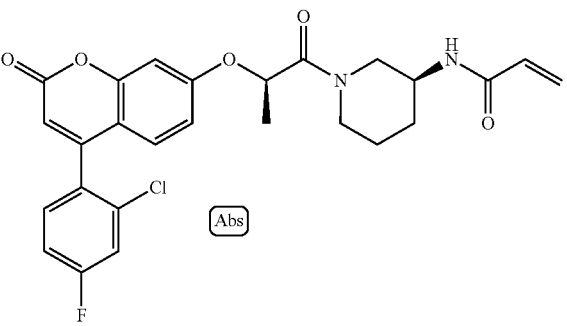 [SMILES: C=CC(=O)N[C@H]1CCCN(C(=O)[C@@H](C)Oc2ccc3c(-c4ccc(F)cc4Cl)cc(=O)oc3c2)C1] [Abs] | (R)-1E | (400 MHz, CDCl$_3$) δ 7.32-7.22 (m, 2H), 7.13 (t, 1H), 7.02-6.64 (m, 3H), 6.38-6.12 (m, 3H), 5.97-5.43 (m, 2H), 5.11-5.00 (m, 1H), 4.10-3.76 (m, 3H), 3.51-3.33 (m, 2H), 2.05-1.73 (m, 2H), 1.72-1.54 (m, 5H). | 96% |
| 166 | 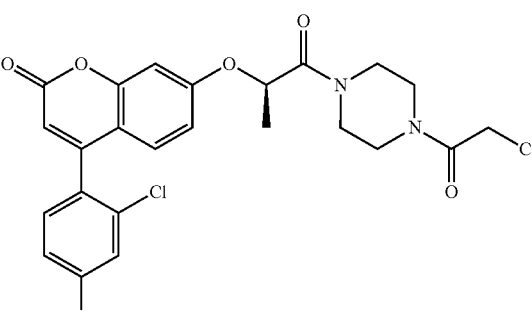 | (R)-1E | (400 MHz, CDCl$_3$) δ 7.33-7.26 (m, 2H), 7.19-7.11 (m, 1H), 7.03-6.96 (m, 1H), 6.90-6.75 (m, 2H), 6.22 (s, 1H), 5.04 (q, 1H), 4.06 (d, 2H), 3.84-3.39 (m, 8H), 1.67 (d, 3H). | 100% |

TABLE 3-continued
Compounds of formula (I) of the invention
| Ex | Structure | BB | ¹H-NMR | LC purity %ee |
|---|---|---|---|---|
| 167 | 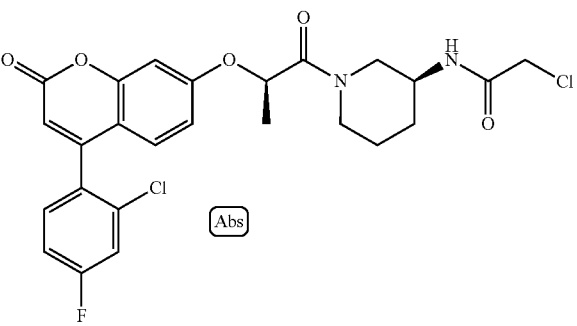 [SMILES: C[C@@H](Oc1ccc2c(-c3ccc(F)cc3Cl)cc(=O)oc2c1)C(=O)N1CCC[C@H](NC(=O)CCl)C1] | (R)-1E | (400 MHz, CDCl₃) δ 7.32-7.27 (m, 2H), 7.13 (td, 1H), 7.00-6.94 (m, 1H), 6.92-6.73 (m, 2H), 6.61-6.46 (m, 1H), 6.27-6.12 (m, 1H), 5.06 (qd, 1H), 4.15-3.90 (m, 4H), 3.88-3.44 (m, 2H), 3.31-3.00 (m, 1H), 2.06-1.73 (m, 2H), 1.68 (d, 5H). | 100% |
| 168 | 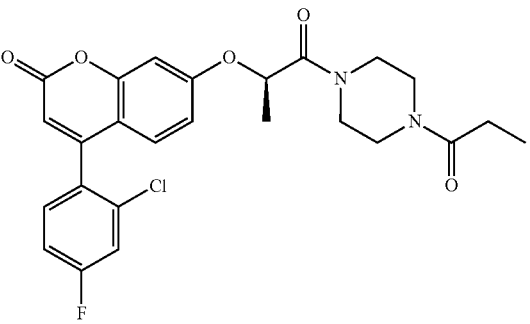 [SMILES: CCC(=O)N1CCN(C(=O)[C@@H](C)Oc2ccc3c(-c4ccc(F)cc4Cl)cc(=O)oc3c2)CC1] | (R)-1E | (400 MHz, CDCl₃) δ 7.34-7.26 (m, 2H), 7.18-7.10 (m, 1H), 6.98 (d, 1H), 6.89-6.74 (m, 2H), 6.21 (s, 1H), 5.04 (q, 1H), 3.78-3.15 (m, 8H), 2.40-2.26 (m, 2H), 1.66 (d, 3H), 1.15 (t, 3H). | 96% |
| 169 | 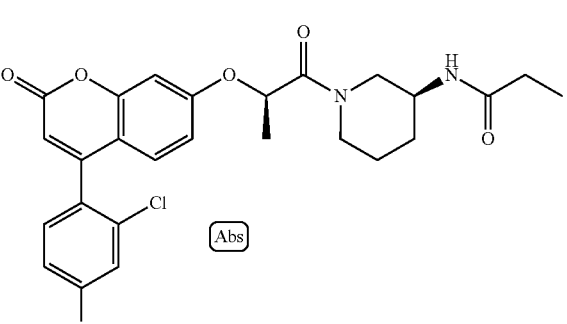 | (R)-1E | (400 MHz, CDCl₃) δ 7.34-7.26 (m, 2H), 7.13 (t, 1H), 7.03-6.64 (m, 3H), 6.23-6.15 (m, 1H), 5.59-5.26 (m, 1H), 5.14-4.98 (m, 1H), 4.04-3.71 (m, 3H), 3.50-3.16 (m, 1H), 2.33-1.90 (m, 3H), 1.88-1.45 (m, 7H), 1.20-0.98 (m, 3H). | 100% |
| 170 | 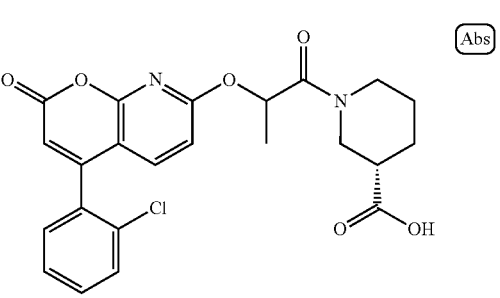 [SMILES: CC(Oc1ccc2c(-c3ccccc3Cl)cc(=O)oc2n1)C(=O)N1CCC[C@H](C(=O)O)C1] | 15E | (400 MHz, DMSO-d₆) δ 7.69-7.64 (m, 1H), 7.61-7.50 (m, 2H), 7.50-7.44 (m, 1H), 7.39-7.33 (m, 1H), 6.85 (dd, 1H), 6.41-6.37 (m, 1H), 5.73 (q, 1H), 4.01-3.88 (m, 2H), 3.41-3.02 (m, 1H), 2.99-2.58 (m, 2H), 2.29 (d, 1H), 2.03 (dd, 1H), 1.82-1.54 (m, 2H), 1.43 (t, 3H). | 94% |

TABLE 3-continued

Compounds of formula (I) of the invention

| Ex | Structure | BB | ¹H-NMR | LC purity %ee |
|---|---|---|---|---|
| 171 | 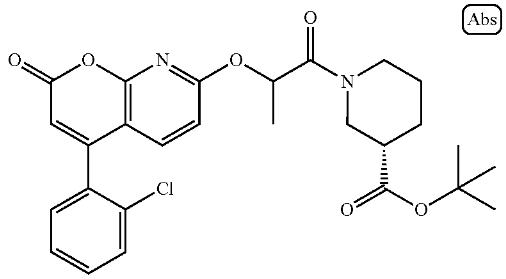 [SMILES: CC(Oc1ccc2c(-c3ccccc3Cl)cc(=O)oc2n1)C(=O)N1CCC[C@H](C(=O)OC(C)(C)C)C1] | 15E | (400 MHz, DMSO-d₆) δ 7.69 (d, 1H), 7.58 (dt, 2H), 7.49 (s, 1H), 7.39 (dd, 1H), 6.87 (d, 1H), 6.45-6.41 (m, 1H), 5.88-5.70 (m, 1H), 4.18 (s, 1H), 3.88 (d, 1H), 3.04-2.77 (m, 1H), 2.33 (s, 1H), 2.10-1.86 (m, 2H), 1.83-1.57 (m, 2H), 1.49-1.42 (m, 4H), 1.42-1.33 (m, 9H). | 99% |
| 172 | 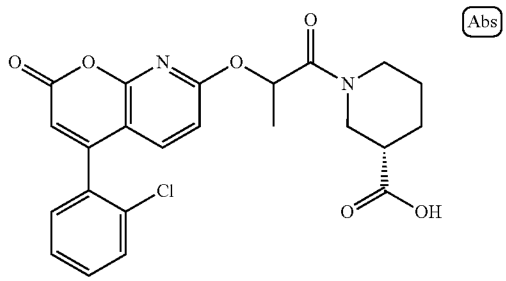 [SMILES: CC(Oc1ccc2c(-c3ccccc3Cl)cc(=O)oc2n1)C(=O)N1CCC[C@H](C(=O)O)C1] | 15E | (400 MHz, DMSO-d₆) δ 12.38 (br. s, 1H), 7.71-7.66 (m, 1H), 7.62-7.46 (m, 3H), 7.38 (dd, 1H), 6.86 (d, 1H), 6.44-6.39 (m, 1H), 5.85-6.68 (m, 1H), 4.40-4.06 (m, 1H), 3.94 (d, 1H), 3.17 (s, 1H), 2.94-2.60 (m, 1H), 2.33 (s, 1H), 2.07 (d, 2H), 1.83-1.54 (m, 2H), 1.45-1.41 (m, 3H). | 100% |
| 173 | 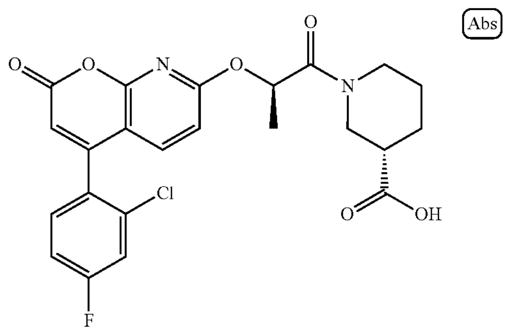 [SMILES: C[C@@H](Oc1ccc2c(-c3ccc(F)cc3Cl)cc(=O)oc2n1)C(=O)N1CCC[C@H](C(=O)O)C1] | 14E | (400 MHz, DMSO-d₆) δ 12.37 (br. s, 1H), 7.71 (dq, 1H), 7.64-7.51 (m, 1H), 7.51-7.38 (m, 2H), 6.87 (dd, 1H), 6.43 (d, 1H), 6.00-5.57 (m, 1H), 4.24 (dd, 1H), 3.95 (d, 1H), 3.23-2.58 (m, 2H), 2.40-2.28 (m, 1H), 2.17-1.89 (m, 2H), 1.82-1.55 (m, 2H), 1.45 (d, 3H). | 100% ee 100% |
| 174 | 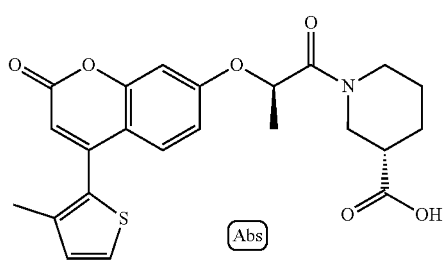 [SMILES: Cc1ccsc1-c1cc(=O)oc2cc(O[C@H](C)C(=O)N3CCC[C@H](C(=O)O)C3)ccc12] | (R)-13E | (300 MHz, CD₃OD) δ 7.46 (d, 1H), 7.29 (t, 1H), 7.01-6.75 (m, 3H), 6.13 (d, 1H), 5.37 (dq, 1H), 4.30-3.56 (m, 3H), 3.37-2.97 (m, 1H), 2.44 (d, 1H), 2.06 (s, 3H), 2.01-1.78 (m, 3H), 1.76-1.36 (m, 4H). | 99% |
| 175 | 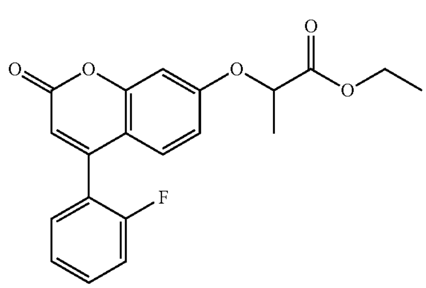 [SMILES: CCOC(=O)C(C)Oc1ccc2c(-c3ccccc3F)cc(=O)oc2c1] | 13B | (400 MHz, CDCl₃) δ 7.53-7.48 (m, 1H), 7.39-7.25 (m, 2H), 7.29-7.18 (m, 1H), 7.17 (dd, 1H), 6.83-6.78 (m, 2H), 6.27 (s, 1H), 4.80 (q, 1H), 4.24 (q, 2H), 1.66 (d, 3H), 1.29 (t, 3H). | 100% |

TABLE 3-continued

Compounds of formula (I) of the invention

| Ex | Structure | BB | ¹H-NMR | LC purity %ee |
|---|---|---|---|---|
| 176 | 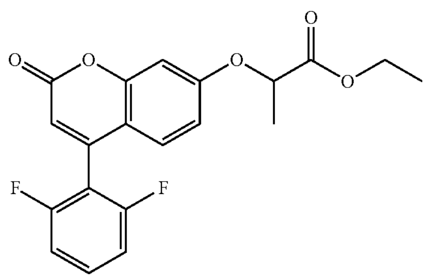 [SMILES: CCOC(=O)C(C)Oc1ccc2c(-c3c(F)cccc3F)cc(=O)oc2c1] | 14B | (400 MHz, CDCl₃) δ 7.47-7.35 (m, 1H), 7.00 (ddt, 3H), 6.78-6.69 (m, 2H), 6.24 (s, 1H), 4.78-4.68 (m, 1H), 4.17 (qd, 2H), 1.59 (dd, 3H), 1.21 (t, 3H). | 100% |
| 177 | 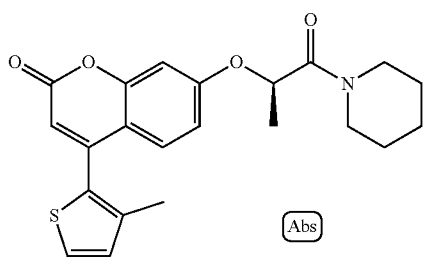 [SMILES: Cc1ccsc1-c1cc(=O)oc2cc(O[C@H](C)C(=O)N3CCCCC3)ccc12] | (R)-13E | (400 MHz, DMSO-d₆) δ 7.74 (d, 1H), 7.35 (d, 1H), 7.12 (d, 1H), 6.94-6.85 (m, 2H), 6.27 (s, 1H), 5.45 (q, 1H), 3.62-3.32 (m, 4H), 2.14 (s, 3H), 1.69-1.39 (m, 9H). | 98% |
| 178 | 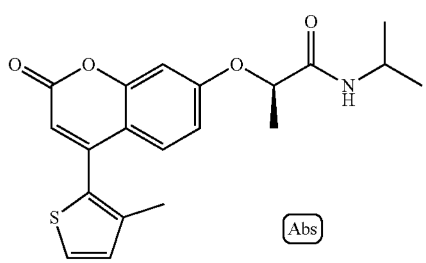 [SMILES: Cc1ccsc1-c1cc(=O)oc2cc(O[C@H](C)C(=O)NC(C)C)ccc12] | (R)-13E | (400 MHz, DMSO-d₆) δ 8.00 (d, 1H), 7.72 (d, 1H), 7.33 (d, 1H), 7.10 (d, 1H), 6.97-6.88 (m, 2H), 6.25 (s, 1H), 4.80 (q, 1H), 3.85 (dp, 1H), 2.12 (s, 3H), 1.44 (d, 3H), 1.04 (dd, 6H). | 98% |
| 179 | 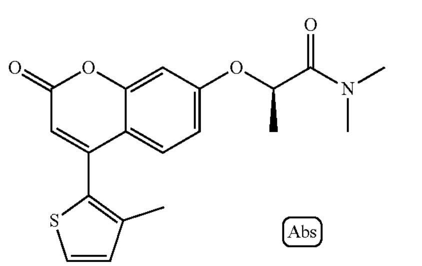 [SMILES: Cc1ccsc1-c1cc(=O)oc2cc(O[C@H](C)C(=O)N(C)C)ccc12] | (R)-13E | (400 MHz, DMSO-d₆) δ 7.75-7.70 (m, 1H), 7.32 (d, 1H), 7.10 (dd, 1H), 6.91-6.83 (m, 2H), 6.25 (s, 1H), 5.41 (q, 1H), 3.08 (s, 3H), 2.83 (s, 3H), 2.13 (d, 3H), 1.44 (d, 3H). | 98% |
| 180 | 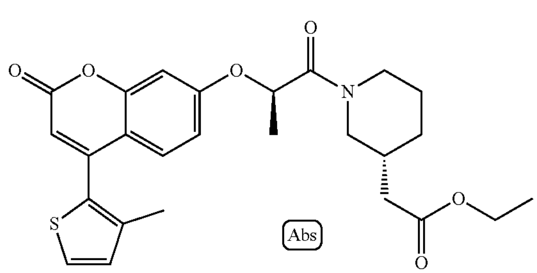 [SMILES: CCOC(=O)C[C@H]1CCCN(C(=O)[C@@H](C)Oc2ccc3c(-c4sccc4C)cc(=O)oc3c2)C1] | (R)-13E | (400 MHz, DMSO-d₆) δ 7.72 (d, 1H), 7.38-7.28 (m, 1H), 7.10 (d, 1H), 6.88 (t, 2H), 6.25 (s, 1H), 5.41 (dd, 1H), 4.23-3.76 (m, 4H), 3.00 (dt, 1H), 2.36-2.14 (m, 2H), 2.12 (s, 3H), 1.84-1.38 (m, 7H), 1.30-1.19 (m, 3H), 1.14 (t, 3H). | 98% |

TABLE 3-continued

Compounds of formula (I) of the invention

| Ex | Structure | BB | ¹H-NMR | LC purity %ee |
|---|---|---|---|---|
| 181 | 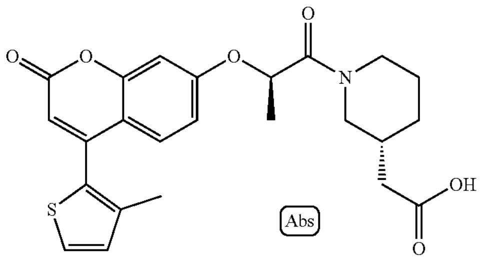 [SMILES: Cc1ccsc1-c1cc(=O)oc2cc(O[C@H](C)C(=O)N3CCC[C@H](CC(=O)O)C3)ccc12] | (R)-13E | (400 MHz, DMSO-d$_6$) δ 7.74 (d, 1H), 7.34 (dd, 1H), 7.12 (d, 1H), 6.99-6.83 (m, 2H), 6.27 (s, 1H), 5.44 (dd, 1H), 4.27-3.78 (m, 2H), 3.09-2.84 (m, 1H), 2.14 (s, 5H), 1.87-1.41 (m, 7H), 1.24 (s, 2H). | 100% |
| 182 | 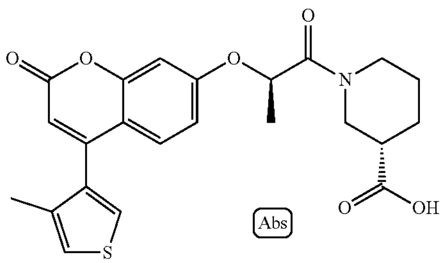 [SMILES: Cc1cscc1-c1cc(=O)oc2cc(O[C@H](C)C(=O)N3CCC[C@H](C(=O)O)C3)ccc12] | (R)-16E | (400 MHz, DMSO-d$_6$) δ 7.69 (d, 1H), 7.42 (dd, 1H), 7.15 (dd, 1H), 7.00-6.79 (m, 2H), 6.19 (d, 1H), 5.55-5.42 (m, 1H), 4.29 (d, 0.5H), 3.83 (t, 1H), 3.70-3.48 (m, 1H), 3.25-2.77 (m, 1.5H), 2.36-2.22 (m, 1H), 2.08 (s, 3H), 1.95 (dd, 1H), 1.81-1.41 (m, 6H). | 100% |
| 183 | 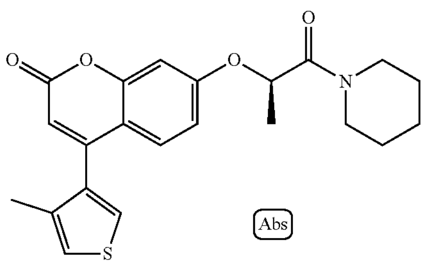 [SMILES: Cc1cscc1-c1cc(=O)oc2cc(O[C@H](C)C(=O)N3CCCCC3)ccc12] | (R)-16E | (400 MHz, DMSO-d$_6$) δ 7.69 (d, 1H), 7.42 (dq, 1H), 7.15 (dd, 1H), 6.90 (dd, 1H), 6.85 (ddd, 1H), 6.20 (d, 1H), 5.45 (q, 1H), 3.62-3.33 (m, 4H), 2.08 (d, 3H), 1.68-1.39 (m, 9H). | 100% |
| 184 | 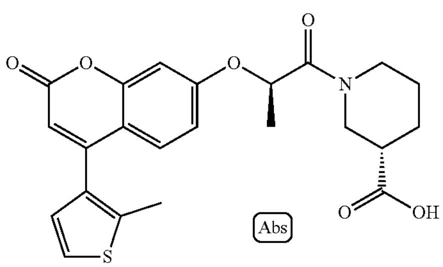 [SMILES: Cc1sccc1-c1cc(=O)oc2cc(O[C@H](C)C(=O)N3CCC[C@H](C(=O)O)C3)ccc12] | (R)-17E | (400 MHz, DMSO-d$_6$) δ 7.69 (d, 1H), 7.42 (dq, 1H), 7.15 (dd, 1H), 6.90 (dd, 1H), 6.85 (ddd, 1H), 6.20 (d, 1H), 5.45 (q, 1H), 3.62-3.33 (m, 4H), 2.08 (d, 3H), 1.68-1.39 (m, 9H). | 100% |
| 185 | 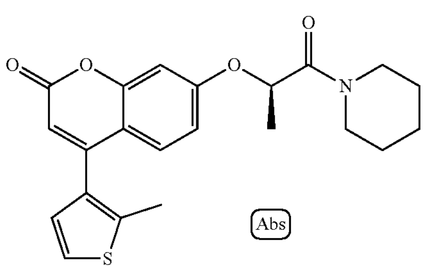 [SMILES: Cc1sccc1-c1cc(=O)oc2cc(O[C@H](C)C(=O)N3CCCCC3)ccc12] | (R)-17E | (400 MHz, DMSO-d$_6$) δ 7.52 (d, 1H), 7.27-7.13 (m, 1H), 7.08 (d, 1H), 6.99-6.80 (m, 2H), 6.20 (s, 1H), 5.57-5.39 (m, 1H), 4.33-3.06 (m, 4H), 2.93-2.70 (m, 1H), 2.37 (s, 3H), 2.34-2.21 (m, 1H), 2.05-1.85 (m, 1H), 1.81-1.40 (m, 6H). | 100% |

The IUPAC chemical names for the compounds shown in Table 3 are provided in Table 4 below.

4. Homogeneous TR-FRET Assay for HTS and Activity Determination

The TR-FRET assay was basically conducted as described in WO2016/193,231A1, especially as described in example 1 (hereby incorporated by reference). With respect to the background of the mitochondrial transcription it is referred to Falkenberg et al. (2002) and Posse et al. (Posse et al., 2015). The method monitors the activity of mitochondrial RNA-polymerase via detection of the formation of its product, a 407 bp long RNA sequence. Detection of the product is facilitated by hybridization of two DNA-oligonucleotide probes to specific and adjacent sequences within the RNA product sequence. Upon annealing of the probes, two fluorophores that are coupled directly to an acceptor nucleotide probe (ATTO647, 5') or introduced via a coupled streptavidin interacting with a biotinylated donor nucleotide probe on the other side (Europium cryptate, 3') are brought into sufficient proximity to serve as a fluorescence-donor-acceptor pair as generally described in Walters and Namchuk (2003). Thus, a FRET signal at 665 nm is generated upon excitation at 340 nm.

Briefly, the protocol described here was applied for screening and activity determination in a low-volume 384-well microtiter plate with non-binding surface. For high-throughput application in the 1536-well microtiter plate format, volumes of the reagent mixes were adjusted, maintaining the volumetric ratio. Proteins POLRMT (NM_172551.3), TFAM (NM_009360.4) and TFB2 M (NM_008249.4) were diluted from their stocks to working concentrations of 150 nM, 1.8 µM and 330 nM respectively, in a dilution buffer containing 100 mM Tris-HCl pH 8.0, 200 mM NaCl, 10% (v/v) glycerole, 2 mM glutathione (GSH), 0.5 mM EDTA and 0.1 mg/mL BSA. Protein dilutions and template DNA, comprising a pUC18 plasmid encoding the mitochondrial light strand promoter, restriction linearized proximal to the promoter 3'-end (pUC-LSP), were mixed at the twofold final assay-concentration in a reaction buffer, containing 10 mM Tris-HCl pH 7.5, 10 mM $MgCl_2$, 40 mM NaCl, 2 mM GSH, 0.01% (w/v) Tween-20 and 0.1 mg/mL BSA.

5 µL of this mix were dispensed, depending on the chosen microtiter plate format, using multi-channel pipettes or a Multidrop® dispenser (Thermo Fisher Scientific, Waltham Mass.) into the wells of a microtiter plate and incubated at room temperature (RT) for 10 min. Chemical compounds under scrutiny in the assay were applied using contact-free acoustic droplet-dispensing (Echo520® Labcyte Inc., Sunnyvale Calif.) from 10 mM compound stocks in 100% DMSO, to a final concentration of 10 µM or in serial dilution series of the required concentration range. Equal amounts of DMSO without any compound were added to positive control samples, followed by an incubation step at RT for 10 min.

The enzymatic reaction was started by the addition of 5 µL of a mix of dNTPs in reaction buffer to a final concentration of 500 µM each. No nucleotide mix was added to negative control samples. The content of the wells was mixed using a VarioTeleshaker™ (Thermo Fisher Scientific, Waltham Mass.) at 1,500 rpm for 45 sec after which the microtiter plate was centrifuged at 500×g for 1 min. The samples were incubated for 2 h at RT with humidity control to avoid evaporation. The detection reagents were prepared in a buffer that was composed, such that the enzymatic reaction was terminated due to chelating of Mg-ions and increased ionic strength, containing 50 mM Tris-HCl pH 7.5, 700 mM NaCl, 20 mM EDTA, and 0.01% (w/v) Tween-20. Importantly Eu-cryptate-coupled streptavidin had to be pre-incubated with a 100-fold molar excess of a random sequence oligonucleotide for 10 min at RT in the dark to block unspecific binding of single stranded RNA to the protein. Subsequently, the blocked streptavidin(—Eu) was mixed with the DNA-probes on ice and kept away from light until use.

At the end of the enzymatic reaction time 10 µL detection reagent mix was added, such that the final concentration of fluorescent-donor probe (bio-5'-AACACATCTCT(-bio)GC-CAAACCCCA-bio-3'), fluorescent-acceptor probe (ATTO647N-5'-ACAAAGAACCCTAACACCAG-3') and streptavidin(—Eu) in each assay well was 1 nM, 3 nM, and 1 nM respectively. Assay plates were again mixed and centrifuged as above and stored at RT, protected from light for at least 2 h or until binding of the DNA probes to RNA product and binding of streptavidin(—Eu) to the biotinylated DNA probe led to the development of the maximal FRET signal. The generated signal was measured with an EnVision plate reader, including TRF light unit (Perkin Elmer, Waltham Mass.), using excitation at 320 nm, an integration time of 200 µs and a delay time of 100 µs, prior to detection at 620 nm and 665 nm. The ratio of donor- and acceptor-fluorescence was used to assess the specific FRET signal, as a measure of the generated product content (i.e. enzymatic activity).

5. Quantitative Real Time-PCR to Assess Cellular Activity

Quantitative real-time PCR (qRT-PCR), based on the TaqMan™ (Thermo Fisher Scientific, Waltham Mass.) technology, was carried out essentially as described in (Heid et al., 1996). HeLa cells were plated one day before compound treatment in RPMI medium supplemented with 10% Fetal Calf Serum and 2 mM L-glutamine. Cells were incubated with dilution series of compounds or vehicle (DMSO) for 4 h, prior to harvest and extraction of the RNA using the RNeasy Mini Kit (Qiagen, Hilden D), according to the manufacturer's instructions. RNA concentrations were measured spectroscopically, using a NanoDrop-2000 (Thermo Fisher Scientific, Waltham Mass.) and normalized prior to cDNA synthesis, using a 'High-Capacity cDNA Reverse Transcription Kit' (Thermo Fisher Scientific, Waltham Mass.). qRT-PCR was carried out using the 'TaqMan Fast Advance Master Mix' (Thermo Fisher Scientific, Waltham Mass.) on a 7500 Fast Real-Time PCR machine (Applied Biosystems, Foster City Calif.)

For these measurements, three genes were used to compare the effect of the scrutinized compounds in relation to their concentration. The POLRMT-gene was used to detect potential influences on nuclear transcription. Mitochondrial transcription in vivo was monitored by measurements 7S RNA. The TBP (TATA-box binding protein) gene was employed as the control (housekeeping gene) during qRT-PCR. The short-lived mitochondrial 7S RNA, which is not post-transcriptionally stabilized, allowed us to monitor rapid changes in mitochondrial transcription activity following compound addition. Biological triplicates were analyzed using the comparative CT Method ($\Delta\Delta Ct$) method (Bubner and Baldwin, 2004) and reported as Rq % values (Rq=Relative quantification=$2-\Delta\Delta Ct$).

6. Biological Activities of Compounds

Activities of compounds are listed in Table 1 together with compound number and IUPAC names as determined by the homogeneous TR-FRET assay for mitochondrial transcription activity according to Example 4 and the quantitative real time-PCR assay of inhibition of mitochondrial transcription according to Example 5 were grouped according to the following scheme:

| mitochondrial transcription activity (IC-50) | <20 nM +++ | 20 nM ≤ x < 100 nM ++ | 100 nM ≤ x < 1 µM + | 1 µM ≤ x < 5 µM (+) |
|---|---|---|---|---|
| cellular qPCR assay IMT (IC-50) | <10 nM +++ | 10 nM ≤ x < 50 nM ++ | 50 nM ≤ x < 500 nM + | 500 nM ≤ x < 5 µM (+) |

TABLE 4

IUPAC chemical names and biological activities

| Ex | IUPAC Name | mitochondrial transcription activity | cellular qPCR assay |
|---|---|---|---|
| 1 | 7-[1-methyl-2-oxo-2-(1-piperidyl)ethoxy]-4-(o-tolyl)chromen-2-one | +++ | +++ |
| 2 | 4-(2-chlorophenyl)-7-[1-methyl-2-oxo-2-(1-piperidyl)ethoxy]chromen-2-one | +++ | +++ |
| 3 | (3S)-1-[2-[4-(o-tolyl)-2-oxo-chromen-7-yl]oxypropanoyl]piperidine-3-carboxylic acid | +++ | |
| 4 | 2-[4-(o-tolyl)-2-oxo-chromen-7-yl]oxy-N-(2-pyridyl)propanamide | +++ | |
| 5 | 7-(1-methyl-2-oxo-2-pyrrolidin-1-yl-ethoxy)-4-(o-tolyl)chromen-2-one | +++ | |
| 6 | methyl 1-[2-[4-(o-tolyl)-2-oxo-chromen-7-yl]oxypropanoyl]piperidine-3-carboxylate | +++ | |
| 7 | methyl 1-[2-[4-(2-chlorophenyl)-2-oxo-chromen-7-yl]oxypropanoyl]piperidine-3-carboxylate | +++ | |
| 8 | 1-[2-[4-(o-tolyl)-2-oxo-chromen-7-yl]oxypropanoyl]piperidine-3-carboxylic acid | +++ | +++ |
| 9 | 1-[2-[4-(2-chlorophenyl)-2-oxo-chromen-7-yl]oxypropanoyl]piperidine-3-carboxylic acid | +++ | +++ |
| 10 | 1-[2-[4-(o-tolyl)-2-oxo-chromen-7-yl]oxypropanoyl]piperidine-3-sulfonic acid | +++ | |
| 11 | 1-[2-[4-(2-chlorophenyl)-2-oxo-chromen-7-yl]oxypropanoyl]piperidine-3-sulfonic acid | +++ | |
| 12 | 1-[2-[4-(o-tolyl)-2-oxo-chromen-7-yl]oxypropanoyl]piperidine-3-sulfonamide | +++ | +++ |
| 13 | 4-(2-chlorophenyl)-7-(1-methyl-2-oxo-2-pyrrolidin-1-yl-ethoxy)chromen-2-one | +++ | |
| 14 | (3S)-1-[(2R)-2-[4-(2-chloro-4-fluoro-phenyl)-2-oxo-chromen-7-yl]oxypropanoyl]piperidine-3-carboxylic acid | +++ | +++ |
| 15 | 1-[2-[4-(2-chlorophenyl)-2-oxo-chromen-7-yl]oxypropanoyl]-N-methyl-piperidine-3-carboxamide | +++ | +++ |
| 16 | ethyl (3S)-1-[2-[4-(2-chlorophenyl)-2-oxo-chromen-7-yl]oxypropanoyl]piperidine-3-carboxylate | +++ | |
| 17 | ethyl (3S)-1-[2-[4-(o-tolyl)-2-oxo-chromen-7-yl]oxypropanoyl]piperidine-3-carboxylate | +++ | |
| 18 | N-methyl-1-[2-[4-(o-tolyl)-2-oxo-chromen-7-yl]oxypropanoyl]piperidine-3-sulfonamide | +++ | +++ |
| 19 | N-[4-(2-hydroxyethyl)phenyl]-2-[4-(o-tolyl)-2-oxo-chromen-7-yl]oxy-propanamide | +++ | |
| 20 | 1-[2-[4-(2-chlorophenyl)-2-oxo-chromen-7-yl]oxypropanoyl]-N-methyl-piperidine-3-sulfonamide | +++ | |
| 21 | N-methyl-1-[2-[4-(o-tolyl)-2-oxo-chromen-7-yl]oxypropanoyl]piperidine-3-carboxamide | +++ | +++ |
| 22 | (3S)-1-[2-[4-(o-tolyl)-2-oxo-chromen-7-yl]oxypropanoyl]pyrrolidine-3-carboxylic acid | +++ | |
| 23 | (3S)-1-[(2R)-2-[4-(2-chlorophenyl)-2-oxo-chromen-7-yl]oxypropanoyl]piperidine-3-carboxylic acid | +++ | +++ |
| 24 | 1-[2-[4-(2-chlorophenyl)-2-oxo-chromen-7-yl]oxypropanoyl]piperidine-3-sulfonamide | +++ | +++ |
| 25 | N-cyclopropyl-2-[4-(o-tolyl)-2-oxo-chromen-7-yl]oxy-propanamide | +++ | +++ |
| 26 | 2-[4-(2-chlorophenyl)-2-oxo-chromen-7-yl]oxy-N-cyclopropyl-propanamide | +++ | +++ |
| 27 | (3S)-1-[(2R)-2-[4-(o-tolyl)-2-oxo-chromen-7-yl]oxypropanoyl]piperidine-3-carboxylic acid | +++ | +++ |

TABLE 4-continued

IUPAC chemical names and biological activities

| Ex | IUPAC Name | mitochondrial transcription activity | cellular qPCR assay |
|---|---|---|---|
| 28 | (3S)-1-[(2R)-2-[4-(2-chlorophenyl)-2-oxo-chromen-7-yl]oxypropanoyl]piperidine-3-carbonitrile | +++ | |
| 29 | (3S)-1-[2-[4-(2-chlorophenyl)-2-oxo-chromen-7-yl]oxypropanoyl]pyrrolidine-3-carboxylic acid | +++ | |
| 30 | 7-[(1R)-1-methyl-2-oxo-2-(1-piperidyl)ethoxy]-4-(o-tolyl)chromen-2-one | +++ | |
| 31 | 2-[4-(2-chlorophenyl)-2-oxo-chromen-7-yl]oxy-N-(2-pyridyl)propanamide | +++ | |
| 32 | (3S)-1-[(2R)-2-[4-(o-tolyl)-2-oxo-chromen-7-yl]oxypropanoyl]piperidine-3-carbonitrile | +++ | |
| 33 | (3S)-1-[2-[4-(2-chlorophenyl)-2-oxo-chromen-7-yl]oxypropanoyl]piperidine-3-carboxylic acid | +++ | +++ |
| 34 | 4-(2-chlorophenyl)-7-[(1R)-1-methyl-2-oxo-2-(1-piperidyl)ethoxy]chromen-2-one | +++ | |
| 35 | 2-[4-(2-chlorophenyl)-2-oxo-chromen-7-yl]oxy-N-[4-(2-hydroxyethyl)phenyl]propanamide | +++ | |
| 36 | (2R)-N-isopropyl-2-[4-(o-tolyl)-2-oxo-chromen-7-yl]oxy-propanamide | +++ | +++ |
| 37 | 1-[2-[4-(2-chloro-4-fluoro-phenyl)-2-oxo-chromen-7-yl]oxypropanoyl]-3-methyl-piperidine-3-carboxylic acid | +++ | +++ |
| 38 | N,N-dimethyl-2-[4-(o-tolyl)-2-oxo-chromen-7-yl]oxy-propanamide | +++ | +++ |
| 39 | 4-(2-chlorophenyl)-7-[1-methyl-2-oxo-2-[3-(2H-tetrazol-5-yl)-1-piperidyl]ethoxy]chromen-2-one | +++ | |
| 40 | ethyl 2-[4-(2-chlorophenyl)-2-oxo-chromen-7-yl]oxypropanoate | +++ | |
| 41 | 1-[2-[4-(o-tolyl)-2-oxo-chromen-7-yl]oxypropanoyl]piperidine-3-carbonitrile | +++ | |
| 42 | 7-[1-methyl-2-oxo-2-[3-(2H-tetrazol-5-yl)-1-piperidyl]ethoxy]-4-(o-tolyl)chromen-2-one | +++ | ++ |
| 43 | 3-methyl-1-[2-[4-(o-tolyl)-2-oxo-chromen-7-yl]oxypropanoyl]piperidine-3-carboxylic acid | +++ | |
| 44 | (2R)-N,N-dimethyl-2-[4-(o-tolyl)-2-oxo-chromen-7-yl]oxy-propanamide | +++ | |
| 45 | (2R)-2-[4-(2-chlorophenyl)-2-oxo-chromen-7-yl]oxy-N,N-dimethyl-propanamide | +++ | |
| 46 | (3R)-1-[2-[4-(2-chlorophenyl)-2-oxo-chromen-7-yl]oxypropanoyl]piperidine-3-carboxylic acid | +++ | |
| 47 | (3S)-1-[2-[4-(2-chloro-4-fluoro-phenyl)-2-oxo-chromen-7-yl]oxypropanoyl]piperidine-3-carboxylic acid | +++ | +++ |
| 48 | 1-[2-[4-(2-chlorophenyl)-2-oxo-chromen-7-yl]oxypropanoyl]piperidine-3-carbonitrile | +++ | |
| 49 | 2-[4-(2-chloro-3-fluoro-phenyl)-2-oxo-chromen-7-yl]oxy-N-isopropyl-propanamide | +++ | |
| 50 | (3S)-1-[2-[4-(2-chloro-3-fluoro-phenyl)-2-oxo-chromen-7-yl]oxypropanoyl]piperidine-3-carboxylic acid | +++ | |
| 51 | 2-[4-(2-chlorophenyl)-2-oxo-chromen-7-yl]oxy-N-methyl-propanamide | +++ | |
| 52 | 1-[2-[4-(2-chloro-3-fluoro-phenyl)-2-oxo-chromen-7-yl]oxypropanoyl]piperidine-3-sulfonamide | +++ | |
| 53 | (3R)-1-[2-[4-(o-tolyl)-2-oxo-chromen-7-yl]oxypropanoyl]piperidine-3-carboxylic acid | +++ | |

TABLE 4-continued

IUPAC chemical names and biological activities

| Ex | IUPAC Name | mitochondrial transcription activity | cellular qPCR assay |
|---|---|---|---|
| 54 | 1-[2-[4-(2-chlorophenyl)-2-oxo-chromen-7-yl]oxypropanoyl]-3-methyl-piperidine-3-carboxylic acid | +++ | +++ |
| 55 | isopropyl (2R)-2-[4-(o-tolyl)-2-oxo-chromen-7-yl]oxypropanoate | +++ | |
| 56 | (2R)-2-[4-(2-chlorophenyl)-2-oxo-chromen-7-yl]oxy-N-isopropyl-propanamide | ++ | +++ |
| 57 | ethyl 2-[4-(2-chloro-3-fluoro-phenyl)-2-oxo-chromen-7-yl]oxypropanoate | ++ | |
| 58 | ethyl 2-[4-(o-tolyl)-2-oxo-chromen-7-yl]oxypropanoate | ++ | |
| 59 | 2-[1-[2-[4-(2-chlorophenyl)-2-oxo-chromen-7-yl]oxypropanoyl]-4-piperidyl]acetic acid | ++ | ++ |
| 60 | 2-[1-[2-[4-(o-tolyl)-2-oxo-chromen-7-yl]oxypropanoyl]-4-piperidyl]acetic acid | ++ | |
| 61 | 2-[4-(2-chloro-3-fluoro-phenyl)-2-oxo-chromen-7-yl]oxy-N-cyclopropyl-propanamide | ++ | |
| 62 | N-isopropyl-2-[4-(o-tolyl)-2-oxo-chromen-7-yl]oxy-propanamide | ++ | +++ |
| 63 | 1-[2-[4-(o-tolyl)-2-oxo-chromen-7-yl]oxypropanoyl]pyrrolidine-3-sulfonamide | ++ | |
| 64 | isopropyl (2R)-2-[4-(2-chlorophenyl)-2-oxo-chromen-7-yl]oxypropanoate | ++ | |
| 65 | 2-[4-(2-chloro-4-fluoro-phenyl)-2-oxo-chromen-7-yl]oxy-N-isopropyl-propanamide | ++ | |
| 66 | 2-[1-[2-[4-(2-chlorophenyl)-2-oxo-chromen-7-yl]oxypropanoyl]-3-piperidyl]acetic acid | ++ | +++ |
| 67 | (3R)-1-[2-[4-(2-chlorophenyl)-2-oxo-chromen-7-yl]oxypropanoyl]-N,N-dimethyl-piperidine-3-carboxamide | ++ | |
| 68 | 2-[4-(2-chloro-3-fluoro-phenyl)-2-oxo-chromen-7-yl]oxy-N-ethyl-propanamide | ++ | |
| 69 | 1-[2-[4-(2-chloro-4-fluoro-phenyl)-2-oxo-chromen-7-yl]oxypropanoyl]piperidine-3-sulfonamide | ++ | +++ |
| 70 | 2-[4-(2-chlorophenyl)-2-oxo-chromen-7-yl]oxy-N-isopropyl-propanamide | ++ | +++ |
| 71 | 7-[2-(4,4-difluoro-1-piperidyl)-1-methyl-2-oxo-ethoxy]-4-(o-tolyl)chromen-2-one | ++ | |
| 72 | 2-[1-[2-[4-(o-tolyl)-2-oxo-chromen-7-yl]oxypropanoyl]-3-piperidyl]acetic acid | ++ | |
| 73 | 7-[1-methyl-2-[3-(methylsulfonimidoyl)-1-piperidyl]-2-oxo-ethoxy]-4-(o-tolyl)chromen-2-one | ++ | |
| 74 | 4-(2-chlorophenyl)-7-[2-(4,4-difluoro-1-piperidyl)-1-methyl-2-oxo-ethoxy]chromen-2-one | ++ | |
| 75 | ethyl 1-[2-[4-(2-chlorophenyl)-2-oxo-chromen-7-yl]oxypropanoyl]-3-methyl-piperidine-3-carboxylate | ++ | |
| 76 | (3S)-1-[2-[4-(2-chlorophenyl)-2-oxo-chromen-7-yl]oxypropanoyl]-N,N-dimethyl-piperidine-3-carboxamide | ++ | |
| 77 | 1-[2-[4-(2-chlorophenyl)-2-oxo-chromen-7-yl]oxypropanoyl]pyrrolidine-3-sulfonamide | ++ | |
| 78 | (3R)-N,N-dimethyl-1-[2-[4-(o-tolyl)-2-oxo-chromen-7-yl]oxypropanoyl]piperidine-3-carboxamide | ++ | +++ |
| 79 | 4-(2-chlorophenyl)-7-[1-methyl-2-[3-(methylsulfonimidoyl)-1-piperidyl]-2-oxo-ethoxy]chromen-2-one | ++ | +++ |
| 80 | methyl 2-[1-[2-[4-(2-chlorophenyl)-2-oxo-chromen-7-yl]oxypropanoyl]-4-piperidyl]acetate | ++ | + |
| 81 | ethyl 2-[4-(2-bromophenyl)-2-oxo-chromen-7-yl]oxypropanoate | ++ | ++ |
| 82 | ethyl 2-[4-(2-chloro-4-fluoro-phenyl)-2-oxo-chromen-7-yl]oxypropanoate | ++ | |

TABLE 4-continued

IUPAC chemical names and biological activities

| Ex | IUPAC Name | mitochondrial transcription activity | cellular qPCR assay |
|---|---|---|---|
| 83 | methyl 2-[1-[2-[4-(o-tolyl)-2-oxo-chromen-7-yl]oxypropanoyl]-4-piperidyl]acetate | ++ | |
| 84 | (3S)-N,N-dimethyl-1-[2-[4-(o-tolyl)-2-oxo-chromen-7-yl]oxypropanoyl]piperidine-3-carboxamide | ++ | ++ |
| 85 | N-ethyl-2-[4-(o-tolyl)-2-oxo-chromen-7-yl]oxy-propanamide | ++ | ++ |
| 86 | ethyl 2-[1-[2-[4-(2-chlorophenyl)-2-oxo-chromen-7-yl]oxypropanoyl]-3-piperidyl]acetate | ++ | ++ |
| 87 | ethyl 2-[1-[2-[4-(o-tolyl)-2-oxo-chromen-7-yl]oxypropanoyl]-3-piperidyl]acetate | ++ | |
| 88 | ethyl 3-methyl-1-[2-[4-(o-tolyl)-2-oxo-chromen-7-yl]oxypropanoyl]piperidine-3-carboxylate | ++ | |
| 89 | 2-[4-(2-bromophenyl)-2-oxo-chromen-7-yl]oxy-N,N-dimethyl-propanamide | ++ | +++ |
| 90 | 2-[4-(2-chloro-4-fluoro-phenyl)-2-oxo-chromen-7-yl]oxy-N-cyclopropyl-propanamide | ++ | |
| 91 | 2-[4-(2-chloro-4-fluoro-phenyl)-2-oxo-chromen-7-yl]oxy-N-ethyl-propanamide | ++ | +++ |
| 92 | isopropyl 2-[4-(2-bromophenyl)-2-oxo-chromen-7-yl]oxypropanoate | ++ | +++ |
| 93 | 2-[4-(2-chlorophenyl)-2-oxo-chromen-7-yl]oxy-N,N-dimethyl-propanamide | ++ | +++ |
| 94 | 2-[4-(2-chloro-3-fluoro-phenyl)-2-oxo-chromen-7-yl]oxypropanoic acid | ++ | |
| 95 | ethyl 1-[2-[4-(2-chloro-4-fluoro-phenyl)-2-oxo-chromen-7-yl]oxypropanoyl]-3-methyl-piperidine-3-carboxylate | + | |
| 96 | 2-[4-(2-chlorophenyl)-2-oxo-chromen-7-yl]oxypropanoic acid | + | |
| 97 | 2-[4-(o-tolyl)-2-oxo-chromen-7-yl]oxypropanoic acid | + | |
| 98 | 2-[4-(2-chlorophenyl)-2-oxo-chromen-7-yl]oxy-N-ethyl-propanamide | + | +++ |
| 99 | 2-[4-(2-chloro-4-fluoro-phenyl)-2-oxo-chromen-7-yl]oxypropanoic acid | + | |
| 100 | methyl 2-[(3S)-1-[(2R)-2-[4-(2-chlorophenyl)-2-oxo-chromen-7-yl]oxypropanoyl]-3-piperidyl]acetate | +++ | |
| 101 | methyl 2-[(3R)-1-[(2R)-2-[4-(2-chlorophenyl)-2-oxo-chromen-7-yl]oxypropanoyl]-3-piperidyl]acetate | +++ | |
| 102 | 2-[(3S)-1-[(2R)-2-[4-(2-chlorophenyl)-2-oxo-chromen-7-yl]oxypropanoyl]-3-piperidyl]acetic acid | +++ | |
| 103 | 2-[(3R)-1-[(2R)-2-[4-(2-chlorophenyl)-2-oxo-chromen-7-yl]oxypropanoyl]-3-piperidyl]acetic acid | +++ | |
| 104 | methyl 2-[(3R)-1-[(2R)-2-[4-(2-chloro-4-fluoro-phenyl)-2-oxo-chromen-7-yl]oxypropanoyl]-3-piperidyl]acetate | +++ | ++ |
| 105 | methyl 2-[(3S)-1-[(2R)-2-[4-(2-chloro-4-fluoro-phenyl)-2-oxo-chromen-7-yl]oxypropanoyl]-3-piperidyl]acetate | ++ | ++ |
| 106 | 2-[(3R)-1-[(2R)-2-[4-(2-chloro-4-fluoro-phenyl)-2-oxo-chromen-7-yl]oxypropanoyl]-3-piperidyl]acetic acid | +++ | +++ |
| 107 | 2-[(3S)-1-[(2R)-2-[4-(2-chloro-4-fluoro-phenyl)-2-oxo-chromen-7-yl]oxypropanoyl]-3-piperidyl]acetic acid | +++ | +++ |
| 108 | (3R)-1-[(2R)-2-[4-(2-chloro-4-fluoro-phenyl)-2-oxo-chromen-7-yl]oxypropanoyl]piperidine-3-carboxylic acid | +++ | |
| 109 | ethyl (3S)-1-[2-[4-(2-chlorophenyl)-2-oxo-chromen-7-yl]oxybutanoyl]piperidine-3-carboxylate | ++ | |

TABLE 4-continued

IUPAC chemical names and biological activities

| Ex | IUPAC Name | mitochondrial transcription activity | cellular qPCR assay |
|---|---|---|---|
| 110 | (3S)-1-[2-[4-(2-chlorophenyl)-2-oxo-chromen-7-yl]oxybutanoyl]piperidine-3-carboxylic acid | +++ | +++ |
| 111 | ethyl (3S)-1-[(2R)-2-[4-(2-chloro-4-fluoro-phenyl)-2-oxo-chromen-7-yl]oxypropanoyl] piperidine-3-carboxylate | ++ | + |
| 112 | 2-[4-(2-chlorophenyl)-2-oxo-chromen-7-yl]oxy-2-methyl-propanoic acid | + | |
| 113 | ethyl 2-[4-(2-chlorophenyl)-2-oxo-chromen-7-yl]oxy-2-methyl-propanoate | + | |
| 114 | 2-[4-(2-chlorophenyl)-2-oxo-chromen-7-yl]oxy-N-isopropyl-2-methyl-propanamide | + | ++ |
| 115 | N-isopropyl-2-methyl-2-[4-(o-tolyl)-2-oxo-chromen-7-yl]oxy-propanamide | + | ++ |
| 116 | (3S)-1-[2-[4-(2-chlorophenyl)-2-oxo-chromen-7-yl]oxy-2-methyl-propanoyl]piperidine-3-carboxylic acid | + | (+) |
| 117 | isopropyl (3S)-1-[(2R)-2-[4-(2-chloro-4-fluoro-phenyl)-2-oxo-chromen-7-yl]oxypropanoyl] piperidine-3-carboxylate | ++ | + |
| 118 | tert-butyl (3S)-1-[(2R)-2-[4-(2-chloro-4-fluoro-phenyl)-2-oxo-chromen-7-yl]oxypropanoyl] piperidine-3-carboxylate | ++ | + |
| 119 | 2-morpholinoethyl (3S)-1-[(2R)-2-[4-(2-chloro-4-fluoro-phenyl)-2-oxo-chromen-7-yl] oxypropanoyl]piperidine-3-carboxylate | | +++ |
| 120 | heptyl (3S)-1-[(2R)-2-[4-(2-chloro-4-fluoro-phenyl)-2-oxo-chromen-7-yl]oxypropanoyl] piperidine-3-carboxylate | + | +++ |
| 121 | isopropoxycarbonyloxymethyl (3S)-1-[(2R)-2-[4-(2-chloro-4-fluoro-phenyl)-2-oxo-chromen-7-yl]oxypropanoyl]piperidine-3-carboxylate | ++ | +++ |
| 122 | (3S)-N-methyl-1-[(2R)-2-[4-(2-chloro-4-fluoro-phenyl)-2-oxo-chromen-7-yl]oxypropanoyl piperidine-3-carboxamide | ++ | +++ |
| 123 | isopropyl 2-[(3R)-1-[(2R)-2-[4-(2-chloro-4-fluoro-phenyl)-2-oxo-chromen-7-yl]oxypropanoyl]-3-piperidyl]acetate | ++ | +++ |
| 124 | tert-butyl 2-[(3R)-1-[(2R)-2-[4-(2-chloro-4-fluoro-phenyl)-2-oxo-chromen-7-yl]oxypropanoyl]-3-piperidyl]acetate | ++ | +++ |
| 125 | 2-morpholinoethyl 2-[(3R)-1-[(2R)-2-[4-(2-chloro-4-fluoro-phenyl)-2-oxo-chromen-7-yl] oxypropanoyl]-3-piperidyl]acetate | +++ | +++ |
| 126 | heptyl 2-[(3R)-1-[(2R)-2-[4-(2-chloro-4-fluoro-phenyl)-2-oxo-chromen-7-yl]oxypropanoyl]-3-piperidyl]acetate | + | +++ |
| 127 | isopropoxycarbonyloxymethyl 2-[(3R)-1-[(2R)-2-[4-(2-chloro-4-fluoro-phenyl)-2-oxo-chromen-7-yl]oxypropanoyl]-3-piperidyl]acetate | ++ | +++ |
| 128 | 2-[(3R)-1-[(2R)-2-[4-(2-chloro-4-fluoro-phenyl)-2-oxo-chromen-7-yl]oxypropanoyl]-3-piperidyl]-N-methyl-acetamide | +++ | +++ |
| 129 | methyl 1-[(2R)-2-[4-(2-chloro-4-fluoro-phenyl)-2-oxo-chromen-7-yl]oxypropanoyl]piperidine-4-carboxylate | +++ | |
| 130 | (2R)-2-[4-(2-chloro-4-fluoro-phenyl)-2-oxo-chromen-7-yl]oxy-N-[4-(hydroxymethyl)phenyl]propanamide | +++ | |
| 131 | 1-[(2R)-2-[4-(2-chloro-4-fluoro-phenyl)-2-oxo-chromen-7-yl]oxypropanoyl]piperidine-4-carboxylic acid | ++ | |

TABLE 4-continued

IUPAC chemical names and biological activities

| Ex | IUPAC Name | mitochondrial transcription activity | cellular qPCR assay |
|---|---|---|---|
| 132 | (3S)-1-[(2R)-2-[4-(2-chloro-4-fluoro-phenyl)-2-oxo-chromen-7-yl]oxypropanoyl]piperidine-3-carboxamide | +++ | |
| 133 | 2-[(3R)-1-[(2R)-2-[4-(2-chloro-4-fluoro-phenyl)-2-oxo-chromen-7-yl]oxypropanoyl]-3-piperidyl]acetamide | +++ | |
| 134 | (3S)-1-[(2R)-2-[4-(2-ethylphenyl)-2-oxo-chromen-7-yl]oxypropanoyl]piperidine-3-carboxylic acid | +++ | |
| 135 | methyl (2S)-4-[(2R)-2-[4-(2-chloro-4-fluoro-phenyl)-2-oxo-chromen-7-yl]oxypropanoyl]piperazine-2-carboxylate | + | |
| 136 | methyl (2R)-4-[(2R)-2-[4-(2-chloro-4-fluoro-phenyl)-2-oxo-chromen-7-yl]oxypropanoyl]piperazine-2-carboxylate | ++ | ++ |
| 137 | methyl 1-methyl-4-[rac-(2R)-2-[4-(2-chloro-4-fluoro-phenyl)-2-oxo-chromen-7-yl]oxypropanoyl]piperazine-2-carboxylate | + | |
| 138 | (2S)-4-[(2R)-2-[4-(2-chloro-4-fluoro-phenyl)-2-oxo-chromen-7-yl]oxypropanoyl]piperazine-2-carboxylic acid | ++ | |
| 139 | 3-[[(2R)-2-[4-(2-chloro-4-fluoro-phenyl)-2-oxo-chromen-7-yl]oxypropanoyl]amino]benzoic acid | +++ | + |
| 140 | (2R)-2-[4-(2-chloro-4-fluoro-phenyl)-2-oxo-chromen-7-yl]oxy-N-[4-(2-methoxyethyl)phenyl]propanamide | + | |
| 141 | 4-[[(2R)-2-[4-(2-chloro-4-fluoro-phenyl)-2-oxo-chromen-7-yl]oxypropanoyl]amino]benzoic acid | +++ | + |
| 142 | methyl 2-[(3R)-1-[(2R)-2-[4-(2-chloro-4-fluoro-phenyl)-2-oxo-chromen-7-yl]oxypropanoyl]pyrrolidin-3-yl]acetate | ++ | |
| 143 | methyl 5-[[(2R)-2-[4-(2-chloro-4-fluoro-phenyl)-2-oxo-chromen-7-yl]oxypropanoyl]amino]pyridine-3-carboxylate | + | |
| 144 | methyl 2-[(3S)-1-[(2R)-2-[4-(2-chloro-4-fluoro-phenyl)-2-oxo-chromen-7-yl]oxypropanoyl]pyrrolidin-3-yl]acetate | ++ | |
| 145 | 2-[(3R)-1-[(2R)-2-[4-(2-chloro-4-fluoro-phenyl)-2-oxo-chromen-7-yl]oxypropanoyl]pyrrolidin-3-yl]acetic acid | ++ | +++ |
| 146 | methyl 2-[[(2R)-2-[4-(2-chloro-4-fluoro-phenyl)-2-oxo-chromen-7-yl]oxypropanoyl]amino]pyridine-4-carboxylate | + | |
| 147 | 2-[(3S)-1-[(2R)-2-[4-(2-chloro-4-fluoro-phenyl)-2-oxo-chromen-7-yl]oxypropanoyl]pyrrolidin-3-yl]acetic acid | +++ | ++ |
| 148 | 5-[[(2R)-2-[4-(2-chloro-4-fluoro-phenyl)-2-oxo-chromen-7-yl]oxypropanoyl]amino]pyridine-3-carboxylic acid | +++ | |
| 149 | methyl 6-[[(2R)-2-[4-(2-chloro-4-fluoro-phenyl)-2-oxo-chromen-7-yl]oxypropanoyl]amino]pyridine-2-carboxylate | ++ | + |
| 150 | (2R)-4-[(2R)-2-[4-(2-chloro-4-fluoro-phenyl)-2-oxo-chromen-7-yl]oxypropanoyl]piperazine-2-carboxylic acid | ++ | |
| 151 | 6-[[(2R)-2-[4-(2-chloro-4-fluoro-phenyl)-2-oxo-chromen-7-yl]oxypropanoyl]amino]pyridine-2-carboxylic acid | +++ | |
| 152 | 2-[[(2R)-2-[4-(2-chloro-4-fluoro-phenyl)-2-oxo-chromen-7-yl]oxypropanoyl]amino]pyridine-4-carboxylic acid | + | |

TABLE 4-continued

IUPAC chemical names and biological activities

| Ex | IUPAC Name | mitochondrial transcription activity | cellular qPCR assay |
|---|---|---|---|
| 153 | methyl 5-[[(2R)-2-[4-(2-chloro-4-fluoro-phenyl)-2-oxo-chromen-7-yl]oxypropanoyl]amino]pyridine-2-carboxylate | ++ | |
| 154 | 5-[[(2R)-2-[4-(2-chloro-4-fluoro-phenyl)-2-oxo-chromen-7-yl]oxypropanoyl]amino]pyridine-2-carboxylic acid | +++ | |
| 155 | 6-[[(2R)-2-[4-(2-chloro-4-fluoro-phenyl)-2-oxo-chromen-7-yl]oxypropanoyl]amino]pyridine-3-carboxylic acid | +++ | +++ |
| 156 | methyl 4-[[(2R)-2-[4-(2-chloro-4-fluoro-phenyl)-2-oxo-chromen-7-yl]oxypropanoyl]amino]pyridine-2-carboxylate | ++ | |
| 157 | methyl (3S)-1-[(2R)-2-[4-(2-chloro-4-fluoro-phenyl)-2-oxo-chromen-7-yl]oxypropanoyl]pyrrolidine-3-carboxylate | ++ | |
| 158 | (3S)-1-[(2R)-2-[4-(4-fluoro-2-methyl-phenyl)-2-oxo-chromen-7-yl]oxypropanoyl]piperidine-3-carboxylic acid | +++ | |
| 159 | (3S)-1-[(2R)-2-[4-(2-chloro-4-fluoro-phenyl)-2-oxo-chromen-7-yl]oxypropanoyl]pyrrolidine-3-carboxylic acid | ++ | (+) |
| 160 | 4-[[(2R)-2-[4-(2-chloro-4-fluoro-phenyl)-2-oxo-chromen-7-yl]oxypropanoyl]amino]pyridine-2-carboxylic acid | +++ | |
| 161 | 1-methyl-4-[rac-(2R)-2-[4-(2-chloro-4-fluoro-phenyl)-2-oxo-chromen-7-yl]oxypropanoyl]piperazine-2-carboxylic acid | + | (+) |
| 162 | (3S)-1-[(2R)-2-[4-(2-cyanophenyl)-2-oxo-chromen-7-yl]oxypropanoyl]piperidine-3-carboxylic acid | ++ | |
| 163 | (3S)-1-[(2R)-2-[4-(2,6-dichlorophenyl)-2-oxo-chromen-7-yl]oxypropanoyl]piperidine-3-carboxylic acid | + | |
| 164 | 4-(2-chloro-4-fluoro-phenyl)-7-[(1R)-1-methyl-2-oxo-2-(4-prop-2-enoylpiperazin-1-yl)ethoxy]chromen-2-one | +++ | +++ |
| 165 | N-[(3S)-1-[(2R)-2-[4-(2-chloro-4-fluoro-phenyl)-2-oxo-chromen-7-yl]oxypropanoyl]-3-piperidyl]prop-2-enamide | +++ | +++ |
| 166 | 7-[(1R)-2-[4-(2-chloroacetyl)piperazin-1-yl]-1-methyl-2-oxo-ethoxy]-4-(2-chloro-4-fluoro-phenyl)chromen-2-one | +++ | +++ |
| 167 | 2-chloro-N-[(3S)-1-[(2R)-2-[4-(2-chloro-4-fluoro-phenyl)-2-oxo-chromen-7-yl]oxypropanoyl]-3-piperidyl]acetamide | +++ | +++ |
| 168 | 4-(2-chloro-4-fluoro-phenyl)-7-[(1R)-1-methyl-2-oxo-2-(4-propanoylpiperazin-1-yl)ethoxy]chromen-2-one | +++ | +++ |
| 169 | N-[(3S)-1-[(2R)-2-[4-(2-chloro-4-fluoro-phenyl)-2-oxo-chromen-7-yl]oxypropanoyl]-3-piperidyl]propanamide | +++ | +++ |
| 170 | rac-(3S)-1-[2-[4-(2-chlorophenyl)-2-oxo-pyrano[2,3-b]pyridin-7-yl]oxypropanoyl]piperidine-3-carboxylic acid | ++ | + |
| 171 | tert-butyl rac-(3S)-1-[2-[4-(2-chlorophenyl)-2-oxo-pyrano[2,3-b]pyridin-7-yl]oxypropanoyl]piperidine-3-carboxylate | + | |
| 172 | (3S)-1-[(2R)-2-[4-(2-chlorophenyl)-2-oxo-pyrano[2,3-b]pyridin-7-yl]oxypropanoyl]piperidine-3-carboxylic acid | ++ | + |

TABLE 4-continued

IUPAC chemical names and biological activities

| Ex | IUPAC Name | mitochondrial transcription activity | cellular qPCR assay |
|---|---|---|---|
| 173 | (3S)-1-[(2R)-2-[4-(2-chloro-4-fluoro-phenyl)-2-oxo-pyrano[2,3-b]pyridin-7-yl]oxypropanoyl]piperidine-3-carboxylic acid | ++ | + |
| 174 | (3S)-1-[(2R)-2-[4-(3-methyl-2-thienyl)-2-oxo-chromen-7-yl]oxypropanoyl]piperidine-3-carboxylic acid | ++ | +++ |
| 175 | ethyl 2-[4-(2-fluorophenyl)-2-oxo-chromen-7-yl]oxypropanoate | + | |
| 176 | ethyl 2-[4-(2,6-difluorophenyl)-2-oxo-chromen-7-yl]oxypropanoate | (+) | |
| 177 | 7-[(1R)-1-methyl-2-oxo-2-(1-piperidyl)ethoxy]-4-(3-methyl-2-thienyl)chromen-2-one | ++ | +++ |
| 178 | (2R)-N-isopropyl-2-[4-(3-methyl-2-thienyl)-2-oxo-chromen-7-yl]oxy-propanamide | + | ++ |
| 179 | (2R)-N,N-dimethyl-2-[4-(3-methyl-2-thienyl)-2-oxo-chromen-7-yl]oxy-propanamide | + | ++ |
| 180 | ethyl 2-[(3R)-1-[(2R)-2-[4-(3-methyl-2-thienyl)-2-oxo-chromen-7-yl]oxypropanoyl]-3-piperidyl]acetate | ++ | +++ |
| 181 | 2-[(3R)-1-[(2R)-2-[4-(3-methyl-2-thienyl)-2-oxo-chromen-7-yl]oxypropanoyl]-3-piperidyl]acetic acid | ++ | ++ |
| 182 | (3S)-1-[(2R)-2-[4-(4-methyl-3-thienyl)-2-oxo-chromen-7-yl]oxypropanoyl]piperidine-3-carboxylic acid | +++ | +++ |
| 183 | 7-[(1R)-1-methyl-2-oxo-2-(1-piperidyl)ethoxy]-4-(4-methyl-3-thienyl)chromen-2-one | +++ | +++ |
| 184 | 7-[1-methyl-2-oxo-2-(1-piperidyl)ethoxy]-4-(2-methyl-3-thienyl)chromen-2-one | + + | +++ |
| 185 | rac-(3S)-1-[2-[4-(2-methyl-3-thienyl)-2-oxo-chromen-7-yl]oxypropanoyl]piperidine-3-carboxylic acid | + + | ++ |

7. Therapeutic Effect on Human A2780 Ovary Carcinoma Xenograft in Nude Mice

A2780 ovary carcinoma cells ($1\times10^7$ cells in 100 μL of PBS/Matrigel), isolated during exponential growth phase from in vitro cell culture, were transplanted s.c. into each female nude mouse at day 0. Mice were kept under strictly controlled and standardized barrier conditions in IVC as described in Table 5.

TABLE 5

Standardized barrier conditions

| Subject | Conditions |
|---|---|
| Animals, gender and strain | Female NMRI: nu/nu mice (Janvier, France) |
| Age | 9-11 weeks |
| Body weight | 25.1 to 32.6 g (mean 28.4 ± 2.0 g) at the start of treatment |
| Supplier | EPO |
| Environmental conditions | Strictly controlled and standardized barrier conditions. IVC System Tecniplast DCC (TECNIPLAST DEUTSCHLAND GMBH) |
| Caging | Macrolon Type-II wire-mesh bottom |
| Feed type | Ssniff NM, Soest, Germany |
| Drinking water | Autoclaved tap water in water bottles (acidified to pH 4 with HCl) |
| Feeding and drinking time | Ad libitum 24 hours per day |
| Room temperature | 22 ± 1° C. |
| Relative humidity | 50 ± 10% |
| Light period | Artificial: 12 hours dark/12 hours light rhythm (light 06:00 to 18:00) |
| Health control | The health of the mice was examined at the start of the experiment and twice per day during the experiment |
| Identification | Ear mark and cage labels |
| Tumor model | Human ovary carcinoma cell line A2780 (ECACC 931125) |

In addition to the number of mice needed to build the groups necessary for the experiment, 8 additional mice were transplanted to have a sufficient number of satellite animals to improve stratification. Mice were stratified at day 7, when the mean tumor volume (TV) was 0.213±0.061 cm³, (median TV=0.206 cm³) into groups A-D with 8 mice each. 8 mice were excluded because of their tumor size.

The test compound 14 and vehicle were stored at room temperature and in the dark until use. Immediately before use, compound 14 was dissolved to obtain an injection solution to be sufficient for one week of treatment. The treatments were indicated as described in Table 6. Body weight (BWC) and tumor volume (TV) were monitored two to three times per week. Mean tumor weight±S.D. (RTV) was calculated. Mice of groups B, C and D were treated again at the end of the study period and blood samples were taken to generate plasma 1 h prior and 1 h post treatment. In addition, tumor and tissue samples were isolated, divided into two parts and snap frozen in liquid nitrogen from mice of groups A, C and D. Mice of group B had to be sacrificed at day 27 (QDx21) because of their too large tumor size. Mice of groups A, C and D were sacrificed at day 34 (QDx28 for times 28. Gross autopsy was performed from all mice.

(50 mg/kg) had no significant effect, the higher doses (100 and 200 mg/kg) were significantly more active regarding tumor growth inhibition (see FIG. 1A).

8. Therapeutic Effect on Human DLD-1 Colon Carcinoma Xenograft in the Nude Mice

DLD-1 colon carcinoma cells (5×10⁶ cells in 100 μL of PBS/Matrigel), isolated during exponential growth phase from in vitro cell culture, were transplanted s.c. into each female BALB/c nude mouse at day 0. Mice were kept under strictly controlled and standardized barrier conditions in IVC.

The test compound 14 and vehicle were stored at room temperature and in the dark until use. Immediately before use, compound 14 was dissolved to obtain a solution to be sufficient for one week of treatment. The treatments were indicated as described in Table 7. Sorafenib) (Nexavar®, which is an approved multi-kinase inhibitor/cytostatic from

TABLE 6

Groups and treatments

| Group | Mice (n) | Treatment | Route schedule | Schedule | Dose (total dose) [mg/kg] | BWC* (at day 27) [g] (Nadir in %, day) | Tumor growth inhibition (D 27)** Mean TV [cm³, ± S.D.] (p-values#) | RTV | Weight [g] (% of control) |
|---|---|---|---|---|---|---|---|---|---|
| A | 8 | vehicle | p.o. | QD × 28 | — | 32.3 ± 2.7 | 0.944 ± 0.425 | 4.8 | 0.833 ± 0.168 |
| B | 8 | cmp. 14 | p.o. | QD × 21 | 30 | 30.8 ± 2.3 (−0.8; D 18) | 1.300 ± 0.942 (n.s.) | 6.8 | 0.629 ± 0.456 (75.5) |
| C | 8 | cmp 14 | p.o. | QD × 28 | 100 | 29.5 ± 1.7 (−3.5; D 18) | 0.715 ± 0.800 (n.s.) | 5.1 | 0.491 ± 0.349 (60,0) |
| D | 8 | cmp 14 | p.o. | QD × 28 | 200 | 30.3 ± 2.2 (−3.2; D 18) | 0.232 ± 0.112# (0.000) | 1.1 | 0.141 ± 0.120 (16.99) |
| E | 8 | | | satellites | | | | | |

*mean body weight ± S.D. at day 27 and the nadir of body weight change (in parenthesis, together with day of measurement).
**tumor volume ± S.D. the relative tumor volume at day 27 compared to D 7 (start of treatment) as well as mean tumor weight +/− S.D.
statistical evaluation performed with U-test of Mann and Whitney using the Windows program STATISTICA 6. A significance level of p < 0.05 was used to identify significantly different data.

Results

Tolerability: Treatment with compound 14 was well tolerated with only a slight and transient body weight loss with a nadir at day 18 after treatment with the higher doses (see FIG. 1B), but no signs of toxicity were observed. Autopsy at the end revealed no abnormal observations.

Therapeutic effect: All mice treated with compound 14 showed a dose-dependent tumor growth inhibition, as indicated by optimum T/C values of 88.3% (50 mg/kg), 59.2% (100 mg/kg) and 24.9% (200 mg/kg). While the lowest dose Bayer A G, was used as a positive control. Body weight and tumor volume (TV) were monitored two to three times per week.

Mice of groups 3, 4 and 5 were treated again at the end of the study period and blood samples were taken to generate plasma 1 h prior and 1 h post treatment. In addition, tumor and tissue samples were isolated, divided into two parts and snap frozen in liquid nitrogen. Mice of groups 1-5 were sacrificed at day 39. Gross autopsy was performed from all mice.

TABLE 7

Groups and Treatments

| Group | Treatment | Total dose given on each dosing (mg/kg) | Dose volume per administration | Dosing schedule | Admin. route | No. of mice | Tumor Collection |
|---|---|---|---|---|---|---|---|
| 1 | Control | 0 mg/kg | 10 μL/g | QD × 28 days | p.o. | 8 | Yes |
| 2 | Sorafenib | 30 mg/kg | 10 μL/g | QD × 28 days | p.o. | 8 | Yes |

TABLE 7-continued

| | | Groups and Treatments | | | | | |
|---|---|---|---|---|---|---|---|
| Group | Treatment | Total dose given on each dosing (mg/kg) | Dose volume per administration | Dosing schedule | Admin. route | No. of mice | Tumor Collection |
| 3 | cmp 14 | 30 mg/kg | 10 µL/g | QD × 28 days | p.o. | 8 | Yes |
| 4 | cmp 14 | 100 mg/kg | 10 µL/g | QD × 28 days | p.o. | 8 | Yes |
| 5 | cmp 14 | 200 mg/kg | 10 µL/g | QD × 28 days | p.o. | 8 | Yes |

Results

Tolerability: Treatment with compound 14 was also well tolerated in the DLD-1 colon carcinoma tumor model with similar body weight loss as the control mice for the low and medium dose of compound 14, and a moderate body weight loss with high dose of compound 14, but no signs of toxicity were observed. Autopsy at the end revealed no abnormal observations. Mice treated with Sorafenib showed severe body weight loss of the course of the treatment (see FIG. 2B).

Therapeutic effect: Also in the DLD-1 colon carcinoma tumor model all mice treated with compound 14 showed a dose-dependent tumor growth inhibition. The lowest dose (50 mg/kg) had a minor effect, the higher doses (100 and 200 mg/kg) were significantly more active regarding tumor growth inhibition and showed a similar cytostatic effect as the positive control sorafenib (see FIG. 2A).

Taking the significantly higher loss of body weight for the Sorafenib group into consideration, compound 14 seems to have a broader therapeutic index than Sorafenib, i.e. having a similar cytostatic effect at a better tolerability.

9. Inhibition of Various Cancer Cell Lines In Vitro

The CellTiter-Glo Luminescent Cell Viability Assay (Promega) is a homogeneous method of determining the number of viable cells in culture. It is based on quantification of ATP, indicating the presence of metabolically active cells.

Cells were seeded on day 1 at cell numbers that assure assay linearity and optimal signal intensity. After incubation for 3 h in humidified chambers at 37° C./5% $CO_2$ compounds/DMSO were added at different concentrations. Cells were further incubated for 72 h at 37° C. and 5% $CO_2$. Cells treated with the compound vehicle DMSO were used as positive controls and cells treated with 10 µM Staurosporine served as negative controls. At day 4 the CellTiter Glo Reagent was prepared according to the instructions of the kit (Promega Inc.): Reagent was mixed 1:1 with cell culture medium. Thereon, mixture and assay plates were equilibrated at room temperature for 20 min. Equal volumes of the reagent-medium-mixture was added to the volume of culture medium present in each well.

The plates were mixed at ~200 rpm for 2 minutes on an orbital shaker. The microplates were then incubated at room temperature for 10 minutes for stabilization of the luminescent signal. Following incubation the luminescence is recorded on a Victor microplate reader (Perkin Elmer) using 200 ms integration time. The data were then analyzed with Excel using the XLFIT Plugin (dose response Fit 205) for $IC_{50}$-determination. As quality control the Z'-factor was calculated from 16 positive and negative control values. Only assay results showing a Z'-factor≥0.5 were used for further analysis.

TABLE 8

| | CellTiter GLO viability assay | | | | | | | | |
|---|---|---|---|---|---|---|---|---|---|
| IC50 (µM) incubation time 144 h | CA-46 (lymphoma) | HEC-59 (endometrial) | HRT-18 (colon) | NCI-H1299 (lung) | NCI-H23 (lung) | NCI-H596 (lung) | SW403 (colon) | SW48 (colon) | SW948 (colon) |
| Compound 38 | (++) | (−) | (+++) | (++) | (+) | (+) | (++) | (+) | (++) |
| Compound 47 | (++) | (−) | (+++) | (++) | (−) | (+) | (++) | (++) | (++) |
| Compound 14 | (+++) | (−) | (+++) | (++) | (+) | (+) | (+++) | (++) | (++) |

(−) = low sensitivity/resistance: x > 10 µM
(+) = moderate sensitivity: 10 µM ≥ x > 1 µM
(++) = good sensitivity: 1 µM ≥ x > 0.1 µM
(+++) = very good sensitivity: 0.1 µM ≥ x Results:

The tested cell lines from the cell panel showed different IC50 values for the tested POLRMT inhibitors (compounds 38, 47 and 14), see Table 8. The HEC-59 cell line was resistant to all three inhibitors, the NCl-H23 was resistant to compound 47. The NCl-H23 cell line showed a moderate sensitivity with respect to compounds 14 and 38. The NCl-H596 cell line showed a moderate sensitivity versus all three compounds. All other tested cell lines showed a good or a very good sensitivity versus all three compounds. The most sensitive cell line in this assay was HRT-18.

Comparing the compounds, Compound 14 was the most active one with the highest activity on three cell lines (CA-46, HRT-18, SW403), whereas both compound 38 and 47 had the highest activity on one cell line (HRT-18). Compound 38 and 47 were mostly comparable with the exceptions that compound 38 was more active on NCl-H23 cells, whereas compound 47 was more active on SW48 cells.

Literature

ARIAANS, G., JALVING, M., VRIES, E. G. & JONG, S. 2017. Anti-tumor effects of everolimus and metformin are complementary and glucose-dependent in breast cancer cells. *BMC Cancer*, 17, 232.

ARNOLD, J. J., SMIDANSKY, E. D., MOUSTAFA, I. M. & CAMERON, C. E. 2012. Human mitochondrial RNA polymerase: structure-function, mechanism and inhibition. *Biochim Biophys Acta*, 1819, 948-60.

BEHERA, M. A., DAI, Q., GARDE, R., SANER, C., JUNGHEIM, E. & PRICE, T. M. 2009. Progesterone stimulates mitochondrial activity with subsequent inhibition of apoptosis in MCF-10A benign breast epithelial cells. *Am J Physiol Endocrinol Metab*, 297, E1089-96.

BHAT, M., SONENBERG, N. & GORES, G. J. 2013. The mTOR pathway in hepatic malignancies. *Hepatology*, 58, 810-8.

BRALHA, F. N., LIYANAGE, S. U., HURREN, R., WANG, X., SON, M. H., FUNG, T. A., CHINGCUANCO, F. B., TUNG, A. Y., ANDREAZZA, A. C., PSARIANOS, P., SCHIMMER, A. D., SALMENA, L. & LAPOSA, R. R. 2015. Targeting mitochondrial RNA polymerase in acute myeloid leukemia. *Oncotarget*, 6, 37216-28.

BRECHT, K., RIEBEL, V., COUTTET, P., PAECH, F., WOLF, A., CHIBOUT, S. D., POGNAN, F., KRAHENBUHL, S. & UTENG, M. 2017. Mechanistic insights into selective killing of OXPHOS-dependent cancer cells by arctigenin. *Toxicol In Vitro*, 40, 55-65.

BUBNER, B. & BALDWIN, I. T. 2004. Use of real-time PCR for determining copy number and zygosity in transgenic plants. *Plant Cell Rep*, 23, 263-71.

CARO, P., KISHAN, A. U., NORBERG, E., STANLEY, I. A., CHAPUY, B., FICARRO, S. B., POLAK, K., TONDERA, D., GOUNARIDES, J., YIN, H., ZHOU, F., GREEN, M. R., CHEN, L., MONTI, S., MARTO, J. A., SHIPP, M. A. & DANIAL, N. N. 2012. Metabolic signatures uncover distinct targets in molecular subsets of diffuse large B cell lymphoma. *Cancer Cell*, 22, 547-60.

CARROLL, S. S., TOMASSINI, J. E., BOSSERMAN, M., GETTY, K., STAHLHUT, M. W., ELDRUP, A. B., BHAT, B., HALL, D., SIMCOE, A. L., LAFEMINA, R., RUTKOWSKI, C. A., WOLANSKI, B., YANG, Z., MIGLIACCIO, G., DE FRANCESCO, R., KUO, L. C., MACCOSS, M. & OLSEN, D. B. 2003. Inhibition of hepatitis C virus RNA replication by 2'-modified nucleoside analogs. *J Biol Chem*, 278, 11979-84.

DENISE, C., PAOLI, P., CALVANI, M., TADDEI, M. L., GIANNONI, E., KOPETZ, S., KAZMI, S. M., PIA, M. M., PETTAZZONI, P., SACCO, E., CASELLI, A., VANONI, M., LANDRISCINA, M., CIRRI, P. & CHIARUGI, P. 2015. 5-fluorouracil resistant colon cancer cells are addicted to OXPHOS to survive and enhance stem-like traits. *Oncotarget*, 6, 41706-21.

DÖRR, J. R., YU, Y., MILANOVIC, M., BEUSTER, G., ZASADA, C., DABRITZ, J. H., LISEC, J., LENZE, D., GERHARDT, A., SCHLEICHER, K., KRATZAT, S., PURFURST, B., WALENTA, S., MUELLER-KLIESER, W., GRALER, M., HUMMEL, M., KELLER, U., BUCK, A. K., DORKEN, B., WILLMITZER, L., REIMANN, M., KEMPA, S., LEE, S. & SCHMITT, C. A. 2013. Synthetic lethal metabolic targeting of cellular senescence in cancer therapy. *Nature*, 501, 421-5.

FALKENBERG, M., GASPARI, M., RANTANEN, A., TRIFUNOVIC, A., LARSSON, N. G. & GUSTAFSSON, C. M. 2002. Mitochondrial transcription factors B1 and B2 activate transcription of human mtDNA. *Nat Genet*, 31, 289-94.

FULDA, S., GALLUZZI, L. & KROEMER, G. 2010. Targeting mitochondria for cancer therapy. *Nat Rev Drug Discov*, 9, 447-64.

GOSSELIN, F., BRITTON, R. A., DAVIES, I. W., DOLMAN, S. J., GAUVREAU, D., HOERRNER, R. S., HUGHES, G., JANEY, J., LAU, S., MOLINARO, C., NADEAU, C., O'SHEA, P. D., PALUCKI, M. & SIDLER, R. 2010. A practical synthesis of 5-lipoxygenase inhibitor MK-0633. *J Org Chem*, 75, 4154-60.

HANAN, E. J., VAN ABBEMA, A., BARRETT, K., BLAIR, W. S., BLANEY, J., CHANG, C., EIGENBROT, C., FLYNN, S., GIBBONS, P., HURLEY, C. A., KENNY, J. R., KULAGOWSKI, J., LEE, L., MAGNUSON, S. R., MORRIS, C., MURRAY, J., PASTOR, R. M., RAWSON, T., SIU, M., ULTSCH, M., ZHOU, A., SAMPATH, D. & LYSSIKATOS, J. P. 2012. Discovery of potent and selective pyrazolopyrimidine janus kinase 2 inhibitors. *J Med Chem*, 55, 10090-107.

HAQ, R., SHOAG, J., ANDREU-PEREZ, P., YOKOYAMA, S., EDELMAN, H., ROWE, G. C., FREDERICK, D. T., HURLEY, A. D., NELLORE, A., KUNG, A. L., WARGO, J. A., SONG, J. S., FISHER, D. E., ARANY, Z. & WIDLUND, H. R. 2013. Oncogenic BRAF regulates oxidative metabolism via PGC1alpha and MITF. *Cancer Cell*, 23, 302-15.

HAYNES, D. A., JONES, W. & MOTHERWELL, W. D. S. 2005. Occurrence of pharmaceutically acceptable anions and cations in the Cambridge Structural Database. *Journal of Pharmaceutical Sciences*, 94, 2111-2120.

HEID, C. A., STEVENS, J., LIVAK, K. J. & WILLIAMS, P. M. 1996. Real time quantitative PCR. *Genome Res*, 6, 986-94.

HSU, P. P. & SABATINI, D. M. 2008. Cancer cell metabolism: Warburg and beyond. *Cell*, 134, 703-7.

KLOMP, J. A., PETILLO, D., NIEMI, N. M., DYKEMA, K. J., CHEN, J., YANG, X. J., SAAF, A., ZICKERT, P., ALY, M., BERGERHEIM, U., NORDENSKJOLD, M., GAD, S., GIRAUD, S., DENOUX, Y., YONNEAU, L., MEJEAN, A., VASILIU, V., RICHARD, S., MACKEIGAN, J. P., TEH, B. T. & FURGE, K. A. 2010. Birt-Hogg-Dube renal tumors are genetically distinct from other renal neoplasias and are associated with up-regulation of mitochondrial gene expression. *BMC Med Genomics*, 3, 59.

LEONETTI, F., FAVIA, A., RAO, A., ALIANO, R., PALUSZCAK, A., HARTMANN, R. W. & CAROTTI, A. 2004. Design, synthesis, and 3D QSAR of novel potent and selective aromatase inhibitors. *J Med Chem*, 47, 6792-803.

LING, S., SONG, L., FAN, N., FENG, T., LIU, L., YANG, X., WANG, M., LI, Y., TIAN, Y., ZHAO, F., LIU, Y., HUANG, Q., HOU, Z., XU, F., SHI, L. & LI, Y. 2017. Combination of metformin and sorafenib suppresses proliferation and induces autophagy of hepatocellular carcinoma via targeting the mTOR pathway. *Int J Oncol*, 50, 297-309.

MITSUNOBU, O. & YAMADA, M. 1967. Preparation of Esters of Carboxylic and Phosphoric Acid via Quaternary Phosphonium Salts. *Bulletin of the Chemical Society of Japan*, 40, 2380-2382.

NADJI, M., GOMEZ-FERNANDEZ, C., GANJEIAZAR, P. & MORALES, A. R. 2005. Immunohistochemistry of estrogen and progesterone receptors reconsidered: experience with 5,993 breast cancers. *Am J Clin Pathol*, 123, 21-7.

PELICANO, H., MARTIN, D. S., XU, R. H. & HUANG, P. 2006. Glycolysis inhibition for anticancer treatment. *Oncogene*, 25, 4633-46.

PELICANO, H., ZHANG, W., LIU, J., HAMMOUDI, N., DAI, J., XU, R. H., PUSZTAI, L. & HUANG, P. 2014.

Mitochondrial dysfunction in some triple-negative breast cancer cell lines: role of mTOR pathway and therapeutic potential. *Breast Cancer Res*, 16, 434.

POSSE, V., SHAHZAD, S., FALKENBERG, M., HALLBERG, B. M. & GUSTAFSSON, C. M. 2015. TEFM is a potent stimulator of mitochondrial transcription elongation in vitro. *Nucleic Acids Res*, 43, 2615-24.

RODRIGUES, M. F., OBRE, E., DE MELO, F. H., SANTOS, G. C., JR., GALINA, A., JASIULIONIS, M. G., ROSSIGNOL, R., RUMJANEK, F. D. & AMOEDO, N. D. 2016. Enhanced OXPHOS, glutaminolysis and beta-oxidation constitute the metastatic phenotype of melanoma cells. *Biochem J*, 473, 703-15.

RODRIGUEZ-ENRIQUEZ, S., HERNANDEZ-ESQUIVEL, L., MARIN-HERNANDEZ, A., EL HAFIDI, M., GALLARDO-PEREZ, J. C., HERNANDEZ-RESENDIZ, I., RODRIGUEZ-ZAVALA, J. S., PACHECO-VELAZQUEZ, S. C. & MORENO-SANCHEZ, R. 2015. Mitochondrial free fatty acid beta-oxidation supports oxidative phosphorylation and proliferation in cancer cells. *Int J Biochem Cell Biol*, 65, 209-21.

ROESCH, A., VULTUR, A., BOGESKI, I., WANG, H., ZIMMERMANN, K. M., SPEICHER, D., KORBEL, C., LASCHKE, M. W., GIMOTTY, P. A., PHILIPP, S. E., KRAUSE, E., PATZOLD, S., VILLANUEVA, J., KREPLER, C., FUKUNAGA-KALABIS, M., HOTH, M., BASTIAN, B. C., VOGT, T. & HERLYN, M. 2013. Overcoming intrinsic multidrug resistance in melanoma by blocking the mitochondrial respiratory chain of slow-cycling JARID1B(high) cells. *Cancer Cell*, 23, 811-25.

SALEM, A. F., WHITAKER-MENEZES, D., LIN, Z., MARTINEZ-OUTSCHOORN, U. E., TANOWITZ, H. B., AL-ZOUBI, M. S., HOWELL, A., PESTELL, R. G., SOTGIA, F. & LISANTI, M. P. 2012. Two-compartment tumor metabolism: autophagy in the tumor microenvironment and oxidative mitochondrial metabolism (OXPHOS) in cancer cells. *Cell Cycle*, 11, 2545-56.

SANCHEZ-ALVAREZ, R., MARTINEZ-OUTSCHOORN, U. E., LAMB, R., HULIT, J., HOWELL, A., GANDARA, R., SARTINI, M., RUBIN, E., LISANTI, M. P. & SOTGIA, F. 2013. Mitochondrial dysfunction in breast cancer cells prevents tumor growth: understanding chemoprevention with metformin. *Cell Cycle*, 12, 172-82.

SCARPULLA, R. C. 2008. Transcriptional paradigms in mammalian mitochondrial biogenesis and function. *Physiol Rev*, 88, 611-38.

SCATENA, R., BOTTONI, P., PONTOGLIO, A., MASTROTOTARO, L. & GIARDINA, B. 2008. Glycolytic enzyme inhibitors in cancer treatment. *Expert Opin Investig Drugs*, 17, 1533-45.

SCHÖCKEL, L., GLASAUER, A., BASIT, F., BITSCHAR, K., TRUONG, H., ERDMANN, G., ALGIRE, C., HAGEBARTH, A., WILLEMS, P. H., KOPITZ, C., KOOPMAN, W. J. & HEROULT, M. 2015. Targeting mitochondrial complex I using BAY 87-2243 reduces melanoma tumor growth. *Cancer Metab*, 3, 11.

SIEGEL, R. L., MILLER, K. D. & JEMAL, A. 2016. Cancer statistics, 2016. *CA Cancer J Clin*, 66, 7-30.

TISDALE, M. J. 2002. Cachexia in cancer patients. *Nat Rev Cancer*, 2, 862-71.

VANDER HEIDEN, M. G., CANTLEY, L. C. & THOMPSON, C. B. 2009. Understanding the Warburg effect: the metabolic requirements of cell proliferation. *Science*, 324, 1029-33.

WALTERS, W. P. & NAMCHUK, M. 2003. Designing screens: how to make your hits a hit. *Nat Rev Drug Discov*, 2, 259-66.

WANROOIJ, S. & FALKENBERG, M. 2010. The human mitochondrial replication fork in health and disease. *Biochim Biophys Acta*, 1797, 1378-88.

WEINBERG, S. E. & CHANDEL, N. S. 2015. Targeting mitochondria metabolism for cancer therapy. *Nat Chem Biol*, 11, 9-15.

WHITAKER-MENEZES, D., MARTINEZ-OUTSCHOORN, U. E., LIN, Z., ERTEL, A., FLOMENBERG, N., WITKIEWICZ, A. K., BIRBE, R. C., HOWELL, A., PAVLIDES, S., GANDARA, R., PESTELL, R. G., SOTGIA, F., PHILP, N. J. & LISANTI, M. P. 2011. Evidence for a stromalepithelial "lactate shuttle" in human tumors: MCT4 is a marker of oxidative stress in cancer-associated fibroblasts. *Cell Cycle*, 10, 1772-83.

YEUNG, K. Y., DICKINSON, A., DONOGHUE, J. F., POLEKHINA, G., WHITE, S. J., GRAMMATOPOULOS, D. K., MCKENZIE, M., JOHNS, T. G. & ST JOHN, J. C. 2014. The identification of mitochondrial DNA variants in glioblastoma multiforme. *Acta Neuropathol Commun*, 2, 1.

WO 2016/146,583 A1
WO 2016/193,231 A1

---

The invention claimed is:

1. A compound of the general formula (I)

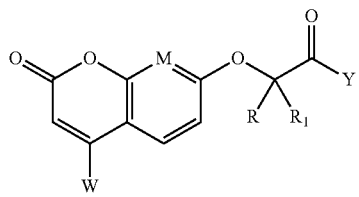

wherein

R is —$C_1$-$C_4$-alkyl;

$R_1$ is —H, or -methyl;

M is CH or N;

W is

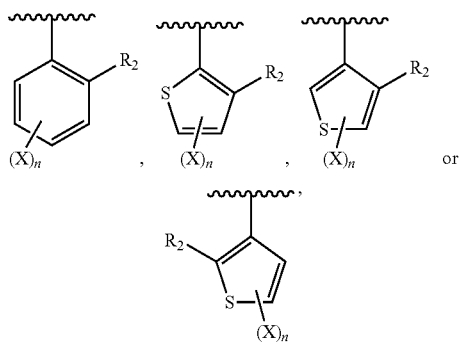

wherein $R_2$ is $C_1$-$C_4$-alkyl, -halogen, —CN;

X is -halogen, or —CN;

n=0, 1, or 2;

Y is —$NR_3R_4$ wherein $R_3$ is —H, or —$C_1$-$C_4$-alkyl, and $R_4$ is —$C_1$-$C_4$-alkyl or —$C_3$-$C_6$-cycloalkyl; or an unsubstituted or substituted pyridine residue; or an unsubstituted or substituted phenyl residue; or Y is —$NR_3R_4$ with N, $R_3$ and $R_4$ forming an unsubstituted or substituted 5- or 6-membered saturated heterocycle; or Y is —$OR_{11}$, with $R_{11}$ is —H or —$C_1$-$C_4$-alkyl;

or a pharmaceutically or veterinary acceptable salt, hydrate or solvate thereof.

2. The compound of claim 1, wherein

R is —$C_1$-$C_4$-alkyl;

$R_1$ is —H, or -methyl;

M is —CH;

W is

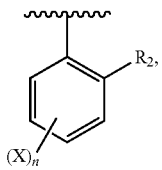

wherein $R_2$ is methyl, -halogen, —CN;

X is -halogen, or —CN;

n=0, 1, or 2;

Y is —$NR_3R_4$ wherein $R_3$ is —H, or —$C_1$-$C_4$-alkyl, and $R_4$ is —$C_1$-$C_4$-alkyl or —$C_3$-$C_6$-cycloalkyl; or an unsubstituted or substituted pyridine residue; or an unsubstituted or substituted phenyl residue;

Y is —$NR_3R_4$ with N, $R_3$ and $R_4$ forming an unsubstituted or substituted 5- or 6-membered saturated heterocycle; or Y is —$OR_{11}$, with $R_{11}$ is —H or —$C_1$-$C_4$-alkyl;

or a pharmaceutically or veterinary acceptable salt, hydrate or solvate thereof.

3. The compound of claim 1, wherein Y is —$NR_3R_4$, wherein $R_3$ is —H, or —$C_1$-$C_4$-alkyl, and $R_4$ is a pyridine residue; or a phenyl residue substituted with —$(CH_2)_pOH$ with p=1 or 2; or —$C_1$-$C_4$-alkyl or —$C_3$-$C_6$-cycloalkyl.

4. The compound of claim 1, wherein N, $R_3$ and $R_4$ together form an unsubstituted or substituted piperidine, piperazine or pyrrolidine residue, each optionally and independently substituted with one or more of the following residues:

—$C_1$-$C_4$-alkyl;

—$(CH_2)_m$—$COOR_5$ with $R_5$ is —H, —$C_1$-$C_8$-alkyl, —$C_2$-$C_4$-alkyl-N-morpholine or the group

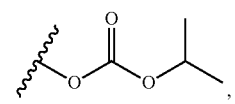

—$(CH_2)_mCONR_6R_7$ with $R_6$ and $R_7$ is independently —H, or —$C_1$-$C_4$-alkyl;

—CO—($C_2$-$C_4$-alkenyl); —CO—$CH_2$—Cl; —CO—$CH_2$—$CH_3$;

NH—CO—($C_2$-$C_4$-alkenyl); —NH—CO—$CH_2$—Cl; —NH—CO—$CH_2$—$CH_3$;

—F;

—CN;

—$SO_3H$;

—$SO_2NR_8R_9$ with $R_8$ and $R_9$ independently are —H, or —$C_1$-$C_4$-alkyl;

—$SONHR_{10}$ with $R_{10}$ is —$C_1$-$C_4$-alkyl; or

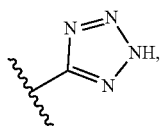 [SMILES: *c1nn[nH]n1]

and
m=0, 1, or 2.

5. The compound according to claim 1, wherein N, $R_3$ and $R_4$ together form an unsubstituted or substituted piperidine or pyrrolidine residue, each optionally and independently substituted with one or more of the following residues:
—$C_1$-$C_4$-alkyl;
—$(CH_2)_m$—$COOR_5$ with $R_5$ is —H, —$C_1$-$C_8$-alkyl, —$C_2$-$C_4$-alkyl-N-morpholine or the group

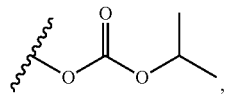

—$(CH_2)_m CONR_6 R_7$ with $R_6$ and $R_7$ is independently —H, or —$C_1$-$C_4$-alkyl;
—F;
—CN;
—$SO_3H$;
—$SO_2 NR_8 R_9$ with $R_5$ and $R_9$ independently are —H, or —$C_1$-$C_4$-alkyl;
—$SONHR_{10}$ with $R_{10}$ is —$C_1$-$C_4$-alkyl; or

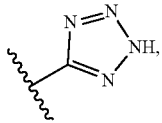 [SMILES: *c1nn[nH]n1]

and
m=0, 1, or 2.

6. The compound according to claim 1, wherein
R is -methyl;
$R_1$ is —H;
m=0, or 1;
W is

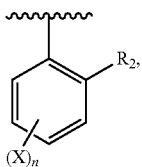

wherein
$R_2$ is methyl, or —Cl;
X is —F with n=1;
Y is —$NR_3 R_4$
wherein
$R_3$ is —H, and
$R_4$ is a pyridine residue,
a phenyl residue substituted at the para position;
or with
N, $R_3$ and $R_4$ forming together a piperidine residue, or a pyrrolidine residue, each optionally and independently substituted with one of the following residues:
—COOH, —$COOCH_3$, —$COOC_2H_5$,
—$CH_2COOH$, —$CH_2COOCH_3$,
—$CH_2COOCH_2CH_3$, —$CONH_2$, —$CONHCH_3$,
—$CON(CH_3)_2$, —$CH_2CONHCH_3$, —$SO_2NH_2$,
—$SO_2NHCH_3$, or —CN.

7. The compound according to claim 1, wherein
R is (R)-methyl;
$R_1$ is —H;
W is

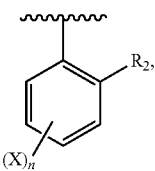

with
$R_2$ is methyl, or Cl;
X is —F with n=1;
Y is —$NR_3 R_4$
with
N, $R_3$ and $R_4$ forming a piperidine residue, or a pyrrolidine residue, each optionally and independently substituted with one of the following residues:
—COOH, —$CH_2COOH$, —$CONHCH_3$,
—$CH_2CONHCH_3$, —$SO_2NH_2$, —$SO_2NHCH_3$, or —CN.

8. The compound according to claim 4, wherein the piperidine residue or the pyrrolidine residue is substituted at the 3-position.

9. The compound according to claim 1, wherein X is at the para-position of the phenyl ring.

10. The compound of claim 1, wherein
R is -methyl or -ethyl;
$R_1$ is —H;
M is CH or N;
W is

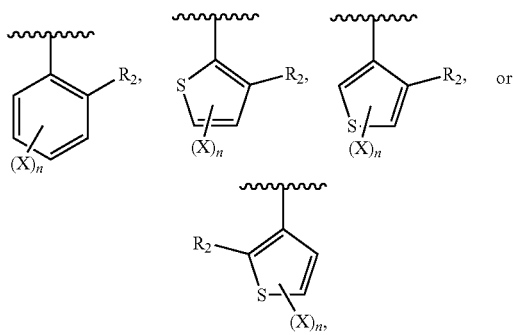

wherein
$R_2$ is -methyl, -ethyl, —Cl, or —Br;
X is —Cl, or —F;
n=0, 1 or 2;
Y is —$NR_3 R_4$ wherein
$R_3$ is —H or -methyl, and
$R_4$ is -methyl, -ethyl, -isopropyl, or -cyclopropyl; or
an unsubstituted or substituted pyridine residue; or
an unsubstituted or a phenyl residue substituted at the para position; or Y is —NR₃R₄ with N, R₃ and R₄ forming an unsubstituted or substituted 5- or 6-membered saturated heterocycle; or Y is —OR₁₁, wherein R₁₁ is -methyl, -ethyl, or -isopropyl.

11. The compound of claim 1, wherein
R is -methyl;
R₁ is —H;
M is —CH:
W is

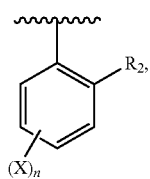

wherein
R₂ is -methyl, —Cl, or —Br;
X is —F;
n=1 or 2;
Y is —NR₃R₄, wherein
R₃ is —H or -methyl, and
R₄ is -methyl, -ethyl, -isopropyl, or -cyclopropyl; or an unsubstituted or substituted pyridine residue; or an unsubstituted or a substituted phenyl residue, substituted at the para position;
Y is —NR₃R₄ with N, R₃ and R₄ forming an unsubstituted or substituted 5- or 6-membered saturated heterocycle; or
Y is —OR₁₁, wherein R₁₁ is -methyl, -ethyl, or -isopropyl.

12. The compound of claim 4, wherein
R₅ is —H, -methyl, -ethyl, -isopropyl, -tert-butyl, -n-heptyl, 2-morpholinoethyl or -isopropoxycarbonyloxymethyl;
R₁₀ is -methyl; and
m is 0 or 1.

13. The compound of formula (I) according to claim 1, selected from
7-[1-methyl-2-oxo-2-(1-piperidyl)ethoxy]-4-(o-tolyl) chromen-2-one, 4-(2-chlorophenyl)-7-[1-methyl-2-oxo-2-(1-piperidyl)ethoxy]chromen-2-one,
(3S)-1-[2-[4-(o-tolyl)-2-oxo-chromen-7-yl]oxypropanoyl]piperidine-3-carboxylic acid,
2-[4-(o-tolyl)-2-oxo-chromen-7-yl]oxy-N-(2-pyridyl) propanamide,
7-(1-methyl-2-oxo-2-pyrrolidin-1-yl-ethoxy)-4-(o-tolyl) chromen-2-one,
methyl -1-[2-[4-(o-tolyl)-2-oxo-chromen-7-yl]oxypropanoyl]piperidine-3-carboxylate,
methyl -1-[2-[4-(2-chlorophenyl)-2-oxo-chromen-7-yl] oxypropanoyl]piperidine-3-carboxylate,
1-[2-[4-(o-tolyl)-2-oxo-chromen-7-yl]oxypropanoyl]piperidine-3-carboxylic acid,
1-[2-[4-(2-chlorophenyl)-2-oxo-chromen-7-yl]oxypropanoyl]piperidine-3-carboxylic acid,
1-[2-[4-(o-tolyl)-2-oxo-chromen-7-yl]oxypropanoyl]piperidine-3-sulfonic acid,
1-[2-[4-(2-chlorophenyl)-2-oxo-chromen-7-yl]oxypropanoyl]piperidine-3-sulfonic acid,
1-[2-[4-(o-tolyl)-2-oxo-chromen-7-yl]oxypropanoyl]piperidine-3-sulfonamide,
4-(2-chlorophenyl)-7-(1-methyl-2-oxo-2-pyrrolidin-1-yl-ethoxy)chromen-2-one,
(3S)-1-[(2R)-2-[4-(2-chloro-4-fluoro-phenyl)-2-oxo-chromen-7-yl]oxypropanoyl]piperidine-3-carboxylic acid,
1-[2-[4-(2-chlorophenyl)-2-oxo-chromen-7-yl]oxypropanoyl]-N-methyl-piperidine-3-carboxamide,
ethyl (3S)-1-[2-[4-(2-chlorophenyl)-2-oxo-chromen-7-yl] oxypropanoyl]piperidine-3-carboxylate,
ethyl (3S)-1-[2-[4-(o-tolyl)-2-oxo-chromen-7-yl]oxypropanoyl]piperidine-3-carboxylate,
N-methyl-1-[2-[4-(o-tolyl)-2-oxo-chromen-7-yl]oxypropanoyl]piperidine-3-sulfonamide,
N-[4-(2-hydroxyethyl)phenyl]-2-[4-(o-tolyl)-2-oxo-chromen-7-yl]oxy-propanamide,
1-[2-[4-(2-chlorophenyl)-2-oxo-chromen-7-yl]oxypropanoyl]-N-methyl-piperidine-3-sulfonamide,
N-methyl-1-[2-[4-(o-tolyl)-2-oxo-chromen-7-yl]oxypropanoyl]piperidine-3-carboxamide,
(3S)-1-[2-[4-(o-tolyl)-2-oxo-chromen-7-yl]oxypropanoyl]pyrrolidine-3-carboxylic acid,
(3S)-1-[(2R)-2-[4-(2-chlorophenyl)-2-oxo-chromen-7-yl] oxypropanoyl]piperidine-3-carboxylic acid,
1-[2-[4-(2-chlorophenyl)-2-oxo-chromen-7-yl]oxypropanoyl]piperidine-3-sulfonamide,
N-cyclopropyl-2-[4-(o-tolyl)-2-oxo-chromen-7-yl]oxy-propanamide,
2-[4-(2-chlorophenyl)-2-oxo-chromen-7-yl]oxy-N-cyclopropyl-propanamide,
(3S)-1-[(2R)-2-[4-(o-tolyl)-2-oxo-chromen-7-yl]oxypropanoyl]piperidine-3-carboxylic acid,
(3S)-1-[(2R)-2-[4-(2-chlorophenyl)-2-oxo-chromen-7-yl] oxypropanoyl]piperidine-3-carbonitrile,
(3S)-1-[2-[4-(2-chlorophenyl)-2-oxo-chromen-7-yl]oxy-propanoyl]pyrrolidine-3-carboxylic acid,
7-[(1R)-1-methyl-2-oxo-2-(1-piperidyl)ethoxy]-4-(o-tolyl)chromen-2-one,
2-[4-(2-chlorophenyl)-2-oxo-chromen-7-yl]oxy-N-(2-pyridyl)propanamide,
(3S)-1-[(2R)-2-[4-(o-tolyl)-2-oxo-chromen-7-yl]oxypropanoyl]piperidine-3-carbonitrile,
(3S)-1-[2-[4-(2-chlorophenyl)-2-oxo-chromen-7-yl]oxy-propanoyl]piperidine-3-carboxylic acid,
4-(2-chlorophenyl)-7-[(1R)-1-methyl-2-oxo-2-(1-piperidyl)ethoxy]chromen-2-one,
2-[4-(2-chlorophenyl)-2-oxo-chromen-7-yl]oxy-N-[4-(2-hydroxyethyl)phenyl]propanamide,
(2R)—N-isopropyl-2-[4-(o-tolyl)-2-oxo-chromen-7-yl] oxy-propanamide,
1-[2-[4-(2-chloro-4-fluoro-phenyl)-2-oxo-chromen-7-yl] oxypropanoyl]-3-methyl-piperidine-3-carboxylic acid,
N,N-dimethyl-2-[4-(o-tolyl)-2-oxo-chromen-7-yl]oxy-propanamide,
4-(2-chlorophenyl)-7-[1-methyl-2-oxo-2-[3-(2H-tetrazol-5-yl)-1-piperidyl]ethoxy]chromen-2-one,
ethyl 2-[4-(2-chlorophenyl)-2-oxo-chromen-7-yl]oxypropanoate,
1-[2-[4-(o-tolyl)-2-oxo-chromen-7-yl]oxypropanoyl]piperidine-3-carbonitrile,
7-[1-methyl-2-oxo-2-[3-(2H-tetrazol-5-yl)-1-piperidyl] ethoxy]-4-(o-tolyl)chromen-2-one,
3-methyl-1-[2-[4-(o-tolyl)-2-oxo-chromen-7-yl]oxypropanoyl]piperidine-3-carboxylic acid,
(2R)—N,N-dimethyl-2-[4-(o-tolyl)-2-oxo-chromen-7-yl] oxy-propanamide,
(2R)-2-[4-(2-chlorophenyl)-2-oxo-chromen-7-yl]oxy-N, N-dimethyl-propanamide,
(3R)-1-[2-[4-(2-chlorophenyl)-2-oxo-chromen-7-yl] oxypropanoyl]piperidine-3-carboxylic acid, (3S)-1-[2-[4-(2-chloro-4-fluoro-phenyl)-2-oxo-chromen-7-yl]oxypropanoyl]piperidine-3-carboxylic acid,
1-[2-[4-(2-chlorophenyl)-2-oxo-chromen-7-yl]oxypropanoyl]piperidine-3-carbonitrile,
2-[4-(2-chloro-3-fluoro-phenyl)-2-oxo-chromen-7-yl]oxy-N-isopropyl-propanamide,
(3S)-1-[2-[4-(2-chloro-3-fluoro-phenyl)-2-oxo-chromen-7-yl]oxypropanoyl]piperidine-3-carboxylic acid,
2-[4-(2-chlorophenyl)-2-oxo-chromen-7-yl]oxy-N-methyl-propanamide,
1-[2-[4-(2-chloro-3-fluoro-phenyl)-2-oxo-chromen-7-yl]oxypropanoyl]piperidine-3-sulfonamide,
(3R)-1-[2-[4-(o-tolyl)-2-oxo-chromen-7-yl]oxypropanoyl]piperidine-3-carboxylic acid,
1-[2-[4-(2-chlorophenyl)-2-oxo-chromen-7-yl]oxypropanoyl]-3-methyl-piperidine-3-carboxylic acid,
isopropyl (2R)-2-[4-(o-tolyl)-2-oxo-chromen-7-yl]oxypropanoate,
(2R)-2-[4-(2-chlorophenyl)-2-oxo-chromen-7-yl]oxy-N-isopropyl-propanamide,
ethyl 2-[4-(2-chloro-3-fluoro-phenyl)-2-oxo-chromen-7-yl]oxypropanoate,
ethyl 2-[4-(o-tolyl)-2-oxo-chromen-7-yl]oxypropanoate,
2-[1-[2-[4-(2-chlorophenyl)-2-oxo-chromen-7-yl]oxypropanoyl]-4-piperidyl]acetic acid,
2-[1-[2-[4-(o-tolyl)-2-oxo-chromen-7-yl]oxypropanoyl]-4-piperidyl]acetic acid,
2-[4-(2-chloro-3-fluoro-phenyl)-2-oxo-chromen-7-yl]oxy-N-cyclopropyl-propanamide,
N-isopropyl-2-[4-(o-tolyl)-2-oxo-chromen-7-yl]oxy-propanamide,
1-[2-[4-(o-tolyl)-2-oxo-chromen-7-yl]oxypropanoyl]pyrrolidine-3-sulfonamide, isopropyl (2R)-2-[4-(2-chlorophenyl)-2-oxo-chromen-7-yl]oxypropanoate,
2-[4-(2-chloro-4-fluoro-phenyl)-2-oxo-chromen-7-yl]oxy-N-isopropyl-propanamide,
2-[1-[2-[4-(2-chlorophenyl)-2-oxo-chromen-7-yl]oxypropanoyl]-3-piperidyl]acetic acid,
(3R)-1-[2-[4-(2-chlorophenyl)-2-oxo-chromen-7-yl]oxypropanoyl]-N,N-dimethyl-piperidine-3-carboxamide,
2-[4-(2-chloro-3-fluoro-phenyl)-2-oxo-chromen-7-yl]oxy-N-ethyl-propanamide,
1-[2-[4-(2-chloro-4-fluoro-phenyl)-2-oxo-chromen-7-yl]oxypropanoyl]piperidine-3-sulfonamide,
2-[4-(2-chlorophenyl)-2-oxo-chromen-7-yl]oxy-N-isopropyl-propanamide,
7-[2-(4,4-difluoro-1-piperidyl)-1-methyl-2-oxo-ethoxy]-4-(o-tolyl)chromen-2-one,
2-[1-[2-[4-(o-tolyl)-2-oxo-chromen-7-yl]oxypropanoyl]-3-piperidyl]acetic acid,
7-[1-methyl-2-[3-(methyl sulfonimidoyl]-1-piperidyl]-2-oxo-ethoxy]-4-(o-tolyl)chromen-2-one,
4-(2-chlorophenyl)-7-[2-(4,4-difluoro-1-piperidyl)-1-methyl-2-oxo-ethoxy]chromen-2-one,
ethyl 1-[2-[4-(2-chlorophenyl)-2-oxo-chromen-7-yl]oxypropanoyl]-3-methyl-piperidine-3-carboxylate,
(3S)-1-[2-[4-(2-chlorophenyl)-2-oxo-chromen-7-yl]oxypropanoyl]-N,N-dimethyl-piperidine-3-carboxamide,
1-[2-[4-(2-chlorophenyl)-2-oxo-chromen-7-yl]oxypropanoyl]pyrrolidine-3-sulfonamide,
(3R)-N,N-dimethyl-1-[2-[4-(o-tolyl)-2-oxo-chromen-7-yl]oxypropanoyl]piperidine-3-carboxamide,
4-(2-chlorophenyl)-7-[1-methyl-2-[3-(methylsulfonimidoyl]-1-piperidyl]-2-oxo-ethoxy]chromen-2-one,
methyl 2-[1-[2-[4-(2-chlorophenyl)-2-oxo-chromen-7-yl]oxypropanoyl]-4-piperidyl]acetate,
ethyl 2-[4-(2-bromophenyl)-2-oxo-chromen-7-yl]oxypropanoate,
ethyl 2-[4-(2-chloro-4-fluoro-phenyl)-2-oxo-chromen-7-yl]oxypropanoate,
methyl 2-[1-[2-[4-(o-tolyl)-2-oxo-chromen-7-yl]oxypropanoyl]-4-piperidyl]acetate,
(3S)—N,N-dimethyl-1-[2-[4-(o-tolyl)-2-oxo-chromen-7-yl]oxypropanoyl]piperidine-3-carboxamide,
N-ethyl-2-[4-(o-tolyl)-2-oxo-chromen-7-yl]oxy-propanamide,
ethyl 2-[1-[2-[4-(2-chlorophenyl)-2-oxo-chromen-7-yl]oxypropanoyl]-3-piperidyl]acetate,
ethyl 2-[1-[2-[4-(o-tolyl)-2-oxo-chromen-7-yl]oxypropanoyl]-3-piperidyl]acetate,
ethyl 3-methyl-1-[2-[4-(o-tolyl)-2-oxo-chromen-7-yl]oxypropanoyl]piperidine-3-carboxylate,
2-[4-(2-bromophenyl)-2-oxo-chromen-7-yl]oxy-N,N-dimethyl-propanamide,
2-[4-(2-chloro-4-fluoro-phenyl)-2-oxo-chromen-7-yl]oxy-N-cyclopropyl-propanamide,
2-[4-(2-chloro-4-fluoro-phenyl)-2-oxo-chromen-7-yl]oxy-N-ethyl-propanamide, isopropyl 2-[4-(2-bromophenyl)-2-oxo-chromen-7-yl]oxypropanoate,
2-[4-(2-chlorophenyl)-2-oxo-chromen-7-yl]oxy-N,N-dimethyl-propanamide,
2-[4-(2-chloro-3-fluoro-phenyl)-2-oxo-chromen-7-yl]oxypropanoic acid,
ethyl 1-[2-[4-(2-chloro-4-fluoro-phenyl)-2-oxo-chromen-7-yl]oxypropanoyl]-3-methyl-piperidine-3-carboxylate,
2-[4-(2-chlorophenyl)-2-oxo-chromen-7-yl]oxypropanoic acid,
2-[4-(o-tolyl)-2-oxo-chromen-7-yl]oxypropanoic acid,
2-[4-(2-chlorophenyl)-2-oxo-chromen-7-yl]oxy-N-ethyl-propanamide,
2-[4-(2-chloro-4-fluoro-phenyl)-2-oxo-chromen-7-yl]oxypropanoic acid,
methyl 2-[(3S)-1-[(2R)-2-[4-(2-chlorophenyl)-2-oxo-chromen-7-yl]oxypropanoyl]-3-piperidyl]acetate,
methyl 2-[(3R)-1-[(2R)-2-[4-(2-chlorophenyl)-2-oxo-chromen-7-yl]oxypropanoyl]-3-piperidyl]acetate,
2-[(3S)-1-[(2R)-2-[4-(2-chlorophenyl)-2-oxo-chromen-7-yl]oxypropanoyl]-3-piperidyl]acetic acid,
2-[(3R)-1-[(2R)-2-[4-(2-chlorophenyl)-2-oxo-chromen-7-yl]oxypropanoyl]-3-piperidyl]acetic acid,
methyl 2-[(3R)-1-[(2R)-2-[4-(2-chloro-4-fluoro-phenyl)-2-oxo-chromen-7-yl]oxypropanoyl]-3-piperidyl]acetate,
methyl 2-[(3S)-1-[(2R)-2-[4-(2-chloro-4-fluoro-phenyl)-2-oxo-chromen-7-yl]oxypropanoyl]-3-piperidyl]acetate,
2-[(3R)-1-[(2R)-2-[4-(2-chloro-4-fluoro-phenyl)-2-oxo-chromen-7-yl]oxypropanoyl]-3-piperidyl]acetic acid,
2-[(3S)-1-[(2R)-2-[4-(2-chloro-4-fluoro-phenyl)-2-oxo-chromen-7-yl]oxypropanoyl]-3-piperidyl]acetic acid,
(3R)-1-[(2R)-2-[4-(2-chloro-4-fluoro-phenyl)-2-oxo-chromen-7-yl]oxypropanoyl]piperidine-3-carboxylic acid,
ethyl (3S)-1-[2-[4-(2-chlorophenyl)-2-oxo-chromen-7-yl]oxybutanoyl]piperidine-3-carboxylate,
(3S)-1-[2-[4-(2-chlorophenyl)-2-oxo-chromen-7-yl]oxybutanoyl]piperidine-3-carboxylic acid,
ethyl (3S)-1-[(2R)-2-[4-(2-chloro-4-fluoro-phenyl)-2-oxo-chromen-7-yl]oxypropanoyl]piperidine-3-carboxylate,
2-[4-(2-chlorophenyl)-2-oxo-chromen-7-yl]oxy-2-methyl-propanoic acid, ethyl 2-[4-(2-chlorophenyl)-2-oxo-chromen-7-yl]oxy-2-methyl-propanoate,
2-[4-(2-chlorophenyl)-2-oxo-chromen-7-yl]oxy-N-isopropyl-2-methyl-propanamide,
N-isopropyl-2-methyl-2-[4-(o-tolyl)-2-oxo-chromen-7-yl]oxy-propanamide,
(3S)-1-[2-[4-[4-(2-chlorophenyl)-2-oxo-chromen-7-yl]oxy-2-methyl-propanoyl]piperidine-3-carboxylic acid,
isopropyl (3S)-1-[(2R)-2-[4-(2-chloro-4-fluoro-phenyl)-2-oxo-chromen-7-yl]oxypropanoyl]piperidine-3-carboxylate,
tert-butyl (3S)-1-[(2R)-2-[4-(2-chloro-4-fluoro-phenyl)-2-oxo-chromen-7-yl]oxypropanoyl]piperidine-3-carboxylate,
2-morpholinoethyl (3S)-1-[(2R)-2-[4-(2-chloro-4-fluoro-phenyl)-2-oxo-chromen-7-yl]oxypropanoyl]piperidine-3-carboxylate,
heptyl (3S)-1-[(2R)-2-[4-(2-chloro-4-fluoro-phenyl)-2-oxo-chromen-7-yl]oxypropanoyl]piperidine-3-carboxylate,
isopropoxycarbonyloxymethyl (3S)-1-[(2R)-2-[4-(2-chloro-4-fluoro-phenyl)-2-oxo-chromen-7-yl]oxypropanoyl]piperidine-3-carboxylate,
(3S)—N-methyl-1-[(2R)-2-[4-(2-chloro-4-fluoro-phenyl)-2-oxo-chromen-7-yl]oxypropanoyl piperidine-3-carboxamide,
isopropyl 2-[(3R)-1-[(2R)-2-[4-(2-chloro-4-fluoro-phenyl)-2-oxo-chromen-7-yl]oxypropanoyl]-3-piperidyl]acetate,
tert-butyl 2-[(3R)-1-[(2R)-2-[4-(2-chloro-4-fluoro-phenyl)-2-oxo-chromen-7-yl]oxypropanoyl]-3-piperidyl]acetate,
2-morpholinoethyl 2-[(3R)-1-[(2R)-2-[4-(2-chloro-4-fluoro-phenyl)-2-oxo-chromen-7-yl]oxypropanoyl]-3-piperidyl]acetate,
heptyl 2-[(3R)-1-[(2R)-2-[4-(2-chloro-4-fluoro-phenyl)-2-oxo-chromen-7-yl]oxypropanoyl]-3-piperidyl]acetate,
isopropoxycarbonyloxymethyl 2-[(3R)-1-[(2R)-2-[4-(2-chloro-4-fluoro-phenyl)-2-oxo-chromen-7-yl]oxypropanoyl]-3-piperidyl]acetate, and
2-[(3R)-1-[(2R)-2-[4-(2-chloro-4-fluoro-phenyl)-2-oxo-chromen-7-yl]oxypropanoyl]-3-piperidyl]-N-methyl-acetamide,
methyl 1-[(2R)-2-[4-(2-chloro-4-fluoro-phenyl)-2-oxo-chromen-7-yl]oxypropanoyl]piperidine-4-carboxylate,
(2R)-2-[4-(2-chloro-4-fluoro-phenyl)-2-oxo-chromen-7-yl]oxy-N-[4-(hydroxymethyl) phenyl]propanamide,
1-[(2R)-2-[4-(2-chloro-4-fluoro-phenyl)-2-oxo-chromen-7-yl]oxypropanoyl]piperidine-4-carboxylic acid,
(3S)-1-[(2R)-2-[4-(2-chloro-4-fluoro-phenyl)-2-oxo-chromen-7-yl]oxypropanoyl]piperidine-3-carboxamide,
2-[(3R)-1-[(2R)-2-[4-(2-chloro-4-fluoro-phenyl)-2-oxo-chromen-7-yl]oxypropanoyl]-3-piperidyl]acetamide,
(3S)-1-[(2R)-2-[4-(2-ethylphenyl)-2-oxo-chromen-7-yl]oxypropanoyl]piperidine-3-carboxylic acid,
methyl (2S)-4-[(2R)-2-[4-(2-chloro-4-fluoro-phenyl)-2-oxo-chromen-7-yl]oxypropanoyl]piperazine-2-carboxylate,
methyl (2R)-4-[(2R)-2-[4-(2-chloro-4-fluoro-phenyl)-2-oxo-chromen-7-yl]oxypropanoyl]piperazine-2-carboxylate,
methyl 1-methyl-4-[rac-(2R)-2-[4-(2-chloro-4-fluoro-phenyl)-2-oxo-chromen-7-yl]oxypropanoyl]piperazine-2-carboxylate,
(2S)-4-[(2R)-2-[4-(2-chloro-4-fluoro-phenyl)-2-oxo-chromen-7-yl]oxypropanoyl]piperazine-2-carboxylic acid,
3-[[(2R)-2-[4-(2-chloro-4-fluoro-phenyl)-2-oxo-chromen-7-yl]oxypropanoyl]amino]benzoic acid,
(2R)-2-[4-(2-chloro-4-fluoro-phenyl)-2-oxo-chromen-7-yl]oxy-N-[4-(2-methoxyethyl) phenyl]propanamide,
4-[[(2R)-2-[4-(2-chloro-4-fluoro-phenyl)-2-oxo-chromen-7-yl]oxypropanoyl]amino]benzoic acid,
methyl 2-[(3R)-1-[(2R)-2-[4-(2-chloro-4-fluoro-phenyl)-2-oxo-chromen-7-yl]oxypropanoyl]pyrrolidin-3-yl]acetate,
methyl 5-[[(2R)-2-[4-(2-chloro-4-fluoro-phenyl)-2-oxo-chromen-7-yl]oxypropanoyl]amino]pyridine-3-carboxylate,
methyl 2-[(3S)-1-[(2R)-2-[4-(2-chloro-4-fluoro-phenyl)-2-oxo-chromen-7-yl]oxypropanoyl]pyrrolidin-3-yl]acetate,
2-[(3R)-1-[(2R)-2-[4-(2-chloro-4-fluoro-phenyl)-2-oxo-chromen-7-yl]oxypropanoyl]pyrrolidin-3-yl]acetic acid,
methyl 2-[[(2R)-2-[4-(2-chloro-4-fluoro-phenyl)-2-oxo-chromen-7-yl]oxypropanoyl]amino]pyridine-4-carboxylate,
2-[(3S)-1-[(2R)-2-[4-(2-chloro-4-fluoro-phenyl)-2-oxo-chromen-7-yl]oxypropanoyl]pyrrolidin-3-yl]acetic acid,
5-[[(2R)-2-[4-(2-chloro-4-fluoro-phenyl)-2-oxo-chromen-7-yl]oxypropanoyl]amino]pyridine-3-carboxylic acid,
methyl 6-[[(2R)-2-[4-(2-chloro-4-fluoro-phenyl)-2-oxo-chromen-7-yl]oxypropanoyl]amino]pyridine-2-carboxylate,
(2R)-4-[(2R)-2-[4-(2-chloro-4-fluoro-phenyl)-2-oxo-chromen-7-yl]oxypropanoyl]piperazine-2-carboxylic acid,
6-[[(2R)-2-[4-(2-chloro-4-fluoro-phenyl)-2-oxo-chromen-7-yl]oxypropanoyl]amino]pyridine-2-carboxylic acid,
2-[[(2R)-2-[4-(2-chloro-4-fluoro-phenyl)-2-oxo-chromen-7-yl]oxypropanoyl]amino]pyridine-4-carboxylic acid,
methyl 5-[[(2R)-2-[4-(2-chloro-4-fluoro-phenyl)-2-oxo-chromen-7-yl]oxypropanoyl]amino]pyridine-2-carboxylate,
5-[[(2R)-2-[4-(2-chloro-4-fluoro-phenyl)-2-oxo-chromen-7-yl]oxypropanoyl]amino]pyridine-2-carboxylic acid,
5-[[(2R)-2-[4-(2-chloro-4-fluoro-phenyl)-2-oxo-chromen-7-yl]oxypropanoyl]amino]pyridine-2-carboxylic acid,
6-[[(2R)-2-[4-(2-chloro-4-fluoro-phenyl)-2-oxo-chromen-7-yl]oxypropanoyl]amino]pyridine-3-carboxylic acid,
methyl 4-[[(2R)-2-[4-(2-chloro-4-fluoro-phenyl)-2-oxo-chromen-7-yl]oxypropanoyl]amino]pyridine-2-carboxylate,
methyl (3S)-1-[(2R)-2-[4-(2-chloro-4-fluoro-phenyl)-2-oxo-chromen-7-yl]oxypropanoyl]pyrrolidine-3-carboxylate,
(3S)-1-[(2R)-2-[4-(4-fluoro-2-methyl-phenyl)-2-oxo-chromen-7-yl]oxypropanoyl]piperidine-3-carboxylic acid,
(3S)-1-[(2R)-2-[4-(2-chloro-4-fluoro-phenyl)-2-oxo-chromen-7-yl]oxypropanoyl]pyrrolidine-3-carboxylic acid, 4-[[(2R)-2-[4-(2-chloro-4-fluoro-phenyl)-2-oxo-chromen-7-yl]oxypropanoyl]amino]pyridine-2-carboxylic acid,
1-methyl-4-[rac-(2R)-2-[4-(2-chloro-4-fluoro-phenyl)-2-oxo-chromen-7-yl]oxypropanoyl]piperazine-2-carboxylic acid,
(3S)-1-[(2R)-2-[4-(2-cyanophenyl)-2-oxo-chromen-7-yl]oxypropanoyl]piperidine-3-carboxylic acid,
(3S)-1-[(2R)-2-[4-(2,6-dichlorophenyl)-2-oxo-chromen-7-yl]oxypropanoyl]piperidine-3-carboxylic acid,
4-(2-chloro-4-fluoro-phenyl)-7-[(1R)-1-methyl-2-oxo-2-(4-prop-2-enoylpiperazin-1-yl)ethoxy]chromen-2-one,
N-[(3S)-1-[(2R)-2-[4-(2-chloro-4-fluoro-phenyl)-2-oxo-chromen-7-yl]oxypropanoyl]-3-piperidyl]prop-2-enamide,
7-[(1R)-2-[4-(2-chloroacetyl)piperazin-1-yl]-1-methyl-2-oxo-ethoxy]-4-(2-chloro-4-fluoro-phenyl)chromen-2-one,
2-chloro-N-[(3S)-1-[(2R)-2-[4-(2-chloro-4-fluoro-phenyl)-2-oxo-chromen-7-yl]oxypropanoyl]-3-piperidyl]acetamide,
4-(2-chloro-4-fluoro-phenyl)-7-[(1R)-1-methyl-2-oxo-2-(4-propanoylpiperazin-1-yl) ethoxy]chromen-2-one,
N-[(3S)-1-[(2R)-2-[4-(2-chloro-4-fluoro-phenyl)-2-oxo-chromen-7-yl]oxypropanoyl]-3-piperidyl]propanamide,
rac-(3S)-1-[2-[4-(2-chlorophenyl)-2-oxo-pyrano[2,3-b]pyridin-7-yl]oxypropanoyl]piperidine-3-carboxylic acid,
tert-butyl rac-(3S)-1-[2-[4-(2-chlorophenyl)-2-oxo-pyrano[2,3-b]pyridin-7-yl]oxypropanoyl]piperidine-3-carboxylate,
(3S)-1-[(2R)-2-[4-(2-chlorophenyl)-2-oxo-pyrano[2,3-b]pyridin-7-yl]oxypropanoyl]piperidine-3-carboxylic acid,
(3S)-1-[(2R)-2-[4-(2-chloro-4-fluoro-phenyl)-2-oxo-pyrano[2,3-b]pyridin-7-yl]oxypropanoyl]piperidine-3-carboxylic acid,
(3S)-1-[(2R)-2-[4-(3-methyl-2-thienyl)-2-oxo-chromen-7-yl]oxypropanoyl]piperidine-3-carboxylic acid,
ethyl 2-[4-(2-fluorophenyl)-2-oxo-chromen-7-yl]oxypropanoate, and
ethyl 2-[4-(2,6-difluorophenyl)-2-oxo-chromen-7-yl]oxypropanoate,
or a pharmaceutically or veterinary acceptable salt, hydrate or solvate thereof.

14. A pharmaceutical composition comprising a compound of claim 1 and pharmaceutically or veterinary acceptable carriers and/or excipients.

15. A process for manufacturing a compound according to claim 1 comprising the steps of:
(a) reacting a compound of formula (A)

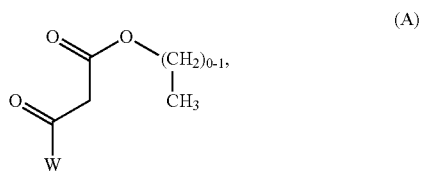

(A)

wherein W is as defined in claim 1,
with resorcin or 2,6-dihydroxypyridine to obtain a compound of formula (B)

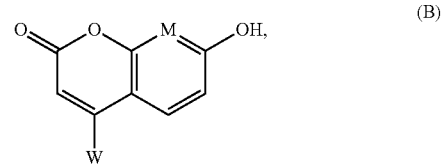

(B)

wherein W and M are as defined in claim 1, or
(a1) reacting a compound of formula (K)

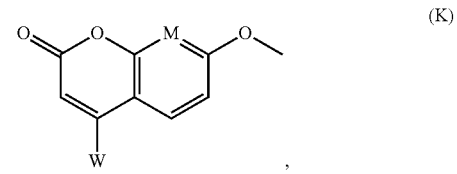

(K)

wherein W and M are as defined in claim 1,
with boron tribromide to obtain a compound of formula (B)

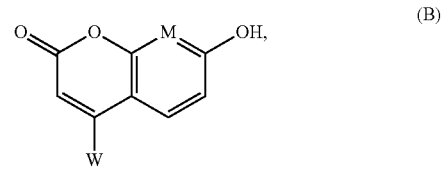

(B)

wherein W and M are as defined in claim 1, and
(b) alkylating a compound of formula (B) as defined above with an alkylating agent,
to obtain a compound of formula (C)

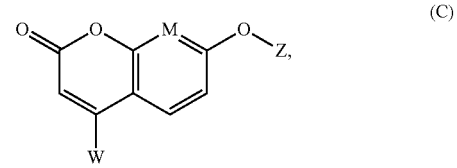

(C)

wherein W, M and Z are as defined above.

16. A process for manufacturing a compound according to claim 1, wherein Y is —NR$_3$R$_4$ as defined in claim 1, comprising the steps of:
(a) hydrolyzing a compound of formula (D)

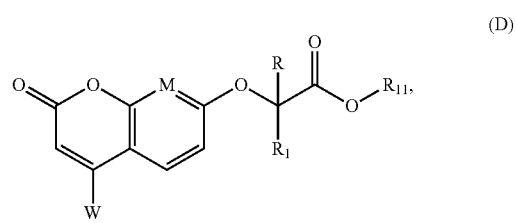

(D)

wherein W, M, R, R$_1$, and R$_{11}$ are as defined in claim 1 to obtain a compound of formula (E)

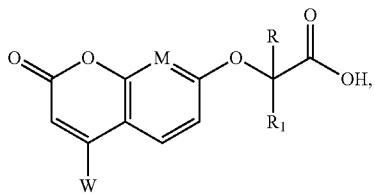
(E)

wherein W, M, R, and $R_1$ are as defined in claim 1, and (b) amidating the compound of formula (E) to obtain a compound of formula (F)

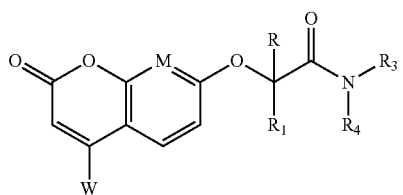
(F)

wherein W, M, R, $R_1$, $R_3$, and $R_4$, are as defined in claim 1.

17. A method of treating cancer comprising administering a therapeutically effective amount of a compound of claim 1.

18. A method of treating cancer comprising administering a therapeutically effective amount of a compound of claim 1 in simultaneous, alternating or subsequent combination with an additional cancer therapy.

19. The method of claim 17, wherein the cancer is selected from the group consisting of melanoma, metastatic melanoma, pancreatic cancer, hepatocellular carcinoma, lymphoma, acute myeloid leukemia, breast cancer, glioblastoma, cervical cancer, renal cancer, colorectal cancer or ovarian cancer.

20. The method of claim 19, wherein the additional cancer therapy is selected from the group consisting of chemotherapy, immunotherapy, hormone therapy, stem cell transplantation therapy, radiation therapy and surgery.

* * * * *

UNITED STATES PATENT AND TRADEMARK OFFICE
CERTIFICATE OF CORRECTION

PATENT NO. : 11,111,238 B2
APPLICATION NO. : 16/648348
DATED : September 7, 2021
INVENTOR(S) : Raffaella Di Lucrezia et al.

It is certified that error appears in the above-identified patent and that said Letters Patent is hereby corrected as shown below:

In the Claims

Claim 5, Line 29 of Column 187, "-$SO_2NR_8R_9$ with $R_5$ and $R_9$ independently are -H, or" should be -- -$SO_2NR_8R_9$ with $R_8$ and $R_9$ independently are -H, or--

Signed and Sealed this
Twelfth Day of July, 2022

Katherine Kelly Vidal
*Director of the United States Patent and Trademark Office*